US012239704B2

(12) United States Patent
Cook et al.

(10) Patent No.: US 12,239,704 B2
(45) Date of Patent: Mar. 4, 2025

(54) RECOMBINANT NON-PATHOGENIC MAREK'S DISEASE VIRUS CONSTRUCTS ENCODING MULTIPLE HETEROLOGOUS ANTIGENS

(71) Applicant: Intervet Inc., Madison, NJ (US)

(72) Inventors: Stephanie M. Cook, Omaha, NE (US); Mohamad Morsey, Omaha, NE (US); Ian Tarpey, St. Ives (GB)

(73) Assignee: INTERVET INC., Rahway, NJ (US)

( * ) Notice: Subject to any disclaimer, the term of this patent is extended or adjusted under 35 U.S.C. 154(b) by 479 days.

(21) Appl. No.: 17/544,044

(22) Filed: Dec. 7, 2021

(65) Prior Publication Data

US 2022/0088187 A1 Mar. 24, 2022

Related U.S. Application Data

(63) Continuation of application No. 16/753,133, filed as application No. PCT/EP2018/077725 on Oct. 11, 2018, now Pat. No. 11,229,698.

(60) Provisional application No. 62/729,673, filed on Sep. 11, 2018, provisional application No. 62/571,524, filed on Oct. 12, 2017.

(51) Int. Cl.

| | |
|---|---|
| ***A61K 39/255*** | (2006.01) |
| ***A61K 39/00*** | (2006.01) |
| ***A61K 39/17*** | (2006.01) |
| ***A61P 31/20*** | (2006.01) |
| ***C12N 15/86*** | (2006.01) |

(52) U.S. Cl.

CPC ............ *A61K 39/255* (2013.01); *A61K 39/17* (2013.01); *A61P 31/20* (2018.01); *C12N 15/86* (2013.01); *A61K 2039/5254* (2013.01); *A61K 2039/5256* (2013.01); *A61K 2039/552* (2013.01); *A61K 2039/70* (2013.01)

(58) Field of Classification Search

None

See application file for complete search history.

(56) References Cited

U.S. PATENT DOCUMENTS

| | | | |
|---|---|---|---|
| 5,187,087 | A | 2/1993 | Sondermeijer et al. |
| 5,733,554 | A | 3/1998 | Audonnet et al. |
| 5,830,745 | A | 11/1998 | Hock et al. |
| 5,834,305 | A | 11/1998 | Cochran et al. |
| 5,853,733 | A | 12/1998 | Cochran et al. |

(Continued)

FOREIGN PATENT DOCUMENTS

| | | | |
|---|---|---|---|
| CN | 1472315 | A | 2/2004 |
| CN | 101210248 | A | 7/2008 |

(Continued)

OTHER PUBLICATIONS

Hein R, Koopman R, Garcia M, Armour N, Dunn JR, Barbosa T, Martinez A. Review of Poultry Recombinant Vector Vaccines. Avian Dis. Sep. 2021;65(3):438-452. (Year: 2021).*

(Continued)

*Primary Examiner* — Michelle S Horning

(74) *Attorney, Agent, or Firm* — JONES DAY

(57) ABSTRACT

The present invention discloses novel recombinant multivalent non-pathogenic Marek's Disease virus constructs that encode and express foreign antigens from three or more (Continued)

avian viruses, along with methods of the use of the multivalent poultry virus vaccines.

12 Claims, 5 Drawing Sheets

Specification includes a Sequence Listing.

(56) References Cited

U.S. PATENT DOCUMENTS

| | | | | |
|---|---|---|---|---|
| 5,928,648 | A | 7/1999 | Cochran | |
| 5,961,982 | A | 10/1999 | Cochran | |
| 5,965,138 | A | 10/1999 | Cochran et al. | |
| 5,980,906 | A | 11/1999 | Audonnet et al. | |
| 6,121,043 | A | 9/2000 | Cochran et al. | |
| 6,183,753 | B1 | 2/2001 | Cochran et al. | |
| 6,299,882 | B1 | 10/2001 | Junker | |
| 6,875,856 | B2 | 4/2005 | Wild et al. | |
| 6,913,751 | B2 | 7/2005 | Cochran et al. | |
| 8,932,604 | B2 | 1/2015 | Cook et al. | |
| 9,114,108 | B2 | 8/2015 | Bublot et al. | |
| 9,409,954 | B2 | 8/2016 | Cook et al. | |
| 9,555,016 | B2 | 1/2017 | Makridakis | |
| 9,555,096 | B2 | 1/2017 | Bublot et al. | |
| 9,770,502 | B2 | 9/2017 | Bublot et al. | |
| 10,188,720 | B2 | 1/2019 | Esaki et al. | |
| 10,308,956 | B2 | 6/2019 | Verstegen et al. | |
| 10,323,257 | B2 | 6/2019 | Bublot et al. | |
| 10,655,146 | B2 | 5/2020 | Esaki et al. | |
| 10,813,991 | B2 | 10/2020 | Reddy et al. | |
| 10,822,620 | B2 | 11/2020 | Bublot et al. | |
| 11,058,761 | B2 | 7/2021 | Mebatsion et al. | |
| 11,123,425 | B2 | 9/2021 | Fujisawa et al. | |
| 11,229,698 | B2 | 1/2022 | Cook et al. | |
| 11,596,687 | B2 * | 3/2023 | Cook | A61P 31/22 |
| 2008/0233146 | A1 | 9/2008 | Sato | |
| 2014/0147465 | A1 | 5/2014 | Bublot et al. | |
| 2018/0163230 | A1 | 6/2018 | Bublot et al. | |
| 2021/0010033 | A1 | 1/2021 | Bublot et al. | |
| 2021/0386854 | A1 | 12/2021 | Ameiss et al. | |

FOREIGN PATENT DOCUMENTS

| | | | |
|---|---|---|---|
| CN | 103589693 | A | 2/2014 |
| CN | 103874508 | A | 6/2014 |
| CN | 103890183 | A | 6/2014 |
| CN | 104364381 | A | 2/2015 |
| CN | 107002097 | A | 8/2017 |
| EP | 728842 | A2 | 8/1996 |
| EP | 1298139 | B1 | 5/2007 |
| EP | 2644702 | A1 | 10/2013 |
| EP | 3041939 | B1 | 3/2019 |
| EP | 3554536 | A1 | 10/2019 |
| EP | 3708670 | A1 | 9/2020 |
| JP | 2015500631 | A | 1/2015 |
| JP | 2015500806 | A | 1/2015 |
| RU | 2593950 | C2 | 8/2016 |
| RU | 2624037 | C2 | 6/2017 |
| WO | 198704463 | A1 | 7/1987 |
| WO | 199203554 | A1 | 3/1992 |
| WO | 1996005291 | A1 | 2/1996 |
| WO | 1998037216 | A1 | 8/1998 |
| WO | 2000061736 | A2 | 10/2000 |
| WO | 2013057235 | A1 | 4/2013 |
| WO | 2013057236 | A1 | 4/2013 |
| WO | 2013082317 | A2 | 6/2013 |
| WO | 2013082327 | A1 | 6/2013 |
| WO | WO 2013144355 | A1 | 10/2013 |
| WO | 2016102647 | A1 | 6/2016 |
| WO | 2017216287 | A1 | 12/2017 |
| WO | 2018112051 | A1 | 6/2018 |
| WO | 2020127964 | A1 | 6/2020 |
| WO | 2021257706 | A1 | 12/2021 |
| WO | 2022079160 | A2 | 4/2022 |

OTHER PUBLICATIONS

U.S. Appl. No. 16/753,133, filed Apr. 2, 2020.

Afonso, et al., The Genome of Turkey Herpesvirus, Journal of Virology, 2001, 971-978, 75-2.

Bobrovskaya, Irina Vladimirovna, Antigenic Properties of Infectious and Thermoinactivated Vaccine Preparations of Marek's Disease Virus Strains, Shchyolkovo, 2000, 1-28, N/A (Machine Translation).

Bobrovskaya, Irina Vladimirovna, Antigenic Properties of Infectious and Thermoinactivated Vaccine Preparations of Marek's Disease Virus Strains, Shchyolkovo, 2000, 1-31, N/A.

Dartiel, et al., Herpesvirus of Turkey Recombinant Viruses Expressing Infectious Bursal Disease Virus (IBDV) VP2 Immunogen Induce Protection Against an IBDV Virulent Challenge in Chickens, Virology, 1995, 481-490, 211.

Fuchs, et al., Molecular Biology of Avian Infectious Laryngotracheitis Virus, Veterinary Research, 2007, 261-279, 38.

Hao, X. et al., Research Progress in Herpesvirus of Turkey Vectored Avian Influenza Vaccines, China Poultry, 2015, 48-52, 37(21).

Hao, Xiaoli et al., Research Progress in Herpesvirus of Turkey Vectored Avian influenza Vaccines, China Poultry, 2015, 48-52, 37(21) (Machine Translation).

International Search report for PCT/EP2018/077725 dated Nov. 28, 2018, 18 pages.

Johnson, et al., Protection Against Infectious Laryngotracheitis by In Ovo Vaccination with Commercially Available Viral Vector Recombinant Vaccines, Avian Diseases, 2010, 1251-1259, 54.

Kingham, et al., The Genome of Herpesvirus of Turkeys: Comparative Analysis with Marek's Disease Viruses, Journal of General Virology, 2001, 1123-1135, 82.

Murthy, et al., Pathogenesis of Marek's Disease: Effect of Immunization with Inactivated Viral and Tumor-Associated Antigens, Infection and Immunity, 1979, pp. 547-533, 26-2.

Petherbridge, et al., Cloning of Gallid Herpesvirus 3 (Marek's Disease Virus Serotype-2), Journal of Virological Methods, 2009, 11-17, 158.

Sondermeijer, et al., Avian Herpesvirus as a Live Viral Vector for the Expression of Heterologous Antigens, Vaccine, 1993, 349-358, 11.

Sun, et al., Protection of Chickens from Newcastle Disease and Infectious Laryngotracheitis with A Recombinant Fowlpox Virus Co-Expressing the F, HN Genes of Newcastle Disease Virus and GB Gene of Infectious Laryngotracheitis Virus, Avian Diseases, 2008, 111-117, 52.

Tsukamoto, et al., Complete, Long-Lasting Protection Against Lethal Infectious Bursal Disease Virus Challenge by a Single Vaccination with an Avian Herepesvirus Vector Expressing VP2 Antigens, Journal of Virology, 2002, 5637-5645, 76-11.

Van Zijl, et al., Regeneration of Herpesviruses from Molecularly Cloned Subgenomic Fragments, Journal of Virology, 1988, 2191-2195, 62-6.

Wild, et al., A Genomic map of Infectious Laryngotracheitis Virus and the Sequence and Organization of Genes Present in the Unique Short and Flanking Regions, Virus Genes, 1996, 107-116, 12-2.

Wu, et al., Molecular Detection and Differentiation of Infectious Bursal Disease Virus, Avian Diseases, 2007, 515-526, 51.

Hein et al., 2011, "Issues of the Poultry Recombinant Viral Vector Vaccines which May Cause an Effect on the Economic Benefits of those Vaccines," Sep. 16, 2011 [online], [retrieved on Aug. 18, 2024]. Retrieved from the Internet <URL: https://en.engormix.com/poultry-industry/poultry-vaccines/issues-poultry-recombinant-viral_a34922/> (8 pages).

Starostina, 2016, "IBD Vaccination: HVT Vector Vaccine or Live?" May 11, 2016 [online], [retrieved on Aug. 18, 2024]. Retrieved from the Internet <URL: https://www.thepoultrysite.com/news/2016/05/ibd-vaccination-hvt-vector-vaccine-or-live> (8 pages).

* cited by examiner

HVT/IBDV/ILT/NDV 670-14 Construct

SEQUENCE LISTING

<160> NUMBER OF SEQ ID NOS: 32

<210> SEQ ID NO 1
<211> LENGTH: 1134
<212> TYPE: DNA
<213> ORGANISM: Infectious Laryngotracheitis virus

<400> SEQUENCE: 1
atggaccgcc atttattttt gaggaatgct ttttggacta tcgtactgct ttcttccttc 60
gctagccaga gcaccgccgc cgtcacgtac gactacattt taggccgtcg cgcgctcgac 120
gcgctaacca taccggcggt tggcccgtat aacagatacc tcactagggt atcaagaggc 180
tgcgacgttg tcgagctcaa cccgatttct aacgtggacg acatgatatc ggcggccaaa 240
gaaaaagaga aggggggccc tttcgaggcc tccgtcgtct ggttctacgt gattaagggc 300
gacgacggcg aggacaagta ctgtccaatc tatagaaaag agtacaggga atgtggcgac 360
gtacaactgc tatctgaatg cgccgttcaa tctgcacaga tgtgggcagt ggactatgtt 420
cctagcaccc ttgtatcgcg aaatggcgcg ggactgacta tattctcccc cactgctgcg 480
ctctctggcc aatacttgct gaccctgaaa atcgggagat ttgcgcaaac agctctcgta 540
actctagaag ttaacgatcg ctgtttaaag atcgggtcgc agcttaactt tttaccgtcg 600
aaatgctgga caacagaaca gtatcagact ggatttcaag gcgaacacct ttatccgatc 660
gcagacacca atacacgaca cgcggacgac gtatatcggg gatacgaaga tattctgcag 720
cgctggaata atttgctgag gaaaaagaat cctagcgcgc cagaccctcg tccagatagc 780
gtcccgcaag aaattcccgc tgtaaccaag aaagcggaag ggcgcacccc ggacgcagaa 840
agcagcgaaa agaaggcccc tccagaagac tcggaggacg acatgcaggc agaggcttct 900
ggagaaaatc ctgccgccct ccccgaagac gacgaagtcc ccgaggacac cgagcacgat 960
gatccaaact cggatcctga ctattacaat gacatgcccg ccgtgatccc ggtggaggag 1020
actactaaaa gttctaatgc cgtctccatg cccatattcg cggcgttcgt agcctgcgcg 1080
gtcgcgctcg tggggctact ggtttggagc atcgtaaaat gcgcgcgtag ctaa 1134

<210> SEQ ID NO 2
<211> LENGTH: 377
<212> TYPE: PRT
<213> ORGANISM: Infectious Laryngotracheitis virus

<400> SEQUENCE: 2

```
Met Asp Arg His Leu Phe Leu Arg Asn Ala Phe Trp Thr Ile Val Leu
1               5                   10                  15

Leu Ser Ser Phe Ala Ser Gln Ser Thr Ala Ala Val Thr Tyr Asp Tyr
            20                  25                  30

Ile Leu Gly Arg Arg Ala Leu Asp Ala Leu Thr Ile Pro Ala Val Gly
        35                  40                  45

Pro Tyr Asn Arg Tyr Leu Thr Arg Val Ser Arg Gly Cys Asp Val Val
    50                  55                  60

Glu Leu Asn Pro Ile Ser Asn Val Asp Asp Met Ile Ser Ala Ala Lys
65                  70                  75                  80

Glu Lys Glu Lys Gly Gly Pro Phe Glu Ala Ser Val Val Trp Phe Tyr
                85                  90                  95

Val Ile Lys Gly Asp Asp Gly Glu Asp Lys Tyr Cys Pro Ile Tyr Arg
            100                 105                 110

Lys Glu Tyr Arg Glu Cys Gly Asp Val Gln Leu Leu Ser Glu Cys Ala
        115                 120                 125

Val Gln Ser Ala Gln Met Trp Ala Val Asp Tyr Val Pro Ser Thr Leu
    130                 135                 140

Val Ser Arg Asn Gly Ala Gly Leu Thr Ile Phe Ser Pro Thr Ala Ala
145                 150                 155                 160

Leu Ser Gly Gln Tyr Leu Leu Thr Leu Lys Ile Gly Arg Phe Ala Gln
                165                 170                 175

Thr Ala Leu Val Thr Leu Glu Val Asn Asp Arg Cys Leu Lys Ile Gly
            180                 185                 190

Ser Gln Leu Asn Phe Leu Pro Ser Lys Cys Trp Thr Thr Glu Gln Tyr
        195                 200                 205

Gln Thr Gly Phe Gln Gly Glu His Leu Tyr Pro Ile Ala Asp Thr Asn
    210                 215                 220

Thr Arg His Ala Asp Asp Val Tyr Arg Gly Tyr Glu Asp Ile Leu Gln
225                 230                 235                 240

Arg Trp Asn Asn Leu Leu Arg Lys Lys Asn Pro Ser Ala Pro Asp Pro
                245                 250                 255

Arg Pro Asp Ser Val Pro Gln Glu Ile Pro Ala Val Thr Lys Lys Ala
            260                 265                 270

Glu Gly Arg Thr Pro Asp Ala Glu Ser Ser Glu Lys Lys Ala Pro Pro
        275                 280                 285

Glu Asp Ser Glu Asp Asp Met Gln Ala Glu Ala Ser Gly Glu Asn Pro
    290                 295                 300

Ala Ala Leu Pro Glu Asp Asp Glu Val Pro Glu Asp Thr Glu His Asp
305                 310                 315                 320

Asp Pro Asn Ser Asp Pro Asp Tyr Tyr Asn Asp Met Pro Ala Val Ile
                325                 330                 335

Pro Val Glu Glu Thr Thr Lys Ser Ser Asn Ala Val Ser Met Pro Ile
            340                 345                 350

Phe Ala Ala Phe Val Ala Cys Ala Val Ala Leu Val Gly Leu Leu Val
        355                 360                 365

Trp Ser Ile Val Lys Cys Ala Arg Ser
    370                 375
```

<210> SEQ ID NO 3
<211> LENGTH: 1089
<212> TYPE: DNA
<213> ORGANISM: Infectious Laryngotracheitis virus

<400> SEQUENCE: 3

```
atggcatcgc tacttggaac tctggctctc cttgccgcga cgctcgcacc cttcggcgcg     60
atgggaatcg tgatcactgg aaatcacgtc tccgccagga ttgacgacga tcacatcgtg    120
atcgtcgcgc ctcgccccga agctacaatt caactgcagc tatttttcat gcctggccag    180
agaccccaca aaccctactc aggaaccgtc cgcgtcgcgt ttcggtctga tataacaaac    240
cagtgctacc aggaacttag cgaggagcgc tttgaaaatt gcactcatcg atcgtcttct    300
gtttttgtcg gctgtaaagt gaccgagtac acgttctccg cctcgaacag actaaccgga    360
cctccacacc cgtttaagct cactatacga aatcctcgtc cgaacgacag cgggatgttc    420
tacgtaattg ttcggctaga cgacaccaaa gaacccattg acgtcttcgc gatccaacta    480
tcggtgtatc aattcgcgaa caccgccgcg actcgcggac tctattccaa ggcttcgtgt    540
cgcaccttcg gattacctac cgtccaactt gaggcctatc tcaggaccga ggaaagttgg    600
cgcaactggc aagcgtacgt tgccacggag gccacgacga ccagcgccga ggcgacaacc    660
ccgacgcccg tcactgcaac cagcgcctcc gaacttgaag cggaacactt tacctttccc    720
tggctagaaa atggcgtgga tcattacgaa ccgacacccg caaacgaaaa ttcaaacgtt    780
actgtccgtc tcgggacaat gagccctacg ctaattgggg taaccgtggc tgccgtcgtg    840
agcgcaacga tcggcctcgt cattgtaatt tccatcgtca ccagaaacat gtgcaccccg    900
caccgaaaat tagacacggt ctcgcaagac gacgaagaac gttcccaaac tagaagggaa    960
tcgcgaaaat ttggacccat ggttgcgtgc gaaataaaca agggggctga ccaggatagt   1020
gaacttgtgg aactggttgc gattgttaac ccgtctgcgc taagctcgcc cgactcaata   1080
aaaatgtga                                                           1089
```

<210> SEQ ID NO 4
<211> LENGTH: 362
<212> TYPE: PRT
<213> ORGANISM: Infectious Laryngotracheitis virus

<400> SEQUENCE: 4

```
Met Ala Ser Leu Leu Gly Thr Leu Ala Leu Leu Ala Ala Thr Leu Ala
1               5                   10                  15

Pro Phe Gly Ala Met Gly Ile Val Ile Thr Gly Asn His Val Ser Ala
            20                  25                  30

Arg Ile Asp Asp Asp His Ile Val Ile Val Ala Pro Arg Pro Glu Ala
        35                  40                  45

Thr Ile Gln Leu Gln Leu Phe Phe Met Pro Gly Gln Arg Pro His Lys
    50                  55                  60

Pro Tyr Ser Gly Thr Val Arg Val Ala Phe Arg Ser Asp Ile Thr Asn
65                  70                  75                  80

Gln Cys Tyr Gln Glu Leu Ser Glu Glu Arg Phe Glu Asn Cys Thr His
                85                  90                  95

Arg Ser Ser Ser Val Phe Val Gly Cys Lys Val Thr Glu Tyr Thr Phe
            100                 105                 110

Ser Ala Ser Asn Arg Leu Thr Gly Pro Pro His Pro Phe Lys Leu Thr
        115                 120                 125

Ile Arg Asn Pro Arg Pro Asn Asp Ser Gly Met Phe Tyr Val Ile Val
    130                 135                 140

Arg Leu Asp Asp Thr Lys Glu Pro Ile Asp Val Phe Ala Ile Gln Leu
145                 150                 155                 160

Ser Val Tyr Gln Phe Ala Asn Thr Ala Ala Thr Arg Gly Leu Tyr Ser
```

```
                165                 170                 175

Lys Ala Ser Cys Arg Thr Phe Gly Leu Pro Thr Val Gln Leu Glu Ala
            180                 185                 190

Tyr Leu Arg Thr Glu Glu Ser Trp Arg Asn Trp Gln Ala Tyr Val Ala
        195                 200                 205

Thr Glu Ala Thr Thr Thr Ser Ala Glu Ala Thr Thr Pro Thr Pro Val
    210                 215                 220

Thr Ala Thr Ser Ala Ser Glu Leu Glu Ala Glu His Phe Thr Phe Pro
225                 230                 235                 240

Trp Leu Glu Asn Gly Val Asp His Tyr Glu Pro Thr Pro Ala Asn Glu
                245                 250                 255

Asn Ser Asn Val Thr Val Arg Leu Gly Thr Met Ser Pro Thr Leu Ile
            260                 265                 270

Gly Val Thr Val Ala Ala Val Val Ser Ala Thr Ile Gly Leu Val Ile
        275                 280                 285

Val Ile Ser Ile Val Thr Arg Asn Met Cys Thr Pro His Arg Lys Leu
    290                 295                 300

Asp Thr Val Ser Gln Asp Asp Glu Glu Arg Ser Gln Thr Arg Arg Glu
305                 310                 315                 320

Ser Arg Lys Phe Gly Pro Met Val Ala Cys Glu Ile Asn Lys Gly Ala
                325                 330                 335

Asp Gln Asp Ser Glu Leu Val Glu Leu Val Ala Ile Val Asn Pro Ser
            340                 345                 350

Ala Leu Ser Ser Pro Asp Ser Ile Lys Met
        355                 360
```

<210> SEQ ID NO 5
<211> LENGTH: 1362
<212> TYPE: DNA
<213> ORGANISM: Infectious bursal disease virus

<400> SEQUENCE: 5

```
atgacaaacc tgcaagatca aacccaacag attgttccgt tcatacggag ccttctgatg      60

ccaacaaccg gaccggcgtc cattccggac gacaccctgg agaagcacac tctcaggtca     120

gagacctcga cctacaattt gactgtgggg gacacagggt cagggctaat tgtctttttc     180

cctggattcc ctggctcaat tgtgggtgct cactacacac tgcagagcaa tgggaactac     240

aagttcgatc agatgctcct gactgcccag aacctaccgg ccagctacaa ctactgcaga     300

ctagtgagtc ggagtctcac agtgaggtca agcacactcc ctggtggcgt ttatgcacta     360

aacggcacca taaacgccgt gaccttccaa ggaagcctga gtgaactgac agatgttagc     420

tacaatgggt tgatgtctgc aacagccaac atcaacgaca aaattgggaa tgtcctggta     480

ggggaagggg tcactgtcct cagcctaccc acatcatatg atcttgggta tgtgaggctt     540

ggtgacccca ttcccgctat agggcttgac ccaaaaatgg tagctacatg cgacagcagt     600

gacaggccca gagtctacac cataactgca gccgatgatt accaattctc atcacagtac     660

caaccaggtg ggtaacaat cacactgttc tcagccaaca ttgatgctat cacaagcctc     720

agcattgggg gagagctcgt gtttcaaaca agcgtccaag gccttgtact gggcgccacc     780

atctacctta taggctttga tgggactgcg gtaatcacca gagctgtggc cgcagataat     840

gggctgacgg ccggcaccga caatcttatg ccattcaatc ttgtcattcc aaccaatgag     900

ataacccagc caatcacatc catcaaactg gagatagtga cctccaaaag tggtggtcag     960

gcaggggatc agatgtcatg gtcggcaagt gggagcctag cagtgacgat ccatggtggc    1020
```

```
aactatccag gggccctccg tcccgtcaca ctagtagcct acgaaagagt ggcaacagga   1080

tccgtcgtta cggtcgctgg ggtgagtaac ttcgagctga ttccaaatcc tgaactagca   1140

aagaacctgg ttacagaata cggccgattt gacccaggag ccatgaacta cacaaaattg   1200

atactgagtg agagggaccg tcttggcatc aagaccgtct ggccaacaag ggagtacact   1260

gattttcgtg agtacttcat ggaggtggcc gacctcaact ctcccctgaa gattgcagga   1320

gcatttggct tcaaagacat aatccgggct ataaggaggt aa                      1362
```

<210> SEQ ID NO 6
<211> LENGTH: 453
<212> TYPE: PRT
<213> ORGANISM: Infectious bursal disease virus

<400> SEQUENCE: 6

```
Met Thr Asn Leu Gln Asp Gln Thr Gln Gln Ile Val Pro Phe Ile Arg
1               5                   10                  15

Ser Leu Leu Met Pro Thr Thr Gly Pro Ala Ser Ile Pro Asp Asp Thr
            20                  25                  30

Leu Glu Lys His Thr Leu Arg Ser Glu Thr Ser Thr Tyr Asn Leu Thr
        35                  40                  45

Val Gly Asp Thr Gly Ser Gly Leu Ile Val Phe Phe Pro Gly Phe Pro
    50                  55                  60

Gly Ser Ile Val Gly Ala His Tyr Thr Leu Gln Ser Asn Gly Asn Tyr
65                  70                  75                  80

Lys Phe Asp Gln Met Leu Leu Thr Ala Gln Asn Leu Pro Ala Ser Tyr
                85                  90                  95

Asn Tyr Cys Arg Leu Val Ser Arg Ser Leu Thr Val Arg Ser Ser Thr
            100                 105                 110

Leu Pro Gly Gly Val Tyr Ala Leu Asn Gly Thr Ile Asn Ala Val Thr
        115                 120                 125

Phe Gln Gly Ser Leu Ser Glu Leu Thr Asp Val Ser Tyr Asn Gly Leu
    130                 135                 140

Met Ser Ala Thr Ala Asn Ile Asn Asp Lys Ile Gly Asn Val Leu Val
145                 150                 155                 160

Gly Glu Gly Val Thr Val Leu Ser Leu Pro Thr Ser Tyr Asp Leu Gly
                165                 170                 175

Tyr Val Arg Leu Gly Asp Pro Ile Pro Ala Ile Gly Leu Asp Pro Lys
            180                 185                 190

Met Val Ala Thr Cys Asp Ser Ser Asp Arg Pro Arg Val Tyr Thr Ile
        195                 200                 205

Thr Ala Ala Asp Asp Tyr Gln Phe Ser Ser Gln Tyr Gln Pro Gly Gly
    210                 215                 220

Val Thr Ile Thr Leu Phe Ser Ala Asn Ile Asp Ala Ile Thr Ser Leu
225                 230                 235                 240

Ser Ile Gly Gly Glu Leu Val Phe Gln Thr Ser Val Gln Gly Leu Val
                245                 250                 255

Leu Gly Ala Thr Ile Tyr Leu Ile Gly Phe Asp Gly Thr Ala Val Ile
            260                 265                 270

Thr Arg Ala Val Ala Ala Asp Asn Gly Leu Thr Ala Gly Thr Asp Asn
        275                 280                 285

Leu Met Pro Phe Asn Leu Val Ile Pro Thr Asn Glu Ile Thr Gln Pro
    290                 295                 300

Ile Thr Ser Ile Lys Leu Glu Ile Val Thr Ser Lys Ser Gly Gly Gln
```

-continued

```
305                 310                 315                 320

Ala Gly Asp Gln Met Ser Trp Ser Ala Ser Gly Ser Leu Ala Val Thr
                325                 330                 335

Ile His Gly Gly Asn Tyr Pro Gly Ala Leu Arg Pro Val Thr Leu Val
            340                 345                 350

Ala Tyr Glu Arg Val Ala Thr Gly Ser Val Val Thr Val Ala Gly Val
        355                 360                 365

Ser Asn Phe Glu Leu Ile Pro Asn Pro Glu Leu Ala Lys Asn Leu Val
    370                 375                 380

Thr Glu Tyr Gly Arg Phe Asp Pro Gly Ala Met Asn Tyr Thr Lys Leu
385                 390                 395                 400

Ile Leu Ser Glu Arg Asp Arg Leu Gly Ile Lys Thr Val Trp Pro Thr
                405                 410                 415

Arg Glu Tyr Thr Asp Phe Arg Glu Tyr Phe Met Glu Val Ala Asp Leu
            420                 425                 430

Asn Ser Pro Leu Lys Ile Ala Gly Ala Phe Gly Phe Lys Asp Ile Ile
        435                 440                 445

Arg Ala Ile Arg Arg
    450


<210> SEQ ID NO 7
<211> LENGTH: 1662
<212> TYPE: DNA
<213> ORGANISM: Newcastle disease virus

<400> SEQUENCE: 7

atgggcccca gaccttctac caagaaccca gtacctatga tgctgactgt ccgagtcgcg      60

ctggtactga gttgcatctg tccggcaaac tccattgatg gcaggcctct tgcggctgca     120

ggaattgtgg ttacaggaga caaagccgtc aacatataca cctcatccca gacaggatca     180

atcatagtta agctcctccc gaatctgccc aaggataagg aggcatgtgc gaaagccccc     240

ttggatgcat acaacaggac attgaccact ttgctcaccc cccttggtga ctctatccgt     300

aggatacaag agtctgtgac tacatctgga ggggggagac aggggcgcct tataggcgcc     360

attattggcg gtgtggctct tggggttgca actgccgcac aaataacagc ggccgcagct     420

ctgatacaag ccaaacaaaa tgctgccaac atcctccgac ttaaagagag cattgccgca     480

accaatgagg ctgtgcatga ggtcactgac ggattatcgc aactagcagt ggcagttggg     540

aagatgcagc agtttgttaa tgaccaattt aataaaacag ctcaggaatt agactgcatc     600

aaaattgcac agcaagttgg tgtagagctc aacctgtacc taaccgaatt gactacagta     660

ttcggaccac aaatcacttc acctgcttta aacaagctga ctattcaggc actttacaat     720

ctagctggtg gaaatatgga ttacttattg actaagttag gtgtagggaa caatcaactc     780

agctcattaa tcggtagcgg cttaatcacc ggtaacccta ttctatacga ctcacagact     840

caactcttgg gtatacaggt aactctacct tcagtcggga agctaaataa tatgcgtgcc     900

acctacttgg aaaccttatc cgtaagcaca accaggggat ttgcctcggc acttgtccca     960

aaagtggtga cacaggtcgg ttctgtgata gaagaacttg acacctcata ctgtatagaa    1020

actgacttac atttatattg tacaagaata gtaacgttcc ctatgtcccc tggtatttat    1080

tcctgcttga gcggcaatac gtcggcctgt atgtactcaa agaccgaagg cgcacttact    1140

acaccataca tgactatcaa aggttcagtc atcgccaact gcaagatgac aacatgtaga    1200

tgtgtaaacc ccccgggtat catatcgcaa aactatggag aagccgtgtc tctaatagat    1260
```

aaacaatcat gcaatgtttt atccttaggc gggataactt taaggctcag tggggaattc 1320
gatgtaactt atcagaagaa tatctcaata caagattctc aagtaataat aacaggcaat 1380
cttgatatct caactgagct tgggaatgtc aacaactcga tcagtaatgc tttgaataag 1440
ttagaggaaa gcaacagaaa actagacaaa gtcaatgtca aactgactag cacatctgct 1500
ctcattacct atatcgtgtt gactatcata tctcttgttt ttggtatact tagcctgatt 1560
ctagcatgct acctaatgta caagcaaaag gcgcaacaaa agaccttatt atggcttggg 1620
aataatactc tagatcagat gagagccact acaaaaatgt ga 1662

<210> SEQ ID NO 8
<211> LENGTH: 553
<212> TYPE: PRT
<213> ORGANISM: Newcastle disease virus

<400> SEQUENCE: 8

Met Gly Pro Arg Pro Ser Thr Lys Asn Pro Val Pro Met Met Leu Thr
1 5 10 15

Val Arg Val Ala Leu Val Leu Ser Cys Ile Cys Pro Ala Asn Ser Ile
20 25 30

Asp Gly Arg Pro Leu Ala Ala Ala Gly Ile Val Val Thr Gly Asp Lys
35 40 45

Ala Val Asn Ile Tyr Thr Ser Ser Gln Thr Gly Ser Ile Ile Val Lys
50 55 60

Leu Leu Pro Asn Leu Pro Lys Asp Lys Glu Ala Cys Ala Lys Ala Pro
65 70 75 80

Leu Asp Ala Tyr Asn Arg Thr Leu Thr Thr Leu Leu Thr Pro Leu Gly
85 90 95

Asp Ser Ile Arg Arg Ile Gln Glu Ser Val Thr Thr Ser Gly Gly Gly
100 105 110

Arg Gln Gly Arg Leu Ile Gly Ala Ile Ile Gly Gly Val Ala Leu Gly
115 120 125

Val Ala Thr Ala Ala Gln Ile Thr Ala Ala Ala Ala Leu Ile Gln Ala
130 135 140

Lys Gln Asn Ala Ala Asn Ile Leu Arg Leu Lys Glu Ser Ile Ala Ala
145 150 155 160

Thr Asn Glu Ala Val His Glu Val Thr Asp Gly Leu Ser Gln Leu Ala
165 170 175

Val Ala Val Gly Lys Met Gln Gln Phe Val Asn Asp Gln Phe Asn Lys
180 185 190

Thr Ala Gln Glu Leu Asp Cys Ile Lys Ile Ala Gln Gln Val Gly Val
195 200 205

Glu Leu Asn Leu Tyr Leu Thr Glu Leu Thr Thr Val Phe Gly Pro Gln
210 215 220

Ile Thr Ser Pro Ala Leu Asn Lys Leu Thr Ile Gln Ala Leu Tyr Asn
225 230 235 240

Leu Ala Gly Gly Asn Met Asp Tyr Leu Leu Thr Lys Leu Gly Val Gly
245 250 255

Asn Asn Gln Leu Ser Ser Leu Ile Gly Ser Gly Leu Ile Thr Gly Asn
260 265 270

Pro Ile Leu Tyr Asp Ser Gln Thr Gln Leu Leu Gly Ile Gln Val Thr
275 280 285

Leu Pro Ser Val Gly Lys Leu Asn Asn Met Arg Ala Thr Tyr Leu Glu
290 295 300

-continued

```
Thr Leu Ser Val Ser Thr Thr Arg Gly Phe Ala Ser Ala Leu Val Pro
305                 310                 315                 320

Lys Val Val Thr Gln Val Gly Ser Val Ile Glu Glu Leu Asp Thr Ser
                325                 330                 335

Tyr Cys Ile Glu Thr Asp Leu His Leu Tyr Cys Thr Arg Ile Val Thr
            340                 345                 350

Phe Pro Met Ser Pro Gly Ile Tyr Ser Cys Leu Ser Gly Asn Thr Ser
        355                 360                 365

Ala Cys Met Tyr Ser Lys Thr Glu Gly Ala Leu Thr Thr Pro Tyr Met
    370                 375                 380

Thr Ile Lys Gly Ser Val Ile Ala Asn Cys Lys Met Thr Thr Cys Arg
385                 390                 395                 400

Cys Val Asn Pro Pro Gly Ile Ile Ser Gln Asn Tyr Gly Glu Ala Val
                405                 410                 415

Ser Leu Ile Asp Lys Gln Ser Cys Asn Val Leu Ser Leu Gly Gly Ile
            420                 425                 430

Thr Leu Arg Leu Ser Gly Glu Phe Asp Val Thr Tyr Gln Lys Asn Ile
        435                 440                 445

Ser Ile Gln Asp Ser Gln Val Ile Ile Thr Gly Asn Leu Asp Ile Ser
    450                 455                 460

Thr Glu Leu Gly Asn Val Asn Asn Ser Ile Ser Asn Ala Leu Asn Lys
465                 470                 475                 480

Leu Glu Glu Ser Asn Arg Lys Leu Asp Lys Val Asn Val Lys Leu Thr
                485                 490                 495

Ser Thr Ser Ala Leu Ile Thr Tyr Ile Val Leu Thr Ile Ile Ser Leu
            500                 505                 510

Val Phe Gly Ile Leu Ser Leu Ile Leu Ala Cys Tyr Leu Met Tyr Lys
        515                 520                 525

Gln Lys Ala Gln Gln Lys Thr Leu Leu Trp Leu Gly Asn Asn Thr Leu
    530                 535                 540

Asp Gln Met Arg Ala Thr Thr Lys Met
545                 550
```

<210> SEQ ID NO 9
<211> LENGTH: 1698
<212> TYPE: DNA
<213> ORGANISM: Newcastle disease virus

<400> SEQUENCE: 9

```
atggatcgat cccggttggc gccctccagg tgcaggatgg gctccagacc ttctaccaag      60

aacccagcac ctatgatgct gactatccgg gtcgcgctgg tactgagttg catctgtccg     120

gcaaactcca ttgatggcag gcctcttgca gctgcaggaa ttgtggttac aggagacaaa     180

gcagtcaaca tatacacctc atcccagaca ggatcaatca tagttaagct cctcccgaat     240

ctgccaaagg ataaggaggc atgtgcgaaa gccccccttgg atgcatacaa caggacattg     300

accactttgc tcaccccct tggtgactct atccgtagga tacaagagtc tgtgactaca     360

tctggagggg ggagacaggg gcgccttata ggcgccatta ttggcggtgt ggctcttggg     420

gttgcaactg ccgcacaaat aacagcggcc gcagctctga tacaagccaa acaaaatgct     480

gccaacatcc tccgacttaa agagagcatt gccgcaacca atgaggctgt gcatgaggtc     540

actgacggat tatcgcaact agcagtggca gttgggaaga tgcagcagtt cgttaatgac     600

caatttaata aaacagctca ggaattagac tgcatcaaaa ttgcacagca agttggtgta     660

gagctcaacc tgtacctaac cgaatcgact acagtattcg gaccacaaat cacttcacct     720
```

```
gccttaaaca agctgactat tcaggcactt tacaatctag ctggtgggaa tatggattac    780

ttattgacta agttaggtat agggaacaat caactcagct cattaatcgg tagcggctta    840

atcaccggta accctattct atacgactca cagactcaac tcttgggtat acaggtaact    900

ctaccttcag tcgggaacct aaataatatg cgtgccacct acttggaaac cttatccgta    960

agcacaacca ggggatttgc ctcggcactt gtcccaaaag tggtgacacg ggtcggttct   1020

gtgatagaag aacttgacac ctcatactgt atagaaactg acttagattt atattgtaca   1080

agaatagtaa cgttccctat gtcccctggt atttactcct gcttgagcgg caatacatcg   1140

gcctgtatgt actcaaagac cgaaggcgca cttactacac catatatgac tatcaaaggc   1200

tcagtcatcg ctaactgcaa gatgacaaca tgtagatgtg taaacccccc gggtatcata   1260

tcgcaaaact atggagaagc cgtgtctcta atagataaac aatcatgcaa tgttttatcc   1320

ttaggcggga taactttaag gctcagtggg gaattcgatg taacttatca gaagaatatc   1380

tcaatacaag attctcaagt aataataaca ggcaatcttg atatctcaac tgagcttggg   1440

aatgtcaaca actcgatcag taatgccttg aataagttag aggaaagcaa cagaaaacta   1500

gacaaagtca atgtcaaact gaccagcaca tctgctctca ttacctatat cgttttgact   1560

atcatatctc ttgtttttgg tatacttagc ctgattctag catgctacct aatgtacaag   1620

caaaaggcgc aacaaaagac cttattatgg cttgggaata ataccctaga tcagatgaga   1680

gccactacaa aaatgtga                                                 1698
```

<210> SEQ ID NO 10
<211> LENGTH: 565
<212> TYPE: PRT
<213> ORGANISM: Newcastle disease virus

<400> SEQUENCE: 10

```
Met Asp Arg Ser Arg Leu Ala Pro Ser Arg Cys Arg Met Gly Ser Arg
1               5                   10                  15

Pro Ser Thr Lys Asn Pro Ala Pro Met Met Leu Thr Ile Arg Val Ala
            20                  25                  30

Leu Val Leu Ser Cys Ile Cys Pro Ala Asn Ser Ile Asp Gly Arg Pro
        35                  40                  45

Leu Ala Ala Ala Gly Ile Val Val Thr Gly Asp Lys Ala Val Asn Ile
    50                  55                  60

Tyr Thr Ser Ser Gln Thr Gly Ser Ile Ile Val Lys Leu Leu Pro Asn
65                  70                  75                  80

Leu Pro Lys Asp Lys Glu Ala Cys Ala Lys Ala Pro Leu Asp Ala Tyr
                85                  90                  95

Asn Arg Thr Leu Thr Thr Leu Leu Thr Pro Leu Gly Asp Ser Ile Arg
            100                 105                 110

Arg Ile Gln Glu Ser Val Thr Thr Ser Gly Gly Gly Arg Gln Gly Arg
        115                 120                 125

Leu Ile Gly Ala Ile Ile Gly Gly Val Ala Leu Gly Val Ala Thr Ala
    130                 135                 140

Ala Gln Ile Thr Ala Ala Ala Ala Leu Ile Gln Ala Lys Gln Asn Ala
145                 150                 155                 160

Ala Asn Ile Leu Arg Leu Lys Glu Ser Ile Ala Ala Thr Asn Glu Ala
                165                 170                 175

Val His Glu Val Thr Asp Gly Leu Ser Gln Leu Ala Val Ala Val Gly
            180                 185                 190
```

-continued

```
Lys Met Gln Gln Phe Val Asn Asp Gln Phe Asn Lys Thr Ala Gln Glu
        195                 200                 205

Leu Asp Cys Ile Lys Ile Ala Gln Gln Val Gly Val Glu Leu Asn Leu
    210                 215                 220

Tyr Leu Thr Glu Ser Thr Thr Val Phe Gly Pro Gln Ile Thr Ser Pro
225                 230                 235                 240

Ala Leu Asn Lys Leu Thr Ile Gln Ala Leu Tyr Asn Leu Ala Gly Gly
                245                 250                 255

Asn Met Asp Tyr Leu Leu Thr Lys Leu Gly Ile Gly Asn Asn Gln Leu
            260                 265                 270

Ser Ser Leu Ile Gly Ser Gly Leu Ile Thr Gly Asn Pro Ile Leu Tyr
        275                 280                 285

Asp Ser Gln Thr Gln Leu Leu Gly Ile Gln Val Thr Leu Pro Ser Val
    290                 295                 300

Gly Asn Leu Asn Asn Met Arg Ala Thr Tyr Leu Glu Thr Leu Ser Val
305                 310                 315                 320

Ser Thr Thr Arg Gly Phe Ala Ser Ala Leu Val Pro Lys Val Val Thr
                325                 330                 335

Arg Val Gly Ser Val Ile Glu Glu Leu Asp Thr Ser Tyr Cys Ile Glu
            340                 345                 350

Thr Asp Leu Asp Leu Tyr Cys Thr Arg Ile Val Thr Phe Pro Met Ser
        355                 360                 365

Pro Gly Ile Tyr Ser Cys Leu Ser Gly Asn Thr Ser Ala Cys Met Tyr
    370                 375                 380

Ser Lys Thr Glu Gly Ala Leu Thr Thr Pro Tyr Met Thr Ile Lys Gly
385                 390                 395                 400

Ser Val Ile Ala Asn Cys Lys Met Thr Thr Cys Arg Cys Val Asn Pro
                405                 410                 415

Pro Gly Ile Ile Ser Gln Asn Tyr Gly Glu Ala Val Ser Leu Ile Asp
            420                 425                 430

Lys Gln Ser Cys Asn Val Leu Ser Leu Gly Gly Ile Thr Leu Arg Leu
        435                 440                 445

Ser Gly Glu Phe Asp Val Thr Tyr Gln Lys Asn Ile Ser Ile Gln Asp
    450                 455                 460

Ser Gln Val Ile Ile Thr Gly Asn Leu Asp Ile Ser Thr Glu Leu Gly
465                 470                 475                 480

Asn Val Asn Asn Ser Ile Ser Asn Ala Leu Asn Lys Leu Glu Glu Ser
                485                 490                 495

Asn Arg Lys Leu Asp Lys Val Asn Val Lys Leu Thr Ser Thr Ser Ala
            500                 505                 510

Leu Ile Thr Tyr Ile Val Leu Thr Ile Ile Ser Leu Val Phe Gly Ile
        515                 520                 525

Leu Ser Leu Ile Leu Ala Cys Tyr Leu Met Tyr Lys Gln Lys Ala Gln
    530                 535                 540

Gln Lys Thr Leu Leu Trp Leu Gly Asn Asn Thr Leu Asp Gln Met Arg
545                 550                 555                 560

Ala Thr Thr Lys Met
                565
```

<210> SEQ ID NO 11
<211> LENGTH: 527
<212> TYPE: DNA
<213> ORGANISM: Infectious Laryngotracheitis virus

<400> SEQUENCE: 11

```
aaacagctgt actacagagt aaccgatgga agaacatcgg tccagctaat gtgcctgtcg     60

tgcacgagcc attctccgga accttactgt cttttcgaca cgtctcttat agcgagggaa    120

aaagatatcg cgccagagtt atactttacc tctgatccgc aaacggcata ctgcacaata    180

actctgccgt ccggcgttgt tccgagattc gaatggagcc ttaataatgt ttcactgccg    240

gaatatttga cggccacgac cgttgtttcg cataccgctg gccaaagtac agtgtggaag    300

agcagcgcga gagcaggcga ggcgtggatt tctggccggg gaggcaatat atacgaatgc    360

accgtcctca tctcagacgg cactcgcgtt actacgcgaa aggagaggtg cttaacaaac    420

acatggattg cggtggaaaa cggtgctgct caggcgcagc tgtattcact cttttctgga    480

cttgtgtcag gattatgcgg gagcatatct gctttgtacg caacgct                  527
```

<210> SEQ ID NO 12
<211> LENGTH: 264
<212> TYPE: DNA
<213> ORGANISM: Infectious Laryngotracheitis virus

<400> SEQUENCE: 12

```
tgactattac aatgacatgc ccgccgtgat cccggtggag gagactacta aaagttctaa     60

tgccgtctcc atgcccatat tcgcggcgtt cgtagcctgc gcggtcgcgc tcgtggggct    120

actggtttgg agcatcgtaa aatgcgcgcg tagctaatcg agcctagaat aggtggtttc    180

ttcctacatg ccacgcctca cgctcataat ataaatcaca tggaatagca taccaatgcc    240

tattcattgg gacgttcgaa aagc                                           264
```

<210> SEQ ID NO 13
<211> LENGTH: 1391
<212> TYPE: DNA
<213> ORGANISM: Mouse cytomegalovirus 1

<400> SEQUENCE: 13

```
aactccgccc gttttatgac tagaaccaat agtttttaat gccaaatgca ctgaaatccc     60

ctaatttgca aagccaaacg ccccctatgt gagtaatacg gggacttttt acccaatttc    120

ccacgcggaa agccccctaa tacactcata tggcatatga atcagcacgg tcatgcactc    180

taatggcggc ccatagggac tttccacata gggggcgttc accatttccc agcatagggg    240

tggtgactca atggccttta cccaagtaca ttgggtcaat gggaggtaag ccaatgggtt    300

tttcccatta ctggcaagca cactgagtca aatgggactt tccactgggt tttgcccaag    360

tacattgggt caatgggagg tgagccaatg ggaaaaaccc attgctgcca agtacactga    420

ctcaataggg actttccaat gggtttttcc attgttggca agcatataag gtcaatgtgg    480

gtgagtcaat agggactttc cattgtattc tgcccagtac ataaggtcaa taggggtga     540

atcaacagga aagtcccatt ggagccaagt acactgcgtc aatagggact ttccattggg    600

ttttgcccag tacataaggt caatagggga tgagtcaatg ggaaaaaccc attggagcca    660

agtacactga ctcaataggg actttccatt gggttttgcc cagtacataa ggtcaatagg    720

gggtgagtca acaggaaagt tccattggag ccaagtacat tgagtcaata gggactttcc    780

aatgggtttt gcccagtaca taaggtcaat gggaggtaag ccaatgggtt tttcccatta    840

ctggcacgta tactgagtca ttagggactt tccaatgggt tttgcccagt acataaggtc    900

aataggggtg aatcaacagg aaagtcccat tggagccaag tacactgagt caatagggac    960

tttccattgg gttttgccca gtacaaaagg tcaatagggg gtgagtcaat gggtttttcc   1020
```

cattattggc acgtacataa ggtcaatagg ggtgagtcat tgggtttttc cagccaattt 1080
aattaaaacg ccatgtactt tcccaccatt gacgtcaatg ggctattgaa actaatgcaa 1140
cgtgaccttt aaacggtact ttcccatagc tgattaatgg gaaagtaccg ttctcgagcc 1200
aatacacgtc aatgggaagt gaaagggcag ccaaaacgta acaccgcccc ggttttcccc 1260
tggaaattcc atattggcac gcattctatt ggctgagctg cgttctacgt gggtataaga 1320
ggcgcgacca gcgtcggtac cgtcgcagtc ttcggtctga ccaccgtaga acgcagagct 1380
cctcgctgca g 1391

<210> SEQ ID NO 14
<211> LENGTH: 301
<212> TYPE: DNA
<213> ORGANISM: Human cytomegalovirus

<400> SEQUENCE: 14
ggcagtacat ctacgtatta gtcatcgcta ttaccatggt gatgcggttt tggcagtaca 60
tcaatgggcg tggatagcgg tttgactcac ggggatttcc aagtctccac cccattgacg 120
tcaatgggag tttgttttgg caccaaaatc aacgggactt tccaaaatgt cgtaacaact 180
ccgccccatt gacgcaaatg ggcggtaggc gtgtacggtg ggaggtctat ataagcagag 240
ctcgtttagt gaaccgtcag atcgcctgga gacgccatcc acgctgtttt gacctccata 300
g 301

<210> SEQ ID NO 15
<211> LENGTH: 360
<212> TYPE: DNA
<213> ORGANISM: Human cytomegalovirus

<400> SEQUENCE: 15
cgcgccaggt caattccctg gcattatgcc cagtacatga ccttatggga ctttcctact 60
tggcagtaca tctacgtatt agtcatcgct attaccatgg tgatgcggtt ttggcagtac 120
atcaatgggc gtggatagcg gtttgactca cggggatttc caagtctcca ccccattgac 180
gtcaatggga gtttgttttg gcaccaaaat caacgggact ttccaaaatg tcgtaacaac 240
tccgccccat tgacgcaaat gggcggtagc gtgtacggtg ggaggtctat ataagcagag 300
ctcgtttagt gaaccgtcag atcgcctgga gacgccatcc acgctgtttt gacctccata 360

<210> SEQ ID NO 16
<211> LENGTH: 1191
<212> TYPE: DNA
<213> ORGANISM: Human cytomegalovirus

<400> SEQUENCE: 16
gtgaataata aaatgtgtgt ttgtccgaaa tacgcgtttg agatttctgt cccgactaaa 60
ttcatgtcgc gcgatagtgg tgtttatcgc cgatagagat ggcgatattg gaaaaatcga 120
tatttgaaaa tatggcatat tgaaaatgtc gccgatgtga gtttctgtgt aactgatatc 180
gccatttttc caaaagttga tttttgggca tacgcgatat ctggcgatac gcttatatcg 240
tttacggggg atggcgatag acgcctttgg tgacttgggc gattctgtgt gtcgcaaata 300
tcgcagtttc gatataggtg acagacgata tgaggctata tcgccgatag aggcgacatc 360
aagctggcac atggccaatg catatcgatc tatacattga atcaatattg gccattagcc 420
atattattca ttggttatat agcataaatc aatattggct attggccatt gcatacgttg 480
tatccatatc ataatatgta catttatatt ggctcatgtc caacattacc gccatgttga 540

```
cattgattat tgactagtta ttaatagtaa tcaattacgg ggtcattagt tcatagccca    600

tatatggagt tccgcgttac ataacttacg gtaaatggcc cgcctggctg accgcccaac    660

gacccccgcc cattgacgtc aataatgacg tatgttccca tagtaacgcc aatagggact    720

ttccattgac gtcaatgggt ggagtattta cggtaaactg cccacttggc agtacatcaa    780

gtgtatcata tgccaagtac gccccctatt gacgtcaatg acggtaaatg gcccgcctgg    840

cattatgccc agtacatgac cttatgggac tttcctactt ggcagtacat ctacgtatta    900

gtcatcgcta ttaccatggt gatgcggttt tggcagtaca tcaatgggcg tggatagcgg    960

tttgactcac ggggatttcc aagtctccac cccattgacg tcaatgggag tttgttttgg   1020

caccaaaatc aacgggactt tccaaaatgt cgtaacaact ccgccccatt gacgcaaatg   1080

ggcggtaggc gtgtacggtg ggaggtctat ataagcagag ctcgtttagt gaaccgtcag   1140

atcgcctgga gacgccatcc acgctgtttt gacctccata gaagacaccg g            1191
```

<210> SEQ ID NO 17
<211> LENGTH: 692
<212> TYPE: DNA
<213> ORGANISM: Gallus gallus
<220> FEATURE:
<221> NAME/KEY: misc_feature
<222> LOCATION: (141)..(143)
<223> OTHER INFORMATION: n is a, c, g, or t

<400> SEQUENCE: 17

```
cgcgccggat cagatctcca tggtcgaggt gagccccacg ttctgcttca ctctccccat     60

ctcccccccc tccccacccc caattttgta tttatttatt ttttaattat tttgtgcagc    120

gatgggggcg gggggggggg nnncgcgcgc caggcggggc ggggcggggc gaggggcggg    180

gcggggcgag gcggagaggt gcggcggcag ccaatcagag cggcgcgctc cgaaagtttc    240

cttttatggc gaggcggcgg cggcggcggc cctataaaaa gcgaagcgcg cggcgggcgg    300

gagtcgctgc gcgctgcctt cgccccgtgc cccgctccgc cgccgcctcg cgccgcccgc    360

cccggctctg actgaccgcg ttactcccac aggtgagcgg gcgggacggc ccttctcctc    420

cgggctgtaa ttagcggcag gaaggaaatg ggcggggagg gccttcgtgc gtcgccgcgc    480

cgccgtcccc ttctccctct ccagcctcgg ggctgtccgc ggggggacgg ctgccttcgg    540

gggggacggg gcagggcggg gttcggcttc tggcgtgtga ccggcggctc tagagcctct    600

gctaaccatg ttcatgcctt cttctttttc ctacagctcc tgggcaacgt gctggttatt    660

gtgctgtctc atcattttgg caaagaattg ca                                  692
```

<210> SEQ ID NO 18
<211> LENGTH: 55
<212> TYPE: DNA
<213> ORGANISM: Feline herpesvirus 1

<400> SEQUENCE: 18

```
caataaacat agcatacgtt atgacatggt ctaccgcgtc ttatatgggg acgac          55
```

<210> SEQ ID NO 19
<211> LENGTH: 370
<212> TYPE: DNA
<213> ORGANISM: herpes simplex virus

<400> SEQUENCE: 19

```
gatccataat tgattgacgg gagatggggg aggctaactg aaacacggaa ggagacaata     60
```

-continued ccggaaggaa cccgcgctat gacggcaata aaaagacaga ataaaacgca cgggtgttgg 120
gtcgtttgtt cataaacgcg gggttcggtc ccagggctgg cactctgtcg ataccccacc 180
gagaccccat tggggccaat acgcccgcgt ttcttccttt tccccacccc accccccaag 240
ttcgggtgaa ggcccagggc tcgcagccaa cgtcggggcg gcaggccctg ccatagccac 300
tggccccgtg ggttagggac ggggtccccc atggggaatg gtttatggtt cgtgggggtt 360
attattttga 370

<210> SEQ ID NO 20
<211> LENGTH: 199
<212> TYPE: DNA
<213> ORGANISM: Simian virus 40

<400> SEQUENCE: 20
agcttcagac atgataagat acattgatga gtttggacaa accacaacta gaatgcagtg 60
aaaaaaatgc tttatttgtg aaatttgtga tgctattgct ttatttgtaa ccattataag 120
ctgcaataaa caagttaaca acaacaattg cattcatttt atgtttcagg ttcaggggga 180
ggtgtgggag gtttttttcg 199

<210> SEQ ID NO 21
<211> LENGTH: 15252
<212> TYPE: DNA
<213> ORGANISM: Artificial Sequence
<220> FEATURE:
<223> OTHER INFORMATION: Expression cassette

<400> SEQUENCE: 21
ggcgcgccac tggagaacgg catgaccgca aaaggcgttg tagagatcga tcccacgaac 60
tctcaggcga tcgtgtcagt cgccataaac agcgacgatc gtctccagga tctgaacggt 120
tttcttctca acgatcatca gtatatgagg aactgaacct gatatttagc cgagggaaac 180
gcaggttaaa aaccctatca agcgattgcg attttcgcgt atctagtaaa aatagatggg 240
cttcggtact agccttcgcc gccaactctg aatatgccct tcgtggacct catataacat 300
ggcattgttt gttggatgcg gggccggaat taagaagaac attcgaaata cgagcaaaaa 360
tttcggccct ggcatgtgct gcgcgagaat cggtacttcg gggagaaagt tttatcggag 420
ctttgggtag tgcagaggaa actctatctt ggttgaaaat gcatgcgacc ctgcacttga 480
ttctggttaa ccacgatcca atttttaaga cggctggcgc ggtcctagat aacctccgct 540
taaaactagc cccaatattg atgtgcagat ataacacaga aaaacgatca atggaagaca 600
tgctacggcg gtcatctccc gaagacatca ccgattccct aacaatgtgc ctgattatgt 660
tatcgcgcat tcgtcgtacc atgcgcaccg caggaaataa atatagctat atgatagatc 720
caatgaatcg tatgtctaat tacactccag gcgaatgtat gacaggtata ttgcgatata 780
ttgacgaaca tgctagaagg tgtcctgatc acatatgtaa tttgtatatc acatgtacac 840
ttatgccgat gtatgtgcac gggcgatatt tctattgtaa ttcatttttt tgttagtaaa 900
ctaccacagg ctgtccggaa atctaagtta atgaataaag tagatggtta atactcattg 960
cttagaattg gactactttt aattctcttt aatgttcgta ttaaataaaa acatctttaa 1020
taaacttcag cctcttcgct tattgtagaa attgagtatt caaaatcatg ttcaaagccg 1080
tcttcggaga gtgtactcgc cacggtggtt ggaacatcac tatgtctaca cgtcaaattt 1140
aagcacgtca ggtctgtcga ggacaagaaa tggttaacta gtgtttcaat tattcttata 1200
aacgttaagc attgtaagcc ccccggccgt ccgcagcaac aatttactag tatgccgtgg 1260

-continued

```
gctccgggac tatcacggat gtccaattcg cacatgcata taatttttct agggtctctc   1320
atttcgagaa atcttcgggg atccatcagc aatgcgggct gtagtcccga ttcccgtttc   1380
aaatgaaggt gctccaacac ggtcttcaaa gcaaccggca taccagcaaa cacagactgc   1440
aactccccgc tgcaatgatt ggttataaac agtaatctgt cttctggaag tatatttcgc   1500
ccgacaatcc acggcgcccc caaagttaaa aaccatccat gtgtatttgc gtcttctctg   1560
ttaaaagaat attgactggc attttcccgt tgaccgccag atatccaaag tacagcacga   1620
tgttgcacgg acgactttgc agtcaccagc cttcctttcc acccccccac caacaaaatg   1680
tttatcgtag gacccatatc cgtaataagg atgggtctgg cagcaacccc ataggcgcct   1740
cggcgtggta gttctcgagg ccttaagctt aaggatcccc caactccgcc cgttttatga   1800
ctagaaccaa tagtttttaa tgccaaatgc actgaaatcc cctaatttgc aaagccaaac   1860
gcccccctatg tgagtaatac ggggactttt tacccaattt cccacgcgga aagcccccta   1920
atacactcat atggcatatg aatcagcacg gtcatgcact ctaatggcgg cccataggga   1980
ctttccacat agggggcgtt caccatttcc cagcataggg gtggtgactc aatggccttt   2040
acccaagtac attgggtcaa tgggaggtaa gccaatgggt ttttcccatt actggcaagc   2100
acactgagtc aaatgggact ttccactggg ttttgcccaa gtacattggg tcaatgggag   2160
gtgagccaat gggaaaaacc cattgctgcc aagtacactg actcaatagg gactttccaa   2220
tgggtttttc cattgttggc aagcatataa ggtcaatgtg ggtgagtcaa tagggacttt   2280
ccattgtatt ctgcccagta cataaggtca ataggggggtg aatcaacagg aaagtcccat   2340
tggagccaag tacactgcgt caatagggac tttccattgg gttttgccca gtacataagg   2400
tcaatagggg atgagtcaat gggaaaaacc cattggagcc aagtacactg actcaatagg   2460
gactttccat tgggttttgc ccagtacata aggtcaatag gggggtgagtc aacaggaaag   2520
ttccattgga gccaagtaca ttgagtcaat agggactttc caatgggttt tgcccagtac   2580
ataaggtcaa tgggaggtaa gccaatgggt ttttcccatt actggcacgt atactgagtc   2640
attagggact ttccaatggg ttttgcccag tacataaggt caataggggt gaatcaacag   2700
gaaagtccca ttggagccaa gtacactgag tcaataggga ctttccattg ggttttgccc   2760
agtacaaaag gtcaataggg ggtgagtcaa tgggtttttc ccattattgg cacgtacata   2820
aggtcaatag ggtgagtca ttgggttttt ccagccaatt taattaaaac gccatgtact   2880
ttcccaccat tgacgtcaat gggctattga aactaatgca acgtgacctt taaacggtac   2940
tttcccatag ctgattaatg ggaaagtacc gttctcgagc caatacacgt caatgggaag   3000
tgaaagggca gccaaaacgt aacaccgccc cggttttccc ctggaaattc catattggca   3060
cgcattctat tggctgagct gcgttctacg tgggtataag aggcgcgacc agcgtcggta   3120
ccgtcgcagt cttcggtctg accaccgtag aacgcagagc tcctcgctgc aggcggccgc   3180
tctagaactc gtcgatcgca gcgatgacaa acctgcaaga tcaaacccaa cagattgttc   3240
cgttcatacg gagccttctg atgccaacaa ccggaccggc gtccattccg gacgacaccc   3300
tggagaagca cactctcagg tcagagacct cgacctacaa tttgactgtg ggggacacag   3360
ggtcagggct aattgtcttt ttccctggat tccctggctc aattgtgggt gctcactaca   3420
cactgcagag caatgggaac tacaagttcg atcagatgct cctgactgcc cagaacctac   3480
cggccagcta caactactgc agactagtga gtcggagtct cacagtgagg tcaagcacac   3540
tccctggtgg cgtttatgca ctaaacggca ccataaacgc cgtgaccttc caaggaagcc   3600
```

-continued tgagtgaact gacagatgtt agctacaatg ggttgatgtc tgcaacagcc aacatcaacg 3660
acaaaattgg gaatgtcctg gtaggggaag ggtcactgt cctcagccta cccacatcat 3720
atgatcttgg gtatgtgagg cttggtgacc ccattcccgc tatagggctt gacccaaaaa 3780
tggtagctac atgcgacagc agtgacaggc ccagagtcta caccataact gcagccgatg 3840
attaccaatt ctcatcacag taccaaccag gtggggtaac aatcacactg ttctcagcca 3900
acattgatgc tatcacaagc ctcagcattg ggggagagct cgtgtttcaa acaagcgtcc 3960
aaggccttgt actgggcgcc accatctacc ttataggctt tgatgggact gcggtaatca 4020
ccagagctgt ggccgcagat aatgggctga cggccggcac cgacaatctt atgccattca 4080
atcttgtcat tccaaccaat gagataaccc agccaatcac atccatcaaa ctggagatag 4140
tgacctccaa aagtggtggt caggcagggg atcagatgtc atggtcggca agtgggagcc 4200
tagcagtgac gatccatggt ggcaactatc caggggccct ccgtcccgtc acactagtag 4260
cctacgaaag agtggcaaca ggatccgtcg ttacggtcgc tggggtgagt aacttcgagc 4320
tgattccaaa tcctgaacta gcaaagaacc tggttacaga atacggccga tttgacccag 4380
gagccatgaa ctacacaaaa ttgatactga gtgagaggga ccgtcttggc atcaagaccg 4440
tctggccaac aagggagtac actgattttc gtgagtactt catggaggtg gccgacctca 4500
actctcccct gaagattgca ggagcatttg gcttcaaaga cataatccgg gctataagga 4560
ggtagatcca gacatgataa gatacattga tgagtttgga caaaccacaa ctagaatgca 4620
gtgaaaaaaa tgctttattt gtgaaatttg tgatgctatt gctttatttg taaccattat 4680
aagctgcaat aaacaagtta acaacaacaa ttgcattcat tttatgtttc aggttcaggg 4740
ggaggtgtgg gaggtttttt cggatcctct agagtcgacg gcagagtcgc agacgcccct 4800
attggacgtc aaaattgtag aggtgaagtt ttcaaacgat ggcgaagtaa cggcgacttg 4860
cgtttccacc gtcaaatctc cctatagggt agaaactaat tggaaagtag acctcgtaga 4920
tgtaatggat gaaatttctg ggaacagtcc cgccggggtt tttaacagta atgagaaatg 4980
gcagaaacag ctgtactaca gagtaaccga tggaagaaca tcggtccagc taatgtgcct 5040
gtcgtgcacg agccattctc cggaacctta ctgtcttttc gacacgtctc ttatagcgag 5100
ggaaaaagat atcgcgccag agttatactt tacctctgat ccgcaaacgg catactgcac 5160
aataactctg ccgtccggcg ttgttccgag attcgaatgg agccttaata atgtttcact 5220
gccggaatat ttgacggcca cgaccgttgt ttcgcatacc gctggccaaa gtacagtgtg 5280
gaagagcagc gcgagagcag gcgaggcgtg gatttctggc cggggaggca atatatacga 5340
atgcaccgtc ctcatctcag acggcactcg cgttactacg cgaaaggaga ggtgcttaac 5400
aaacacatgg attgcggtgg aaaacggtgc tgctcaggcg cagctgtatt cactcttttc 5460
tggacttgtg tcaggattat gcgggagcat atctgctttg tacgcaacgc tatggaccgc 5520
catttatttt tgaggaatgc tttttggact atcgtactgc tttcttcctt cgctagccag 5580
agcaccgccg ccgtcacgta cgactacatt ttaggccgtc gcgcgctcga cgcgctaacc 5640
ataccggcgg ttggcccgta taacagatac ctcactaggg tatcaagagg ctgcgacgtt 5700
gtcgagctca acccgatttc taacgtggac gacatgatat cggcggccaa agaaaaagag 5760
aaggggggcc ctttcgaggc ctccgtcgtc tggttctacg tgattaaggg cgacgacggc 5820
gaggacaagt actgtccaat ctatagaaaa gagtacaggg aatgtggcga cgtacaactg 5880
ctatctgaat gcgccgttca atctgcacag atgtgggcag tggactatgt tcctagcacc 5940
cttgtatcgc gaaatggcgc gggactgact atattctccc ccactgctgc gctctctggc 6000

```
caatacttgc tgaccctgaa aatcgggaga tttgcgcaaa cagctctcgt aactctagaa   6060
gttaacgatc gctgtttaaa gatcgggtcg cagcttaact ttttaccgtc gaaatgctgg   6120
acaacagaac agtatcagac tggatttcaa ggcgaacacc tttatccgat cgcagacacc   6180
aatacacgac acgcggacga cgtatatcgg ggatacgaag atattctgca gcgctggaat   6240
aatttgctga ggaaaaagaa tcctagcgcg ccagaccctc gtccagatag cgtcccgcaa   6300
gaaattcccg ctgtaaccaa gaaagcggaa gggcgcaccc cggacgcaga aagcagcgaa   6360
aagaaggccc ctccagaaga ctcggaggac gacatgcagg cagaggcttc tggagaaaat   6420
cctgccgccc tccccgaaga cgacgaagtc cccgaggaca ccgagcacga tgatccaaac   6480
tcggatcctg actattacaa tgacatgccc gccgtgatcc cggtggagga gactactaaa   6540
agttctaatg ccgtctccat gcccatattc gcggcgttcg tagcctgcgc ggtcgcgctc   6600
gtggggctac tggtttggag catcgtaaaa tgcgcgcgta gctaatcgag cctagaatag   6660
gtggtttctt cctacatgcc acgcctcacg ctcataatat aaatcacatg gaatagcata   6720
ccaatgccta ttcattggga cgttcgaaaa gcatggcatc gctacttgga actctggctc   6780
tccttgccgc gacgctcgca cccttcggcg cgatgggaat cgtgatcact ggaaatcacg   6840
tctccgccag gattgacgac gatcacatcg tgatcgtcgc gcctcgcccc gaagctacaa   6900
ttcaactgca gctatttttc atgcctggcc agagacccca caaaccctac tcaggaaccg   6960
tccgcgtcgc gtttcggtct gatataacaa accagtgcta ccaggaactt agcgaggagc   7020
gctttgaaaa ttgcactcat cgatcgtctt ctgtttttgt cggctgtaaa gtgaccgagt   7080
acacgttctc cgcctcgaac agactaaccg gacctccaca cccgtttaag ctcactatac   7140
gaaatcctcg tccgaacgac agcgggatgt tctacgtaat tgttcggcta gacgacacca   7200
aagaacccat tgacgtcttc gcgatccaac tatcggtgta tcaattcgcg aacaccgccg   7260
cgactcgcgg actctattcc aaggcttcgt gtcgcacctt cggattacct accgtccaac   7320
ttgaggccta tctcaggacc gaggaaagtt ggcgcaactg gcaagcgtac gttgccacgg   7380
aggccacgac gaccagcgcc gaggcgacaa ccccgacgcc cgtcactgca accagcgcct   7440
ccgaacttga agcggaacac tttacctttc cctggctaga aaatggcgtg gatcattacg   7500
aaccgacacc cgcaaacgaa aattcaaacg ttactgtccg tctcgggaca atgagcccta   7560
cgctaattgg ggtaaccgtg gctgccgtcg tgagcgcaac gatcggcctc gtcattgtaa   7620
tttccatcgt caccagaaac atgtgcaccc cgcaccgaaa attagacacg gtctcgcaag   7680
acgacgaaga acgttcccaa actagaaggg aatcgcgaaa atttggaccc atggttgcgt   7740
gcgaaataaa caagggggct gaccaggata gtgaacttgt ggaactggtt gcgattgtta   7800
acccgtctgc gctaagctcg cccgactcaa taaaaatgtg attaagtctg aatgtggctc   7860
tccaatcatt tcgattctct aatctcccaa tcctctcaaa aggggcagta tcggacacgg   7920
actgggaggg gcgtacacga tagttatatg gtacagcaga ggcctctgaa cacttaggag   7980
gagaattcag ccggggagag cccctgttga gtaggcttgg gagcatattg caggatgaac   8040
atgttagtga tagttctcgc ctcttgtctt gcgcgcctaa cttttgcgac gcgacacgtc   8100
ctctttttgg aaggcactca ggctgtcctc ggggaagatg atcccagaaa cgttccggaa   8160
gggactgtaa tcaaatggac aaaagtcctg cggaacgcgt gcaagatgaa ggcggccgat   8220
gtctgctctt cgcctaacta ttgctttcat gatttaattt acgacggagg aaagaaagac   8280
tgcccgcccg cgggacccct gtctgcaaac ctggtaattt tactaaagcg cggcgaaagc   8340
```

-continued

```
ttcccgggtt aattaaggcc ctcgaggata catccaaaga ggttgagtat tctctctaca   8400
cttcttgtta aatggaaagt gcatttgctt gttcttacaa tcggcccgag tctcgttcac   8460
agcgcctcgt tcacacttaa accacaaata gtctacaggc tatatgggag ccagactgaa   8520
actcacatat gactaatatt cgggggtgtt agtcacgtgt agcccattgt gtgcatataa   8580
cgatgttgga cgcgtcctta ttcgcggtgt acttgatact atggcagcga gcatgggata   8640
ttcatcctcg tcatcgttaa catctctacg ggttcagaat gtttggcatg tcgtcgatcc   8700
tttgcccatc gttgcaaatt acaagtccga tcgccatgac cgcgataagc ctgtaccatg   8760
tggcattagg gtgacatctc gatcatacat tataagacca acgtgcgagt cttccaaaga   8820
cctgcacgcc ttcttcttcg gattgtcaac gggttcttca gaatctatgc ccatatctgg   8880
cgttgagacc attgtgcgtt taatgaacaa taaagcggca tgccatggaa aggagggctg   8940
cagatctcca ttttctcacg ccactatcct ggacgctgta gacgataatt ataccatgaa   9000
tatagagggg gtatgtttcc actgccactg tgatgataag ttttctccag attgttggat   9060
atctgcattt tctgctgccg aacaaacttc atcgctatgc aaagagatgc gtgtgtacac   9120
gcgccggtgg agtatacggg aaactaaatg ttcatagagg tctttgggct atatgttatt   9180
aaataaaata attgaccagt gaacaatttg tttaatgtta gtttattcaa tgcattggtt   9240
gcaaatattc attacttctc caatcccagg tcattcttta gcgagatgat gttatgacat   9300
tgctgtgaaa attactacag gatatatttt taagatgcag gagtaacaat gtgcatagta   9360
ggcgtagtta tcgcagacgt gcaacgcttc gcatttgagt taccgaagtg cccaacagtg   9420
ctgcggttat ggtttatgcg cacagaatcc atgcatgtcc taattgaacc atccgatttt   9480
tcttttaatc gcgatcgatg tttgggcaac tgcgttattt cagatctaaa aaatttaccc   9540
tttatgacca tcacatctct ctggctcata ccccgcttgg ataagatatc atgtagattc   9600
cgccctaaga aatgcaaact aacattattg tcggttccat atacacttcc atcttgtcct   9660
tcgaaaataa caaactcgcg caatagaccg tccgtacatg catggccgat gtgtgtcaac   9720
atcattggtc tgctagatcc cgatgggacg aatcgtacag tcgtcgctcc agcattggca   9780
aaaatcccca gataccctcc atgcggcaaa tctaaattgc gaccccgaag agactgcacc   9840
aaagtcttat cgacgcacgc tgattttttt gaacagcggg agcccattat cttcagtgga   9900
gcgtagacgg gcgaggctaa ttatgtgaca tagcaacact gcatgtatgt ttttataaat   9960
caataagagt acataattta ttacgtatca tttccgtttg taatatactg tatacatcat  10020
ccacactatt agtcagcact agcgcgcggg cgcacgttac aatagcagcg tgcccgttat  10080
ctatattgtc cgatatttac acataacatt tcatcgacat gattaaatac ctaagtactg  10140
cacacagatg tttaatgtat atcgtcatat aaattatatc gctaggacag acccaaacga  10200
cctttatccc aaacagtcag atcctcttct caagtgtcga tttctgttat ggaatatgca  10260
taccctggcc cagaaattgc acgcacgagc gtagtgaatg cgtcattggt tttacattta  10320
aaggctaaat gcacaaattc tttagacgac agcacatcgt taaatagcat ctctagcgtt  10380
cttatgaatg ctaagcattg gagtcctcct ggtcggccac aataacagct gagtatcata  10440
ccctgagctc cggggttgtc gcacatagcg gattcgtata aacataggat tttccgcgaa  10500
tccatcagtt gcaaaaatct gttaggctcc atcaacaacg ctggatttac ttcagatcca  10560
cgcgtaaagt aatggtgctc gaataccgtt tttagagttg tcggcatttc aaggaacaaa  10620
gaattcattt cttcattgca acgacgcgcc agaaatccca agacctcttt gggtagtatg  10680
ttcttgccta taaaacacgg cgttccaagt gccaggaacc acgcatgtgt tactgttggg  10740
```

-continued

```
gcgtattcag aaataaagcg gggtttatgc ggcttttgaa gctcggatat ccaaagtatc  10800
gcttgctgat gaacgagcga tgtagctgtt acaaaacctc ctttccatcc tccagtcaac  10860
ataatattta tcggcctacc tatgtccgta ataagtattg gtcgggcaat tattccgtat  10920
gaggtcttgc aggaataagc tcttagggac agccagcttg gatatggtgc gaaacagacc  10980
ttctcggctt cagaatgtcg ctccgcagtc tcttcgtgtc ggtgcatctt agatccacca  11040
tcaatgtgtg cagcattgac tcccgcccgt cgaatattcc ttttgttacg atgcagtaat  11100
gagcacgatc atgggcgggg cgatgacgtt ctatttgcat gtctgcgaac aatttgcgtc  11160
agtcatacag ctatggagtg ggccatttct ggccgtcaac ttaaaaacgc gaaccgcaga  11220
catatgtatt tgcatgcaaa gacgtatctt cgtatttctg ggcatcttca aatgctctgg  11280
ccaatatggc aatgaatttg gattcgtttg acgccgatgg tatgcagtgc aaatgtgcca  11340
atagcccaca tccgaaaaag ttatttgtca tacaagcagg tgttaagtag caatcacata  11400
aaggcaccag acgcctcatg gcatcataat gaatagctcc ttctccccac tggaaccact  11460
gacaaaatct gcgagtatat tccgcaaacc acattttatt tctcatagaa actaccctaa  11520
atccttttaa cgggaagaag aatcctagat agtgcttgaa gtcatgactg ttactgctgc  11580
aataacactg tatattattt ataaattccg tttgtctagg tatctgatgt aggcattccg  11640
atccctttac tattgcgtct tcacgaccaa atgggaatgc gccaaaatcc ccacacctca  11700
tcaccctgga ggcagattgt gtattattaa tatccgccga ttgaagcaca aaacggtacg  11760
gtactgttcc taattctggt atagattcta tggtcaaaag tctgcatatc cccgacattg  11820
ccatgagatc acacagtcca agtagcatgt ttattgagtc actcagactg tcaacgtccc  11880
tcgccgcacc accaatcgaa aataaagtat ctacgcaagt tatagctccg cattttctat  11940
cgctagcagc aatcgcgacg caaaacataa aggccatgtt gggatttgaa ctctctgggg  12000
ggcttgttat cttctgcacc gtcgcagtcg cagttttccg aaatttatgt ctaatatatt  12060
ttccggccgt gctccaatcg gccgaaaaga atctgcgtat taccagactc attgacgggc  12120
cgataaagac cataaaacaa aattcctgtg cactccctcc tccagttttg ccatcgtcca  12180
agtcccgtaa ctttttttgc gtttcgagga gcaagcgttc gttatcccta cccacacttg  12240
ttttccaccg ttttcttatt ataagcggtt gtatcgccaa cgcgtcaccg caggttgtca  12300
catacagtga tggcatactt gaacgtgcaa caacgcgctc gctttgcaaa tctaagtcat  12360
tgaccatcaa atcgcgttga gaggatagcc aggcatcttt tttcctagta tggtgacggt  12420
gcagccaccc caactcagtt cttgtaaaaa aagctattgg cgggaattta tgttctgagg  12480
tgcattctat atttatgagt ccatcaaatg ccattaacca gattcgtatt ttttcgctcg  12540
acccggcatc actatggata caataccttt ctatggccca tttcagctct cgaaccaacc  12600
acacggacaa ttgactaaca taagtatgat ctttatcaca gtcgcaccca tctgagttat  12660
atttatggca tccgagcgct cttactgtac ggtcggatac acccatggtt tttcctttat  12720
atagtcgggt tatagtctgt cgggtttggc ggtagcacgg agtagtttga tttttaagaa  12780
tcgaaaaccg gcttggagag accactgtcg aatatttgtc cgtatactct acacgtgagt  12840
gttgtccatt cctaggtata ttcatctgtt cggatacctt caattgctgt tcaggcataa  12900
ccttaaagca tatgttatgt tgtacatcaa aacttggtga gttatgttcg attgccgcgc  12960
ataaagaatc gtacatgagc gtttctgcta acatactatc tatattctca cacgcccctg  13020
catatactgt tcctattcca aattcacgtt ttgccccatc ggctatctgc tcccaaaaag  13080
```

-continued

```
ttgtaatata ggtgccgctg ggtgcgaaat tttcatcagt tgtattcctg ataaactgaa  13140
tcactttaca taatttttgc cacatatctg cgtgcagcca tagtatcgaa cccgtgggct  13200
cggagacgac agtgcgtaca atgggtattt tacctttccc caacaaaata atggtataca  13260
agttaggtcc gtacctagac cttaatgttt ccaattcttc tgaatcactg cactctcgta  13320
ggggagtaac ggtaataatt tcgtctctga gccccgtttt gcgttgaaaa ctaatcacat  13380
tagataatgt gcaatcggtt tcttttatcc ggatacatct aagtattatg acatcggtgg  13440
tcattgtttc catcaacgac catcttttac gatcgcccat actactcatg gacgttgtcg  13500
gtgttgaaaa atcaccagaa ttgcaacgga tctctgggta ccatgctgct gatggaattg  13560
gcggttttaa ttgttgtttc agtctattat tgctatcttt ggcggggttg aataatgtgg  13620
ggggagagtg attgcaggaa tccgaatggg tcaataaaac gaccgtgctc cgttctgccg  13680
gcgccgatcc gattgaagct atatacttcg cttctctccc cacttttcca atttgatccg  13740
gaaataaaac ggccccggac aacagtatcg tacgatccgg atccggatcc tgcttgccta  13800
cagaagaatc aacatctcgc cccaatattc tggtcaaaac tggctcgctc atggcaacgc  13860
ggacgtttcc cccggtggcc agtcttaatg gttaatgttc ttttcggcaa tcttatacat  13920
cagcgggttg cgtgaatact ggtcacagtt cagtcattta ctacacacca gcaatacgac  13980
gacggacagt accgtcccga cgaacgcgac gcccaaaatt gctatcgcga ccgcgtccga  14040
ggcgatgtcg tacgggcggt gcggggttgg atcctcggca aagagatcct cgtaattcgg  14100
cggtgggagc ggagggtaaa gacgcgggtg gggatctccc tccggaccgc gcgccgggcg  14160
cggttcgaaa atgctttccg cctcgctcag tgtcaacgcc aagtattcgg gcgggctggg  14220
ggccggaata tctcccgcga cttcttctat cggcgcggaa ttggagtcgc ggtcgtggcg  14280
cgcttctagc gtcgtcaacg gaagtccatt ttcggggtct cccggtgggc gttcagcgtc  14340
catcgtcgta tatgctctaa cacacgtctc gctatattaa aaaaaagaag agtatcggtc  14400
agtgtcgagt gtcgccgaca atgtcgcgag ttctcggcga tttaattttt ggaactgctc  14460
cctatgaatc ccgtaactgt agcgcccgcg cagaaagccg ccatcagacc aactacgtgt  14520
ctgttcgatg tttgcccgcc gatcgcttta ccgattaagg ttccggcgag aaatgacatg  14580
ctcgatccaa gaacaaagtt tttcgcggta aacaacaaca tagttaccgt gcgagatgga  14640
gaaaccacat ctcccgaatt agtagaggaa agcccgcgct gtcggtttgg ggacatatcg  14700
atctttttttg tgtttttcct aggacccttt tgccagatcg tacaaagtcg cgtcttatga  14760
gcggacgttc ttactgcagc tcggtaggag tggggcaggg ttagatttcg tcggcgtttc  14820
ggccccccgta tgcgccgcgc caccctcttc gccgagctct ttatgcgcgg tgggggtgag  14880
cgcttccgga gttgcgatct ccgatctcga gccgcagccc ggcggtgtct ctttcagtgg  14940
agcgttagcg ccatcatgtg gttcgtggcg gtggaaaggc tattatgtgt taggggagag  15000
accacgtgat cggcatgcaa atgagcaagg cgaacgcgtc agcgttcgca ctgcgaacca  15060
ataatatata tattatacta ttggctttag gtgcgaacgt ccggctagtc caatagcggg  15120
gtcgcgtttc gtaccacgtg ttatagaccg ccctaaactc gcactcgggg gtccggccgc  15180
gcccagacag ggcggagacg tgccacaggg gctttaaaac accgcttcgg gcaccgttca  15240
tctcggcgcg cc                                                      15252
```

<210> SEQ ID NO 22
<211> LENGTH: 12692
<212> TYPE: DNA
<213> ORGANISM: Artificial Sequence
<220> FEATURE:
<223> OTHER INFORMATION: Expression cassette

<400> SEQUENCE: 22
ctcgcgcgtt tcggtgatga cggtgaaaac ctctgacaca tgcagctccc ggagacggtc 60
acagcttgtc tgtaagcgga tgccgggagc agacaagccc gtcagggcgc gtcagcgggt 120
gttggcgggt gtcggggctg gcttaactat gcggcatcag agcagattgt actgagagtg 180
caccatatcg acgctctccc ttatgcgact cctgcattag gaagcagccc agtagtaggt 240
tgaggccgtt gagcaccgcc gccgcaagga atggtgcatg caaggagatg gcgcccaaca 300
gtcccccggc cacggggcct gccaccatac ccacgccgaa acaagcgctc atgagcccga 360
agtggcgagc ccgatcttcc ccatcggtga tgtcggcgat ataggcgcca gcaaccgcac 420
ctgtggcgcc ggtgatgccg gccacgatgc gtccggcgta gaggatctgg ctagcgatga 480
ccctgctgat tggttcgctg accatttccg gggtgcggaa cggcgttacc agaaactcag 540
aaggttcgtc caaccaaacc gactctgacg gcagtttacg agagagatga tagggtctgc 600
ttcagtaagc cagatgctac acaattaggc ttgtacatat tgtcgttaga acgcggctac 660
aattaataca taaccttatg tatcatacac atacgattta ggtgacacta tagaatacaa 720
gctagcttgg gctgcaggtc gactctagag gatcgttaat taacgatccc cgggcgagct 780
cgaattccag actaaatgcc ccggcccaat ttgtcaagtg tgcagtcacg gaggcgtcga 840
ccgtgtcccc ggcattaaac aggaaagcgt taaagttttt gaatgttagg tcacaggtac 900
aaacataaat gtttgtacaa acaggtaaca ggtacaaaca taaatgcccc ggcataaatg 960
tcccttacgg cggatcgaaa cgacattagg catactcggg taccattttg cattccgatc 1020
agcacggatg aaattaggca ggaatgcggt ttatattatg cggcattgga caaacgatat 1080
ggcattgatt ggcagtttat gaatgtcttc atgttgggcg taaacggatt cctattggtt 1140
cagaagacaa cgacgatata tttagagaga aaaagctacc cagcatagga taaacacaca 1200
ttgagcattg agagacatag gtatcggtat ggatgggaaa actacacacg tgaacaccaa 1260
acgacttata tactcgagcg gtgatactac tgagcaagaa tgcactgcat ctgagccact 1320
gaatgaagac tgtgatgaaa atgtgaccat cgatggaatt ggagaagaat atgcgcagtt 1380
cttcatgtcc ccgcaatggg tcccaaatct acatcgcttg agcgaggata ccaaaaaggt 1440
ataccgatgt atggtttcca acagactcaa ttattttccc tattatgagg cgttcaggcg 1500
gtctttgttt gatatgtata tgctaggtcg gttggggcgt cgacttaagc gatctgactg 1560
ggagactatt atgcatctgt caccaacgca aagtcggcgt ctacatagaa ctttaagatt 1620
tgtggagcgt agaattatcc catctaacag ttatatacgc acatcgggcc acgttccgcc 1680
ttcgagggca cttccgacag atacgaattt aaagatggat gaataattaa attggaaaga 1740
gtaactacat taatcgagcg tcatgacggc gtcccgtgaa aatgggaatt ttctactcga 1800
aacaccgtga catttgacag acctggaatt gttattctga tatatagtgg gtgtgtctgg 1860
ccggcaacat acataatgtg catgcgaaac cactttttca gtgtacgctg acattgtgca 1920
acacggaggg gtagcatcta catacaatat atgttgatta atgattggag aaaaaactat 1980
gcagctcgcc gatcatatgg ctaactcgcc ttcgtctata tggcggaccc cgcgggaaaa 2040
atcgacgtac catctgattt acaacaccag taatgaacat gtcgcatccc tgcccagatc 2100
tgtgcgccca ttggcgcgga tcgttgtgaa tgccgccgaa acacttcagg tcggtatgag 2160
agccgggagg ccgccatcag caggagtttg gcgagaggtg tttgatagaa tgatgacagc 2220

```
cttccgtgac cacgagccta ctgcgacatt taatgctgca aatcccatta gaaaaatggt   2280
cgagacagtt ctacagaata atgaagagcc cccgcggacg catgctgaaa tgggtaatcg   2340
ccttatgaac attatgtact ggtgttgctt gggacacgca ggacaatgct cgatatggca   2400
gttgtacgag acgaatcagg ccattttaag tttattagat gaagtggtta tcggcacaac   2460
aaatcccttt tgcaccctcg agcaatactg gaagccatta tgcaccgcaa tcgccaacaa   2520
ggggacctca tcgcttgttg aggatgccaa agtggccgag tacctggtta gcatgcgcaa   2580
attgatataa cataggcacg ctctgatgtt acagaccaca ataccgcata catttattgt   2640
aaggttgtta ataaaggttt attctatgta agactacaat actttcgaca ttgcttgtat   2700
acatattaaa tactttctca agttcctatt acataaaatg ggatctatca ttacattcgt   2760
taagagtctg gataatttta ctgtttgcca gcttcgatct tggaacgtac tgtggatagt   2820
gccttacttg gaatcgtgaa aatttgaaac gtccattatt tggatatctt ccggttgtcc   2880
catatcccgc cctggtaccg ctcggatacc ttgcccgtat ggattcgtat tgacagtcgc   2940
gcaatcgggg accaacaacg cgtgggtcca cactcattcg gaaattttcc gatgattctg   3000
aatatttatt gccgctcgtt acgagtcgtt ggacatatct gtaatacatt tcttcttctg   3060
aaggatcgct gcacatttga tctatacatt ggccaggatg ttcaagtctc agatgttgca   3120
ttctggcaca gcacaacttt atggcatttc cgatgtaatc gtccggcagc cctgggggag   3180
ttctatattc gcatattggg atggtaagga caatagcaga tctcgcaacc tccagggagg   3240
ctataataac gtttttaaag gatggatttc tcataaaaat ctgtcgcaaa ttacactgag   3300
aatatccttt actagcgccg attgagagca tcgtcgtcca attttctaaa tggaaagaaa   3360
acaaggcggg caagagtgtt ccaaacattt tcattttcgg cgaatctctc aaatcccatg   3420
gcgtgcaatt gattgcaaaa ttggcacttc cgttcacgtt tgtatctcca aactctaaga   3480
cacttttaat tgaaaaacta cgttctagtg tggaaagaaa cctataggca gaccatagaa   3540
ctatttgaca ccacatatct ttttgtatgt caaactgacc atgatcgtat gttgctgaat   3600
gcactagggc aattcgctcg cgcgactcca tacattgaat aattccacac gtcagctcat   3660
cggttagcaa ggtccagtag ttgaagtcat ttatttttcc ccgcggctgg ccaaatctac   3720
ctctgggaat atccaagttg tcgaatatga tcgcaccggc tctggtcatg gtgaaggaac   3780
tgtagcataa agacgcaggt atcatagggg taatattttt ttattcactc acatactaaa   3840
agtaacgcat attagcacca tgtatgggct atcaattgac atttgcgtag cactacatca   3900
cgattatgta caacataatg ggacaacata tggcaagtag atgcaatttc ctcacactag   3960
ttgggtttat ctactattga attttcccct atctgtgata cacttgggag cctctacaag   4020
catattgcca tcatgtacgt ttttatctac tgtcttaacg cccatgggaa cggaggcgtc   4080
gtcgtcatgt attggacggc aacataggca gcaacacaaa ttgcgtttag gtggggtgca   4140
tgtggactcg ataccaagcc cctgcagctg gggaacgtct ggtggagagc cgataatttg   4200
atatacgcac gccatattac tgtcgttgaa gtacgcctta tcttctatgt tttcaaattt   4260
aggttcccaa gtggacgtga gaagtgtttg tatctcacat ggaatggccc aaggcattcc   4320
agcccaggtg cctggtactt taatggcaaa caaacgtttt ggtagaggta ttgattctat   4380
tgcagttctg cagatatctg cagccccgag tatccacagg ctatacgata cgttatcgga   4440
ggcaagcttc gcgccaggtc aattccctgg cattatgccc agtacatgac cttatgggac   4500
tttcctactt ggcagtacat ctacgtatta gtcatcgcta ttaccatggt gatgcggttt   4560
tggcagtaca tcaatgggcg tggatagcgg tttgactcac ggggatttcc aagtctccac   4620
```

cccattgacg tcaatgggag tttgttttgg caccaaaatc aacgggactt tccaaaatgt 4680
cgtaacaact ccgccccatt gacgcaaatg ggcggtagcg tgtacggtgg gaggtctata 4740
taagcagagc tcgtttagtg aaccgtcaga tcgcctggag acgccatcca cgctgttttg 4800
acctccatag aagacaccgg ttgcgccgcc accatgggcc ccagaccttc taccaagaac 4860
ccagtaccta tgatgctgac tgtccgagtc gcgctggtac tgagttgcat ctgtccggca 4920
aactccattg atggcaggcc tcttgcggct gcaggaattg tggttacagg agacaaagcc 4980
gtcaacatat acacctcatc ccagacagga tcaatcatag ttaagctcct cccgaatctg 5040
cccaaggata aggaggcatg tgcgaaagcc ccccttggatg catacaacag gacattgacc 5100
actttgctca cccccccttgg tgactctatc cgtaggatac aagagtctgt gactacatct 5160
ggagggggga gacaggggcg ccttataggc gccattattg gcggtgtggc tcttggggtt 5220
gcaactgccg cacaaataac agcggccgca gctctgatac aagccaaaca aaatgctgcc 5280
aacatcctcc gacttaaaga gagcattgcc gcaaccaatg aggctgtgca tgaggtcact 5340
gacggattat cgcaactagc agtggcagtt gggaagatgc agcagtttgt taatgaccaa 5400
tttaataaaa cagctcagga attagactgc atcaaaattg cacagcaagt tggtgtagag 5460
ctcaacctgt acctaaccga attgactaca gtattcggac cacaaatcac ttcacctgct 5520
ttaaacaagc tgactattca ggcactttac aatctagctg gtggaaatat ggattactta 5580
ttgactaagt taggtgtagg gaacaatcaa ctcagctcat taatcggtag cggcttaatc 5640
accggtaacc ctattctata cgactcacag actcaactct tgggtataca ggtaactcta 5700
ccttcagtcg ggaagctaaa taatatgcgt gccacctact tggaaacctt atccgtaagc 5760
acaaccaggg gatttgcctc ggcacttgtc ccaaaagtgg tgacacaggt cggttctgtg 5820
atagaagaac ttgacacctc atactgtata gaaactgact tacatttata ttgtacaaga 5880
atagtaacgt tccctatgtc ccctggtatt tattcctgct tgagcggcaa tacgtcggcc 5940
tgtatgtact caaagaccga aggcgcactt actacaccat acatgactat caaaggttca 6000
gtcatcgcca actgcaagat gacaacatgt agatgtgtaa accccccggg tatcatatcg 6060
caaaactatg gagaagccgt gtctctaata gataaacaat catgcaatgt tttatcctta 6120
ggcgggataa ctttaaggct cagtggggaa ttcgatgtaa cttatcagaa gaatatctca 6180
atacaagatt ctcaagtaat aataacaggc aatcttgata tctcaactga gcttgggaat 6240
gtcaacaact cgatcagtaa tgctttgaat aagttagagg aaagcaacag aaaactagac 6300
aaagtcaatg tcaaactgac tagcacatct gctctcatta cctatatcgt gttgactatc 6360
atatctcttg tttttggtat acttagcctg attctagcat gctacctaat gtacaagcaa 6420
aaggcgcaac aaaagacctt attatggctt gggaataata ctctagatca gatgagagcc 6480
actacaaaaa tgtgaggatc tctcgaggaa ttctagatcc cacgtcacta ttgtatactc 6540
tatattatac tctatgttat actctgtaat cctactcaat aaacgtgtca cgcctgtgaa 6600
accgtactaa gtctcccgtg tcttcttatc accatcaggt gacatcctcg cccaggctgt 6660
caatcatgcc ggtatcgatt ccagtagcac cggccccacg ctgacaaccc actcttgcag 6720
cgttagcagc gcccctctta acaagccgac ccccaccagc gtcgcggtta ctaacactcc 6780
tctccccgac ctgcaactag taagcttgcc tccgattcta gcattacata gccggtcagt 6840
agatcctgcc attcggtagc gcaaccggct acatcttcaa acagtctcac aataaatgca 6900
tctctcgttc ctgccaatcc ggaaccgggc ataccactcc cgcctgccga tttaattctc 6960

-continued

```
acaattgggc gatgccggcg gggcaaaacg aatgtggatt tggcaaaccg acacaggtct   7020
gctgtacgga ctaatatggg cacacccaca tcattcttca gatgctccat gcattgttct   7080
atgagaaaga tccatagggt ggaggcagcg tcacgagatc gcccaggcaa tcgatcgcat   7140
tcgtctagta aagtgacgag agttatcatg cacacaccca tgcccacgcc ttccgaataa   7200
ctggagctgt ggaagatcgg aaacgtcttt ttgactgccg gtctcgtact actttcgcac   7260
aggtgtatac ccggacgcgt actatatatt ttatatcatc caacgtccga aattacatac   7320
gtggcggcga tggaagtaga tgttgagtct tcgaaagtaa gtgcctcgaa tatgggtatt   7380
gtctgtgaaa atatcgaaag cggtacgacg gttgcagaac cgtcgatgtc gccagatact   7440
agtaacaata gcttcgataa cgaagacttc cgtgggcctg aatacgatgt ggagataaat   7500
accagaaaat ctgctaatct tgatcgtatg gaatcttcgt gccgtgaaca acgagcggcg   7560
tgcgaacttc gaaagtgttc gtgtcctacg tctgccgtgc gcatgcaata cagtattctt   7620
tcatctctcg ctccgggttc agagggtcat gtatatatat gtactagata cggggacgcg   7680
gaccaaaaaa aatgcatagt gaaggcagtc gttggaggaa agaatcccgg gagggaagtg   7740
gatattttaa aaaccatctc acataaatca attataaaat taatccatgc ctataaatgg   7800
aaaaatgttg tgtgtatggc aatgcgtgta tatcgttatg atcttttcac atatattgac   7860
ggagtcggcc ctatgcccct tcaacagatg atctatattc aacgtggact actagaggcg   7920
ctagcataca tacatgaaag gggcatcatt caccgagacg taaagacgga gaatatattc   7980
ttggataatc acgaaaatgc agttttgggt gacttcggtg ctgcatgcca actaggagat   8040
tgtatagata cgccccaatg ttacggttgg agcggaactg tggaaacaaa ttcgccggaa   8100
ttatctgcac ttgatccgta ttgcacaaaa acagatattt ggagtgccgg attggttcta   8160
tatgagatgg caattaaaaa tgtaccattg tttagtaagc aggtgaaaag ttcgggatct   8220
cagctgagat ccataatacg gtgcatgcaa gtgcatgaac tggagtttcc ccgcaacgat   8280
tctaccaacc tctgtaaaca tttcaaacaa tatgcggttc gtgtacgacc gccttatacc   8340
attcctcgag ttataagaaa tggggggatg ccaatggatg ttgaatatgt catttctaaa   8400
atgcttacgt ttgaccagga gttcagacct tctgctaagg aaatattgaa tatgccccta   8460
tttactaagg cgccgattaa cctgcttaat atcacaccct ctgacagtgt ctaacggtat   8520
acaggcggga gcgggtcgtg gcgtcatcat caccacttga gaatttatat tttgaattgt   8580
tgattgataa attaacctga ttcattgaga actgaaacgc catattggtt tcttggatat   8640
gtctacaaca attagttaaa ttgctatgtt ctactgcgag taacatttga taagttgtaa   8700
gagacgggcg actcatgtcg aagttgacga atataaagta cataacgtgt ttagaatacc   8760
cagaatccga atagtccgcg gggcgtctt ctcgcgtgag taccaaatac tgagttgaac   8820
ttgaaaatgc taaatctgtg acactctttg tgtgatgatt attgtcacca cttcgaagat   8880
ggcttcgaca ttcatgatgt tctggtgttt gtttggaatc gtaatagcgc ttgtttcgtc   8940
caagtctgac aacaaagaaa atctgaagaa ttatatcacg gataagtcaa ccaatattag   9000
aatacccacg ccattatttg tatcaacgga aaactcttat cccacaaaac atgtaatcta   9060
cgatgaaaac tgtggcttcg ctgtactcaa tcctataagt gaccccaaat atgtcctttt   9120
gagccagctt ctaatgggaa ggcgcaaata tgatgcgacg gtcgcgtggt ttgttctcgg   9180
taaaatgtgt gccagattaa tatatttgcg cgaattttat aactgctcga caaatgagcc   9240
ttttggcaca tgttctatga gctctcctgg atggtgggac aggcgctacg tctcaaccag   9300
tttcatttct cgcgacgaat tacagctggt ttttgcagcg ccgtcccgag aattagatgg   9360
```

```
tttatatacg cgcgtagtag ttgtcaacgg ggactttact acggccgata taatgtttaa   9420
tgttaaagtg gcatgtgcct tttcaaagac tggaatagaa gatgatacat tatgcaaacc   9480
ctttcatttc tttgccaatg caacattgca caatttaacc atgattagat cggtaactct   9540
tcgagcgcac gaaagccatt taaaggaatg ggtggcacgg agaggtggta acgtccctgc   9600
agtgctactt gagtctacca tgtatcatgc atccaatctg cctagaaatt tcagggattt   9660
ctacataaag tctccagatg attataagta taatcaccta gatgggccat ctgtaatgct   9720
catcactgac agacctagtg aagatttgga tgggaggctc gttcaccaaa gtgacatttt   9780
tactactaca agtcctataa aacaggtccg gtatgaagag catcagtcac atacaaagca   9840
gtatcctgta aacaaaatac aagctataat ttttttgata gggttaggct cgttcattgg   9900
aagcatattc gtagttttgg tagtatggat tatacgcaga tattgcaatg gagcgcggag   9960
tggggggaacg ccccccagtc ctcgccggta tgtgtatacc aggctatgat cacgtgtgaa  10020
acttgggcgg acctgtatca tatgtacacc gtccctattc gtttatagcc agtacgtgtt  10080
atctgcacat agaggaacat gtgtcatact gggatcgcat gcatggtatg tgtgactcta  10140
atattattct gtatcataat aaaaacacag tgcatggtat atagaggatc gctggtaagc  10200
actacggtag accaatcggc tcagattgca ttctttggca tcgataccgt tgttaattta  10260
tatggcaaag tcttgttcat gggagatcag tatttggagg aaatatactc tggaacgatg  10320
gaaatactca aatggaatca agctaaccgc tgctattcta ttgcgcatgc aacatattac  10380
gccgactgtc ctataatcag ttctacggta ttcagaggat gccgggacgc cgttgtttat  10440
actaggcccc acagcagaat tcgtaatcat ggtcatagct gtttcctgtg tgaaattgtt  10500
atccgctcac aattccacac aacatacgag ccggaagcat aaagtgtaaa gcctggggtg  10560
cctaatgagt gagctaactc acattaattg cgttgcgctc actgcccgct ttccagtcgg  10620
gaaacctgtc gtgccagctg cattaatgaa tcggccaacg cgcggggaga ggcggtttgc  10680
gtattgggcg ctcttccgct tcctcgctca ctgactcgct gcgctcggtc gttcggctgc  10740
ggcgagcggt atcagctcac tcaaaggcgg taatacggtt atccacagaa tcaggggata  10800
acgcaggaaa gaacatgtga gcaaaaggcc agcaaaaggc caggaaccgt aaaaaggccg  10860
cgttgctggc gtttttccat aggctccgcc cccctgacga gcatcacaaa aatcgacgct  10920
caagtcagag gtggcgaaac ccgacaggac tataaagata ccaggcgttt ccccctggaa  10980
gctccctcgt gcgctctcct gttccgaccc tgccgcttac cggatacctg tccgcctttc  11040
tcccttcggg aagcgtggcg ctttctcaat gctcacgctg taggtatctc agttcggtgt  11100
aggtcgttcg ctccaagctg ggctgtgtgc acgaaccccc cgttcagccc gaccgctgcg  11160
ccttatccgg taactatcgt cttgagtcca acccggtaag acacgactta tcgccactgg  11220
cagcagccac tggtaacagg attagcagag cgaggtatgt aggcggtgct acagagttct  11280
tgaagtggtg gcctaactac ggctacacta gaaggacagt atttggtatc tgcgctctgc  11340
tgaagccagt taccttcgga aaaagagttg gtagctcttg atccggcaaa caaaccaccg  11400
ctggtagcgg tggttttttt gtttgcaagc agcagattac gcgcagaaaa aaaggatctc  11460
aagaagatcc tttgatcttt tctacggggt ctgacgctca gtggaacgaa aactcacgtt  11520
aagggatttt ggtcatgaga ttatcaaaaa ggatcttcac ctagatcctt ttaaattaaa  11580
aatgaagttt taaatcaatc taaagtatat atgagtaaac ttggtctgac agttaccaat  11640
gcttaatcag tgaggcacct atctcagcga tctgtctatt tcgttcatcc atagttgcct  11700
```

```
gactccccgt cgtgtagata actacgatac gggagggctt accatctggc cccagtgctg  11760

caatgatacc gcgagaccca cgctcaccgg ctccagattt atcagcaata aaccagccag  11820

ccggaagggc cgagcgcaga agtggtcctg caactttatc cgcctccatc cagtctatta  11880

attgttgccg ggaagctaga gtaagtagtt cgccagttaa tagtttgcgc aacgttgttg  11940

ccattgctac aggcatcgtg gtgtcacgct cgtcgtttgg tatggcttca ttcagctccg  12000

gttcccaacg atcaaggcga gttacatgat cccccatgtt gtgcaaaaaa gcggttagct  12060

ccttcggtcc tccgatcgtt gtcagaagta agttggccgc agtgttatca ctcatggtta  12120

tggcagcact gcataattct cttactgtca tgccatccgt aagatgcttt tctgtgactg  12180

gtgagtactc aaccaagtca ttctgagaat agtgtatgcg gcgaccgagt tgctcttgcc  12240

cggcgtcaat acgggataat accgcgccac atagcagaac tttaaaagtg ctcatcattg  12300

gaaaacgttc ttcggggcga aaactctcaa ggatcttacc gctgttgaga tccagttcga  12360

tgtaacccac tcgtgcaccc aactgatctt cagcatcttt tactttcacc agcgtttctg  12420

ggtgagcaaa aacaggaagg caaaatgccg caaaaaaggg aataagggcg acacggaaat  12480

gttgaatact catactcttc ctttttcaat attattgaag catttatcag ggttattgtc  12540

tcatgagcgg atacatattt gaatgtattt agaaaaataa acaaataggg gttccgcgca  12600

catttccccg aaaagtgcca cctgacgtct aagaaaccat tattatcatg acattaacct  12660

ataaaaatag gcgtatcacg aggccctttc gt                                12692
```

```
<210> SEQ ID NO 23
<211> LENGTH: 14113
<212> TYPE: DNA
<213> ORGANISM: Artificial Sequence
<220> FEATURE:
<223> OTHER INFORMATION: Expression cassette

<400> SEQUENCE: 23

gaattccaga ctaaatgccc cggcccaatt tgtcaagtgt gcagtcacgg aggcgtcgac     60

cgtgtccccg gcattaaaca ggaaagcgtt aaagtttttg aatgttaggt cacaggtaca    120

aacataaatg tttgtacaaa caggtaacag gtacaaacat aaatgccccg gcataaatgt    180

cccttacggc ggatcgaaac gacattaggc atactcgggt accattttgc attccgatca    240

gcacggatga aattaggcag gaatgcggtt tatattatgc ggcattggac aaacgatatg    300

gcattgattg gcagtttatg aatgtcttca tgttgggcgt aaacggattc ctattggttc    360

agaagacaac gacgatatat ttagagagaa aaagctaccc agcataggat aaacacacat    420

tgagcattga gagacatagg tatcggtatg gatgggaaaa ctacacacgt gaacaccaaa    480

cgacttatat actcgagcgg tgatactact gagcaagaat gcactgcatc tgagccactg    540

aatgaagact gtgatgaaaa tgtgaccatc gatggaattg gagaagaata tgcgcagttc    600

ttcatgtccc cgcaatgggt cccaaatcta catcgcttga gcgaggatac caaaaaggta    660

taccgatgta tggtttccaa cagactcaat tattttccct attatgaggc gttcaggcgg    720

tctttgtttg atatgtatat gctaggtcgg ttggggcgtc gacttaagcg atctgactgg    780

gagactatta tgcatctgtc accaacgcaa agtcggcgtc tacatagaac tttaagattt    840

gtggagcgta gaattatccc atctaacagt tatatacgca catcgggcca cgttccgcct    900

tcgagggcac ttccgacaga tacgaattta aagatggatg aataattaaa ttggaaagag    960

taactacatt aatcgagcgt catgacggcg tcccgtgaaa atgggaattt tctactcgaa   1020

acaccgtgac atttgacaga cctggaattg ttattctgat atatagtggg tgtgtctggc   1080
```

cggcaacata cataatgtgc atgcgaaacc actttttcag tgtacgctga cattgtgcaa 1140
cacggagggg tagcatctac atacaatata tgttgattaa tgattggaga aaaaactatg 1200
cagctcgccg atcatatggc taactcgcct tcgtctatat ggcggacccc gcgggaaaaa 1260
tcgacgtacc atctgattta caacaccagt aatgaacatg tcgcatccct gcccagatct 1320
gtgcgcccat tggcgcggat cgttgtgaat gccgccgaaa cacttcaggt cggtatgaga 1380
gccgggaggc cgccatcagc aggagtttgg cgagaggtgt ttgatagaat gatgacagcc 1440
ttccgtgacc acgagcctac tgcgacattt aatgctgcaa atcccattag aaaaatggtc 1500
gagacagttc tacagaataa tgaagagccc ccgcggacgc atgctgaaat gggtaatcgc 1560
cttatgaaca ttatgtactg gtgttgcttg ggacacgcag gacaatgctc gatatggcag 1620
ttgtacgaga cgaatcaggc cattttaagt ttattagatg aagtggttat cggcacaaca 1680
aatccctttt gcaccctcga gcaatactgg aagccattat gcaccgcaat cgccaacaag 1740
gggacctcat cgcttgttga ggatgccaaa gtggccgagt acctggttag catgcgcaaa 1800
ttgatataac ataggcacgc tctgatgtta cagaccacaa taccgcatac atttattgta 1860
aggttgttaa taaaggttta ttctatgtaa gactacaata ctttcgacat tgcttgtata 1920
catattaaat actttctcaa gttcctatta cataaaatgg gatctatcat tacattcgtt 1980
aagagtctgg ataattttac tgtttgccag cttcgatctt ggaacgtact gtggatagtg 2040
ccttacttgg aatcgtgaaa atttgaaacg tccattattt ggatatcttc cggttgtccc 2100
atatcccgcc ctggtaccgc tcggatacct tgcccgtatg gattcgtatt gacagtcgcg 2160
caatcgggga ccaacaacgc gtgggtccac actcattcgg aaattttccg atgattctga 2220
atatttattg ccgctcgtta cgagtcgttg gacatatctg taatacattt cttcttctga 2280
aggatcgctg cacatttgat ctatacattg gccaggatgt tcaagtctca gatgttgcat 2340
tctggcacag cacaacttta tggcatttcc gatgtaatcg tccggcagcc ctgggggagt 2400
tctatattcg catattggga tggtaaggac aatagcagat ctcgcaacct ccagggaggc 2460
tataataacg tttttaaagg atggatttct cataaaaatc tgtcgcaaat tacactgaga 2520
atatccttta ctagcgccga ttgagagcat cgtcgtccaa ttttctaaat ggaaagaaaa 2580
caaggcgggc aagagtgttc caaacatttt catttttcggc gaatctctca aatcccatgg 2640
cgtgcaattg attgcaaaat tggcacttcc gttcacgttt gtatctccaa actctaagac 2700
acttttaatt gaaaaactac gttctagtgt ggaaagaaac ctataggcag accatagaac 2760
tatttgacac cacatatctt tttgtatgtc aaactgacca tgatcgtatg ttgctgaatg 2820
cactagggca attcgctcgc gcgactccat acattgaata attccacacg tcagctcatc 2880
ggttagcaag gtccagtagt tgaagtcatt tatttttccc cgcggctggc caaatctacc 2940
tctgggaata tccaagttgt cgaatatgat cgcaccggct ctggtcatgg tgaaggaact 3000
gtagcataaa gacgcaggta tcataggggt aatatttttt tattcactca catactaaaa 3060
gtaacgcata ttagcaccat gtatgggcta tcaattgaca tttgcgtagc actacatcac 3120
gattatgtac aacataatgg gacaacatat ggcaagtaga tgcaatttcc tcacactagt 3180
tgggtttatc tactattgaa ttttccccta tctgtgatac acttgggagc ctctacaagc 3240
atattgccat catgtacgtt tttatctact gtcttaacgc ccatgggaac ggaggcgtcg 3300
tcgtcatgta ttggacggca acataggcag caacacaaat tgcgtttagg tggggtgcat 3360
gtggactcga taccaagccc ctgcagctgg ggaacgtctg gtggagagcc gataatttga 3420

-continued

```
tatacgcacg ccatattact gtcgttgaag tacgccttat cttctatgtt ttcaaattta   3480
ggttcccaag tggacgtgag aagtgtttgt atctcacatg gaatggccca aggcattcca   3540
gcccaggtgc ctggtacttt aatggcaaac aaacgttttg gtagaggtat tgattctatt   3600
gcagttctgc agatatctgc agccccgagt atccacaggc tatacgatac gttatcggag   3660
gcaagctgcg gccgctctag aactagtgga tcccccgggc tgcagcccaa tgtggaattc   3720
gcccttgcac attgttactc ctgcatctta aaaatatatc ctgtagtaat tttcacagca   3780
atgtcataac atcatctcgc taaagaatga cctgggattg gagaagtaat gaatatttgc   3840
aaccaatgca ttgaataaac taacattaaa cgaattcact agtggatccc ccaactccgc   3900
ccgttttatg actagaacca atagttttta atgccaaatg cactgaaatc ccctaatttg   3960
caaagccaaa cgccccctat gtgagtaata cggggacttt ttacccaatt tcccacgcgg   4020
aaagcccct aatacactca tatggcatat gaatcagcac ggtcatgcac tctaatggcg   4080
gcccataggg actttccaca tagggggcgt tcaccatttc ccagcatagg ggtggtgact   4140
caatggcctt tacccaagta cattgggtca atgggaggta agccaatggg tttttcccat   4200
tactggcaag cacactgagt caaatgggac tttccactgg gttttgccca agtacattgg   4260
gtcaatggga ggtgagccaa tgggaaaaac ccattgctgc caagtacact gactcaatag   4320
ggactttcca atgggttttt ccattgttgg caagcatata aggtcaatgt gggtgagtca   4380
atagggactt tccattgtat tctgcccagt acataaggtc aatagggggt gaatcaacag   4440
gaaagtccca ttggagccaa gtacactgcg tcaataggga ctttccattg ggttttgccc   4500
agtacataag gtcaataggg gatgagtcaa tgggaaaaac ccattggagc caagtacact   4560
gactcaatag ggactttcca ttgggttttg cccagtacat aaggtcaata ggggtgagt   4620
caacaggaaa gttccattgg agccaagtac attgagtcaa tagggacttt ccaatgggtt   4680
ttgcccagta cataaggtca atgggaggta agccaatggg tttttcccat tactggcacg   4740
tatactgagt cattagggac tttccaatgg gttttgccca gtacataagg tcaatagggg   4800
tgaatcaaca ggaaagtccc attggagcca agtacactga gtcaataggg actttccatt   4860
gggttttgcc cagtacaaaa ggtcaatagg gggtgagtca atgggttttt cccattattg   4920
gcacgtacat aaggtcaata ggggtgagtc attgggtttt tccagccaat ttaattaaaa   4980
cgccatgtac tttcccacca ttgacgtcaa tgggctattg aaactaatgc aacgtgacct   5040
ttaaacggta ctttcccata gctgattaat gggaaagtac cgttctcgag ccaatacacg   5100
tcaatgggaa gtgaaagggc agccaaaacg taacaccgcc ccggttttcc cctggaaatt   5160
ccatattggc acgcattcta ttggctgagc tgcgttctac gtgggtataa gaggcgcgac   5220
cagcgtcggt accgtcgcag tcttcggtct gaccaccgta gaacgcagag ctcctcgctg   5280
caggcggccg ctctagaact cgtcgatcgc agcgatgaca aacctgcaag atcaaaccca   5340
acagattgtt ccgttcatac ggagccttct gatgccaaca accggaccgg cgtccattcc   5400
ggacgacacc ctggagaagc acactctcag gtcagagacc tcgacctaca atttgactgt   5460
gggggacaca gggtcagggc taattgtctt tttccctgga ttccctggct caattgtggg   5520
tgctcactac acactgcaga gcaatgggaa ctacaagttc gatcagatgc tcctgactgc   5580
ccagaaccta ccggccagct acaactactg cagactagtg agtcggagtc tcacagtgag   5640
gtcaagcaca ctccctggtg gcgtttatgc actaaacggc accataaacg ccgtgacctt   5700
ccaaggaagc ctgagtgaac tgacagatgt tagctacaat gggttgatgt ctgcaacagc   5760
caacatcaac gacaaaattg ggaatgtcct ggtaggggaa ggggtcactg tcctcagcct   5820
```

acccacatca tatgatcttg ggtatgtgag gcttggtgac cccattcccg ctatagggct 5880
tgacccaaaa atggtagcta catgcgacag cagtgacagg cccagagtct acaccataac 5940
tgcagccgat gattaccaat tctcatcaca gtaccaacca ggtggggtaa caatcacact 6000
gttctcagcc aacattgatg ctatcacaag cctcagcatt gggggagagc tcgtgtttca 6060
aacaagcgtc caaggccttg tactgggcgc caccatctac cttataggct ttgatgggac 6120
tgcggtaatc accagagctg tggccgcaga taatgggctg acggccggca ccgacaatct 6180
tatgccattc aatcttgtca ttccaaccaa tgagataacc cagccaatca catccatcaa 6240
actggagata gtgacctcca aaagtggtgg tcaggcaggg gatcagatgt catggtcggc 6300
aagtgggagc ctagcagtga cgatccatgg tggcaactat ccaggggccc tccgtcccgt 6360
cacactagta gcctacgaaa gagtggcaac aggatccgtc gttacggtcg ctggggtgag 6420
taacttcgag ctgattccaa atcctgaact agcaaagaac ctggttacag aatacggccg 6480
atttgaccca ggagccatga actacacaaa attgatactg agtgagaggg accgtcttgg 6540
catcaagacc gtctggccaa caagggagta cactgatttt cgtgagtact tcatggaggt 6600
ggccgacctc aactctcccc tgaagattgc aggagcattt ggcttcaaag acataatccg 6660
ggctataagg aggtaagctt cagacatgat aagatacatt gatgagtttg gacaaaccac 6720
aactagaatg cagtgaaaaa aatgctttat ttgtgaaatt tgtgatgcta ttgctttatt 6780
tgtaaccatt ataagctgca ataaacaagt taacaacaac aattgcattc attttatgtt 6840
tcaggttcag ggggaggtgt gggaggtttt ttcggatcct ctagagtcga cggcagagtc 6900
gcagacgccc ctattggacg tcaaaattgt agaggtgaag ttttcaaacg atggcgaagt 6960
aacggcgact tgcgtttcca ccgtcaaatc tccctatagg gtagaaacta attggaaagt 7020
agacctcgta gatgtaatgg atgaaatttc tgggaacagt cccgccgggg tttttaacag 7080
taatgagaaa tggcagaaac agctgtacta cagagtaacc gatggaagaa catcggtcca 7140
gctaatgtgc ctgtcgtgca cgagccattc tccggaacct tactgtcttt tcgacacgtc 7200
tcttatagcg agggaaaaag atatcgcgcc agagttatac tttacctctg atccgcaaac 7260
ggcatactgc acaataactc tgccgtccgg cgttgttccg agattcgaat ggagccttaa 7320
taatgtttca ctgccggaat atttgacggc cacgaccgtt gtttcgcata ccgctggcca 7380
aagtacagtg tggaagagca gcgcgagagc aggcgaggcg tggatttctg gccggggagg 7440
caatatatac gaatgcaccg tcctcatctc agacggcact cgcgttacta cgcgaaagga 7500
gaggtgctta acaaacacat ggattgcggt ggaaaacggt gctgctcagg cgcagctgta 7560
ttcactcttt tctggacttg tgtcaggatt atgcgggagc atatctgctt tgtacgcaac 7620
gctatggacc gccatttatt tttgaggaat gctttttgga ctatcgtact gctttcttcc 7680
ttcgctagcc agagcaccgc cgccgtcacg tacgactaca ttttaggccg tcgcgcgctc 7740
gacgcgctaa ccataccggc ggttggcccg tataacagat acctcactag ggtatcaaga 7800
ggctgcgacg ttgtcgagct caacccgatt tctaacgtgg acgacatgat atcggcggcc 7860
aaagaaaaag agaagggggg cccctttcgag gcctccgtcg tctggttcta cgtgattaag 7920
ggcgacgacg gcgaggacaa gtactgtcca atctatagaa aagagtacag ggaatgtggc 7980
gacgtacaac tgctatctga atgcgccgtt caatctgcac agatgtgggc agtggactat 8040
gttcctagca cccttgtatc gcgaaatggc gcgggactga ctatattctc ccccactgct 8100
gcgctctctg gccaatactt gctgaccctg aaaatcggga gatttgcgca aacagctctc 8160

```
gtaactctag aagttaacga tcgctgttta aagatcgggt cgcagcttaa ctttttaccg   8220

tcgaaatgct ggacaacaga acagtatcag actggatttc aaggcgaaca cctttatccg   8280

atcgcagaca ccaatacacg acacgcggac gacgtatatc ggggatacga agatattctg   8340

cagcgctgga ataatttgct gaggaaaaag aatcctagcg cgccagaccc tcgtccagat   8400

agcgtcccgc aagaaattcc cgctgtaacc aagaaagcgg aagggcgcac cccggacgca   8460

gaaagcagcg aaaagaaggc ccctccagaa gactcggagg acgacatgca ggcagaggct   8520

tctggagaaa atcctgccgc cctccccgaa gacgacgaag tccccgagga caccgagcac   8580

gatgatccaa actcggatcc tgactattac aatgacatgc ccgccgtgat cccggtggag   8640

gagactacta aaagttctaa tgccgtctcc atgcccatat tcgcggcgtt cgtagcctgc   8700

gcggtcgcgc tcgtggggct actggtttgg agcatcgtaa aatgcgcgcg tagctaatcg   8760

agcctagaat aggtggtttc ttcctacatg ccacgcctca cgctcataat ataaatcaca   8820

tggaatagca taccaatgcc tattcattgg gacgttcgaa aagcatggca tcgctacttg   8880

gaactctggc tctccttgcc gcgacgctcg cacccttcgg cgcgatggga atcgtgatca   8940

ctggaaatca cgtctccgcc aggattgacg acgatcacat cgtgatcgtc gcgcctcgcc   9000

ccgaagctac aattcaactg cagctatttt tcatgcctgg ccagagaccc cacaaaccct   9060

actcaggaac cgtccgcgtc gcgtttcggt ctgatataac aaaccagtgc taccaggaac   9120

ttagcgagga gcgctttgaa aattgcactc atcgatcgtc ttctgttttt gtcggctgta   9180

aagtgaccga gtacacgttc tccgcctcga acagactaac cggacctcca cacccgttta   9240

agctcactat acgaaatcct cgtccgaacg acagcgggat gttctacgta attgttcggc   9300

tagacgacac caaagaaccc attgacgtct tcgcgatcca actatcggtg tatcaattcg   9360

cgaacaccgc cgcgactcgc ggactctatt ccaaggcttc gtgtcgcacc ttcggattac   9420

ctaccgtcca acttgaggcc tatctcagga ccgaggaaag ttggcgcaac tggcaagcgt   9480

acgttgccac ggaggccacg acgaccagcg ccgaggcgac aaccccgacg cccgtcactg   9540

caaccagcgc ctccgaactt gaagcggaac actttacctt tccctggcta gaaaatggcg   9600

tggatcatta cgaaccgaca cccgcaaacg aaaattcaaa cgttactgtc cgtctcggga   9660

caatgagccc tacgctaatt ggggtaaccg tggctgccgt cgtgagcgca acgatcggcc   9720

tcgtcattgt aatttccatc gtcaccagaa acatgtgcac cccgcaccga aaattagaca   9780

cggtctcgca agacgacgaa gaacgttccc aaactagaag ggaatcgcga aaatttggac   9840

ccatggttgc gtgcgaaata aacaaggggg ctgaccagga tagtgaactt gtggaactgg   9900

ttgcgattgt taacccgtct gcgctaagct cgcccgactc aataaaaatg tgattaagtc   9960

tgaatgtggc tctccaatca tttcgattct ctaatctccc aatcctctca aaggggcag  10020

tatcggacac ggactgggag gggcgtacac gatagttata tggtacagca gaggcctctg  10080

aacacttagg aggagaattc agccggggag agcccctgtt gagtaggctt gggagcatat  10140

tgcaggatga acatgttagt gatagttctc gcctcttgtc ttgcgcgcct aacttttgcg  10200

acgcgacacg tcctcttttt ggaaggcact caggctgtcc tcggggaaga tgatcccaga  10260

aacgttccgg aagggactgt aatcaaatgg acaaaagtcc tgcggaacgc gtgcaagatg  10320

aaggcggccg atgtctgctc ttcgcctaac tattgctttc atgatttaat ttacgacgga  10380

ggaaagaaag actgcccgcc cgcgggaccc ctgtctgcaa acctggtaat tttactaaag  10440

cgcggcgaag cttagcttgc ctccgattct agcattacat agccggtcag tagatcctgc  10500

cattcggtag cgcaaccggc tacatcttca aacagtctca cgataaatgc atctctcgtt  10560
```

-continued

```
cctgccaatc cggaaccggg cataccactc ccgcctgccg atttaattct cacaattggg  10620
cgatgccggc ggggcaaaac gaatgtggat ttggcaaacc gacacaggtc tgctgtacgg  10680
actaatatgg gcacacccac atcattcttc agatgctcca tgcattgttc tatgagaaag  10740
atccataggg tggaggcagc gtcacgagat cgcccaggca atcgatcgca ttcgtctagt  10800
aaagtgacga gagttatcat gcacacaccc atgcccacgc cttccgaata actggagctg  10860
tggaagatcg gaaacgtctt tttgactgcc ggtctcgtac tactttcgca caggtgtata  10920
cccggacgcg tactatatat tttatatcat ccaacgtccg aaattacata cgtggcggcg  10980
atggaagtag atgttgagtc ttcgaaagta agtgcctcga atatgggtat tgtctgtgaa  11040
aatatcgaaa gcggtacgac ggttgcagaa ccgtcgatgt cgccagatac tagtaacaat  11100
agcttcgata acgaagactt ccgtgggcct gaatacgatg tggagataaa taccagaaaa  11160
tctgctaatc ttgatcgtat ggaatcttcg tgccgtgaac aacgagcggc gtgcgaactt  11220
cgaaagtgtt cgtgtcctac gtctgccgtg cgcatgcaat acagtattct ttcatctctc  11280
gctccgggtt cagagggtca tgtatatata tgtactagat acggggacgc ggaccaaaaa  11340
aaatgcatag tgaaggcagt cgttggagga aagaatcccg ggagggaagt ggatatttta  11400
aaaaccatct cacataaatc aattataaaa ttaatccatg cctataaatg gaaaaatgtt  11460
gtgtgtatgg caatgcgtgt atatcgttat gatcttttca catatattga cggagtcggc  11520
cctatgcccc ttcaacagat gatctatatt caacgtggac tactagaggc gctagcatac  11580
atacatgaaa ggggcatcat tcaccgagac gtaaagacgg agaatatatt cttggataat  11640
cacgaaaatg cagttttggg tgacttcggt gctgcatgcc aactaggaga ttgtatagat  11700
acgccccaat gttacggttg gagcggaact gtggaaacaa attcgccgga attatctgca  11760
cttgatccgt attgcacaaa aacagatatt tggagtgccg gattggttct atatgagatg  11820
gcaattaaaa atgtaccatt gtttagtaag caggtgaaaa gttcgggatc tcagctgaga  11880
tccataatac ggtgcatgca agtgcatgaa ctggagtttc cccgcaacga ttctaccaac  11940
ctctgtaaac atttcaaaca atatgcggtt cgtgtacgac cgccttatac cattcctcga  12000
gttataagaa atgggggat gccaatggat gttgaatatg tcatttctaa aatgcttacg  12060
tttgaccagg agttcagacc ttctgctaag gaaatattga atatgcccct atttactaag  12120
gcgccgatta acctgcttaa tatcacaccc tctgacagtg tctaacggta tacaggcggg  12180
agcgggtcgt ggcgtcatca tcaccacttg agaatttata ttttgaattg ttgattgata  12240
aattaacctg attcattgag aactgaaacg ccatattggt ttcttggata tgtctacaac  12300
aattagttaa attgctatgt tctactgcga gtaacatttg ataagttgta agagacgggc  12360
gactcatgtc gaagttgacg aatataaagt acataacgtg tttagaatac ccagaatccg  12420
aatagtccgc gggggcgtct tctcgcgtga gtaccaaata ctgagttgaa cttgaaaatg  12480
ctaaatctgt gacactcttt gtgtgatgat tattgtcacc acttcgaaga tggcttcgac  12540
attcatgatg ttctggtgtt tgtttggaat cgtaatagcg cttgtttcgt ccaagtctga  12600
caacaaagaa aatctgaaga attatatcac ggataagtca accaatatta gaatacccac  12660
gccattattt gtatcaacgg aaaactctta tcccacaaaa catgtaatct acgatgaaaa  12720
ctgtggcttc gctgtactca atcctataag tgaccccaaa tatgtccttt tgagccagct  12780
tctaatggga aggcgcaaat atgatgcgac ggtcgcgtgg tttgttctcg gtaaaatgtg  12840
tgccagatta atatatttgc gcgaatttta taactgctcg acaaatgagc cttttggcac  12900
```

atgttctatg agctctcctg gatggtggga caggcgctac gtctcaacca gtttcatttc 12960
tcgcgacgaa ttacagctgg tttttgcagc gccgtcccga gaattagatg gtttatatac 13020
gcgcgtagta gttgtcaacg gggactttac tacggccgat ataatgttta atgttaaagt 13080
ggcatgtgcc ttttcaaaga ctggaataga agatgataca ttatgcaaac cctttcattt 13140
ctttgccaat gcaacattgc acaatttaac catgattaga tcggtaactc ttcgagcgca 13200
cgaaagccat ttaaaggaat gggtggcacg gagaggtggt aacgtccctg cagtgctact 13260
tgagtctacc atgtatcatg catccaatct gcctagaaat ttcagggatt tctacataaa 13320
gtctccagat gattataagt ataatcacct agatgggcca tctgtaatgc tcatcactga 13380
cagacctagt gaagatttgg atgggaggct cgttcaccaa agtgacattt ttactactac 13440
aagtcctata aaacaggtcc ggtatgaaga gcatcagtca catacaaagc agtatcctgt 13500
aaacaaaata caagctataa ttttttgat agggttaggc tcgttcattg gaagcatatt 13560
cgtagttttg gtagtatgga ttatacgcag atattgcaat ggagcgcgga gtgggggaac 13620
gccccccagt cctcgccggt atgtgtatac caggctatga tcacgtgtga aacttgggcg 13680
gacctgtatc atatgtacac cgtccctatt cgtttatagc cagtacgtgt tatctgcaca 13740
tagaggaaca tgtgtcatac tgggatcgca tgcatggtat gtgtgactct aatattattc 13800
tgtatcataa taaaaacaca gtgcatggta tatagaggat cgctggtaag cactacggta 13860
gaccaatcgg ctcagattgc attctttggc atcgataccg ttgttaattt atatggcaaa 13920
gtcttgttca tgggagatca gtatttggag gaaatatact ctggaacgat ggaaatactc 13980
aaatggaatc aagctaaccg ctgctattct attgcgcatg caacatatta cgccgactgt 14040
cctataatca gttctacggt attcagagga tgccgggacg ccgttgttta tactaggccc 14100
cacagcagaa ttc 14113

<210> SEQ ID NO 24
<211> LENGTH: 13064
<212> TYPE: DNA
<213> ORGANISM: Artificial Sequence
<220> FEATURE:
<223> OTHER INFORMATION: Expression cassette
<220> FEATURE:
<221> NAME/KEY: misc_feature
<222> LOCATION: (7401)..(7403)
<223> OTHER INFORMATION: n is a, c, g, or t

<400> SEQUENCE: 24
gaattccaga ctaaatgccc cggcccaatt tgtcaagtgt gcagtcacgg aggcgtcgac 60
cgtgtccccg gcattaaaca ggaaagcgtt aaagtttttg aatgttaggt cacaggtaca 120
aacataaatg tttgtacaaa caggtaacag gtacaaacat aaatgccccg gcataaatgt 180
cccttacggc ggatcgaaac gacattaggc atactcgggt accattttgc attccgatca 240
gcacggatga aattaggcag gaatgcggtt tatattatgc ggcattggac aaacgatatg 300
gcattgattg gcagtttatg aatgtcttca tgttgggcgt aaacggattc ctattggttc 360
agaagacaac gacgatatat ttagagagaa aaagctaccc agcataggat aaacacacat 420
tgagcattga gagacatagg tatcggtatg gatgggaaaa ctacacacgt gaacaccaaa 480
cgacttatat actcgagcgg tgatactact gagcaagaat gcactgcatc tgagccactg 540
aatgaagact gtgatgaaaa tgtgaccatc gatggaattg gagaagaata tgcgcagttc 600
ttcatgtccc cgcaatgggt cccaaatcta catcgcttga gcgaggatac caaaaaggta 660
taccgatgta tggtttccaa cagactcaat tattttccct attatgaggc gttcaggcgg 720

```
tctttgtttg atatgtatat gctaggtcgg ttggggcgtc gacttaagcg atctgactgg    780
gagactatta tgcatctgtc accaacgcaa agtcggcgtc tacatagaac tttaagattt    840
gtggagcgta gaattatccc atctaacagt tatatacgca catcgggcca cgttccgcct    900
tcgagggcac ttccgacaga tacgaattta aagatggatg aataattaaa ttggaaagag    960
taactacatt aatcgagcgt catgacggcg tcccgtgaaa atgggaattt tctactcgaa   1020
acaccgtgac atttgacaga cctggaattg ttattctgat atatagtggg tgtgtctggc   1080
cggcaacata cataatgtgc atgcgaaacc actttttcag tgtacgctga cattgtgcaa   1140
cacggagggg tagcatctac atacaatata tgttgattaa tgattggaga aaaaactatg   1200
cagctcgccg atcatatggc taactcgcct tcgtctatat ggcggacccc gcgggaaaaa   1260
tcgacgtacc atctgattta caacaccagt aatgaacatg tcgcatccct gcccagatct   1320
gtgcgcccat tggcgcggat cgttgtgaat gccgccgaaa cacttcaggt cggtatgaga   1380
gccgggaggc cgccatcagc aggagtttgg cgagaggtgt ttgatagaat gatgacagcc   1440
ttccgtgacc acgagcctac tgcgacattt aatgctgcaa atcccattag aaaaatggtc   1500
gagacagttc tacagaataa tgaagagccc ccgcggacgc atgctgaaat gggtaatcgc   1560
cttatgaaca ttatgtactg gtgttgcttg ggacacgcag gacaatgctc gatatggcag   1620
ttgtacgaga cgaatcaggc cattttaagt ttattagatg aagtggttat cggcacaaca   1680
aatccctttt gcaccctcga gcaatactgg aagccattat gcaccgcaat cgccaacaag   1740
gggacctcat cgcttgttga ggatgccaaa gtggccgagt acctggttag catgcgcaaa   1800
ttgatataac ataggcacgc tctgatgtta cagaccacaa taccgcatac atttattgta   1860
aggttgttaa taaaggttta ttctatgtaa gactacaata ctttcgacat tgcttgtata   1920
catattaaat actttctcaa gttcctatta cataaaatgg gatctatcat tacattcgtt   1980
aagagtctgg ataattttac tgtttgccag cttcgatctt ggaacgtact gtggatagtg   2040
ccttacttgg aatcgtgaaa atttgaaacg tccattattt ggatatcttc cggttgtccc   2100
atatcccgcc ctggtaccgc tcggatacct tgcccgtatg gattcgtatt gacagtcgcg   2160
caatcgggga ccaacaacgc gtgggtccac actcattcgg aaattttccg atgattctga   2220
atatttattg ccgctcgtta cgagtcgttg gacatatctg taatacattt cttcttctga   2280
aggatcgctg cacatttgat ctatacattg gccaggatgt tcaagtctca gatgttgcat   2340
tctggcacag cacaacttta tggcatttcc gatgtaatcg tccggcagcc ctgggggagt   2400
tctatattcg catattggga tggtaaggac aatagcagat ctcgcaacct ccagggaggc   2460
tataataacg tttttaaagg atggatttct cataaaaatc tgtcgcaaat tacactgaga   2520
atatccttta ctagcgccga ttgagagcat cgtcgtccaa ttttctaaat ggaaagaaaa   2580
caaggcgggc aagagtgttc caaacatttt cattttcggc gaatctctca aatcccatgg   2640
cgtgcaattg attgcaaaat tggcacttcc gttcacgttt gtatctccaa actctaagac   2700
acttttaatt gaaaaactac gttctagtgt ggaaagaaac ctataggcag accatagaac   2760
tatttgacac cacatatctt tttgtatgtc aaactgacca tgatcgtatg ttgctgaatg   2820
cactagggca attcgctcgc gcgactccat acattgaata attccacacg tcagctcatc   2880
ggttagcaag gtccagtagt tgaagtcatt tatttttccc cgcggctggc caaatctacc   2940
tctgggaata tccaagttgt cgaatatgat cgcaccggct ctggtcatgg tgaaggaact   3000
gtagcataaa gacgcaggta tcataggggt aatatttttt tattcactca catactaaaa   3060
```

-continued

```
gtaacgcata ttagcaccat gtatgggcta tcaattgaca tttgcgtagc actacatcac   3120
gattatgtac aacataatgg gacaacatat ggcaagtaga tgcaatttcc tcacactagt   3180
tgggtttatc tactattgaa ttttccccta tctgtgatac acttgggagc ctctacaagc   3240
atattgccat catgtacgtt tttatctact gtcttaacgc ccatgggaac ggaggcgtcg   3300
tcgtcatgta ttggacggca acataggcag caacacaaat tgcgtttagg tggggtgcat   3360
gtggactcga taccaagccc ctgcagctgg ggaacgtctg gtggagagcc gataatttga   3420
tatacgcacg ccatattact gtcgttgaag tacgccttat cttctatgtt ttcaaattta   3480
ggttcccaag tggacgtgag aagtgtttgt atctcacatg gaatggccca aggcattcca   3540
gcccaggtgc ctggtacttt aatggcaaac aaacgttttg gtagaggtat tgattctatt   3600
gcagttctgc agatatctgc agccccgagt atccacaggc tatacgatac gttatcggag   3660
gcaagcttaa ttaagtaccg agctcgaatt ggcgcgcccg acggcagagt cgcagacgcc   3720
cctattggac gtcaaaattg tagaggtgaa gttttcaaac gatggcgaag taacggcgac   3780
ttgcgtttcc accgtcaaat ctccctatag ggtagaaact aattggaaag tagacctcgt   3840
agatgtaatg gatgaaattt ctgggaacag tcccgccggg gtttttaaca gtaatgagaa   3900
atggcagaaa cagctgtact acagagtaac cgatggaaga acatcggtcc agctaatgtg   3960
cctgtcgtgc acgagccatt ctccggaacc ttactgtctt ttcgacacgt ctcttatagc   4020
gagggaaaaa gatatcgcgc cagagttata ctttacctct gatccgcaaa cggcatactg   4080
cacaataact ctgccgtccg gcgttgttcc gagattcgaa tggagcctta ataatgtttc   4140
actgccggaa tatttgacgg ccacgaccgt tgtttcgcat accgctggcc aaagtacagt   4200
gtggaagagc agcgcgagag caggcgaggc gtggatttct ggccggggag gcaatatata   4260
cgaatgcacc gtcctcatct cagacggcac tcgcgttact acgcgaaagg agaggtgctt   4320
aacaaacaca tggattgcgg tggaaaacgg tgctgctcag gcgcagctgt attcactctt   4380
ttctggactt gtgtcaggat tatgcgggag catatctgct ttgtacgcaa cgctatggac   4440
cgccatttat ttttgaggaa tgctttttgg actatcgtac tgctttcttc cttcgctagc   4500
cagagcaccg ccgccgtcac gtacgactac attttaggcc gtcgcgcgct cgacgcgcta   4560
accataccgg cggttggccc gtataacaga tacctcacta gggtatcaag aggctgcgac   4620
gttgtcgagc tcaacccgat ttctaacgtg gacgacatga tatcggcggc caaagaaaaa   4680
gagaaggggg gccctttcga ggcctccgtc gtctggttct acgtgattaa gggcgacgac   4740
ggcgaggaca agtactgtcc aatctataga aaagagtaca gggaatgtgg cgacgtacaa   4800
ctgctatctg aatgcgccgt tcaatctgca cagatgtggg cagtggacta tgttcctagc   4860
acccttgtat cgcgaaatgg cgcgggactg actatattct cccccactgc tgcgctctct   4920
ggccaatact tgctgaccct gaaaatcggg agatttgcgc aaacagctct cgtaactcta   4980
gaagttaacg atcgctgttt aaagatcggg tcgcagctta actttttacc gtcgaaatgc   5040
tggacaacag aacagtatca gactggattt caaggcgaac acctttatcc gatcgcagac   5100
accaatacac gacacgcgga cgacgtatat cggggatacg aagatattct gcagcgctgg   5160
aataatttgc tgaggaaaaa gaatcctagc gcgccagacc ctcgtccaga tagcgtcccg   5220
caagaaattc ccgctgtaac caagaaagcg gaagggcgca ccccggacgc agaaagcagc   5280
gaaaagaagg cccctccaga agactcggag gacgacatgc aggcagaggc ttctggagaa   5340
aatcctgccg ccctccccga agacgacgaa gtccccgagg acaccgagca cgatgatcca   5400
aactcggatc ctgactatta caatgacatg cccgccgtga tcccggtgga ggagactact   5460
```

```
aaaagttcta atgccgtctc catgcccata ttcgcggcgt tcgtagcctg cgcggtcgcg   5520
ctcgtggggc tactggtttg gagcatcgta aaatgcgcgc gtagctaatc gagcctagaa   5580
taggtggttt cttcctacat gccacgcctc acgctcataa tataaatcac atggaatagc   5640
ataccaatgc ctattcattg ggacgttcga aaagcatggc atcgctactt ggaactctgg   5700
ctctccttgc cgcgacgctc gcacccttcg gcgcgatggg aatcgtgatc actggaaatc   5760
acgtctccgc caggattgac gacgatcaca tcgtgatcgt cgcgcctcgc cccgaagcta   5820
caattcaact gcagctattt ttcatgcctg gccagagacc ccacaaaccc tactcaggaa   5880
ccgtccgcgt cgcgtttcgg tctgatataa caaaccagtg ctaccaggaa cttagcgagg   5940
agcgctttga aaattgcact catcgatcgt cttctgtttt tgtcggctgt aaagtgaccg   6000
agtacacgtt ctccgcctcg aacagactaa ccggacctcc acacccgttt aagctcacta   6060
tacgaaatcc tcgtccgaac gacagcggga tgttctacgt aattgttcgg ctagacgaca   6120
ccaaagaacc cattgacgtc ttcgcgatcc aactatcggt gtatcaattc gcgaacaccg   6180
ccgcgactcg cggactctat tccaaggctt cgtgtcgcac cttcggatta cctaccgtcc   6240
aacttgaggc ctatctcagg accgaggaaa gttggcgcaa ctggcaagcg tacgttgcca   6300
cggaggccac gacgaccagc gccgaggcga caaccccgac gcccgtcact gcaaccagcg   6360
cctccgaact tgaagcggaa cactttacct ttccctggct agaaaatggc gtggatcatt   6420
acgaaccgac acccgcaaac gaaaattcaa acgttactgt ccgtctcggg acaatgagcc   6480
ctacgctaat tggggtaacc gtggctgccg tcgtgagcgc aacgatcggc ctcgtcattg   6540
taatttccat cgtcaccaga aacatgtgca ccccgcaccg aaaattagac acggtctcgc   6600
aagacgacga agaacgttcc caaactagaa gggaatcgcg aaaatttgga cccatggttg   6660
cgtgcgaaat aaacaagggg gctgaccagg atagtgaact tgtggaactg gttgcgattg   6720
ttaacccgtc tgcgctaagc tcgcccgact caataaaaat gtgattaagt ctgaatgtgg   6780
ctctccaatc atttcgattc tctaatctcc caatcctctc aaaaggggca gtatcggaca   6840
cggactggga ggggcgtaca cgatagttat atggtacagc agaggcctct gaacacttag   6900
gaggagaatt cagccgggga gagcccctgt tgagtaggct tgggagcata ttgcaggatg   6960
aacatgttag tgatagttct cgcctcttgt cttgcgcgcc taacttttgc gacgcgacac   7020
gtcctctttt tggaaggcac tcaggctgtc ctcggggaag atgatcccag aaacgttccg   7080
gaagggactg taatcaaatg gacaaaagtc ctgcggaacg cgtgcaagat gaaggcggcc   7140
gatgtctgct cttcgcctaa ctattgcttt catgatttaa tttacgacgg aggaaagaaa   7200
gactgcccgc ccgcgggacc cctgtctgca aacctggtaa ttttactaaa gcgcggcggg   7260
cgcgccggat cagatctcca tggtcgaggt gagccccacg ttctgcttca ctctccccat   7320
ctcccccccc tccccacccc caattttgta tttatttatt ttttaattat tttgtgcagc   7380
gatgggggcg gggggggggg nnncgcgcgc caggcggggc ggggcggggc gaggggcggg   7440
gcggggcgag gcggagaggt gcggcggcag ccaatcagag cggcgcgctc cgaaagtttc   7500
cttttatggc gaggcggcgg cggcggcggc cctataaaaa gcgaagcgcg cggcgggcgg   7560
gagtcgctgc gcgctgcctt cgccccgtgc cccgctccgc cgccgcctcg cgccgcccgc   7620
cccggctctg actgaccgcg ttactcccac aggtgagcgg gcgggacggc ccttctcctc   7680
cgggctgtaa ttagcggcag gaaggaaatg ggcggggagg gccttcgtgc gtcgccgcgc   7740
cgccgtcccc ttctccctct ccagcctcgg ggctgtccgc ggggggacgg ctgccttcgg   7800
```

gggggacggg gcagggcggg gttcggcttc tggcgtgtga ccggcggctc tagagcctct 7860
gctaaccatg ttcatgcctt cttctttttc ctacagctcc tgggcaacgt gctggttatt 7920
gtgctgtctc atcattttgg caaagaattg cagatctgga tctatgacaa acctgcaaga 7980
tcaaacccaa cagattgttc cgttcatacg gagccttctg atgccaacaa ccggaccggc 8040
gtccattccg gacgacaccc tggagaagca cactctcagg tcagagacct cgacctacaa 8100
tttgactgtg ggggacacag ggtcagggct aattgtcttt ttccctggat tccctggctc 8160
aattgtgggt gctcactaca cactgcagag caatgggaac tacaagttcg atcagatgct 8220
cctgactgcc cagaacctac cggccagcta caactactgc agactagtga gtcggagtct 8280
cacagtgagg tcaagcacac tccctggtgg cgtttatgca ctaaacggca ccataaacgc 8340
cgtgaccttc caaggaagcc tgagtgaact gacagatgtt agctacaatg ggttgatgtc 8400
tgcaacagcc aacatcaacg acaaagttgg gaatgtcctg gtaggggaag ggtcactgt 8460
cctcagccta cccacatcat atgatcttgg gtatgtgagg cttggtgacc ccattcccgc 8520
tatagggctt gacccaaaaa tggtagctac atgcgacagc agtgacaggc ccagagtcta 8580
caccataact gcagccgatg attaccaatt ctcatcacag taccaaccag gtggggtaac 8640
aatcacactg ttctcagcca acattgatgc tatcacaagc ctcagcattg gggagagct 8700
cgtgtttcaa acaagcgtcc aaggccttgt actgggcgcc accatctacc ttataggctt 8760
tgatgggact gcggtaatca ccagagctgt ggccgcagat aatgggctga cggccggcac 8820
cgacaatctt atgccattca atcttgtcat tccaaccaat gagataaccc agccgatcac 8880
atccatcaaa ctggagatag tgacctccaa aagtggtggt caggcagggg atcagatgtc 8940
atggtcggca agtgggagcc tagcagtgac gatccatggt ggcaactatc caggggccct 9000
ccgtcccgtc acactagtag cctacgaaag agtggcaaca ggatccgtcg ttacggtcgc 9060
tggggtgagt aacttcgagc tgatcccaaa tcctgaacta gcaaagaacc tggttacaga 9120
atacggccga tttgacccag gagccatgaa ctacacaaaa ttgatactga gtgagaggga 9180
ccgtcttggc atcaagaccg tctggccaac aagggagtac actgattttc gtgagtactt 9240
catggaggtg gccgacctca actctcccct gaagattgca ggagcatttg gcttcaaaga 9300
cataatccgg gctataagga ggtaagatcc gatctctcga ttaattaaca ataaacatag 9360
catacgttat gacatggtct accgcgtctt atatggggac gacaagcttg cctccgattc 9420
tagcattaca tagccggtca gtagatcctg ccattcggta gcgcaaccgg ctacatcttc 9480
aaacagtctc acgataaatg catctctcgt tcctgccaat ccggaaccgg gcataccact 9540
cccgcctgcc gatttaattc tcacaattgg gcgatgccgg cggggcaaaa cgaatgtgga 9600
tttggcaaac cgacacaggt ctgctgtacg gactaatatg ggcacaccca catcattctt 9660
cagatgctcc atgcattgtt ctatgagaaa gatccatagg gtggaggcag cgtcacgaga 9720
tcgcccaggc aatcgatcgc attcgtctag taaagtgacg agagttatca tgcacacacc 9780
catgcccacg ccttccgaat aactggagct gtggaagatc ggaaacgtct tttgactgc 9840
cggtctcgta ctactttcgc acaggtgtat acccggacgc gtactatata ttttatatca 9900
tccaacgtcc gaaattacat acgtggcggc gatggaagta gatgttgagt cttcgaaagt 9960
aagtgcctcg aatatgggta ttgtctgtga aaatatcgaa agcggtacga cggttgcaga 10020
accgtcgatg tcgccagata ctagtaacaa tagcttcgat aacgaagact tccgtgggcc 10080
tgaatacgat gtggagataa ataccagaaa atctgctaat cttgatcgta tggaatcttc 10140
gtgccgtgaa caacgagcgg cgtgcgaact tcgaaagtgt tcgtgtccta cgtctgccgt 10200

-continued

```
gcgcatgcaa tacagtattc tttcatctct cgctccgggt tcagagggtc atgtatatat  10260
atgtactaga tacggggacg cggaccaaaa aaaatgcata gtgaaggcag tcgttggagg  10320
aaagaatccc gggagggaag tggatatttt aaaaaccatc tcacataaat caattataaa  10380
attaatccat gcctataaat ggaaaaatgt tgtgtgtatg gcaatgcgtg tatatcgtta  10440
tgatcttttc acatatattg acggagtcgg ccctatgccc cttcaacaga tgatctatat  10500
tcaacgtgga ctactagagg cgctagcata catacatgaa aggggcatca ttcaccgaga  10560
cgtaaagacg gagaatatat tcttggataa tcacgaaaat gcagttttgg gtgacttcgg  10620
tgctgcatgc caactaggag attgtataga tacgccccaa tgttacggtt ggagcggaac  10680
tgtggaaaca aattcgccgg aattatctgc acttgatccg tattgcacaa aaacagatat  10740
ttggagtgcc ggattggttc tatatgagat ggcaattaaa aatgtaccat tgtttagtaa  10800
gcaggtgaaa agttcgggat ctcagctgag atccataata cggtgcatgc aagtgcatga  10860
actggagttt ccccgcaacg attctaccaa cctctgtaaa catttcaaac aatatgcggt  10920
tcgtgtacga ccgccttata ccattcctcg agttataaga aatgggggga tgccaatgga  10980
tgttgaatat gtcatttcta aaatgcttac gtttgaccag gagttcagac cttctgctaa  11040
ggaaatattg aatatgcccc tatttactaa ggcgccgatt aacctgctta atatcacacc  11100
ctctgacagt gtctaacggt atacaggcgg gagcgggtcg tggcgtcatc atcaccactt  11160
gagaatttat attttgaatt gttgattgat aaattaacct gattcattga gaactgaaac  11220
gccatattgg tttcttggat atgtctacaa caattagtta aattgctatg ttctactgcg  11280
agtaacattt gataagttgt aagagacggg cgactcatgt cgaagttgac gaatataaag  11340
tacataacgt gtttagaata cccagaatcc gaatagtccg cgggggcgtc ttctcgcgtg  11400
agtaccaaat actgagttga acttgaaaat gctaaatctg tgacactctt tgtgtgatga  11460
ttattgtcac cacttcgaag atggcttcga cattcatgat gttctggtgt ttgtttggaa  11520
tcgtaatagc gcttgtttcg tccaagtctg acaacaaaga aaatctgaag aattatatca  11580
cggataagtc aaccaatatt agaataccca cgccattatt tgtatcaacg gaaaactctt  11640
atcccacaaa acatgtaatc tacgatgaaa actgtggctt cgctgtactc aatcctataa  11700
gtgaccccaa atatgtcctt ttgagccagc ttctaatggg aaggcgcaaa tatgatgcga  11760
cggtcgcgtg gtttgttctc ggtaaaatgt gtgccagatt aatatatttg cgcgaatttt  11820
ataactgctc gacaaatgag ccttttggca catgttctat gagctctcct ggatggtggg  11880
acaggcgcta cgtctcaacc agtttcattt ctcgcgacga attacagctg gtttttgcag  11940
cgccgtcccg agaattagat ggtttatata cgcgcgtagt agttgtcaac ggggacttta  12000
ctacggccga tataatgttt aatgttaaag tggcatgtgc cttttcaaag actggaatag  12060
aagatgatac attatgcaaa ccctttcatt tctttgccaa tgcaacattg cacaatttaa  12120
ccatgattag atcggtaact cttcgagcgc acgaaagcca tttaaaggaa tgggtggcac  12180
ggagaggtgg taacgtccct gcagtgctac ttgagtctac catgtatcat gcatccaatc  12240
tgcctagaaa tttcagggat ttctacataa agtctccaga tgattataag tataatcacc  12300
tagatgggcc atctgtaatg ctcatcactg acagacctag tgaagatttg gatgggaggc  12360
tcgttcacca aagtgacatt tttactacta caagtcctat aaaacaggtc cggtatgaag  12420
agcatcagtc acatacaaag cagtatcctg taaacaaaat acaagctata attttttga   12480
tagggttagg ctcgttcatt ggaagcatat tcgtagtttt ggtagtatgg attatacgca  12540
```

gatattgcaa tggagcgcgg agtgggggaa cgccccccag tcctcgccgg tatgtgtata 12600
ccaggctatg atcacgtgtg aaacttgggc ggacctgtat catatgtaca ccgtccctat 12660
tcgtttatag ccagtacgtg ttatctgcac atagaggaac atgtgtcata ctgggatcgc 12720
atgcatggta tgtgtgactc taatattatt ctgtatcata ataaaaacac agtgcatggt 12780
atatagagga tcgctggtaa gcactacggt agaccaatcg gctcagattg cattctttgg 12840
catcgatacc gttgttaatt tatatggcaa agtcttgttc atgggagatc agtatttgga 12900
ggaaatatac tctggaacga tggaaatact caaatggaat caagctaacc gctgctattc 12960
tattgcgcat gcaacatatt acgccgactg tcctataatc agttctacgg tattcagagg 13020
atgccgggac gccgttgttt atactaggcc ccacagcaga attc 13064

<210> SEQ ID NO 25
<211> LENGTH: 13017
<212> TYPE: DNA
<213> ORGANISM: Artificial Sequence
<220> FEATURE:
<223> OTHER INFORMATION: Expression cassette

<400> SEQUENCE: 25
gaattccaga ctaaatgccc cggcccaatt tgtcaagtgt gcagtcacgg aggcgtcgac 60
cgtgtccccg gcattaaaca ggaaagcgtt aaagtttttg aatgttaggt cacaggtaca 120
aacataaatg tttgtacaaa caggtaacag gtacaaacat aaatgccccg gcataaatgt 180
cccttacggc ggatcgaaac gacattaggc atactcgggt accattttgc attccgatca 240
gcacggatga aattaggcag gaatgcggtt tatattatgc ggcattggac aaacgatatg 300
gcattgattg gcagtttatg aatgtcttca tgttgggcgt aaacggattc ctattggttc 360
agaagacaac gacgatatat ttagagagaa aaagctaccc agcataggat aaacacacat 420
tgagcattga gagacatagg tatcggtatg gatgggaaaa ctacacacgt gaacaccaaa 480
cgacttatat actcgagcgg tgatactact gagcaagaat gcactgcatc tgagccactg 540
aatgaagact gtgatgaaaa tgtgaccatc gatggaattg gagaagaata tgcgcagttc 600
ttcatgtccc cgcaatgggt cccaaatcta catcgcttga gcgaggatac caaaaaggta 660
taccgatgta tggtttccaa cagactcaat tattttccct attatgaggc gttcaggcgg 720
tctttgtttg atatgtatat gctaggtcgg ttggggcgtc gacttaagcg atctgactgg 780
gagactatta tgcatctgtc accaacgcaa agtcggcgtc tacatagaac tttaagattt 840
gtggagcgta gaattatccc atctaacagt tatatacgca catcgggcca cgttccgcct 900
tcgagggcac ttccgacaga tacgaattta aagatggatg aataattaaa ttggaaagag 960
taactacatt aatcgagcgt catgacggcg tcccgtgaaa atgggaattt tctactcgaa 1020
acaccgtgac atttgacaga cctggaattg ttattctgat atatagtggg tgtgtctggc 1080
cggcaacata cataatgtgc atgcgaaacc actttttcag tgtacgctga cattgtgcaa 1140
cacggagggg tagcatctac atacaatata tgttgattaa tgattggaga aaaaactatg 1200
cagctcgccg atcatatggc taactcgcct tcgtctatat ggcggacccc gcgggaaaaa 1260
tcgacgtacc atctgattta caacaccagt aatgaacatg tcgcatccct gcccagatct 1320
gtgcgcccat tggcgcggat cgttgtgaat gccgccgaaa cacttcaggt cggtatgaga 1380
gccgggaggc cgccatcagc aggagtttgg cgagaggtgt ttgatagaat gatgacagcc 1440
ttccgtgacc acgagcctac tgcgacattt aatgctgcaa atcccattag aaaaatggtc 1500
gagacagttc tacagaataa tgaagagccc ccgcggacgc atgctgaaat gggtaatcgc 1560
cttatgaaca ttatgtactg gtgttgcttg ggacacgcag gacaatgctc gatatggcag 1620
ttgtacgaga cgaatcaggc cattttaagt ttattagatg aagtggttat cggcacaaca 1680
aatccctttt gcaccctcga gcaatactgg aagccattat gcaccgcaat cgccaacaag 1740
gggacctcat cgcttgttga ggatgccaaa gtggccgagt acctggttag catgcgcaaa 1800
ttgatataac ataggcacgc tctgatgtta cagaccacaa taccgcatac atttattgta 1860
aggttgttaa taaaggttta ttctatgtaa gactacaata ctttcgacat tgcttgtata 1920
catattaaat actttctcaa gttcctatta cataaaatgg gatctatcat tacattcgtt 1980
aagagtctgg ataattttac tgtttgccag cttcgatctt ggaacgtact gtggatagtg 2040
ccttacttgg aatcgtgaaa atttgaaacg tccattattt ggatatcttc cggttgtccc 2100
atatcccgcc ctggtaccgc tcggatacct tgcccgtatg gattcgtatt gacagtcgcg 2160
caatcgggga ccaacaacgc gtgggtccac actcattcgg aaattttccg atgattctga 2220
atatttattg ccgctcgtta cgagtcgttg gacatatctg taatacattt cttcttctga 2280
aggatcgctg cacatttgat ctatacattg gccaggatgt tcaagtctca gatgttgcat 2340
tctggcacag cacaacttta tggcatttcc gatgtaatcg tccggcagcc ctgggggagt 2400
tctatattcg catattggga tggtaaggac aatagcagat ctcgcaacct ccagggaggc 2460
tataataacg tttttaaagg atggatttct cataaaaatc tgtcgcaaat tacactgaga 2520
atatccttta ctagcgccga ttgagagcat cgtcgtccaa ttttctaaat ggaaagaaaa 2580
caaggcgggc aagagtgttc caaacatttt cattttcggc gaatctctca aatcccatgg 2640
cgtgcaattg attgcaaaat tggcacttcc gttcacgttt gtatctccaa actctaagac 2700
acttttaatt gaaaaactac gttctagtgt ggaaagaaac ctataggcag accatagaac 2760
tatttgacac cacatatctt tttgtatgtc aaactgacca tgatcgtatg ttgctgaatg 2820
cactagggca attcgctcgc gcgactccat acattgaata attccacacg tcagctcatc 2880
ggttagcaag gtccagtagt tgaagtcatt tatttttccc cgcggctggc caaatctacc 2940
tctgggaata tccaagttgt cgaatatgat cgcaccggct ctggtcatgg tgaaggaact 3000
gtagcataaa gacgcaggta tcataggggt aatatttttt tattcactca catactaaaa 3060
gtaacgcata ttagcaccat gtatgggcta tcaattgaca tttgcgtagc actacatcac 3120
gattatgtac aacataatgg gacaacatat ggcaagtaga tgcaatttcc tcacactagt 3180
tgggtttatc tactattgaa ttttccccta tctgtgatac acttgggagc ctctacaagc 3240
atattgccat catgtacgtt tttatctact gtcttaacgc ccatgggaac ggaggcgtcg 3300
tcgtcatgta ttggacggca acataggcag caacacaaat tgcgtttagg tggggtgcat 3360
gtggactcga taccaagccc ctgcagctgg ggaacgtctg gtggagagcc gataatttga 3420
tatacgcacg ccatattact gtcgttgaag tacgccttat cttctatgtt ttcaaattta 3480
ggttcccaag tggacgtgag aagtgtttgt atctcacatg gaatggccca aggcattcca 3540
gcccaggtgc ctggtacttt aatggcaaac aaacgttttg gtagaggtat tgattctatt 3600
gcagttctgc agatatctgc agccccgagt atccacaggc tatacgatac gttatcggag 3660
gcaagcttgt taattaagtc gacggcagag tcgcagacgc ccctattgga cgtcaaaatt 3720
gtagaggtga agttttcaaa cgatggcgaa gtaacggcga cttgcgtttc caccgtcaaa 3780
tctccctata gggtagaaac taattggaaa gtagacctcg tagatgtaat ggatgaaatt 3840
tctgggaaca gtcccgccgg ggtttttaac agtaatgaga aatggcagaa acagctgtac 3900

-continued tacagagtaa ccgatggaag aacatcggtc cagctaatgt gcctgtcgtg cacgagccat 3960
tctccggaac cttactgtct tttcgacacg tctcttatag cgagggaaaa agatatcgcg 4020
ccagagttat actttacctc tgatccgcaa acggcatact gcacaataac tctgccgtcc 4080
ggcgttgttc cgagattcga atggagcctt aataatgttt cactgccgga atatttgacg 4140
gccacgaccg ttgtttcgca taccgctggc caaagtacag tgtggaagag cagcgcgaga 4200
gcaggcgagg cgtggatttc tggccgggga ggcaatatat acgaatgcac cgtcctcatc 4260
tcagacggca ctcgcgttac tacgcgaaag gagaggtgct taacaaacac atggattgcg 4320
gtggaaaacg gtgctgctca ggcgcagctg tattcactct tttctggact tgtgtcagga 4380
ttatgcggga gcatatctgc tttgtacgca acgctatgga ccgccattta tttttgagga 4440
atgctttttg gactatcgta ctgctttctt ccttcgctag ccagagcacc gccgccgtca 4500
cgtacgacta cattttaggc cgtcgcgcgc tcgacgcgct aaccataccg gcggttggcc 4560
cgtataacag atacctcact agggtatcaa gaggctgcga cgttgtcgag ctcaacccga 4620
tttctaacgt ggacgacatg atatcggcgg ccaaagaaaa agagaagggg ggccctttcg 4680
aggcctccgt cgtctggttc tacgtgatta agggcgacga cggcgaggac aagtactgtc 4740
caatctatag aaaagagtac agggaatgtg gcgacgtaca actgctatct gaatgcgccg 4800
ttcaatctgc acagatgtgg gcagtggact atgttcctag caccccttgta tcgcgaaatg 4860 gcgcgggact gactatattc tcccccactg ctgcgctctc tggccaatac ttgctgaccc 4920
tgaaaatcgg gagatttgcg caaacagctc tcgtaactct agaagttaac gatcgctgtt 4980
taaagatcgg gtcgcagctt aactttttac cgtcgaaatg ctggacaaca gaacagtatc 5040
agactggatt tcaaggcgaa cacctttatc cgatcgcaga caccaataca cgacacgcgg 5100
acgacgtata tcggggatac gaagatattc tgcagcgctg gaataatttg ctgaggaaaa 5160
agaatcctag cgcgccagac cctcgtccag atagcgtccc gcaagaaatt cccgctgtaa 5220
ccaagaaagc ggaagggcgc accccggacg cagaaagcag cgaaaagaag gcccctccag 5280
aagactcgga ggacgacatg caggcagagg cttctggaga aaatcctgcc gccctccccg 5340
aagacgacga agtccccgag gacaccgagc acgatgatcc aaactcggat cctgactatt 5400
acaatgacat gcccgccgtg atcccggtgg aggagactac taaaagttct aatgccgtct 5460
ccatgcccat attcgcggcg ttcgtagcct gcgcggtcgc gctcgtgggg ctactggttt 5520
ggagcatcgt aaaatgcgcg cgtagctaat cgagcctaga ataggtggtt tcttcctaca 5580
tgccacgcct cacgctcata atataaatca catggaatag cataccaatg cctattcatt 5640
gggacgttcg aaaagcatgg catcgctact tggaactctg gctctccttg ccgcgacgct 5700 cgcaccccttc ggcgcgatgg gaatcgtgat cactggaaat cacgtctccg ccaggattga 5760
cgacgatcac atcgtgatcg tcgcgcctcg ccccgaagct acaattcaac tgcagctatt 5820
tttcatgcct ggccagagac cccacaaacc ctactcagga accgtccgcg tcgcgtttcg 5880
gtctgatata acaaaccagt gctaccagga acttagcgag gagcgctttg aaaattgcac 5940
tcatcgatcg tcttctgttt ttgtcggctg taaagtgacc gagtacacgt tctccgcctc 6000
gaacagacta accggacctc cacacccgtt taagctcact atacgaaatc ctcgtccgaa 6060
cgacagcggg atgttctacg taattgttcg gctagacgac accaaagaac ccattgacgt 6120
cttcgcgatc caactatcgg tgtatcaatt cgcgaacacc gccgcgactc gcggactcta 6180
ttccaaggct tcgtgtcgca ccttcggatt acctaccgtc caacttgagg cctatctcag 6240
gaccgaggaa agttggcgca actggcaagc gtacgttgcc acggaggcca cgacgaccag 6300

-continued

```
cgccgaggcg acaaccccga cgcccgtcac tgcaaccagc gcctccgaac ttgaagcgga   6360
acactttacc tttccctggc tagaaaatgg cgtggatcat tacgaaccga cacccgcaaa   6420
cgaaaattca aacgttactg tccgtctcgg gacaatgagc cctacgctaa ttggggtaac   6480
cgtggctgcc gtcgtgagcg caacgatcgg cctcgtcatt gtaatttcca tcgtcaccag   6540
aaacatgtgc accccgcacc gaaaattaga cacggtctcg caagacgacg aagaacgttc   6600
ccaaactaga agggaatcgc gaaaatttgg acccatggtt gcgtgcgaaa taaacaaggg   6660
ggctgaccag gatagtgaac ttgtggaact ggttgcgatt gttaacccgt ctgcgctaag   6720
ctcgcccgac tcaataaaaa tgtgattaag tctgaatgtg gctctccaat catttcgatt   6780
ctctaatctc ccaatcctct caaaaggggc agtatcggac acggactggg aggggcgtac   6840
acgatagtta tatggtacag cagaggcctc tgaacactta ggaggagaat tcagccgggg   6900
agagcccctg ttgagtaggc ttgggagcat attgcaggat gaacatgtta gtgatagttc   6960
tcgcctcttg tcttgcgcgc ctaacttttg cgacgcgaca cgtcctcttt ttggaaggca   7020
ctcaggctgt cctcggggaa gatgatccca gaaacgttcc ggaagggact gtaatcaaat   7080
ggacaaaagt cctgcggaac gcgtgcaaga tgaaggcggc cgatgtctgc tcttcgccta   7140
actattgctt tcatgattta atttacgacg gaggaaagaa agactgcccg cccgcgggac   7200
ccctgtctgc aaacctggta attttactaa agcgcggcga aagcttaggt caattccctg   7260
gcattatgcc cagtacatga ccttatggga ctttcctact tggcagtaca tctacgtatt   7320
agtcatcgct attaccatgg tgatgcggtt ttggcagtac atcaatgggc gtggatagcg   7380
gtttgactca cggggatttc caagtctcca ccccattgac gtcaatggga gtttgttttg   7440
gcaccaaaat caacgggact ttccaaaatg tcgtaacaac tccgccccat tgacgcaaat   7500
gggcggtagg cgtgtacggt gggaggtcta tataagcaga gctcgtttag tgaaccgtca   7560
gatcgcctgg agacgccatc cacgctgttt tgacctccat agaagacacc gggcgcgccg   7620
gatctatgac aaacctgcaa gatcaaaccc aacagattgt tccgttcata cggagccttc   7680
tgatgccaac aaccggaccg gcgtccattc cggacgacac cctggagaag cacactctca   7740
ggtcagagac ctcgacctac aatttgactg tgggggacac agggtcaggg ctaattgtct   7800
ttttccctgg attccctggc tcaattgtgg gtgctcacta cacactgcag agcaatggga   7860
actacaagtt cgatcagatg ctcctgactg cccagaacct accggccagc tacaactact   7920
gcagactagt gagtcggagt ctcacagtga ggtcaagcac actccctggt ggcgtttatg   7980
cactaaacgg caccataaac gccgtgacct tccaaggaag cctgagtgaa ctgacagatg   8040
ttagctacaa tgggttgatg tctgcaacag ccaacatcaa cgacaaagtt gggaatgtcc   8100
tggtagggga aggggtcact gtcctcagcc tacccacatc atatgatctt gggtatgtga   8160
ggcttggtga ccccattccc gctatagggc ttgacccaaa aatggtagct acatgcgaca   8220
gcagtgacag gcccagagtc tacaccataa ctgcagccga tgattaccaa ttctcatcac   8280
agtaccaacc aggtggggta acaatcacac tgttctcagc caacattgat gctatcacaa   8340
gcctcagcat tgggggagag ctcgtgtttc aaacaagcgt ccaaggcctt gtactgggcg   8400
ccaccatcta ccttataggc tttgatggga ctgcggtaat caccagagct gtggccgcag   8460
ataatgggct gacggccggc accgacaatc ttatgccatt caatcttgtc attccaacca   8520
atgagataac ccagccgatc acatccatca aactggagat agtgacctcc aaaagtggtg   8580
gtcaggcagg ggatcagatg tcatggtcgg caagtgggag cctagcagtg acgatccatg   8640
```

gtggcaacta tccaggggcc ctccgtcccg tcacactagt agcctacgaa agagtggcaa 8700
caggatccgt cgttacggtc gctggggtga gtaacttcga gctgatccca aatcctgaac 8760
tagcaaagaa cctggttaca gaatacggcc gatttgaccc aggagccatg aactacacaa 8820
aattgatact gagtgagagg gaccgtcttg gcatcaagac cgtctggcca acaagggagt 8880
acactgattt tcgtgagtac ttcatggagg tggccgacct caactctccc ctgaagattg 8940
caggagcatt tggcttcaaa gacataatcc gggctataag gaggtaagat ccataattga 9000
ttgacgggag atgggggagg ctaactgaaa cacggaagga gacaataccg gaaggaaccc 9060
gcgctatgac ggcaataaaa agacagaata aaacgcacgg gtgttgggtc gtttgttcat 9120
aaacgcgggg ttcggtccca gggctggcac tctgtcgata ccccaccgag accccattgg 9180
ggccaatacg cccgcgtttc ttccttttcc ccaccccacc ccccaagttc gggtgaaggc 9240
ccagggctcg cagccaacgt cggggcggca ggccctgcca tagccactgg ccccgtgggt 9300
tagggacggg gtcccccatg gggaatggtt tatggttcgt gggggttatt attttgaagc 9360
ttgcctccga ttctagcatt acatagccgg tcagtagatc ctgccattcg gtagcgcaac 9420
cggctacatc ttcaaacagt ctcacaataa atgcatctct cgttcctgcc aatccggaac 9480
cgggcatacc actcccgcct gccgatttaa ttctcacaat tgggcgatgc cggcggggca 9540
aaacgaatgt ggatttggca aaccgacaca ggtctgctgt acggactaat atgggcacac 9600
ccacatcatt cttcagatgc tccatgcatt gttctatgag aaagatccat agggtggagg 9660
cagcgtcacg agatcgccca ggcaatcgat cgcattcgtc tagtaaagtg acgagagtta 9720
tcatgcacac acccatgccc acgccttccg aataactgga gctgtggaag atcggaaacg 9780
tctttttgac tgccggtctc gtactacttt cgcacaggtg tatacccgga cgcgtactat 9840
atattttata tcatccaacg tccgaaatta catacgtggc ggcgatggaa gtagatgttg 9900
agtcttcgaa agtaagtgcc tcgaatatgg gtattgtctg tgaaaatatc gaaagcggta 9960
cgacggttgc agaaccgtcg atgtcgccag atactagtaa caatagcttc gataacgaag 10020
acttccgtgg gcctgaatac gatgtggaga taaataccag aaaatctgct aatcttgatc 10080
gtatggaatc ttcgtgccgt gaacaacgag cggcgtgcga acttcgaaag tgttcgtgtc 10140
ctacgtctgc cgtgcgcatg caatacagta ttctttcatc tctcgctccg ggttcagagg 10200
gtcatgtata tatatgtact agatacgggg acgcggacca aaaaaaatgc atagtgaagg 10260
cagtcgttgg aggaaagaat cccgggaggg aagtggatat tttaaaaacc atctcacata 10320
aatcaattat aaaattaatc catgcctata aatggaaaaa tgttgtgtgt atggcaatgc 10380
gtgtatatcg ttatgatctt ttcacatata ttgacggagt cggccctatg ccccttcaac 10440
agatgatcta tattcaacgt ggactactag aggcgctagc atacatacat gaaaggggca 10500
tcattcaccg agacgtaaag acggagaata tattcttgga taatcacgaa aatgcagttt 10560
tgggtgactt cggtgctgca tgccaactag gagattgtat agatacgccc caatgttacg 10620
gttggagcgg aactgtggaa acaaattcgc cggaattatc tgcacttgat ccgtattgca 10680
caaaaacaga tatttggagt gccggattgg ttctatatga gatggcaatt aaaaatgtac 10740
cattgtttag taagcaggtg aaaagttcgg gatctcagct gagatccata atacggtgca 10800
tgcaagtgca tgaactggag tttccccgca acgattctac caacctctgt aaacatttca 10860
aacaatatgc ggttcgtgta cgaccgcctt ataccattcc tcgagttata agaaatgggg 10920
ggatgccaat ggatgttgaa tatgtcattt ctaaaatgct tacgtttgac caggagttca 10980
gaccttctgc taaggaaata ttgaatatgc cctatttac taaggcgccg attaacctgc 11040

```
ttaatatcac accctctgac agtgtctaac ggtatacagg cgggagcggg tcgtggcgtc  11100

atcatcacca cttgagaatt tatattttga attgttgatt gataaattaa cctgattcat  11160

tgagaactga aacgccatat tggtttcttg gatatgtcta caacaattag ttaaattgct  11220

atgttctact gcgagtaaca tttgataagt tgtaagagac gggcgactca tgtcgaagtt  11280

gacgaatata aagtacataa cgtgtttaga atacccagaa tccgaatagt ccgcgggggc  11340

gtcttctcgc gtgagtacca aatactgagt tgaacttgaa aatgctaaat ctgtgacact  11400

ctttgtgtga tgattattgt caccacttcg aagatggctt cgacattcat gatgttctgg  11460

tgtttgtttg gaatcgtaat agcgcttgtt tcgtccaagt ctgacaacaa agaaaatctg  11520

aagaattata tcacggataa gtcaaccaat attagaatac ccacgccatt atttgtatca  11580

acggaaaact cttatcccac aaaacatgta atctacgatg aaaactgtgg cttcgctgta  11640

ctcaatccta taagtgaccc caaatatgtc cttttgagcc agcttctaat gggaaggcgc  11700

aaatatgatg cgacggtcgc gtggtttgtt ctcggtaaaa tgtgtgccag attaatatat  11760

ttgcgcgaat tttataactg ctcgacaaat gagccttttg gcacatgttc tatgagctct  11820

cctggatggt gggacaggcg ctacgtctca accagtttca tttctcgcga cgaattacag  11880

ctggtttttg cagcgccgtc ccgagaatta gatggtttat atacgcgcgt agtagttgtc  11940

aacggggact ttactacggc cgatataatg tttaatgtta aagtggcatg tgccttttca  12000

aagactggaa tagaagatga tacattatgc aaaccctttc atttctttgc caatgcaaca  12060

ttgcacaatt taaccatgat tagatcggta actcttcgag cgcacgaaag ccatttaaag  12120

gaatgggtgg cacggagagg tggtaacgtc cctgcagtgc tacttgagtc taccatgtat  12180

catgcatcca atctgcctag aaatttcagg gatttctaca taaagtctcc agatgattat  12240

aagtataatc acctagatgg gccatctgta atgctcatca ctgacagacc tagtgaagat  12300

ttggatggga ggctcgttca ccaaagtgac atttttacta ctacaagtcc tataaaacag  12360

gtccggtatg aagagcatca gtcacataca aagcagtatc ctgtaaacaa aatacaagct  12420

ataatttttt tgatagggtt aggctcgttc attggaagca tattcgtagt tttggtagta  12480

tggattatac gcagatattg caatggagcg cggagtgggg gaacgccccc cagtcctcgc  12540

cggtatgtgt ataccaggct atgatcacgt gtgaaacttg ggcggacctg tatcatatgt  12600

acaccgtccc tattcgttta tagccagtac gtgttatctg cacatagagg aacatgtgtc  12660

atactgggat cgcatgcatg gtatgtgtga ctctaatatt attctgtatc ataataaaaa  12720

cacagtgcat ggtatataga ggatcgctgg taagcactac ggtagaccaa tcggctcaga  12780

ttgcattctt tggcatcgat accgttgtta atttatatgg caaagtcttg ttcatgggag  12840

atcagtattt ggaggaaata tactctggaa cgatggaaat actcaaatgg aatcaagcta  12900

accgctgcta ttctattgcg catgcaacat attacgccga ctgtcctata atcagttcta  12960

cggtattcag aggatgccgg gacgccgttg tttatactag gccccacagc agaattc     13017
```

<210> SEQ ID NO 26
<211> LENGTH: 11017
<212> TYPE: DNA
<213> ORGANISM: Artificial Sequence
<220> FEATURE:
<223> OTHER INFORMATION: Expression cassette

<400> SEQUENCE: 26

```
ggcgcgccac tggagaacgg catgaccgca aaaggcgttg tagagatcga tcccacgaac     60
```

-continued

```
tctcaggcga tcgtgtcagt cgccataaac agcgacgatc gtctccagga tctgaacggt    120
tttcttctca acgatcatca gtatatgagg aactgaacct gatatttagc cgagggaaac    180
gcaggttaaa aaccctatca agcgattgcg attttcgcgt atctagtaaa aatagatggg    240
cttcggtact agccttcgcc gccaactctg aatatgccct tcgtggacct catataacat    300
ggcattgttt gttggatgcg gggccggaat taagaagaac attcgaaata cgagcaaaaa    360
tttcggccct ggcatgtgct gcgcgagaat cggtacttcg gggagaaagt tttatcggag    420
ctttgggtag tgcagaggaa actctatctt ggttgaaaat gcatgcgacc ctgcacttga    480
ttctggttaa ccacgatcca atttttaaga cggctggcgc ggtcctagat aacctccgct    540
taaaactagc cccaatattg atgtgcagat ataacacaga aaaacgatca atggaagaca    600
tgctacggcg gtcatctccc gaagacatca ccgattccct aacaatgtgc ctgattatgt    660
tatcgcgcat tcgtcgtacc atgcgcaccg caggaaataa atatagctat atgatagatc    720
caatgaatcg tatgtctaat tacactccag gcgaatgtat gacaggtata ttgcgatata    780
ttgacgaaca tgctagaagg tgtcctgatc acatatgtaa tttgtatatc acatgtacac    840
ttatgccgat gtatgtgcac gggcgatatt tctattgtaa ttcatttttt tgttagtaaa    900
ctaccacagg ctgtccggaa atctaagtta atgaataaag tagatggtta atactcattg    960
cttagaattg gactactttt aattctcttt aatgttcgta ttaaataaaa acatctttaa   1020
taaacttcag cctcttcgct tattgtagaa attgagtatt caaaatcatg ttcaaagccg   1080
tcttcggaga gtgtactcgc cacggtggtt ggaacatcac tatgtctaca cgtcaaattt   1140
aagcacgtca ggtctgtcga ggacaagaaa tggttaacta gtgtttcaat tattcttata   1200
aacgttaagc attgtaagcc ccccggccgt ccgcagcaac aatttactag tatgccgtgg   1260
gctccgggac tatcacggat gtccaattcg cacatgcata taatttttct agggtctctc   1320
atttcgagaa atcttcgggg atccatcagc aatgcgggct gtagtcccga ttcccgtttc   1380
aaatgaaggt gctccaacac ggtcttcaaa gcaaccggca taccagcaaa cacagactgc   1440
aactccccgc tgcaatgatt ggttataaac agtaatctgt cttctggaag tatatttcgc   1500
ccgacaatcc acggcgcccc caaagttaaa aaccatccat gtgtatttgc gtcttctctg   1560
ttaaaagaat attgactggc attttcccgt tgaccgccag atatccaaag tacagcacga   1620
tgttgcacgg acgactttgc agtcaccagc cttcctttcc acccccccac caacaaaatg   1680
tttatcgtag gacccatatc cgtaataagg atgggtctgg cagcaacccc ataggcgcct   1740
cggcgtggta gttctcgagg ccttaattaa gtaccgagct cgaattggcg cgccaggtca   1800
attccctggc attatgccca gtacatgacc ttatgggact ttcctacttg gcagtacatc   1860
tacgtattag tcatcgctat taccatggtg atgcggtttt ggcagtacat caatgggcgt   1920
ggatagcggt ttgactcacg gggatttcca agtctccacc ccattgacgt caatgggagt   1980
ttgttttggc accaaaatca acgggacttt ccaaaatgtc gtaacaactc cgccccattg   2040
acgcaaatgg gcggtaggcg tgtacggtgg gaggtctata taagcagagc tcgtttagtg   2100
aaccgtcaga tcgcctggag acgccatcca cgctgttttg acctccatag aagacaccgg   2160
gcgcgccgga tccatgggcc ccagaccttc taccaagaac ccagtaccta tgatgctgac   2220
tgtccgagtc gcgctggtac tgagttgcat ctgtccggca aactccattg atggcaggcc   2280
tcttgcggct gcaggaattg tggttacagg agacaaagcc gtcaacatat acacctcatc   2340
ccagacagga tcaatcatag ttaagctcct cccgaatctg cccaaggata aggaggcatg   2400
tgcgaaagcc cccttggatg catacaacag gacattgacc actttgctca ccccccttgg   2460
```

```
tgactctatc cgtaggatac aagagtctgt gactacatct ggaggggga gacaggggcg    2520
ccttataggc gccattattg gcggtgtggc tcttggggtt gcaactgccg cacaaataac  2580
agcggccgca gctctgatac aagccaaaca aaatgctgcc aacatcctcc gacttaaaga  2640
gagcattgcc gcaaccaatg aggctgtgca tgaggtcact gacggattat cgcaactagc  2700
agtggcagtt gggaagatgc agcagtttgt taatgaccaa tttaataaaa cagctcagga  2760
attagactgc atcaaaattg cacagcaagt tggtgtagag ctcaacctgt acctaaccga  2820
attgactaca gtattcggac cacaaatcac ttcacctgct ttaaacaagc tgactattca  2880
ggcactttac aatctagctg gtggaaatat ggattactta ttgactaagt taggtgtagg  2940
gaacaatcaa ctcagctcat taatcggtag cggcttaatc accggtaacc ctattctata  3000
cgactcacag actcaactct tgggtataca ggtaactcta ccttcagtcg ggaacctaaa  3060
taatatgcgt gccacctact tggaaacctt atccgtaagc acaaccaggg gatttgcctc  3120
ggcacttgtc ccaaaagtgg tgacacaggt cggttctgtg atagaagaac ttgacacctc  3180
atactgtata gaaactgact tagatttata ttgtacaaga atagtaacgt tccctatgtc  3240
ccctggtatt tattcctgct tgagcggcaa tacgtcggcc tgtatgtact caaagaccga  3300
aggcgcactt actacaccat acatgactat caaaggttca gtcatcgcca actgcaagat  3360
gacaacatgt agatgtgtaa accccccggg tatcatatcg caaaactatg gagaagccgt  3420
gtctctaata gataaacaat catgcaatgt tttatcctta ggcgggataa ctttaaggct  3480
cagtggggaa ttcgatgtaa cttatcagaa gaatatctca atacaagatt ctcaagtaat  3540
aataacaggc aatcttgata tctcaactga gcttgggaat gtcaacaact cgatcagtaa  3600
tgctttgaat aagttagagg aaagcaacag aaaactagac aaagtcaatg tcaaactgac  3660
tagcacatct gctctcatta cctatatcgt tttgactatc atatctcttg tttttggtat  3720
acttagcccg attctagcat gctacctaat gtacaagcaa aaggcgcaac aaaagacctt  3780
attatggctt gggaataata ctctagatca gatgagagcc actacaaaaa tgtgaggatc  3840
tctcgaggaa ttctagatcc cacgtcacta ttgtatactc tatattatac tctatgttat  3900
actctgtaat cctactcaat aaacgtgtca cgcctgtgaa accgtactaa gtctcccgtg  3960
tcttcttatc accatcaggt gacatcctcg cccaggctgt caatcatgcc ggtatcgatt  4020
ccagtagcac cggccccacg ctgacaaccc actcttgcag cgttagcagc gcccctctta  4080
acaagccgac ccccaccagc gtcgcggtta ctaacactcc tctcccctcg aggatacatc  4140
caaagaggtt gagtattctc tctacacttc ttgttaaatg gaaagtgcat ttgcttgttc  4200
ttacaatcgg cccgagtctc gttcacagcg cctcgttcac acttaaacca caaatagtct  4260
acaggctata tgggagccag actgaaactc acatatgact aatattcggg ggtgttagtc  4320
acgtgtagcc cattgtgtgc atataacgat gttggacgcg tccttattcg cggtgtactt  4380
gatactatgg cagcgagcat gggatattca tcctcgtcat cgttaacatc tctacgggtt  4440
cagaatgttt ggcatgtcgt cgatcctttg cccatcgttg caaattacaa gtccgatcgc  4500
catgaccgcg ataagcctgt accatgtggc attagggtga catctcgatc atacattata  4560
agaccaacgt gcgagtcttc caaagacctg cacgccttct tcttcggatt gtcaacgggt  4620
tcttcagaat ctatgcccat atctggcgtt gagaccattg tgcgtttaat gaacaataaa  4680
gcggcatgcc atggaaagga gggctgcaga tctccatttt ctcacgccac tatcctggac  4740
gctgtagacg ataattatac catgaatata gagggggtat gtttccactg ccactgtgat  4800
```

-continued

```
gataagtttt ctccagattg ttggatatct gcattttctg ctgccgaaca aacttcatcg   4860
ctatgcaaag agatgcgtgt gtacacgcgc cgttgagtat acgggaaact aaatgttcat   4920
agaggtcttt gggctatatg ttattaaata aaataattga ccagtgaaca atttgtttaa   4980
tgttagttta ttcaatgcat tggttgcaaa tattcattac ttctccaatc ccaggtcatt   5040
ctttagcgag atgatgttat gacattgctg tgaaaattac tacaggatat atttttaaga   5100
tgcaggagta acaatgtgca tagtaggcgt agttatcgca gacgtgcaac gcttcgcatt   5160
tgagttaccg aagtgcccaa cagtgctgcg gttatggttt atgcgcacag aatccatgca   5220
tgtcctaatt gaaccatccg atttttcttt taatcgcgat cgttgtttgg gcaactgcgt   5280
tatttcagat ctaaaaaatt taccctttat gaccatcaca tctctctggc tcataccccg   5340
cttggataag atatcatgta gattccgccc taagaaatgc aaactaacat tattgtcggt   5400
tccatataca cttccatctt gtccttcgaa aataacaaac tcgcgcaata gaccgtccgt   5460
acatgcatgg ccgatgtgtg tcaacatcat tggtctgcta gatcccgatg ggacgaatcg   5520
tacagtcgtc gctccagcat tggcaaaaat ccccagatac cctccatgcg gcaaatctaa   5580
attgcgaccc cgaagagact gcaccaaagt cttatcgacg cacgctgatt tttttgaaca   5640
gcgggagccc attatcttca gtggagcgta gacgggcgag gctaattatg tgacatagca   5700
acactgcatg tatgttttta taaatcaata agagtacata atttattacg tatcatttcc   5760
gtttgtaata tactgtatac atcatccaca ctattagtca gcactagcgc gcgggcgcac   5820
gttacaatag cagcgtgccc gttatctata ttgtccgata tttacacata acatttcatc   5880
gacatgatta aatacctaag tactgcacac agatgtttaa tgtatatcgt catataaatt   5940
atatcgctag gacagaccca aacgaccttt atcccaaaca gtcagatcct cttctcaagt   6000
gtcgatttct gttatggaat atgcataccc tggcccagaa attgcacgca cgagcgtagt   6060
gaatgcgtca ttggttttac atttaaaggc taaatgcaca aattctttag acgacagcac   6120
atcgttaaat agcatctcta gcgttcttat gaatgctaag cattggagtc ctcctggtcg   6180
gccacaataa cagctgagta tcatacccctg agctccgggg ttgtcgcaca tagcggattc   6240
gtataaacat aggattttcc gcgaatccat cagttgcaaa aatctgttag gctccatcaa   6300
caacgctgga tttacttcag atccacgcgt aaagtaatgg tgctcgaata ccgtttttag   6360
agttgtcggc atttcaagga acaaagaatt catttcttca ttgcaacgac gcgccagaaa   6420
tcccaagacc tctttgggta gtatgttctt gcctataaaa cacggcgttc caagtgccag   6480
gaaccacgca tgtgttactg ttggggcgta ttcagaaata aagcggggtt tatgcggctt   6540
ttgaagctcg gatatccaaa gtatcgcttg ctgatgaacg agcgatgtag ctgttacaaa   6600
acctcctttc catcctccag tcaacataat atttatcggc ctacctatgt ccgtaataag   6660
tattggtcgg gcaattattc cgtatgaggt cttgcaggaa taagctctta gggacagcca   6720
gcttggatat ggtgcgaaac agaccttctc ggcttcagaa tgtcgctccg cagtctcttc   6780
gtgtcggtgc atcttagatc caccatcaat gtgtgcagca ttgactcccg cccgtcgaat   6840
attccttttg ttacgatgca gtaatgagca cgatcatggg cggggcgatg acgttctatt   6900
tgcatgtctg cgaacaattt gcgtcagtca tacagctatg gagtgggcca tttctggccg   6960
tcaacttaaa aacgcgaacc gcagacatat gtatttgcat gcaaagacgt atcttcgtat   7020
ttctgggcat cttcaaatgc tctggccaat atggcaatga atttggattc gtttgacgcc   7080
gatggtatgc agtgcaaatg tgccaatagc ccacatccga aaaagttatt tgtcatacaa   7140
gcaggtgtta agtagcaatc acataaaggc accagacgcc tcatggcatc ataatgaata   7200
```

gctccttctc cccactggaa ccactgacaa aatctgcgag tatattccgc aaaccacatt 7260
ttatttctca tagaaactac cctaaatcct tttaacggga agaagaatcc tagatagtgc 7320
ttgaagtcat gactgttact gctgcaataa cactgtatat tatttataaa ttccgtttgt 7380
ctaggtatct gatgtaggca ttccgatccc tttactattg cgtcttcacg accaaatggg 7440
aatgcgccaa aatccccaca cctcatcacc ctggaggcag attgtgtatt attaatatcc 7500
gccgattgaa gcacaaaacg gtacggtact gttcctaatt ctggtataga ttctatggtc 7560
aaaagtctgc atatccccga cattgccatg agatcacaca gtccaagtag catgtttatt 7620
gagtcactca gactgtcaac gtccctcgcc gcaccaccaa tcgaaaataa agtatctacg 7680
caagttatag ctccgcattt tctatcgcta gcagcaatcg cgacgcaaaa cataaaggcc 7740
atgttgggat ttgaactctc tggggggctt gttatcttct gcaccgtcgc agtcgcagtt 7800
ttccgaaatt tatgtctaat atattttccg gccgtgctcc aatcggccga aaagaatctg 7860
cgtattacca gactcattga cgggccgata aagaccataa aacaaaattc ctgtgcactc 7920
cctcctccag ttttgccatc gtccaagtcc cgtaactttt tttgcgtttc gaggagcaag 7980
cgttcgttat ccctacccac acttgttttc caccgttttc ttattataag cggttgtatc 8040
gccaacgcgt caccgcaggt tgtcacatac agtgatggca tacttgaacg tgcaacaacg 8100
cgctcgcttt gcaaatctaa gtcattgacc atcaaatcgc gttgagagga tagccaggca 8160
tcttttttcc tagtatggtg acggtgcagc caccccaact cagttcttgt aaaaaaagct 8220
attggcggga atttatgttc tgaggtgcat tctatattta tgagtccatc aaatgccatt 8280
aaccagattc gtatttttttc gctcgacccg gcatcactat ggatacaata cctttctatg 8340
gcccatttca gctctcgaac caaccacacg gacaattgac taacataagt atgatcttta 8400
tcacagtcgc acccatctga gttatattta tggcatccga gcgctcttac tgtacggtcg 8460
gatacaccca tggtttttcc tttatatagt cgggttatag tctgtcgggt ttggcggtag 8520
cacggagtag tttgattttt aagaatcgaa aaccggcttg gagagaccac tgtcgaatat 8580
ttgtccgtat actctacacg tgagtgttgt ccattcctag gtatattcat ctgttcggat 8640
accttcaatt gctgttcagg cataacctta aagcatatgt tatgttgtac atcaaaactt 8700
ggtgagttat gttcgattgc cgcgcataaa gaatcgtaca tgagcgtttc tgctaacata 8760
ctatctatat tctcacacgc ccctgcatat actgttccta ttccaaattc acgttttgcc 8820
ccatcggcta tctgctccca aaaagttgta atataggtgc cgctgggtgc gaaattttca 8880
tcagttgtat tcctgataaa ctgaatcact ttacataatt tttgccacat atctgcgtgc 8940
agccatagta tcgaacccgt gggctcggag acgacagtgc gtacaatggg tattttacct 9000
ttccccaaca aaataatggt atacaagtta ggtccgtacc tagaccttaa tgtttccaat 9060
tcttctgaat cactgcactc tcgtagggga gtaacggtaa taatttcgtc tctgagcccc 9120
gttttgcgtt gaaaactaat cacattagat aatgtgcaat cggtttcttt tatccggata 9180
catctaagta ttatgacatc ggtggtcatt gtttccatca acgaccatct tttacgatcg 9240
cccatactac tcatggacgt tgtcggtgtt gaaaaatcac cagaattgca acggatctct 9300
gggtaccatg ctgctgatgg aattggcggt tttaattgtt gtttcagtct attattgcta 9360
tctttggcgg ggttgaataa tgtgggggga gagtgattgc aggaatccga atgggtcaat 9420
aaaacgaccg tgctccgttc tgccggcgcc gatccgattg aagctatata cttcgcttct 9480
ctccccactt ttccaatttg atccggaaat aaaacggccc cggacaacag tatcgtacga 9540

```
tccggatccg gatcctgctt gcctacagaa gaatcaacat ctcgccccaa tattctggtc   9600

aaaactggct cgctcatggc aacgcggacg tttcccccgg tggccagtct taatggttaa   9660

tgttcttttc ggcaatctta tacatcagcg ggttgcgtga atactggtca cagttcagtc   9720

atttactaca caccagcaat acgacgacgg acagtaccgt cccgacgaac gcgacgccca   9780

aaattgctat cgcgaccgcg tccgaggcga tgtcgtacgg gcggtgcggg gttggatcct   9840

cggcaaagag atcctcgtaa ttcggcggtg ggagcggagg gtaaagacgc gggtggggat   9900

ctccctccgg accgcgcgcc gggcgcggtt cgaaaatgct ttccgcctcg ctcagtgtca   9960

acgccaagta ttcgggcggg ctgggggccg gaatatctcc cgcgacttct tctatcggcg  10020

cggaattgga gtcgcggtcg tggcgcgctt ctagcgtcgt caacggaagt ccattttcgg  10080

ggtctcccgg tgggcgttca gcgtccatcg tcgtatatgc tctaacacac gtctcgctat  10140

attaaaaaaa agaagagtat cggtcagtgt cgagtgtcgc cgacaatgtc gcgagttctc  10200

ggcgatttaa tttttggaac tgctccctat gaatcccgta actgtagcgc ccgcgcagaa  10260

agccgccatc agaccaacta cgtgtctgtt cgatgtttgc ccgccgatcg ctttaccgat  10320

taaggttccg gcgagaaatg acatgctcga tccaagaaca aagtttttcg cggtaaacaa  10380

caacatagtt accgtgcgag atggagaaac cacatctccc gaattagtag aggaaagccc  10440

gcgctgtcgg tttggggaca tatcgatctt ttttgtgttt ttcctaggac ccttttgcca  10500

gatcgtacaa agtcgcgtct tatgagcgga cgttcttact gcagctcggt aggagtgggg  10560

cagggttaga tttcgtcggc gtttcggccc ccgtatgcgc cgcgccaccc tcttcgccga  10620

gctctttatg cgcggtgggg gtgagcgctt ccggagttgc gatctccgat ctcgagccgc  10680

agcccggcgg tgtctctttc agtggagcgt tagcgccatc atgtggttcg tggcggtgga  10740

aaggctatta tgtgttaggg gagagaccac gtgatcggca tgcaaatgag caaggcgaac  10800

gcgtcagcgt tcgcactgcg aaccaataat atatatatta tactattggc tttaggtgcg  10860

aacgtccggc tagtccaata gcggggtcgc gtttcgtacc acgtgttata gaccgcccta  10920

aactcgcact cgggggtccg gccgcgccca gacagggcgg agacgtgcca caggggcttt  10980

aaaacaccgc ttcgggcacc gttcatctcg gcgcgcc                           11017
```

<210> SEQ ID NO 27
<211> LENGTH: 11665
<212> TYPE: DNA
<213> ORGANISM: Artificial Sequence
<220> FEATURE:
<223> OTHER INFORMATION: Expression cassette

<400> SEQUENCE: 27

```
ggcgcgccac tggagaacgg catgaccgca aaaggcgttg tagagatcga tcccacgaac     60

tctcaggcga tcgtgtcagt cgccataaac agcgacgatc gtctccagga tctgaacggt    120

tttcttctca acgatcatca gtatatgagg aactgaacct gatatttagc cgagggaaac    180

gcaggttaaa aaccctatca agcgattgcg attttcgcgt atctagtaaa aatagatggg    240

cttcggtact agccttcgcc gccaactctg aatatgccct tcgtggacct catataacat    300

ggcattgttt gttggatgcg gggccggaat taagaagaac attcgaaata cgagcaaaaa    360

tttcggccct ggcatgtgct gcgcgagaat cggtacttcg gggagaaagt tttatcggag    420

ctttgggtag tgcagaggaa actctatctt ggttgaaaat gcatgcgacc ctgcacttga    480

ttctggttaa ccacgatcca atttttaaga cggctggcgc ggtcctagat aacctccgct    540

taaaactagc cccaatattg atgtgcagat ataacacaga aaaacgatca atggaagaca    600
```

```
tgctacggcg gtcatctccc gaagacatca ccgattccct aacaatgtgc ctgattatgt    660
tatcgcgcat tcgtcgtacc atgcgcaccg caggaaataa atatagctat atgatagatc    720
caatgaatcg tatgtctaat tacactccag gcgaatgtat gacaggtata ttgcgatata    780
ttgacgaaca tgctagaagg tgtcctgatc acatatgtaa tttgtatatc acatgtacac    840
ttatgccgat gtatgtgcac gggcgatatt tctattgtaa ttcatttttt tgttagtaaa    900
ctaccacagg ctgtccggaa atctaagtta atgaataaag tagatggtta atactcattg    960
cttagaattg gactactttt aattctcttt aatgttcgta ttaaataaaa acatctttaa   1020
taaacttcag cctcttcgct tattgtagaa attgagtatt caaaatcatg ttcaaagccg   1080
tcttcggaga gtgtactcgc cacggtggtt ggaacatcac tatgtctaca cgtcaaattt   1140
aagcacgtca ggtctgtcga ggacaagaaa tggttaacta gtgtttcaat tattcttata   1200
aacgttaagc attgtaagcc ccccggccgt ccgcagcaac aatttactag tatgccgtgg   1260
gctccgggac tatcacggat gtccaattcg cacatgcata taatttttct agggtctctc   1320
atttcgagaa atcttcgggg atccatcagc aatgcgggct gtagtcccga ttcccgtttc   1380
aaatgaaggt gctccaacac ggtcttcaaa gcaaccggca taccagcaaa cacagactgc   1440
aactccccgc tgcaatgatt ggttataaac agtaatctgt cttctggaag tatatttcgc   1500
ccgacaatcc acggcgcccc caaagttaaa aaccatccat gtgtatttgc gtcttctctg   1560
ttaaaagaat attgactggc attttcccgt tgaccgccag atatccaaag tacagcacga   1620
tgttgcacgg acgactttgc agtcaccagc cttcctttcc acccccccac caacaaaatg   1680
tttatcgtag gacccatatc cgtaataagg atgggtctgg cagcaacccc ataggcgcct   1740
cggcgtggta gttctcgagg ccttaagctt aaggatcccc caactccgcc cgttttatga   1800
ctagaaccaa tagtttttaa tgccaaatgc actgaaatcc cctaatttgc aaagccaaac   1860
gcccccctatg tgagtaatac ggggactttt tacccaattt cccacgcgga aagcccccta   1920
atacactcat atggcatatg aatcagcacg gtcatgcact ctaatggcgg cccataggga   1980
ctttccacat agggggcgtt caccatttcc cagcataggg gtggtgactc aatggccttt   2040
acccaagtac attgggtcaa tgggaggtaa gccaatgggt ttttcccatt actggcaagc   2100
acactgagtc aaatgggact ttccactggg ttttgcccaa gtacattggg tcaatgggag   2160
gtgagccaat gggaaaaacc cattgctgcc aagtacactg actcaatagg gactttccaa   2220
tgggtttttc cattgttggc aagcatataa ggtcaatgtg ggtgagtcaa tagggacttt   2280
ccattgtatt ctgcccagta cataaggtca ataggggtg aatcaacagg aaagtcccat   2340
tggagccaag tacactgcgt caatagggac tttccattgg gttttgccca gtacataagg   2400
tcaatagggg atgagtcaat gggaaaaacc cattggagcc aagtacactg actcaatagg   2460
gactttccat tgggttttgc ccagtacata aggtcaatag ggggtgagtc aacaggaaag   2520
ttccattgga gccaagtaca ttgagtcaat agggactttc caatgggttt tgcccagtac   2580
ataaggtcaa tgggaggtaa gccaatgggt ttttcccatt actggcacgt atactgagtc   2640
attagggact ttccaatggg ttttgcccag tacataaggt caataggggt gaatcaacag   2700
gaaagtccca ttggagccaa gtacactgag tcaataggga ctttccattg ggttttgccc   2760
agtacaaaag gtcaataggg ggtgagtcaa tgggtttttc ccattattgg cacgtacata   2820
aggtcaatag ggtgagtca ttgggttttt ccagccaatt taattaaaac gccatgtact   2880
ttcccaccat tgacgtcaat gggctattga aactaatgca acgtgacctt taaacggtac   2940
```

-continued

```
tttcccatag ctgattaatg ggaaagtacc gttctcgagc caatacacgt caatgggaag   3000
tgaaagggca gccaaaacgt aacaccgccc cggttttccc ctggaaattc catattggca   3060
cgcattctat tggctgagct gcgttctacg tgggtataag aggcgcgacc agcgtcggta   3120
ccgtcgcagt cttcggtctg accaccgtag aacgcagagc tcctcgctgc aggcggccgc   3180
tctagaactc gtcgatcgca gcgatgacaa acctgcaaga tcaaacccaa cagattgttc   3240
cgttcatacg gagccttctg atgccaacaa ccggaccggc gtccattccg gacgacaccc   3300
tggagaagca cactctcagg tcagagacct cgacctacaa tttgactgtg ggggacacag   3360
ggtcagggct aattgtcttt ttccctggat tccctggctc aattgtgggt gctcactaca   3420
cactgcagag caatgggaac tacaagttcg atcagatgct cctgactgcc cagaacctac   3480
cggccagcta caactactgc agactagtga gtcggagtct cacagtgagg tcaagcacac   3540
tccctggtgg cgtttatgca ctaaacggca ccataaacgc cgtgaccttc caaggaagcc   3600
tgagtgaact gacagatgtt agctacaatg ggttgatgtc tgcaacagcc aacatcaacg   3660
acaaaattgg gaatgtcctg gtaggggaag gggtcactgt cctcagccta cccacatcat   3720
atgatcttgg gtatgtgagg cttggtgacc ccattcccgc tatagggctt gacccaaaaa   3780
tggtagctac atgcgacagc agtgacaggc ccagagtcta caccataact gcagccgatg   3840
attaccaatt ctcatcacag taccaaccag gtggggtaac aatcacactg ttctcagcca   3900
acattgatgc tatcacaagc ctcagcattg gggagagct cgtgtttcaa acaagcgtcc   3960
aaggccttgt actgggcgcc accatctacc ttataggctt tgatgggact gcggtaatca   4020
ccagagctgt ggccgcagat aatgggctga cggccggcac cgacaatctt atgccattca   4080
atcttgtcat tccaaccaat gagataaccc agccaatcac atccatcaaa ctggagatag   4140
tgacctccaa aagtggtggt caggcagggg atcagatgtc atggtcggca agtgggagcc   4200
tagcagtgac gatccatggt ggcaactatc caggggccct ccgtcccgtc acactagtag   4260
cctacgaaag agtggcaaca ggatccgtcg ttacggtcgc tggggtgagt aacttcgagc   4320
tgattccaaa tcctgaacta gcaaagaacc tggttacaga atacggccga tttgacccag   4380
gagccatgaa ctacacaaaa ttgatactga gtgagaggga ccgtcttggc atcaagaccg   4440
tctggccaac aagggagtac actgattttc gtgagtactt catggaggtg gccgacctca   4500
actctcccct gaagattgca ggagcatttg gcttcaaaga cataatccgg gctataagga   4560
ggtagatcca gacatgataa gatacattga tgagtttgga caaaccacaa ctagaatgca   4620
gtgaaaaaaa tgctttattt gtgaaatttg tgatgctatt gctttatttg taaccattat   4680
aagctgcaat aaacaagtta acaacaacaa ttgcattcat tttatgtttc aggttcaggg   4740
ggaggtgtgg gaggtttttt cggatcctct agagtcgagg atacatccaa agaggttgag   4800
tattctctct acacttcttg ttaaatggaa agtgcatttg cttgttctta caatcggccc   4860
gagtctcgtt cacagcgcct cgttcacact taaaccacaa atagtctaca ggctatatgg   4920
gagccagact gaaactcaca tatgactaat attcgggggt gttagtcacg tgtagcccat   4980
tgtgtgcata taacgatgtt ggacgcgtcc ttattcgcgg tgtacttgat actatggcag   5040
cgagcatggg atattcatcc tcgtcatcgt taacatctct acgggttcag aatgtttggc   5100
atgtcgtcga tcctttgccc atcgttgcaa attacaagtc cgatcgccat gaccgcgata   5160
agcctgtacc atgtggcatt agggtgacat ctcgatcata cattataaga ccaacgtgcg   5220
agtcttccaa agacctgcac gccttcttct tcggattgtc aacgggttct tcagaatcta   5280
tgcccatatc tggcgttgag accattgtgc gtttaatgaa caataaagcg gcatgccatg   5340
```

-continued

```
gaaaggaggg ctgcagatct ccattttctc acgccactat cctggacgct gtagacgata   5400
attataccat gaatatagag gggtatgtt tccactgcca ctgtgatgat aagttttctc    5460
cagattgttg gatatctgca ttttctgctg ccgaacaaac ttcatcgcta tgcaaagaga   5520
tgcgtgtgta cacgcgccgg tggagtatac gggaaactaa atgttcatag aggtctttgg   5580
gctatatgtt attaaataaa ataattgacc agtgaacaat ttgtttaatg ttagtttatt   5640
caatgcattg gttgcaaata ttcattactt ctccaatccc aggtcattct ttagcgagat   5700
gatgttatga cattgctgtg aaaattacta caggatatat ttttaagatg caggagtaac   5760
aatgtgcata gtaggcgtag ttatcgcaga cgtgcaacgc ttcgcatttg agttaccgaa   5820
gtgcccaaca gtgctgcggt tatggtttat gcgcacagaa tccatgcatg tcctaattga   5880
accatccgat ttttctttta atcgcgatcg atgtttgggc aactgcgtta tttcagatct   5940
aaaaaattta ccctttatga ccatcacatc tctctggctc ataccccgct tggataagat   6000
atcatgtaga ttccgcccta agaaatgcaa actaacatta ttgtcggttc catatacact   6060
tccatcttgt ccttcgaaaa taacaaactc gcgcaataga ccgtccgtac atgcatggcc   6120
gatgtgtgtc aacatcattg gtctgctaga tcccgatggg acgaatcgta cagtcgtcgc   6180
tccagcattg gcaaaaatcc ccagataccc tccatgcggc aaatctaaat tgcgaccccg   6240
aagagactgc accaaagtct tatcgacgca cgctgatttt tttgaacagc gggagcccat   6300
tatcttcagt ggagcgtaga cgggcgaggc taattatgtg acatagcaac actgcatgta   6360
tgtttttata aatcaataag agtacataat ttattacgta tcatttccgt ttgtaatata   6420
ctgtatacat catccacact attagtcagc actagcgcgc gggcgcacgt tacaatagca   6480
gcgtgcccgt tatctatatt gtccgatatt tacacataac atttcatcga catgattaaa   6540
tacctaagta ctgcacacag atgtttaatg tatatcgtca tataaattat atcgctagga   6600
cagacccaaa cgacctttat cccaaacagt cagatcctct tctcaagtgt cgatttctgt   6660
tatggaatat gcataccctg gcccagaaat tgcacgcacg agcgtagtga atgcgtcatt   6720
ggttttacat ttaaaggcta aatgcacaaa ttctttagac gacagcacat cgttaaatag   6780
catctctagc gttcttatga atgctaagca ttggagtcct cctggtcggc cacaataaca   6840
gctgagtatc ataccctgag ctccggggtt gtcgcacata gcggattcgt ataaacatag   6900
gattttccgc gaatccatca gttgcaaaaa tctgttaggc tccatcaaca acgctggatt   6960
tacttcagat ccacgcgtaa agtaatggtg ctcgaatacc gtttttagag ttgtcggcat   7020
ttcaaggaac aaagaattca tttcttcatt gcaacgacgc gccagaaatc ccaagacctc   7080
tttgggtagt atgttcttgc ctataaaaca cggcgttcca agtgccagga accacgcatg   7140
tgttactgtt ggggcgtatt cagaaataaa gcggggttta tgcggctttt gaagctcgga   7200
tatccaaagt atcgcttgct gatgaacgag cgatgtagct gttacaaaac ctcctttcca   7260
tcctccagtc aacataatat ttatcggcct acctatgtcc gtaataagta ttggtcgggc   7320
aattattccg tatgaggtct tgcaggaata agctcttagg gacagccagc ttggatatgg   7380
tgcgaaacag accttctcgg cttcagaatg tcgctccgca gtctcttcgt gtcggtgcat   7440
cttagatcca ccatcaatgt gtgcagcatt gactcccgcc cgtcgaatat tccttttgtt   7500
acgatgcagt aatgagcacg atcatgggcg gggcgatgac gttctatttg catgtctgcg   7560
aacaatttgc gtcagtcata cagctatgga gtgggccatt tctggccgtc aacttaaaaa   7620
cgcgaaccgc agacatatgt atttgcatgc aaagacgtat cttcgtattt ctgggcatct   7680
```

```
tcaaatgctc tggccaatat ggcaatgaat ttggattcgt ttgacgccga tggtatgcag   7740
tgcaaatgtg ccaatagccc acatccgaaa aagttatttg tcatacaagc aggtgttaag   7800
tagcaatcac ataaaggcac cagacgcctc atggcatcat aatgaatagc tccttctccc   7860
cactggaacc actgacaaaa tctgcgagta tattccgcaa accacatttt atttctcata   7920
gaaactaccc taaatccttt taacgggaag aagaatccta gatagtgctt gaagtcatga   7980
ctgttactgc tgcaataaca ctgtatatta tttataaatt ccgtttgtct aggtatctga   8040
tgtaggcatt ccgatccctt tactattgcg tcttcacgac caaatgggaa tgcgccaaaa   8100
tccccacacc tcatcaccct ggaggcagat tgtgtattat taatatccgc cgattgaagc   8160
acaaaacggt acggtactgt tcctaattct ggtatagatt ctatggtcaa aagtctgcat   8220
atccccgaca ttgccatgag atcacacagt ccaagtagca tgtttattga gtcactcaga   8280
ctgtcaacgt ccctcgccgc accaccaatc gaaaataaag tatctacgca agttatagct   8340
ccgcattttc tatcgctagc agcaatcgcg acgcaaaaca taaaggccat gttgggattt   8400
gaactctctg gggggcttgt tatcttctgc accgtcgcag tcgcagtttt ccgaaattta   8460
tgtctaatat attttccggc cgtgctccaa tcggccgaaa agaatctgcg tattaccaga   8520
ctcattgacg ggccgataaa gaccataaaa caaaattcct gtgcactccc tcctccagtt   8580
ttgccatcgt ccaagtcccg taactttttt tgcgtttcga ggagcaagcg ttcgttatcc   8640
ctacccacac ttgttttcca ccgttttctt attataagcg gttgtatcgc caacgcgtca   8700
ccgcaggttg tcacatacag tgatggcata cttgaacgtg caacaacgcg ctcgctttgc   8760
aaatctaagt cattgaccat caaatcgcgt tgagaggata gccaggcatc tttttcccta   8820
gtatggtgac ggtgcagcca ccccaactca gttcttgtaa aaaaagctat tggcgggaat   8880
ttatgttctg aggtgcattc tatatttatg agtccatcaa atgccattaa ccagattcgt   8940
atttttcgc tcgacccggc atcactatgg atacaatacc tttctatggc ccatttcagc   9000
tctcgaacca accacacgga caattgacta acataagtat gatctttatc acagtcgcac   9060
ccatctgagt tatatttatg gcatccgagc gctcttactg tacggtcgga tacacccatg   9120
gtttttcctt tatatagtcg ggttatagtc tgtcgggttt ggcggtagca cggagtagtt   9180
tgatttttaa gaatcgaaaa ccggcttgga gagaccactg tcgaatattt gtccgtatac   9240
tctacacgtg agtgttgtcc attcctaggt atattcatct gttcggatac cttcaattgc   9300
tgttcaggca taaccttaaa gcatatgtta tgttgtacat caaaacttgg tgagttatgt   9360
tcgattgccg cgcataaaga atcgtacatg agcgtttctg ctaacatact atctatattc   9420
tcacacgccc ctgcatatac tgttcctatt ccaaattcac gttttgcccc atcggctatc   9480
tgctcccaaa aagttgtaat ataggtgccg ctgggtgcga aattttcatc agttgtattc   9540
ctgataaact gaatcacttt acataatttt tgccacatat ctgcgtgcag ccatagtatc   9600
gaacccgtgg gctcggagac gacagtgcgt acaatgggta ttttaccttt ccccaacaaa   9660
ataatggtat acaagttagg tccgtaccta gaccttaatg tttccaattc ttctgaatca   9720
ctgcactctc gtaggggagt aacggtaata atttcgtctc tgagccccgt tttgcgttga   9780
aaactaatca cattagataa tgtgcaatcg gtttctttta tccggataca tctaagtatt   9840
atgacatcgg tggtcattgt ttccatcaac gaccatcttt tacgatcgcc catactactc   9900
atggacgttg tcggtgttga aaaatcacca gaattgcaac ggatctctgg gtaccatgct   9960
gctgatggaa ttggcggttt taattgttgt ttcagtctat tattgctatc tttggcgggg  10020
ttgaataatg tggggggaga gtgattgcag gaatccgaat gggtcaataa aacgaccgtg  10080
```

ctccgttctg ccggcgccga tccgattgaa gctatatact tcgcttctct ccccactttt 10140
ccaatttgat ccggaaataa aacggccccg gacaacagta tcgtacgatc cggatccgga 10200
tcctgcttgc ctacagaaga atcaacatct cgccccaata ttctggtcaa aactggctcg 10260
ctcatggcaa cgcggacgtt tcccccggtg gccagtctta atggttaatg ttcttttcgg 10320
caatcttata catcagcggg ttgcgtgaat actggtcaca gttcagtcat ttactacaca 10380
ccagcaatac gacgacggac agtaccgtcc cgacgaacgc gacgcccaaa attgctatcg 10440
cgaccgcgtc cgaggcgatg tcgtacgggc ggtgcggggt tggatcctcg gcaaagagat 10500
cctcgtaatt cggcggtggg agcggagggt aaagacgcgg gtggggatct ccctccggac 10560
cgcgcgccgg gcgcggttcg aaaatgcttt ccgcctcgct cagtgtcaac gccaagtatt 10620
cgggcgggct gggggccgga atatctcccg cgacttcttc tatcggcgcg gaattggagt 10680
cgcggtcgtg gcgcgcttct agcgtcgtca acggaagtcc attttcgggg tctcccggtg 10740
ggcgttcagc gtccatcgtc gtatatgctc taacacacgt ctcgctatat taaaaaaaag 10800
aagagtatcg gtcagtgtcg agtgtcgccg acaatgtcgc gagttctcgg cgatttaatt 10860
tttggaactg ctccctatga atcccgtaac tgtagcgccc gcgcagaaag ccgccatcag 10920
accaactacg tgtctgttcg atgtttgccc gccgatcgct ttaccgatta aggttccggc 10980
gagaaatgac atgctcgatc caagaacaaa gtttttcgcg gtaaacaaca acatagttac 11040
cgtgcgagat ggagaaacca catctcccga attagtagag gaaagcccgc gctgtcggtt 11100
tggggacata tcgatctttt ttgtgttttt cctaggaccc ttttgccaga tcgtacaaag 11160
tcgcgtctta tgagcggacg ttcttactgc agctcggtag gagtggggca gggttagatt 11220
tcgtcggcgt ttcggccccc gtatgcgccg cgccaccctc ttcgccgagc tctttatgcg 11280
cggtgggggt gagcgcttcc ggagttgcga tctccgatct cgagccgcag cccggcggtg 11340
tctctttcag tggagcgtta gcgccatcat gtggttcgtg gcggtggaaa ggctattatg 11400
tgttagggga gagaccacgt gatcggcatg caaatgagca aggcgaacgc gtcagcgttc 11460
gcactgcgaa ccaataatat atatattata ctattggctt taggtgcgaa cgtccggcta 11520
gtccaatagc ggggtcgcgt ttcgtaccac gtgttataga ccgccctaaa ctcgcactcg 11580
ggggtccggc cgcgcccaga cagggcggag acgtgccaca ggggctttaa aacaccgctt 11640
cgggcaccgt tcatctcggc gcgcc 11665

<210> SEQ ID NO 28
<211> LENGTH: 13253
<212> TYPE: DNA
<213> ORGANISM: Artificial Sequence
<220> FEATURE:
<223> OTHER INFORMATION: Expression cassette

<400> SEQUENCE: 28
aattccagac taaatgcccc ggcccaattt gtcaagtgtg cagtcacgga ggcgtcgacc 60
gtgtccccgg cattaaacag gaaagcgtta aagtttttga atgttaggtc acaggtacaa 120
acataaatgt ttgtacaaac aggtaacagg tacaaacata aatgccccgg cataaatgtc 180
ccttacggcg gatcgaaacg acattaggca tactcgggta ccattttgca ttccgatcag 240
cacggatgaa attaggcagg aatgcggttt atattatgcg gcattggaca aacgatatgg 300
cattgattgg cagtttatga atgtcttcat gttgggcgta aacggattcc tattggttca 360
gaagacaacg acgatatatt tagagagaaa aagctaccca gcataggata aacacacatt 420

-continued

```
gagcattgag agacataggt atcggtatgg atgggaaaac tacacacgtg aacaccaaac    480
gacttatata ctcgagcggt gatactactg agcaagaatg cactgcatct gagccactga    540
atgaagactg tgatgaaaat gtgaccatcg atggaattgg agaagaatat gcgcagttct    600
tcatgtcccc gcaatgggtc ccaaatctac atcgcttgag cgaggatacc aaaaaggtat    660
accgatgtat ggtttccaac agactcaatt attttcccta ttatgaggcg ttcaggcggt    720
ctttgtttga tatgtatatg ctaggtcggt tggggcgtcg acttaagcga tctgactggg    780
agactattat gcatctgtca ccaacgcaaa gtcggcgtct acatagaact ttaagatttg    840
tggagcgtag aattatccca tctaacagtt atatacgcac atcgggccac gttccgcctt    900
cgagggcact tccgacagat acgaatttaa agatggatga ataattaaat tggaaagagt    960
aactacatta atcgagcgtc atgacggcgt cccgtgaaaa tgggaatttt ctactcgaaa   1020
caccgtgaca tttgacagac ctggaattgt tattctgata tatagtgggt gtgtctggcc   1080
ggcaacatac ataatgtgca tgcgaaacca ctttttcagt gtacgctgac attgtgcaac   1140
acggaggggt agcatctaca tacaatatat gttgattaat gattggagaa aaaactatgc   1200
agctcgccga tcatatggct aactcgcctt cgtctatatg gcggaccccg cgggaaaaat   1260
cgacgtacca tctgatttac aacaccagta atgaacatgt cgcatccctg cccagatctg   1320
tgcgcccatt ggcgcggatc gttgtgaatg ccgccgaaac acttcaggtc ggtatgagag   1380
ccgggaggcc gccatcagca ggagtttggc gagaggtgtt tgatagaatg atgacagcct   1440
tccgtgacca cgagcctact gcgacattta atgctgcaaa tcccattaga aaaatggtcg   1500
agacagttct acagaataat gaagagcccc cgcggacgca tgctgaaatg ggtaatcgcc   1560
ttatgaacat tatgtactgg tgttgcttgg gacacgcagg acaatgctcg atatggcagt   1620
tgtacgagac gaatcaggcc attttaagtt tattagatga agtggttatc ggcacaacaa   1680
atccctttg caccctcgag caatactgga agccattatg caccgcaatc gccaacaagg   1740
ggacctcatc gcttgttgag gatgccaaag tggccgagta cctggttagc atgcgcaaat   1800
tgatataaca taggcacgct ctgatgttac agaccacaat accgcataca tttattgtaa   1860
ggttgttaat aaaggtttat tctatgtaag actacaatac tttcgacatt gcttgtatac   1920
atattaaata ctttctcaag ttcctattac ataaaatggg atctatcatt acattcgtta   1980
agagtctgga taattttact gtttgccagc ttcgatcttg gaacgtactg tggatagtgc   2040
cttacttgga atcgtgaaaa tttgaaacgt ccattatttg gatatcttcc ggttgtccca   2100
tatcccgccc tggtaccgct cggatacctt gcccgtatgg attcgtattg acagtcgcgc   2160
aatcggggac caacaacgcg tgggtccaca ctcattcgga aattttccga tgattctgaa   2220
tatttattgc cgctcgttac gagtcgttgg acatatctgt aatacatttc ttcttctgaa   2280
ggatcgctgc acatttgatc tatacattgg ccaggatgtt caagtctcag atgttgcatt   2340
ctggcacagc acaactttat ggcatttccg atgtaatcgt ccggcagccc tgggggagtt   2400
ctatattcgc atattgggat ggtaaggaca atagcagatc tcgcaacctc cagggaggct   2460
ataataacgt ttttaaagga tggatttctc ataaaaatct gtcgcaaatt acactgagaa   2520
tatcctttac tagcgccgat tgagagcatc gtcgtccaat tttctaaatg gaaagaaaac   2580
aaggcgggca agagtgttcc aaacattttc attttcggcg aatctctcaa atcccatggc   2640
gtgcaattga ttgcaaaatt ggcacttccg ttcacgtttg tatctccaaa ctctaagaca   2700
cttttaattg aaaaactacg ttctagtgtg gaaagaaacc tataggcaga ccatagaact   2760
atttgacacc acatatcttt ttgtatgtca aactgaccat gatcgtatgt tgctgaatgc   2820
```

actagggcaa ttcgctcgcg cgactccata cattgaataa ttccacacgt cagctcatcg 2880
gttagcaagg tccagtagtt gaagtcattt atttttcccc gcggctggcc aaatctacct 2940
ctgggaatat ccaagttgtc gaatatgatc gcaccggctc tggtcatggt gaaggaactg 3000
tagcataaag acgcaggtat catagggta atatttttt attcactcac atactaaaag 3060
taacgcatat tagcaccatg tatgggctat caattgacat ttgcgtagca ctacatcacg 3120
attatgtaca acataatggg acaacatatg gcaagtagat gcaatttcct cacactagtt 3180
gggtttatct actattgaat tttcccctat ctgtgataca cttgggagcc tctacaagca 3240
tattgccatc atgtacgttt ttatctactg tcttaacgcc catgggaacg gaggcgtcgt 3300
cgtcatgtat tggacggcaa cataggcagc aacacaaatt gcgtttaggt ggggtgcatg 3360
tggactcgat accaagcccc tgcagctggg gaacgtctgg tggagagccg ataatttgat 3420
atacgcacgc catattactg tcgttgaagt acgccttatc ttctatgttt tcaaatttag 3480
gttcccaagt ggacgtgaga agtgtttgta tctcacatgg aatggcccaa ggcattccag 3540
cccaggtgcc tggtacttta atggcaaaca aacgttttgg tagaggtatt gattctattg 3600
cagttctgca gatatctgca gccccgagta tccacaggct atacgatacg ttatcggagg 3660
caagcttgtt aattaagtcg acggcagagt cgcagacgcc cctattggac gtcaaaattg 3720
tagaggtgaa gttttcaaac gatggcgaag taacggcgac ttgcgtttcc accgtcaaat 3780
ctccctatag ggtagaaact aattggaaag tagacctcgt agatgtaatg gatgaaattt 3840
ctgggaacag tcccgccggg gtttttaaca gtaatgagaa atggcagaaa cagctgtact 3900
acagagtaac cgatggaaga acatcggtcc agctaatgtg cctgtcgtgc acgagccatt 3960
ctccggaacc ttactgtctt ttcgacacgt ctcttatagc gagggaaaaa gatatcgcgc 4020
cagagttata ctttacctct gatccgcaaa cggcatactg cacaataact ctgccgtccg 4080
gcgttgttcc gagattcgaa tggagcctta ataatgtttc actgccggaa tatttgacgg 4140
ccacgaccgt tgtttcgcat accgctggcc aaagtacagt gtggaagagc agcgcgagag 4200
caggcgaggc gtggatttct ggccggggag gcaatatata cgaatgcacc gtcctcatct 4260
cagacggcac tcgcgttact acgcgaaagg agaggtgctt aacaaacaca tggattgcgg 4320
tggaaaacgg tgctgctcag gcgcagctgt attcactctt ttctggactt gtgtcaggat 4380
tatgcgggag catatctgct ttgtacgcaa cgctatggac cgccatttat ttttgaggaa 4440
tgctttttgg actatcgtac tgctttcttc cttcgctagc cagagcaccg ccgccgtcac 4500
gtacgactac attttaggcc gtcgcgcgct cgacgcgcta accataccgg cggttggccc 4560
gtataacaga tacctcacta gggtatcaag aggctgcgac gttgtcgagc tcaacccgat 4620
ttctaacgtg gacgacatga tatcggcggc caaagaaaaa gagaaggggg gccctttcga 4680
ggcctccgtc gtctggttct acgtgattaa gggcgacgac ggcgaggaca agtactgtcc 4740
aatctataga aaagagtaca gggaatgtgg cgacgtacaa ctgctatctg aatgcgccgt 4800
tcaatctgca cagatgtggg cagtggacta tgttcctagc acccttgtat cgcgaaatgg 4860
cgcgggactg actatattct cccccactgc tgcgctctct ggccaatact tgctgaccct 4920
gaaaatcggg agatttgcgc aaacagctct cgtaactcta gaagttaacg atcgctgttt 4980
aaagatcggg tcgcagctta actttttacc gtcgaaatgc tggacaacag aacagtatca 5040
gactggattt caaggcgaac acctttatcc gatcgcagac accaatacac gacacgcgga 5100
cgacgtatat cggggatacg aagatattct gcagcgctgg aataatttgc tgaggaaaaa 5160

-continued

```
gaatcctagc gcgccagacc ctcgtccaga tagcgtcccg caagaaattc ccgctgtaac   5220
caagaaagcg gaagggcgca ccccggacgc agaaagcagc gaaaagaagg cccctccaga   5280
agactcggag gacgacatgc aggcagaggc ttctggagaa aatcctgccg ccctccccga   5340
agacgacgaa gtccccgagg acaccgagca cgatgatcca aactcggatc ctgactatta   5400
caatgacatg cccgccgtga tcccggtgga ggagactact aaaagttcta atgccgtctc   5460
catgcccata ttcgcggcgt tcgtagcctg cgcggtcgcg ctcgtggggc tactggtttg   5520
gagcatcgta aaatgcgcgc gtagctaatc gagcctagaa taggtggttt cttcctacat   5580
gccacgcctc acgctcataa tataaatcac atggaatagc ataccaatgc ctattcattg   5640
ggacgttcga aaagcatggc atcgctactt ggaactctgg ctctccttgc cgcgacgctc   5700
gcacccttcg gcgcgatggg aatcgtgatc actggaaatc acgtctccgc caggattgac   5760
gacgatcaca tcgtgatcgt cgcgcctcgc cccgaagcta caattcaact gcagctattt   5820
ttcatgcctg gccagagacc ccacaaaccc tactcaggaa ccgtccgcgt cgcgtttcgg   5880
tctgatataa caaaccagtg ctaccaggaa cttagcgagg agcgctttga aaattgcact   5940
catcgatcgt cttctgtttt tgtcggctgt aaagtgaccg agtacacgtt ctccgcctcg   6000
aacagactaa ccggacctcc acacccgttt aagctcacta tacgaaatcc tcgtccgaac   6060
gacagcggga tgttctacgt aattgttcgg ctagacgaca ccaaagaacc cattgacgtc   6120
ttcgcgatcc aactatcggt gtatcaattc gcgaacaccg ccgcgactcg cggactctat   6180
tccaaggctt cgtgtcgcac cttcggatta cctaccgtcc aacttgaggc ctatctcagg   6240
accgaggaaa gttggcgcaa ctggcaagcg tacgttgcca cggaggccac gacgaccagc   6300
gccgaggcga caaccccgac gcccgtcact gcaaccagcg cctccgaact tgaagcggaa   6360
cactttacct ttccctggct agaaaatggc gtggatcatt acgaaccgac acccgcaaac   6420
gaaaattcaa acgttactgt ccgtctcggg acaatgagcc ctacgctaat tggggtaacc   6480
gtggctgccg tcgtgagcgc aacgatcggc ctcgtcattg taatttccat cgtcaccaga   6540
aacatgtgca ccccgcaccg aaaattagac acggtctcgc aagacgacga agaacgttcc   6600
caaactagaa gggaatcgcg aaaatttgga cccatggttg cgtgcgaaat aaacaagggg   6660
gctgaccagg atagtgaact tgtggaactg gttgcgattg ttaacccgtc tgcgctaagc   6720
tcgcccgact caataaaaat gtgattaagt ctgaatgtgg ctctccaatc atttcgattc   6780
tctaatctcc caatcctctc aaaaggggca gtatcggaca cggactggga ggggcgtaca   6840
cgatagttat atggtacagc agaggcctct gaacacttag gaggagaatt cagccgggga   6900
gagcccctgt tgagtaggct tgggagcata ttgcaggatg aacatgttag tgatagttct   6960
cgcctcttgt cttgcgcgcc taacttttgc gacgcgacac gtcctctttt tggaaggcac   7020
tcaggctgtc ctcggggaag atgatcccag aaacgttccg gaagggactg taatcaaatg   7080
gacaaaagtc ctgcggaacg cgtgcaagat gaaggcggcc gatgtctgct cttcgcctaa   7140
ctattgcttt catgatttaa tttacgacgg aggaaagaaa gactgcccgc ccgcgggacc   7200
cctgtctgca aacctggtaa ttttactaaa gcgcggcgaa agcttcgcgc caggtcaatt   7260
ccctggcatt atgcccagta catgacctta tgggactttc ctacttggca gtacatctac   7320
gtattagtca tcgctattac catggtgatg cggttttggc agtacatcaa tgggcgtgga   7380
tagcggtttg actcacgggg atttccaagt ctccacccca ttgacgtcaa tgggagtttg   7440
ttttggcacc aaaatcaacg ggactttcca aaatgtcgta acaactccgc cccattgacg   7500
caaatgggcg gtagcgtgta cggtgggagg tctatataag cagagctcgt ttagtgaacc   7560
```

```
gtcagatcgc ctggagacgc catccacgct gttttgacct ccatagaaga caccggttgc   7620
gccgccacca tgggccccag accttctacc aagaacccag tacctatgat gctgactgtc   7680
cgagtcgcgc tggtactgag ttgcatctgt ccggcaaact ccattgatgg caggcctctt   7740
gcggctgcag gaattgtggt tacaggagac aaagccgtca acatatacac ctcatcccag   7800
acaggatcaa tcatagttaa gctcctcccg aatctgccca aggataagga ggcatgtgcg   7860
aaagcccccct tggatgcata caacaggaca ttgaccactt tgctcacccc ccttggtgac   7920
tctatccgta ggatacaaga gtctgtgact acatctggag gggggagaca ggggcgcctt   7980
ataggcgcca ttattggcgg tgtggctctt ggggttgcaa ctgccgcaca aataacagcg   8040
gccgcagctc tgatacaagc caaacaaaat gctgccaaca tcctccgact taaagagagc   8100
attgccgcaa ccaatgaggc tgtgcatgag gtcactgacg gattatcgca actagcagtg   8160
gcagttggga agatgcagca gtttgttaat gaccaattta ataaaacagc tcaggaatta   8220
gactgcatca aaattgcaca gcaagttggt gtagagctca acctgtacct aaccgaattg   8280
actacagtat tcggaccaca aatcacttca cctgctttaa acaagctgac tattcaggca   8340
ctttacaatc tagctggtgg aaatatggat tacttattga ctaagttagg tgtagggaac   8400
aatcaactca gctcattaat cggtagcggc ttaatcaccg gtaaccctat tctatacgac   8460
tcacagactc aactcttggg tatacaggta actctacctt cagtcgggaa gctaaataat   8520
atgcgtgcca cctacttgga aaccttatcc gtaagcacaa ccaggggatt tgcctcggca   8580
cttgtcccaa aagtggtgac acaggtcggt tctgtgatag aagaacttga cacctcatac   8640
tgtatagaaa ctgacttaca tttatattgt acaagaatag taacgttccc tatgtcccct   8700
ggtatttatt cctgcttgag cggcaatacg tcggcctgta tgtactcaaa gaccgaaggc   8760
gcacttacta caccatacat gactatcaaa ggttcagtca tcgccaactg caagatgaca   8820
acatgtagat gtgtaaaccc cccgggtatc atatcgcaaa actatggaga agccgtgtct   8880
ctaatagata aacaatcatg caatgtttta tccttaggcg ggataacttt aaggctcagt   8940
ggggaattcg atgtaactta tcagaagaat atctcaatac aagattctca agtaataata   9000
acaggcaatc ttgatatctc aactgagctt gggaatgtca acaactcgat cagtaatgct   9060
ttgaataagt tagaggaaag caacagaaaa ctagacaaag tcaatgtcaa actgactagc   9120
acatctgctc tcattaccta tatcgtgttg actatcatat ctcttgtttt tggtatactt   9180
agcctgattc tagcatgcta cctaatgtac aagcaaaagg cgcaacaaaa gaccttatta   9240
tggcttggga ataatactct agatcagatg agagccacta caaaaatgtg aggatctctc   9300
gaggaattct agatcccacg tcactattgt atactctata ttatactcta tgttatactc   9360
tgtaatccta ctcaataaac gtgtcacgcc tgtgaaaccg tactaagtct cccgtgtctt   9420
cttatcacca tcaggtgaca tcctcgccca ggctgtcaat catgccggta tcgattccag   9480
tagcaccggc cccacgctga caacccactc ttgcagcgtt agcagcgccc ctcttaacaa   9540
gccgaccccc accagcgtcg cggttactaa cactcctctc cccgacctgc aactagtaag   9600
cttgcctccg attctagcat tacatagccg gtcagtagat cctgccattc ggtagcgcaa   9660
ccggctacat cttcaaacag tctcacaata aatgcatctc tcgttcctgc caatccggaa   9720
ccgggcatac cactcccgcc tgccgattta attctcacaa ttgggcgatg ccggcggggc   9780
aaaacgaatg tggatttggc aaaccgacac aggtctgctg tacggactaa tatgggcaca   9840
cccacatcat tcttcagatg ctccatgcat tgttctatga gaaagatcca tagggtggag   9900
```

```
gcagcgtcac gagatcgccc aggcaatcga tcgcattcgt ctagtaaagt gacgagagtt   9960
atcatgcaca cacccatgcc cacgccttcc gaataactgg agctgtggaa gatcggaaac  10020
gtctttttga ctgccggtct cgtactactt tcgcacaggt gtatacccgg acgcgtacta  10080
tatattttat atcatccaac gtccgaaatt acatacgtgg cggcgatgga agtagatgtt  10140
gagtcttcga aagtaagtgc ctcgaatatg ggtattgtct gtgaaaatat cgaaagcggt  10200
acgacggttg cagaaccgtc gatgtcgcca gatactagta acaatagctt cgataacgaa  10260
gacttccgtg ggcctgaata cgatgtggag ataaatacca gaaaatctgc taatcttgat  10320
cgtatggaat cttcgtgccg tgaacaacga gcggcgtgcg aacttcgaaa gtgttcgtgt  10380
cctacgtctg ccgtgcgcat gcaatacagt attctttcat ctctcgctcc gggttcagag  10440
ggtcatgtat atatatgtac tagatacggg gacgcggacc aaaaaaaatg catagtgaag  10500
gcagtcgttg gaggaaagaa tcccgggagg gaagtggata ttttaaaaac catctcacat  10560
aaatcaatta taaaattaat ccatgcctat aaatggaaaa atgttgtgtg tatggcaatg  10620
cgtgtatatc gttatgatct tttcacatat attgacggag tcggccctat gccccttcaa  10680
cagatgatct atattcaacg tggactacta gaggcgctag catacataca tgaaaggggc  10740
atcattcacc gagacgtaaa gacggagaat atattcttgg ataatcacga aaatgcagtt  10800
ttgggtgact tcggtgctgc atgccaacta ggagattgta tagatacgcc ccaatgttac  10860
ggttggagcg gaactgtgga aacaaattcg ccggaattat ctgcacttga tccgtattgc  10920
acaaaaacag atatttggag tgccggattg gttctatatg agatggcaat taaaaatgta  10980
ccattgttta gtaagcaggt gaaaagttcg ggatctcagc tgagatccat aatacggtgc  11040
atgcaagtgc atgaactgga gtttccccgc aacgattcta ccaacctctg taaacatttc  11100
aaacaatatg cggttcgtgt acgaccgcct tataccattc ctcgagttat aagaaatggg  11160
gggatgccaa tggatgttga atatgtcatt tctaaaatgc ttacgtttga ccaggagttc  11220
agaccttctg ctaaggaaat attgaatatg cccctattta ctaaggcgcc gattaacctg  11280
cttaatatca caccctctga cagtgtctaa cggtatacag gcgggagcgg gtcgtggcgt  11340
catcatcacc acttgagaat ttatattttg aattgttgat tgataaatta acctgattca  11400
ttgagaactg aaacgccata ttggtttctt ggatatgtct acaacaatta gttaaattgc  11460
tatgttctac tgcgagtaac atttgataag ttgtaagaga cgggcgactc atgtcgaagt  11520
tgacgaatat aaagtacata acgtgtttag aatacccaga atccgaatag tccgcggggg  11580
cgtcttctcg cgtgagtacc aaatactgag ttgaacttga aaatgctaaa tctgtgacac  11640
tctttgtgtg atgattattg tcaccacttc gaagatggct tcgacattca tgatgttctg  11700
gtgtttgttt ggaatcgtaa tagcgcttgt ttcgtccaag tctgacaaca aagaaaatct  11760
gaagaattat atcacggata agtcaaccaa tattagaata cccacgccat tatttgtatc  11820
aacggaaaac tcttatccca caaaacatgt aatctacgat gaaaactgtg gcttcgctgt  11880
actcaatcct ataagtgacc ccaaatatgt ccttttgagc cagcttctaa tgggaaggcg  11940
caaatatgat gcgacggtcg cgtggtttgt tctcggtaaa atgtgtgcca gattaatata  12000
tttgcgcgaa ttttataact gctcgacaaa tgagcctttt ggcacatgtt ctatgagctc  12060
tcctggatgg tgggacaggc gctacgtctc aaccagtttc atttctcgcg acgaattaca  12120
gctggttttt gcagcgccgt cccgagaatt agatggttta tatacgcgcg tagtagttgt  12180
caacggggac tttactacgg ccgatataat gtttaatgtt aaagtggcat gtgccttttc  12240
aaagactgga atagaagatg atacattatg caaacccttt catttctttg ccaatgcaac  12300
```

attgcacaat ttaaccatga ttagatcggt aactcttcga gcgcacgaaa gccatttaaa 12360
ggaatgggtg gcacggagag gtggtaacgt ccctgcagtg ctacttgagt ctaccatgta 12420
tcatgcatcc aatctgccta gaaatttcag ggatttctac ataaagtctc cagatgatta 12480
taagtataat cacctagatg ggccatctgt aatgctcatc actgacagac ctagtgaaga 12540
tttggatggg aggctcgttc accaaagtga catttttact actacaagtc ctataaaaca 12600
ggtccggtat gaagagcatc agtcacatac aaagcagtat cctgtaaaca aaatacaagc 12660
tataattttt ttgatagggt taggctcgtt cattggaagc atattcgtag ttttggtagt 12720
atggattata cgcagatatt gcaatggagc gcggagtggg ggaacgcccc ccagtcctcg 12780
ccggtatgtg tataccaggc tatgatcacg tgtgaaactt gggcggacct gtatcatatg 12840
tacaccgtcc ctattcgttt atagccagta cgtgttatct gcacatagag gaacatgtgt 12900
catactggga tcgcatgcat ggtatgtgtg actctaatat tattctgtat cataataaaa 12960
acacagtgca tggtatatag aggatcgctg gtaagcacta cggtagacca atcggctcag 13020
attgcattct ttggcatcga taccgttgtt aatttatatg gcaaagtctt gttcatggga 13080
gatcagtatt tggaggaaat atactctgga acgatggaaa tactcaaatg gaatcaagct 13140
aaccgctgct attctattgc gcatgcaaca tattacgccg actgtcctat aatcagttct 13200
acggtattca gaggatgccg ggacgccgtt gtttatacta ggccccacag cag 13253

<210> SEQ ID NO 29
<211> LENGTH: 12248
<212> TYPE: DNA
<213> ORGANISM: Artificial Sequence
<220> FEATURE:
<223> OTHER INFORMATION: Expression cassette

<400> SEQUENCE: 29
ggcgcgccac tggagaacgg catgaccgca aaaggcgttg tagagatcga tcccacgaac 60
tctcaggcga tcgtgtcagt cgccataaac agcgacgatc gtctccagga tctgaacggt 120
tttcttctca acgatcatca gtatatgagg aactgaacct gatatttagc cgagggaaac 180
gcaggttaaa aaccctatca agcgattgcg attttcgcgt atctagtaaa aatagatggg 240
cttcggtact agccttcgcc gccaactctg aatatgccct tcgtggacct catataacat 300
ggcattgttt gttggatgcg gggccggaat taagaagaac attcgaaata cgagcaaaaa 360
tttcggccct ggcatgtgct gcgcgagaat cggtacttcg gggagaaagt tttatcggag 420
ctttgggtag tgcagaggaa actctatctt ggttgaaaat gcatgcgacc ctgcacttga 480
ttctggttaa ccacgatcca atttttaaga cggctggcgc ggtcctagat aacctccgct 540
taaaactagc cccaatattg atgtgcagat ataacacaga aaaacgatca atggaagaca 600
tgctacggcg gtcatctccc gaagacatca ccgattccct aacaatgtgc ctgattatgt 660
tatcgcgcat tcgtcgtacc atgcgcaccg caggaaataa atatagctat atgatagatc 720
caatgaatcg tatgtctaat tacactccag gcgaatgtat gacaggtata ttgcgatata 780
ttgacgaaca tgctagaagg tgtcctgatc acatatgtaa tttgtatatc acatgtacac 840
ttatgccgat gtatgtgcac gggcgatatt tctattgtaa ttcatttttt tgttagtaaa 900
ctaccacagg ctgtccggaa atctaagtta atgaataaag tagatggtta atactcattg 960
cttagaattg gactactttt aattctcttt aatgttcgta ttaaataaaa acatctttaa 1020
taaacttcag cctcttcgct tattgtagaa attgagtatt caaaatcatg ttcaaagccg 1080

-continued

```
tcttcggaga gtgtactcgc cacggtggtt ggaacatcac tatgtctaca cgtcaaattt   1140
aagcacgtca ggtctgtcga ggacaagaaa tggttaacta gtgtttcaat tattcttata   1200
aacgttaagc attgtaagcc ccccggccgt ccgcagcaac aatttactag tatgccgtgg   1260
gctccgggac tatcacggat gtccaattcg cacatgcata taatttttct agggtctctc   1320
atttcgagaa atcttcgggg atccatcagc aatgcgggct gtagtcccga ttcccgtttc   1380
aaatgaaggt gctccaacac ggtcttcaaa gcaaccggca taccagcaaa cacagactgc   1440
aactccccgc tgcaatgatt ggttataaac agtaatctgt cttctggaag tatatttcgc   1500
ccgacaatcc acggcgcccc caaagttaaa aaccatccat gtgtatttgc gtcttctctg   1560
ttaaaagaat attgactggc attttcccgt tgaccgccag atatccaaag tacagcacga   1620
tgttgcacgg acgactttgc agtcaccagc cttcctttcc acccccccac caacaaaatg   1680
tttatcgtag gacccatatc cgtaataagg atgggtctgg cagcaacccc ataggcgcct   1740
cggcgtggta gttctcgagg ccttaattaa gtcgacggca gagtcgcaga cgcccctatt   1800
ggacgtcaaa attgtagagg tgaagttttc aaacgatggc gaagtaacgg cgacttgcgt   1860
ttccaccgtc aaatctccct atagggtaga aactaattgg aaagtagacc tcgtagatgt   1920
aatggatgaa atttctggga acagtcccgc cggggttttt aacagtaatg agaaatggca   1980
gaaacagctg tactacagag taaccgatgg aagaacatcg gtccagctaa tgtgcctgtc   2040
gtgcacgagc cattctccgg aaccttactg tcttttcgac acgtctctta tagcgaggga   2100
aaaagatatc gcgccagagt tatactttac ctctgatccg caaacggcat actgcacaat   2160
aactctgccg tccggcgttg ttccgagatt cgaatggagc cttaataatg tttcactgcc   2220
ggaatatttg acggccacga ccgttgtttc gcataccgct ggccaaagta cagtgtggaa   2280
gagcagcgcg agagcaggcg aggcgtggat ttctggccgg ggaggcaata tatacgaatg   2340
caccgtcctc atctcagacg gcactcgcgt tactacgcga aaggagaggt gcttaacaaa   2400
cacatggatt gcggtggaaa acggtgctgc tcaggcgcag ctgtattcac tcttttctgg   2460
acttgtgtca ggattatgcg ggagcatatc tgctttgtac gcaacgctat ggaccgccat   2520
ttatttttga ggaatgcttt ttggactatc gtactgcttt cttccttcgc tagccagagc   2580
accgccgccg tcacgtacga ctacatttta ggccgtcgcg cgctcgacgc gctaaccata   2640
ccggcggttg gcccgtataa cagatacctc actagggtat caagaggctg cgacgttgtc   2700
gagctcaacc cgatttctaa cgtggacgac atgatatcgg cggccaaaga aaaagagaag   2760
gggggccctt tcgaggcctc cgtcgtctgg ttctacgtga ttaagggcga cgacggcgag   2820
gacaagtact gtccaatcta tagaaaagag tacagggaat gtggcgacgt acaactgcta   2880
tctgaatgcg ccgttcaatc tgcacagatg tgggcagtgg actatgttcc tagcaccctt   2940
gtatcgcgaa atggcgcggg actgactata ttctccccca ctgctgcgct ctctggccaa   3000
tacttgctga ccctgaaaat cgggagattt gcgcaaacag ctctcgtaac tctagaagtt   3060
aacgatcgct gtttaaagat cgggtcgcag cttaactttt taccgtcgaa atgctggaca   3120
acagaacagt atcagactgg atttcaaggc gaacaccttt atccgatcgc agacaccaat   3180
acacgacacg cggacgacgt atatcgggga tacgaagata ttctgcagcg ctggaataat   3240
ttgctgagga aaaagaatcc tagcgcgcca gaccctcgtc cagatagcgt cccgcaagaa   3300
attcccgctg taaccaagaa agcggaaggg cgcaccccgg acgcagaaag cagcgaaaag   3360
aaggcccctc cagaagactc ggaggacgac atgcaggcag aggcttctgg agaaaatcct   3420
gccgccctcc ccgaagacga cgaagtcccc gaggacaccg agcacgatga tccaaactcg   3480
```

```
gatcctgact attacaatga catgcccgcc gtgatcccgg tggaggagac tactaaaagt   3540
tctaatgccg tctccatgcc catattcgcg gcgttcgtag cctgcgcggt cgcgctcgtg   3600
gggctactgg tttggagcat cgtaaaatgc gcgcgtagct aatcgagcct agaataggtg   3660
gtttcttcct acatgccacg cctcacgctc ataatataaa tcacatggaa tagcatacca   3720
atgcctattc attgggacgt tcgaaaagca tggcatcgct acttggaact ctggctctcc   3780
ttgccgcgac gctcgcaccc ttcggcgcga tgggaatcgt gatcactgga aatcacgtct   3840
ccgccaggat tgacgacgat cacatcgtga tcgtcgcgcc tcgccccgaa gctacaattc   3900
aactgcagct atttttcatg cctggccaga gaccccacaa accctactca ggaaccgtcc   3960
gcgtcgcgtt tcggtctgat ataacaaacc agtgctacca ggaacttagc gaggagcgct   4020
ttgaaaattg cactcatcga tcgtcttctg tttttgtcgg ctgtaaagtg accgagtaca   4080
cgttctccgc ctcgaacaga ctaaccggac ctccacaccc gtttaagctc actatacgaa   4140
atcctcgtcc gaacgacagc gggatgttct acgtaattgt tcggctagac gacaccaaag   4200
aacccattga cgtcttcgcg atccaactat cggtgtatca attcgcgaac accgccgcga   4260
ctcgcggact ctattccaag gcttcgtgtc gcaccttcgg attacctacc gtccaacttg   4320
aggcctatct caggaccgag gaaagttggc gcaactggca agcgtacgtt gccacggagg   4380
ccacgacgac cagcgccgag gcgacaaccc cgacgcccgt cactgcaacc agcgcctccg   4440
aacttgaagc ggaacacttt acctttccct ggctagaaaa tggcgtggat cattacgaac   4500
cgacacccgc aaacgaaaat tcaaacgtta ctgtccgtct cgggacaatg agccctacgc   4560
taattggggt aaccgtggct gccgtcgtga gcgcaacgat cggcctcgtc attgtaattt   4620
ccatcgtcac cagaaacatg tgcaccccgc accgaaaatt agacacggtc tcgcaagacg   4680
acgaagaacg ttcccaaact agaagggaat cgcgaaaatt tggacccatg gttgcgtgcg   4740
aaataaacaa gggggctgac caggatagtg aacttgtgga actggttgcg attgttaacc   4800
cgtctgcgct aagctcgccc gactcaataa aaatgtgatt aagtctgaat gtggctctcc   4860
aatcatttcg attctctaat ctcccaatcc tctcaaaagg ggcagtatcg gacacggact   4920
gggaggggcg tacacgatag ttatatggta cagcagaggc ctctgaacac ttaggaggag   4980
aattcagccg gggagagccc ctgttgagta ggcttgggag catattgcag gatgaacatg   5040
ttagtgatag ttctcgcctc ttgtcttgcg cgcctaactt ttgcgacgcg acacgtcctc   5100
tttttggaag gcactcaggc tgtcctcggg gaagatgatc ccagaaacgt tccggaaggg   5160
actgtaatca aatggacaaa agtcctgcgg aacgcgtgca agatgaaggc ggccgatgtc   5220
tgctcttcgc ctaactattg ctttcatgat ttaatttacg acggaggaaa gaaagactgc   5280
ccgcccgcgg gacccctgtc tgcaaacctg gtaattttac taaagcgcgg cgaaagcttc   5340
ccgggttaat taaggccctc gaggatacat ccaaagaggt tgagtattct ctctacactt   5400
cttgttaaat ggaaagtgca tttgcttgtt cttacaatcg gcccgagtct cgttcacagc   5460
gcctcgttca cacttaaacc acaaatagtc tacaggctat atgggagcca gactgaaact   5520
cacatatgac taatattcgg gggtgttagt cacgtgtagc ccattgtgtg catataacga   5580
tgttggacgc gtccttattc gcggtgtact tgatactatg gcagcgagca tgggatattc   5640
atcctcgtca tcgttaacat ctctacgggt tcagaatgtt tggcatgtcg tcgatccttt   5700
gcccatcgtt gcaaattaca agtccgatcg ccatgaccgc gataagcctg taccatgtgg   5760
cattagggtg acatctcgat catacattat aagaccaacg tgcgagtctt ccaaagacct   5820
```

-continued

```
gcacgccttc ttcttcggat tgtcaacggg ttcttcagaa tctatgccca tatctggcgt   5880
tgagaccatt gtgcgtttaa tgaacaataa agcggcatgc catggaaagg agggctgcag   5940
atctccattt tctcacgcca ctatcctgga cgctgtagac gataattata ccatgaatat   6000
agagggggta tgtttccact gccactgtga tgataagttt tctccagatt gttggatatc   6060
tgcattttct gctgccgaac aaacttcatc gctatgcaaa gagatgcgtg tgtacacgcg   6120
ccgttgagta tacgggaaac taaatgttca tagaggtctt tgggctatat gttattaaat   6180
aaaataattg accagtgaac aatttgttta atgttagttt attcaatgca ttggttgcaa   6240
atattcatta cttctccaat cccaggtcat tctttagcga gatgatgtta tgacattgct   6300
gtgaaaatta ctacaggata tatttttaag atgcaggagt aacaatgtgc atagtaggcg   6360
tagttatcgc agacgtgcaa cgcttcgcat ttgagttacc gaagtgccca acagtgctgc   6420
ggttatggtt tatgcgcaca gaatccatgc atgtcctaat tgaaccatcc gatttttctt   6480
ttaatcgcga tcgttgtttg ggcaactgcg ttatttcaga tctaaaaaat ttacccttta   6540
tgaccatcac atctctctgg ctcatacccc gcttggataa gatatcatgt agattccgcc   6600
ctaagaaatg caaactaaca ttattgtcgg ttccatatac acttccatct tgtccttcga   6660
aaataacaaa ctcgcgcaat agaccgtccg tacatgcatg gccgatgtgt gtcaacatca   6720
ttggtctgct agatcccgat gggacgaatc gtacagtcgt cgctccagca ttggcaaaaa   6780
tccccagata ccctccatgc ggcaaatcta aattgcgacc ccgaagagac tgcaccaaag   6840
tcttatcgac gcacgctgat ttttttgaac agcgggagcc cattatcttc agtggagcgt   6900
agacgggcga ggctaattat gtgacatagc aacactgcat gtatgttttt ataaatcaat   6960
aagagtacat aatttattac gtatcatttc cgtttgtaat atactgtata catcatccac   7020
actattagtc agcactagcg cgcgggcgca cgttacaata gcagcgtgcc cgttatctat   7080
attgtccgat atttacacat aacatttcat cgacatgatt aaatacctaa gtactgcaca   7140
cagatgttta atgtatatcg tcatataaat tatatcgcta ggacagaccc aaacgacctt   7200
tatcccaaac agtcagatcc tcttctcaag tgtcgatttc tgttatggaa tatgcatacc   7260
ctggcccaga aattgcacgc acgagcgtag tgaatgcgtc attggtttta catttaaagg   7320
ctaaatgcac aaattcttta gacgacagca catcgttaaa tagcatctct agcgttctta   7380
tgaatgctaa gcattggagt cctcctggtc ggccacaata acagctgagt atcataccct   7440
gagctccggg gttgtcgcac atagcggatt cgtataaaca taggattttc cgcgaatcca   7500
tcagttgcaa aaatctgtta ggctccatca acaacgctgg atttacttca gatccacgcg   7560
taaagtaatg gtgctcgaat accgttttta gagttgtcgg catttcaagg aacaaagaat   7620
tcatttcttc attgcaacga cgcgccagaa atcccaagac ctctttgggt agtatgttct   7680
tgcctataaa acacggcgtt ccaagtgcca ggaaccacgc atgtgttact gttggggcgt   7740
attcagaaat aaagcggggt ttatgcggct tttgaagctc ggatatccaa agtatcgctt   7800
gctgatgaac gagcgatgta gctgttacaa aacctccttt ccatcctcca gtcaacataa   7860
tatttatcgg cctacctatg tccgtaataa gtattggtcg ggcaattatt ccgtatgagg   7920
tcttgcagga ataagctctt agggacagcc agcttggata tggtgcgaaa cagaccttct   7980
cggcttcaga atgtcgctcc gcagtctctt cgtgtcggtg catcttagat ccaccatcaa   8040
tgtgtgcagc attgactccc gcccgtcgaa tattcctttt gttacgatgc agtaatgagc   8100
acgatcatgg gcggggcgat gacgttctat ttgcatgtct gcgaacaatt tgcgtcagtc   8160
atacagctat ggagtgggcc atttctggcc gtcaacttaa aaacgcgaac cgcagacata   8220
```

-continued

```
tgtatttgca tgcaaagacg tatcttcgta tttctgggca tcttcaaatg ctctggccaa   8280
tatggcaatg aatttggatt cgtttgacgc cgatggtatg cagtgcaaat gtgccaatag   8340
cccacatccg aaaaagttat ttgtcataca agcaggtgtt aagtagcaat cacataaagg   8400
caccagacgc ctcatggcat cataatgaat agctccttct ccccactgga accactgaca   8460
aaatctgcga gtatattccg caaaccacat tttatttctc atagaaacta ccctaaatcc   8520
ttttaacggg aagaagaatc ctagatagtg cttgaagtca tgactgttac tgctgcaata   8580
acactgtata ttatttataa attccgtttg tctaggtatc tgatgtaggc attccgatcc   8640
ctttactatt gcgtcttcac gaccaaatgg gaatgcgcca aaatccccac acctcatcac   8700
cctggaggca gattgtgtat tattaatatc cgccgattga agcacaaaac ggtacggtac   8760
tgttcctaat tctggtatag attctatggt caaaagtctg catatccccg acattgccat   8820
gagatcacac agtccaagta gcatgtttat tgagtcactc agactgtcaa cgtccctcgc   8880
cgcaccacca atcgaaaata aagtatctac gcaagttata gctccgcatt ttctatcgct   8940
agcagcaatc gcgacgcaaa acataaaggc catgttggga tttgaactct ctggggggct   9000
tgttatcttc tgcaccgtcg cagtcgcagt tttccgaaat ttatgtctaa tatattttcc   9060
ggccgtgctc caatcggccg aaaagaatct gcgtattacc agactcattg acgggccgat   9120
aaagaccata aaacaaaatt cctgtgcact ccctcctcca gttttgccat cgtccaagtc   9180
ccgtaacttt ttttgcgttt cgaggagcaa gcgttcgtta tccctaccca cacttgtttt   9240
ccaccgtttt cttattataa gcggttgtat cgccaacgcg tcaccgcagg ttgtcacata   9300
cagtgatggc atacttgaac gtgcaacaac gcgctcgctt tgcaaatcta agtcattgac   9360
catcaaatcg cgttgagagg atagccaggc atcttttttc ctagtatggt gacggtgcag   9420
ccaccccaac tcagttcttg taaaaaaagc tattggcggg aatttatgtt ctgaggtgca   9480
ttctatattt atgagtccat caaatgccat taaccagatt cgtatttttt cgctcgaccc   9540
ggcatcacta tggatacaat acctttctat ggcccatttc agctctcgaa ccaaccacac   9600
ggacaattga ctaacataag tatgatcttt atcacagtcg cacccatctg agttatattt   9660
atggcatccg agcgctctta ctgtacggtc ggatacaccc atggtttttc ctttatatag   9720
tcgggttata gtctgtcggg tttggcggta gcacggagta gtttgatttt taagaatcga   9780
aaaccggctt ggagagacca ctgtcgaata tttgtccgta tactctacac gtgagtgttg   9840
tccattccta ggtatattca tctgttcgga taccttcaat tgctgttcag gcataacctt   9900
aaagcatatg ttatgttgta catcaaaact tggtgagtta tgttcgattg ccgcgcataa   9960
agaatcgtac atgagcgttt ctgctaacat actatctata ttctcacacg cccctgcata  10020
tactgttcct attccaaatt cacgttttgc cccatcggct atctgctccc aaaaagttgt  10080
aatataggtg ccgctgggtg cgaaattttc atcagttgta ttcctgataa actgaatcac  10140
tttacataat ttttgccaca tatctgcgtg cagccatagt atcgaacccg tgggctcgga  10200
gacgacagtg cgtacaatgg gtattttacc tttccccaac aaaataatgg tatacaagtt  10260
aggtccgtac ctagacctta atgtttccaa ttcttctgaa tcactgcact ctcgtagggg  10320
agtaacggta ataatttcgt ctctgagccc cgttttgcgt tgaaaactaa tcacattaga  10380
taatgtgcaa tcggtttctt ttatccggat acatctaagt attatgacat cggtggtcat  10440
tgtttccatc aacgaccatc ttttacgatc gcccatacta ctcatggacg ttgtcggtgt  10500
tgaaaaatca ccagaattgc aacggatctc tgggtaccat gctgctgatg gaattggcgg  10560
```

ttttaattgt tgtttcagtc tattattgct atctttggcg gggttgaata atgtgggggg 10620
agagtgattg caggaatccg aatgggtcaa taaaacgacc gtgctccgtt ctgccggcgc 10680
cgatccgatt gaagctatat acttcgcttc tctccccact tttccaattt gatccggaaa 10740
taaaacggcc ccggacaaca gtatcgtacg atccggatcc ggatcctgct tgcctacaga 10800
agaatcaaca tctcgcccca atattctggt caaaactggc tcgctcatgg caacgcggac 10860 gtttccccg gtggccagtc ttaatggtta atgttctttt cggcaatctt atacatcagc 10920
gggttgcgtg aatactggtc acagttcagt catttactac acaccagcaa tacgacgacg 10980
gacagtaccg tcccgacgaa cgcgacgccc aaaattgcta tcgcgaccgc gtccgaggcg 11040
atgtcgtacg ggcggtgcgg ggttggatcc tcggcaaaga gatcctcgta attcggcggt 11100
gggagcggag ggtaaagacg cgggtgggga tctccctccg gaccgcgcgc cgggcgcggt 11160
tcgaaaatgc tttccgcctc gctcagtgtc aacgccaagt attcgggcgg gctgggggcc 11220
ggaatatctc ccgcgacttc ttctatcggc gcggaattgg agtcgcggtc gtggcgcgct 11280
tctagcgtcg tcaacggaag tccattttcg gggtctcccg gtgggcgttc agcgtccatc 11340
gtcgtatatg ctctaacaca cgtctcgcta tattaaaaaa aagaagagta tcggtcagtg 11400
tcgagtgtcg ccgacaatgt cgcgagttct cggcgattta atttttggaa ctgctcccta 11460
tgaatcccgt aactgtagcg cccgcgcaga aagccgccat cagaccaact acgtgtctgt 11520
tcgatgtttg cccgccgatc gctttaccga ttaaggttcc ggcgagaaat gacatgctcg 11580
atccaagaac aaagtttttc gcggtaaaca acaacatagt taccgtgcga gatggagaaa 11640
ccacatctcc cgaattagta gaggaaagcc cgcgctgtcg gtttggggac atatcgatct 11700
tttttgtgtt tttcctagga ccctttttgcc agatcgtaca aagtcgcgtc ttatgagcgg 11760
acgttcttac tgcagctcgg taggagtggg gcagggttag atttcgtcgg cgtttcggcc 11820
cccgtatgcg ccgcgccacc ctcttcgccg agctctttat gcgcggtggg ggtgagcgct 11880
tccggagttg cgatctccga tctcgagccg cagcccggcg gtgtctcttt cagtggagcg 11940
ttagcgccat catgtggttc gtggcggtgg aaaggctatt atgtgttagg ggagagacca 12000
cgtgatcggc atgcaaatga gcaaggcgaa cgcgtcagcg ttcgcactgc gaaccaataa 12060
tatatatatt atactattgg ctttaggtgc gaacgtccgg ctagtccaat agcggggtcg 12120
cgtttcgtac cacgtgttat agaccgccct aaactcgcac tcgggggtcc ggccgcgccc 12180
agacagggcg gagacgtgcc acaggggctt taaaacaccg cttcgggcac cgttcatctc 12240
ggcgcgcc 12248

<210> SEQ ID NO 30
<211> LENGTH: 13068
<212> TYPE: DNA
<213> ORGANISM: Artificial Sequence
<220> FEATURE:
<223> OTHER INFORMATION: Expression cassette

<400> SEQUENCE: 30
aattccagac taaatgcccc ggcccaattt gtcaagtgtg cagtcacgga ggcgtcgacc 60
gtgtccccgg cattaaacag gaaagcgtta aagtttttga atgttaggtc acaggtacaa 120
acataaatgt ttgtacaaac aggtaacagg tacaaacata aatgccccgg cataaatgtc 180
ccttacggcg gatcgaaacg acattaggca tactcgggta ccattttgca ttccgatcag 240
cacggatgaa attaggcagg aatgcggttt atattatgcg gcattggaca aacgatatgg 300
cattgattgg cagtttatga atgtcttcat gttgggcgta aacggattcc tattggttca 360

```
gaagacaacg acgatatatt tagagagaaa aagctaccca gcataggata aacacacatt    420
gagcattgag agacataggt atcggtatgg atgggaaaac tacacacgtg aacaccaaac    480
gacttatata ctcgagcggt gatactactg agcaagaatg cactgcatct gagccactga    540
atgaagactg tgatgaaaat gtgaccatcg atggaattgg agaagaatat gcgcagttct    600
tcatgtcccc gcaatgggtc ccaaatctac atcgcttgag cgaggatacc aaaaaggtat    660
accgatgtat ggtttccaac agactcaatt attttcccta ttatgaggcg ttcaggcggt    720
ctttgtttga tatgtatatg ctaggtcggt tggggcgtcg acttaagcga tctgactggg    780
agactattat gcatctgtca ccaacgcaaa gtcggcgtct acatagaact ttaagatttg    840
tggagcgtag aattatccca tctaacagtt atatacgcac atcgggccac gttccgcctt    900
cgagggcact tccgacagat acgaatttaa agatggatga ataattaaat tggaaagagt    960
aactacatta atcgagcgtc atgacggcgt cccgtgaaaa tgggaatttt ctactcgaaa   1020
caccgtgaca tttgacagac ctggaattgt tattctgata tatagtgggt gtgtctggcc   1080
ggcaacatac ataatgtgca tgcgaaacca ctttttcagt gtacgctgac attgtgcaac   1140
acggaggggt agcatctaca tacaatatat gttgattaat gattggagaa aaaactatgc   1200
agctcgccga tcatatggct aactcgcctt cgtctatatg gcggaccccg cgggaaaaat   1260
cgacgtacca tctgatttac aacaccagta atgaacatgt cgcatccctg cccagatctg   1320
tgcgcccatt ggcgcggatc gttgtgaatg ccgccgaaac acttcaggtc ggtatgagag   1380
ccgggaggcc gccatcagca ggagtttggc gagaggtgtt tgatagaatg atgacagcct   1440
tccgtgacca cgagcctact gcgacattta atgctgcaaa tcccattaga aaaatggtcg   1500
agacagttct acagaataat gaagagcccc cgcggacgca tgctgaaatg ggtaatcgcc   1560
ttatgaacat tatgtactgg tgttgcttgg gacacgcagg acaatgctcg atatggcagt   1620
tgtacgagac gaatcaggcc attttaagtt tattagatga agtggttatc ggcacaacaa   1680
atccctttg caccctcgag caatactgga agccattatg caccgcaatc gccaacaagg   1740
ggacctcatc gcttgttgag gatgccaaag tggccgagta cctggttagc atgcgcaaat   1800
tgatataaca taggcacgct ctgatgttac agaccacaat accgcataca tttattgtaa   1860
ggttgttaat aaaggtttat tctatgtaag actacaatac tttcgacatt gcttgtatac   1920
atattaaata ctttctcaag ttcctattac ataaaatggg atctatcatt acattcgtta   1980
agagtctgga taattttact gtttgccagc ttcgatcttg gaacgtactg tggatagtgc   2040
cttacttgga atcgtgaaaa tttgaaacgt ccattatttg gatatcttcc ggttgtccca   2100
tatcccgccc tggtaccgct cggatacctt gcccgtatgg attcgtattg acagtcgcgc   2160
aatcggggac caacaacgcg tgggtccaca ctcattcgga aattttccga tgattctgaa   2220
tatttattgc cgctcgttac gagtcgttgg acatatctgt aatacatttc ttcttctgaa   2280
ggatcgctgc acatttgatc tatacattgg ccaggatgtt caagtctcag atgttgcatt   2340
ctggcacagc acaactttat ggcatttccg atgtaatcgt ccggcagccc tgggggagtt   2400
ctatattcgc atattgggat ggtaaggaca atagcagatc tcgcaacctc cagggaggct   2460
ataataacgt ttttaaagga tggatttctc ataaaaatct gtcgcaaatt acactgagaa   2520
tatcctttac tagcgccgat tgagagcatc gtcgtccaat tttctaaatg gaaagaaaac   2580
aaggcgggca agagtgttcc aaacattttc attttcggcg aatctctcaa atcccatggc   2640
gtgcaattga ttgcaaaatt ggcacttccg ttcacgtttg tatctccaaa ctctaagaca   2700
```

-continued

```
cttttaattg aaaaactacg ttctagtgtg gaaagaaacc tataggcaga ccatagaact   2760
atttgacacc acatatcttt ttgtatgtca aactgaccat gatcgtatgt tgctgaatgc   2820
actagggcaa ttcgctcgcg cgactccata cattgaataa ttccacacgt cagctcatcg   2880
gttagcaagg tccagtagtt gaagtcattt atttttcccc gcggctggcc aaatctacct   2940
ctgggaatat ccaagttgtc gaatatgatc gcaccggctc tggtcatggt gaaggaactg   3000
tagcataaag acgcaggtat catagggta atatttttt attcactcac atactaaaag   3060
taacgcatat tagcaccatg tatgggctat caattgacat ttgcgtagca ctacatcacg   3120
attatgtaca acataatggg acaacatatg gcaagtagat gcaatttcct cacactagtt   3180
gggtttatct actattgaat tttcccctat ctgtgataca cttgggagcc tctacaagca   3240
tattgccatc atgtacgttt ttatctactg tcttaacgcc catgggaacg gaggcgtcgt   3300
cgtcatgtat tggacggcaa cataggcagc aacacaaatt gcgtttaggt ggggtgcatg   3360
tggactcgat accaagcccc tgcagctggg gaacgtctgg tggagagccg ataatttgat   3420
atacgcacgc catattactg tcgttgaagt acgccttatc ttctatgttt tcaaatttag   3480
gttcccaagt ggacgtgaga agtgtttgta tctcacatgg aatggcccaa ggcattccag   3540
cccaggtgcc tggtacttta atggcaaaca aacgttttgg tagaggtatt gattctattg   3600
cagttctgca gatatctgca gccccgagta tccacaggct atacgatacg ttatcggagg   3660
caagctgcgg ccgctctaga actagtggat cccccgggct gcagcccaat gtggaattcg   3720
cccttgcaca ttgttactcc tgcatcttaa aaatatatcc tgtagtaatt ttcacagcaa   3780
tgtcataaca tcatctcgct aaagaatgac ctgggattgg agaagtaatg aatatttgca   3840
accaatgcat tgaataaact aacattaaac gaattcacta gtggatcccc caactccgcc   3900
cgttttatga ctagaaccaa tagtttttaa tgccaaatgc actgaaatcc cctaatttgc   3960
aaagccaaac gccccctatg tgagtaatac ggggactttt tacccaattt cccaagcgga   4020
aagcccccta atacactcat atggcatatg aatcagcacg gtcatgcact ctaatggcgg   4080
cccataggga ctttccacat agggggcgtt caccatttcc cagcataggg gtggtgactc   4140
aatggccttt acccaagtac attgggtcaa tgggaggtaa gccaatgggt ttttcccatt   4200
actggcaagc acactgagtc aaatgggact ttccactggg ttttgcccaa gtacattggg   4260
tcaatgggag gtgagccaat gggaaaaacc cattgctgcc aagtacactg actcaatagg   4320
gactttccaa tgggtttttc cattgttggc aagcatataa ggtcaatgtg ggtgagtcaa   4380
tagggacttt ccattgtatt ctgcccagta cataaggtca atagggggtg aatcaacagg   4440
aaagtcccat tggagccaag tacactgcgt caatagggac tttccattgg gttttgccca   4500
gtacataagg tcaatagggg atgagtcaat gggaaaaacc cattggagcc aagtacactg   4560
actcaatagg gactttccat tgggttttgc ccagtacata aggtcaatag ggggtgagtc   4620
aacaggaaag tcccattgga gccaagtaca ttgagtcaat agggactttc caatgggttt   4680
tgcccagtac ataaggtcaa tgggaggtaa gccaatgggt ttttcccatt actggcacgt   4740
atactgagtc attagggact ttccaatggg ttttgcccag tacataaggt caataggggt   4800
gaatcaacag gaaagtccca ttggagccaa gtacactgag tcaataggga ctttccattg   4860
ggttttgccc agtacaaaag gtcaataggg ggtgagtcaa tgggtttttc ccattattgg   4920
cacgtacata aggtcaatag ggtgagtca ttgggttttt ccagccaatt taattaaaac   4980
gccatgtact ttcccaccat tgacgtcaat gggctattga aactaatgca acgtgacctt   5040
taaacggtac tttcccatag ctgattaatg ggaaagtacc gttctcgagc caatacacgt   5100
```

```
caatgggaag tgaaagggca gccaaaacgt aacaccgccc cggttttccc ctggaaattc   5160
catattggca cgcattctat tggctgagct gcgttctacg tgggtataag aggcgcgacc   5220
agcgtcggta ccgtcgcagt cttcggtctg accaccgtag aacgcagagc tcctcgctgc   5280
aggcggccgc tctagaactc gtcgatcgca gcgatgacaa acctgcaaga tcaaacccaa   5340
cagattgttc cgttcatacg gagccttctg atgccaacaa ccggaccggc gtccattccg   5400
gacgacaccc tggagaagca cactctcagg tcagagacct cgacctacaa tttgactgtg   5460
ggggacacag ggtcagggct aattgtcttt ttccctggat tccctggctc aattgtgggt   5520
gctcactaca cactgcagag caatgggaac tacaagttcg atcagatgct cctgactgcc   5580
cagaacctac cggccagcta caactactgc agactagtga gtcggagtct cacagtgagg   5640
tcaagcacac tccctggtgg cgtttatgca ctaaacggca ccataaacgc cgtgaccttc   5700
caaggaagcc tgagtgaact gacagatgtt agctacaatg ggttgatgtc tgcaacagcc   5760
aacatcaacg acaaaattgg gaatgtcctg gtaggggaag gggtcactgt cctcagccta   5820
cccacatcat atgatcttgg gtatgtgagg cttggtgacc ccattcccgc tatagggctt   5880
gacccaaaaa tggtagctac atgcgacagc agtgacaggc ccagagtcta caccataact   5940
gcagccgatg attaccaatt ctcatcacag taccaaccag gtggggtaac aatcacactg   6000
ttctcagcca acattgatgc tatcacaagc ctcagcattg gggagagagct cgtgtttcaa   6060
acaagcgtcc aaggccttgt actgggcgcc accatctacc ttataggctt tgatgggact   6120
gcggtaatca ccagagctgt agccgcagat aatgggctga cggccggcac cgacaatctt   6180
atgccattca atcttgtcat tccaaccaat gagataaccc agccaatcac atccatcaaa   6240
ctggagatag tgacctccaa aagtggtggt caggcagggg atcagatgtc atggtcggca   6300
agtgggagcc tagcagtgac gatccatggt ggcaactatc caggggccct ccgtcccgtc   6360
acactagtag cctacgaaag agtggcaaca ggatccgtcg ttacggtcgc tggggtgagt   6420
aacttcgagc tgattccaaa tcctgaacta gcaaagaacc tggttacaga atacggccga   6480
tttgacccag gagccatgaa ctacacaaaa ttgatactga gtgagaggga ccgtcttggc   6540
atcaagaccg tctggccaac aagggagtac actgattttc gtgagtactt catggaggtg   6600
gccgacctca actctcccct gaagattgca ggagcatttg gcttcaaaga cataatccgg   6660
gctataagga ggtaagcttg atctagagcg gccgcgggga tccagacatg ataagataca   6720
ttgatgagtt tggacaaacc acaactagaa tgcagtgaaa aaaatgcttt atttgtgaaa   6780
tttgtgatgc tattgcttta tttgtaacca ttataagctg caataaacaa gttaacaaca   6840
acaattgcat tcattttatg tttcaggttc agggggaggt gtgggaggtt ttttcggatc   6900
ctctagagtc gacaattatt tcatttaata acatatagcc caaagacctc tatgaacatt   6960
tagtttcccg tatactcaac ggcgcgtgta cacacaaggg cgaattccac agtggatatc   7020
aagcttaatt aagtaccgag ctcgaattgg cgcgccaggt caattccctg gcattatgcc   7080
cagtacatga ccttatggga ctttcctact tggcagtaca tctacgtatt agtcatcgct   7140
attaccatgg tgatgcggtt ttggcagtac atcaatgggc gtggatagcg gtttgactca   7200
cggggatttc caagtctcca ccccattgac gtcaatggga gtttgttttg gcaccaaaat   7260
caacgggact ttccaaaatg tcgtaacaac tccgccccat tgacgcaaat gggcggtagg   7320
cgtgtacggt gggaggtcta tataagcaga gctcgtttag tgaaccgtca gatcgcctgg   7380
agacgccatc cacgctgttt tgacctccat agaagacacc gggcgcgccg gatccatggg   7440
```

-continued

```
ccccagacct tctaccaaga acccagtacc tatgatgctg actgtccgag tcgcgctggt   7500
actgagttgc atctgtccgg caaactccat tgatggcagg cctcttgcgg ctgcaggaat   7560
tgtggttaca ggagacaaag ccgtcaacat atacacctca tcccagacag gatcaatcat   7620
agttaagctc ctcccgaatc tgcccaagga taaggaggca tgtgcgaaag ccccccttgga  7680
tgcatacaac aggacattga ccactttgct caccccccctt ggtgactcta tccgtaggat  7740
acaagagtct gtgactacat ctggaggggg gagacagggg cgccttatag gcgccattat   7800
tggcggtgtg gctcttgggg ttgcaactgc cgcacaaata acagcggccg cagctctgat   7860
acaagccaaa caaaatgctg ccaacatcct ccgacttaaa gagagcattg ccgcaaccaa   7920
tgaggctgtg catgaggtca ctgacggatt atcgcaacta gcagtggcag ttgggaagat   7980
gcagcagttt gttaatgacc aatttaataa aacagctcag gaattagact gcatcaaaat   8040
tgcacagcaa gttggtgtag agctcaacct gtacctaacc gaattgacta cagtattcgg   8100
accacaaatc acttcacctg ctttaaacaa gctgactatt caggcacttt acaatctagc   8160
tggtggaaat atggattact tattgactaa gttaggtgta gggaacaatc aactcagctc   8220
attaatcggt agcggcttaa tcaccggtaa ccctattcta tacgactcac agactcaact   8280
cttgggtata caggtaactc taccttcagt cgggaaccta aataatatgc gtgccaccta   8340
cttggaaacc ttatccgtaa gcacaaccag gggatttgcc tcggcacttg tcccaaaagt   8400
ggtgacacag gtcggttctg tgatagaaga acttgacacc tcatactgta tagaaactga   8460
cttagattta tattgtacaa gaatagtaac gttccctatg tcccctggta tttattcctg   8520
cttgagcggc aatacgtcgg cctgtatgta ctcaaagacc gaaggcgcac ttactacacc   8580
atacatgact atcaaaggtt cagtcatcgc caactgcaag atgacaacat gtagatgtgt   8640
aaacccccccg ggtatcatat cgcaaaacta tggagaagcc gtgtctctaa tagataaaca  8700
atcatgcaat gttttatcct taggcgggat aactttaagg ctcagtgggg aattcgatgt   8760
aacttatcag aagaatatct caatacaaga ttctcaagta ataataacag gcaatcttga   8820
tatctcaact gagcttggga atgtcaacaa ctcgatcagt aatgctttga ataagttaga   8880
ggaaagcaac agaaaactag acaaagtcaa tgtcaaactg actagcacat ctgctctcat   8940
tacctatatc gttttgacta tcatatctct tgtttttggt atacttagcc cgattctagc   9000
atgctaccta atgtacaagc aaaaggcgca acaaaagacc ttattatggc ttgggaataa   9060
tactctagat cagatgagag ccactacaaa aatgtgagga tctctcgagg aattctagat   9120
cccacgtcac tattgtatac tctatattat actctatgtt atactctgta atcctactca   9180
ataaacgtgt cacgcctgtg aaaccgtact aagtctcccg tgtcttctta tcaccatcag   9240
gtgacatcct cgcccaggct gtcaatcatg ccggtatcga ttccagtagc accggcccca   9300
cgctgacaac ccactcttgc agcgttagca gcgcccctct taacaagccg acccccacca   9360
gcgtcgcggt tactaacact cctctccccg acctgcaact agtgcggccg cagcttgcct   9420
ccgattctag cattacatag ccggtcagta gatcctgcca ttcggtagcg caaccggcta   9480
catcttcaaa cagtctcacg ataaatgcat ctctcgttcc tgccaatccg gaaccgggca   9540
taccactccc gcctgccgat ttaattctca caattgggcg atgccggcgg ggcaaaacga   9600
atgtggattt ggcaaaccga cacaggtctg ctgtacggac taatatgggc acacccacat   9660
cattcttcag atgctccatg cattgttcta tgagaaagat ccatagggtg gaggcagcgt   9720
cacgagatcg cccaggcaat cgatcgcatt cgtctagtaa agtgacgaga gttatcatgc   9780
acacacccat gcccacgcct tccgaataac tggagctgtg gaagatcgga aacgtctttt   9840
```

```
tgactgccgg tctcgtacta ctttcgcaca ggtgtatacc cggacgcgta ctatatattt   9900
tatatcatcc aacgtcccga aattacatac gtggcggcga tggaagtaga tgttgagtct   9960
tcgaaagtaa gtgcctcgaa tatgggtatt gtctgtgaaa atatcgaaag cggtacgacg  10020
gttgcagaac cgtcgatgtc gccagatact agtaacaata gcttcgataa cgaagacttc  10080
cgtgggcctg aatacgatgt ggagataaat accagaaaat ctgctaatct tgatcgtatg  10140
gaatcttcgt gccgtgaaca acgagcggcg tgcgaacttc gaaagtgttc gtgtcctacg  10200
tctgccgtgc gcatgcaata cagtattctt tcatctctcg ctccgggttc agagggtcat  10260
gtatatatat gtactagata cggggacgcg gaccaaaaaa aatgcatagt gaaggcagtc  10320
gttggaggaa agaatcccgg gagggaagtg gatattttaa aaaccatctc acataaatca  10380
attataaaat taatccatgc ctataaatgg aaaaatgttg tgtgtatggc aatgcgtgta  10440
tatcgttatg atcttttcac atatattgac ggagtcggcc ctatgcccct tcaacagatg  10500
atctatattc aacgtggact actagaggcg ctagcataca tacatgaaag ggcatcatt   10560
caccgagacg taaagacgga gaatatattc ttggataatc acgaaaatgc agttttgggt  10620
gacttcggtg ctgcatgcca actaggagat tgtatagata cgccccaatg ttacggttgg  10680
agcggaactg tggaaacaaa ttcgccggaa ttatctgcac ttgatccgta ttgcacaaaa  10740
acagatattt ggagtgccgg attggttcta tatgagatgg caattaaaaa tgtaccattg  10800
tttagtaagc aggtgaaaag ttcgggatct cagctgagat ccataatacg gtgcatgcaa  10860
gtgcatgaac tggagtttcc ccgcaacgat tctaccaacc tctgtaaaca tttcaaacaa  10920
tatgcggttc gtgtacgacc gccttatacc attcctcgag ttataagaaa tgggggggatg  10980
ccaatggatg ttgaatatgt catttctaaa atgcttacgt ttgaccagga gttcagacct  11040
tctgctaagg aaatattgaa tatgccccta tttactaagg cgccgattaa cctgcttaat  11100
atcacaccct ctgacagtgt ctaacggtat acaggcggga gcgggtcgtg gcgtcatcat  11160
caccacttga gaatttatat tttgaattgt tgattgataa attaacctga ttcattgaga  11220
actgaaacgc catattggtt tcttggatat gtctacaaca attagttaaa ttgctatgtt  11280
ctactgcgag taacatttga taagttgtaa gagacgggcg actcatgtcg aagttgacga  11340
atataaagta cataacgtgt ttagaatacc cagaatccga atagtccgcg ggggcgtctt  11400
ctcgcgtgag taccaaatac tgagttgaac ttgaaaatgc taaatctgtg acactctttg  11460
tgtgatgatt attgtcacca cttcgaagat ggcttcgaca ttcatgatgt tctggtgttt  11520
gtttggaatc gtaatagcgc ttgtttcgtc caagtctgac aacaaagaaa atctgaagaa  11580
ttatatcacg gataagtcaa ccaatattag aatacccacg ccattatttg tatcaacgga  11640
aaactcttat cccacaaaac atgtaatcta cgatgaaaac tgtggcttcg ctgtactcaa  11700
tcctataagt gaccccaaat atgtcctttt gagccagctt ctaatgggaa ggcgcaaata  11760
tgatgcgacg gtcgcgtggt ttgttctcgg taaaatgtgt gccagattaa tatatttgcg  11820
cgaattttat aactgctcga caaatgagcc ttttggcaca tgttctatga gctctcctgg  11880
atggtgggac aggcgctacg tctcaaccag tttcatttct cgcgacgaat tacagctggt  11940
ttttgcagcg ccgtcccgag aattagatgg tttatatacg cgcgtagtag ttgtcaacgg  12000
ggactttact acggccgata taatgtttaa tgttaaagtg gcatgtgcct tttcaaagac  12060
tggaatagaa gatgatacat tatgcaaacc ctttcatttc tttgccaatg caacattgca  12120
caatttaacc atgattagat cggtaactct tcgagcgcac gaaagccatt taaaggaatg  12180
```

```
ggtggcacgg agaggtggta acgtccctgc agtgctactt gagtctacca tgtatcatgc  12240

atccaatctg cctagaaatt tcagggattt ctacataaag tctccagatg attataagta  12300

taatcaccta gatgggccat ctgtaatgct catcactgac agacctagtg aagatttgga  12360

tgggaggctc gttcaccaaa gtgacatttt tactactaca agtcctataa aacaggtccg  12420

gtatgaagag catcagtcac atacaaagca gtatcctgta aacaaaatac aagctataat  12480

ttttttgata gggttaggct cgttcattgg aagcatattc gtagttttgg tagtatggat  12540

tatacgcaga tattgcaatg gagcgcggag tgggggaacg ccccccagtc ctcgccggta  12600

tgtgtatacc aggctatgat cacgtgtgaa acttgggcgg acctgtatca tatgtacacc  12660

gtccctattc gtttatagcc agtacgtgtt atctgcacat agaggaacat gtgtcatact  12720

gggatcgcat gcatggtatg tgtgactcta atattattct gtatcataat aaaaacacag  12780

tgcatggtat atagaggatc gctggtaagc actacggtag accaatcggc tcagattgca  12840

ttctttggca tcgataccgt tgttaattta tatggcaaag tcttgttcat gggagatcag  12900

tatttggagg aaatatactc tggaacgatg gaaatactca aatggaatca agctaaccgc  12960

tgctattcta ttgcgcatgc aacatattac gccgactgtc ctataatcag ttctacggta  13020

ttcagaggat gccgggacgc cgttgtttat actaggcccc acagcaga              13068
```

<210> SEQ ID NO 31
<211> LENGTH: 14598
<212> TYPE: DNA
<213> ORGANISM: Artificial Sequence
<220> FEATURE:
<223> OTHER INFORMATION: Expression cassette

<400> SEQUENCE: 31

```
cgcgccactg gagaacggca tgaccgcaaa aggcgttgta gagatcgatc ccacgaactc     60

tcaggcgatc gtgtcagtcg ccataaacag cgacgatcgt ctccaggatc tgaacggttt    120

tcttctcaac gatcatcagt atatgaggaa ctgaacctga tatttagccg agggaaacgc    180

aggttaaaaa ccctatcaag cgattgcgat tttcgcgtat ctagtaaaaa tagatgggct    240

tcggtactag ccttcgccgc caactctgaa tatgcccttc gtggacctca tataacatgg    300

cattgtttgt tggatgcggg gccggaatta agaagaacat tcgaaatacg agcaaaaatt    360

tcggccctgg catgtgctgc gcgagaatcg gtacttcggg gagaaagttt tatcggagct    420

ttgggtagtg cagaggaaac tctatcttgg ttgaaaatgc atgcgaccct gcacttgatt    480

ctggttaacc acgatccaat ttttaagacg gctggcgcgg tcctagataa cctccgctta    540

aaactagccc caatattgat gtgcagatat aacacagaaa aacgatcaat ggaagacatg    600

ctacggcggt catctcccga agacatcacc gattccctaa caatgtgcct gattatgtta    660

tcgcgcattc gtcgtaccat gcgcaccgca ggaaataaat atagctatat gatagatcca    720

atgaatcgta tgtctaatta cactccaggc gaatgtatga caggtatatt gcgatatatt    780

gacgaacatg ctagaaggtg tcctgatcac atatgtaatt tgtatatcac atgtacactt    840

atgccgatgt atgtgcacgg gcgatatttc tattgtaatt cattttttttg ttagtaaact    900

accacaggct gtccggaaat ctaagttaat gaataaagta gatggttaat actcattgct    960

tagaattgga ctacttttaa ttctctttaa tgttcgtatt aaataaaaac atctttaata   1020

aacttcagcc tcttcgctta ttgtagaaat tgagtattca aaatcatgtt caaagccgtc   1080

ttcggagagt gtactcgcca cggtggttgg aacatcacta tgtctacacg tcaaatttaa   1140

gcacgtcagg tctgtcgagg acaagaaatg gttaactagt gtttcaatta ttcttataaa   1200
```

-continued

```
cgttaagcat tgtaagcccc ccggccgtcc gcagcaacaa tttactagta tgccgtgggc   1260
tccgggacta tcacggatgt ccaattcgca catgcatata atttttctag ggtctctcat   1320
ttcgagaaat cttcggggat ccatcagcaa tgcgggctgt agtcccgatt cccgtttcaa   1380
atgaaggtgc tccaacacgg tcttcaaagc aaccggcata ccagcaaaca cagactgcaa   1440
ctccccgctg caatgattgg ttataaacag taatctgtct tctggaagta tatttcgccc   1500
gacaatccac ggcgccccca aagttaaaaa ccatccatgt gtatttgcgt cttctctgtt   1560
aaaagaatat tgactggcat tttcccgttg accgccagat atccaaagta cagcacgatg   1620
ttgcacggac gactttgcag tcaccagcct tcctttccac ccccccacca acaaaatgtt   1680
tatcgtagga cccatatccg taataaggat gggtctggca gcaaccccat aggcgcctcg   1740
gcgtggtagt tctcgaggcc ttaattaagt cgacggcaga gtcgcagacg cccctattgg   1800
acgtcaaaat tgtagaggtg aagttttcaa acgatggcga agtaacggcg acttgcgttt   1860
ccaccgtcaa atctccctat agggtagaaa ctaattggaa agtagacctc gtagatgtaa   1920
tggatgaaat ttctgggaac agtcccgccg ggtttttaa cagtaatgag aaatggcaga   1980
aacagctgta ctacagagta accgatggaa gaacatcggt ccagctaatg tgcctgtcgt   2040
gcacgagcca ttctccggaa ccttactgtc ttttcgacac gtctcttata gcgagggaaa   2100
aagatatcgc gccagagtta tactttacct ctgatccgca aacggcatac tgcacaataa   2160
ctctgccgtc cggcgttgtt ccgagattcg aatggagcct taataatgtt tcactgccgg   2220
aatatttgac ggccacgacc gttgtttcgc ataccgctgg ccaaagtaca gtgtggaaga   2280
gcagcgcgag agcaggcgag gcgtggattt ctggccgggg aggcaatata tacgaatgca   2340
ccgtcctcat ctcagacggc actcgcgtta ctacgcgaaa ggagaggtgc ttaacaaaca   2400
catggattgc ggtggaaaac ggtgctgctc aggcgcagct gtattcactc ttttctggac   2460
ttgtgtcagg attatgcggg agcatatctg ctttgtacgc aacgctatgg accgccattt   2520
atttttgagg aatgcttttt ggactatcgt actgctttct tccttcgcta gccagagcac   2580
cgccgccgtc acgtacgact acattttagg ccgtcgcgcg ctcgacgcgc taaccatacc   2640
ggcggttggc ccgtataaca gatacctcac tagggtatca agaggctgcg acgttgtcga   2700
gctcaacccg atttctaacg tggacgacat gatatcggcg gccaaagaaa aagagaaggg   2760
gggccctttc gaggcctccg tcgtctggtt ctacgtgatt aagggcgacg acggcgagga   2820
caagtactgt ccaatctata gaaaagagta cagggaatgt ggcgacgtac aactgctatc   2880
tgaatgcgcc gttcaatctg cacagatgtg ggcagtggac tatgttccta gcacccttgt   2940
atcgcgaaat ggcgcgggac tgactatatt ctcccccact gctgcgctct ctggccaata   3000
cttgctgacc ctgaaaatcg ggagatttgc gcaaacagct ctcgtaactc tagaagttaa   3060
cgatcgctgt ttaaagatcg ggtcgcagct taacttttta ccgtcgaaat gctggacaac   3120
agaacagtat cagactggat ttcaaggcga acacctttat ccgatcgcag acaccaatac   3180
acgacacgcg gacgacgtat atcggggata cgaagatatt ctgcagcgct ggaataattt   3240
gctgaggaaa aagaatccta gcgcgccaga ccctcgtcca gatagcgtcc cgcaagaaat   3300
tcccgctgta accaagaaag cggaagggcg caccccggac gcagaaagca gcgaaaagaa   3360
ggcccctcca gaagactcgg aggacgacat gcaggcagag gcttctggag aaaatcctgc   3420
cgccctcccc gaagacgacg aagtccccga ggacaccgag cacgatgatc caaactcgga   3480
tcctgactat tacaatgaca tgcccgccgt gatcccggtg gaggagacta ctaaaagttc   3540
```

```
taatgccgtc tccatgccca tattcgcggc gttcgtagcc tgcgcggtcg cgctcgtggg   3600
gctactggtt tggagcatcg taaaatgcgc gcgtagctaa tcgagcctag aataggtggt   3660
ttcttcctac atgccacgcc tcacgctcat aatataaatc acatggaata gcataccaat   3720
gcctattcat tgggacgttc gaaaagcatg gcatcgctac ttggaactct ggctctcctt   3780
gccgcgacgc tcgcaccctt cggcgcgatg ggaatcgtga tcactggaaa tcacgtctcc   3840
gccaggattg acgacgatca catcgtgatc gtcgcgcctc gccccgaagc tacaattcaa   3900
ctgcagctat ttttcatgcc tggccagaga ccccacaaac cctactcagg aaccgtccgc   3960
gtcgcgtttc ggtctgatat aacaaaccag tgctaccagg aacttagcga ggagcgcttt   4020
gaaaattgca ctcatcgatc gtcttctgtt tttgtcggct gtaaagtgac cgagtacacg   4080
ttctccgcct cgaacagact aaccggacct ccacacccgt ttaagctcac tatacgaaat   4140
cctcgtccga acgacagcgg gatgttctac gtaattgttc ggctagacga caccaaagaa   4200
cccattgacg tcttcgcgat ccaactatcg gtgtatcaat tcgcgaacac cgccgcgact   4260
cgcggactct attccaaggc ttcgtgtcgc accttcggat tacctaccgt ccaacttgag   4320
gcctatctca ggaccgagga aagttggcgc aactggcaag cgtacgttgc cacggaggcc   4380
acgacgacca gcgccgaggc gacaaccccg acgcccgtca ctgcaaccag cgcctccgaa   4440
cttgaagcgg aacactttac ctttccctgg ctagaaaatg gcgtggatca ttacgaaccg   4500
acacccgcaa acgaaaattc aaacgttact gtccgtctcg ggacaatgag ccctacgcta   4560
attggggtaa ccgtggctgc cgtcgtgagc gcaacgatcg gcctcgtcat tgtaatttcc   4620
atcgtcacca gaaacatgtg caccccgcac cgaaaattag acacggtctc gcaagacgac   4680
gaagaacgtt cccaaactag aagggaatcg cgaaaatttg gacccatggt tgcgtgcgaa   4740
ataaacaagg gggctgacca ggatagtgaa cttgtggaac tggttgcgat tgttaacccg   4800
tctgcgctaa gctcgcccga ctcaataaaa atgtgattaa gtctgaatgt ggctctccaa   4860
tcatttcgat tctctaatct cccaatcctc tcaaaagggg cagtatcgga cacggactgg   4920
gaggggcgta cacgatagtt atatggtaca gcagaggcct ctgaacactt aggaggagaa   4980
ttcagccggg gagagcccct gttgagtagg cttgggagca tattgcagga tgaacatgtt   5040
agtgatagtt ctcgcctctt gtcttgcgcg cctaactttt gcgacgcgac acgtcctctt   5100
tttggaaggc actcaggctg tcctcgggga agatgatccc agaaacgttc cggaagggac   5160
tgtaatcaaa tggacaaaag tcctgcggaa cgcgtgcaag atgaaggcgg ccgatgtctg   5220
ctcttcgcct aactattgct ttcatgattt aatttacgac ggaggaaaga aagactgccc   5280
gcccgcggga cccctgtctg caaacctggt aattttacta aagcgcggcg aaagcttcgc   5340
gccaggtcaa ttccctggca ttatgcccag tacatgacct tatgggactt tcctacttgg   5400
cagtacatct acgtattagt catcgctatt accatggtga tgcggttttg gcagtacatc   5460
aatgggcgtg gatagcggtt tgactcacgg ggatttccaa gtctccaccc cattgacgtc   5520
aatgggagtt tgttttggca ccaaaatcaa cgggactttc caaaatgtcg taacaactcc   5580
gccccattga cgcaaatggg cggtagcgtg tacggtggga ggtctatata agcagagctc   5640
gtttagtgaa ccgtcagatc gcctggagac gccatccacg ctgttttgac ctccatagaa   5700
gacaccggtt gcgccgccac catgggcccc agaccttcta ccaagaaccc agtacctatg   5760
atgctgactg tccgagtcgc gctggtactg agttgcatct gtccggcaaa ctccattgat   5820
ggcaggcctc ttgcggctgc aggaattgtg gttacaggag acaaagccgt caacatatac   5880
acctcatccc agacaggatc aatcatagtt aagctcctcc cgaatctgcc caaggataag   5940
```

gaggcatgtg cgaaagcccc cttggatgca tacaacagga cattgaccac tttgctcacc 6000
ccccttggtg actctatccg taggatacaa gagtctgtga ctacatctgg aggggggaga 6060
caggggcgcc ttataggcgc cattattggc ggtgtggctc ttggggttgc aactgccgca 6120
caaataacag cggccgcagc tctgatacaa gccaaacaaa atgctgccaa catcctccga 6180
cttaaagaga gcattgccgc aaccaatgag gctgtgcatg aggtcactga cggattatcg 6240
caactagcag tggcagttgg gaagatgcag cagtttgtta atgaccaatt taataaaaca 6300
gctcaggaat tagactgcat caaaattgca cagcaagttg gtgtagagct caacctgtac 6360
ctaaccgaat tgactacagt attcggacca caaatcactt cacctgcttt aaacaagctg 6420
actattcagg cactttacaa tctagctggt ggaaatatgg attacttatt gactaagtta 6480
ggtgtaggga acaatcaact cagctcatta atcggtagcg gcttaatcac cggtaaccct 6540
attctatacg actcacagac tcaactcttg ggtatacagg taactctacc ttcagtcggg 6600
aagctaaata atatgcgtgc cacctacttg gaaaccttat ccgtaagcac aaccagggga 6660
tttgcctcgg cacttgtccc aaaagtggtg acacaggtcg gttctgtgat agaagaactt 6720
gacacctcat actgtataga aactgactta catttatatt gtacaagaat agtaacgttc 6780
cctatgtccc ctggtattta ttcctgcttg agcggcaata cgtcggcctg tatgtactca 6840
aagaccgaag gcgcacttac tacaccatac atgactatca aaggttcagt catcgccaac 6900
tgcaagatga caacatgtag atgtgtaaac cccccgggta tcatatcgca aaactatgga 6960
gaagccgtgt ctctaataga taaacaatca tgcaatgttt tatccttagg cgggataact 7020
ttaaggctca gtggggaatt cgatgtaact tatcagaaga atatctcaat acaagattct 7080
caagtaataa taacaggcaa tcttgatatc tcaactgagc ttgggaatgt caacaactcg 7140
atcagtaatg ctttgaataa gttagaggaa agcaacagaa aactagacaa agtcaatgtc 7200
aaactgacta gcacatctgc tctcattacc tatatcgtgt tgactatcat atctcttgtt 7260
tttggtatac ttagcctgat tctagcatgc tacctaatgt acaagcaaaa ggcgcaacaa 7320
aagaccttat tatggcttgg gaataatact ctagatcaga tgagagccac tacaaaaatg 7380
tgaggatctc tcgaggaatt ctagatccca cgtcactatt gtatactcta tattatactc 7440
tatgttatac tctgtaatcc tactcaataa acgtgtcacg cctgtgaaac cgtactaagt 7500
ctcccgtgtc ttcttatcac catcaggtga catcctcgcc caggctgtca atcatgccgg 7560
tatcgattcc agtagcaccg gccccacgct gacaacccac tcttgcagcg ttagcagcgc 7620
ccctcttaac aagccgaccc ccaccagcgt cgcggttact aacactcctc tccccgacct 7680
gcaactagta agcttcccgg gttaattaag gccctcgagg atacatccaa agaggttgag 7740
tattctctct acacttcttg ttaaatggaa agtgcattg cttgttctta caatcggccc 7800
gagtctcgtt cacagcgcct cgttcacact taaaccacaa atagtctaca ggctatatgg 7860
gagccagact gaaactcaca tatgactaat attcgggggt gttagtcacg tgtagcccat 7920
tgtgtgcata taacgatgtt ggacgcgtcc ttattcgcgg tgtacttgat actatggcag 7980
cgagcatggg atattcatcc tcgtcatcgt taacatctct acgggttcag aatgtttggc 8040
atgtcgtcga tcctttgccc atcgttgcaa attacaagtc cgatcgccat gaccgcgata 8100
agcctgtacc atgtggcatt agggtgacat ctcgatcata cattataaga ccaacgtgcg 8160
agtcttccaa agacctgcac gccttcttct tcggattgtc aacgggttct tcagaatcta 8220
tgcccatatc tggcgttgag accattgtgc gtttaatgaa caataaagcg gcatgccatg 8280
gaaaggaggg ctgcagatct ccattttctc acgccactat cctggacgct gtagacgata 8340
attataccat gaatatagag gggtatgtt tccactgcca ctgtgatgat aagttttctc 8400
cagattgttg gatatctgca ttttctgctg ccgaacaaac ttcatcgcta tgcaaagaga 8460
tgcgtgtgta cacgcgccgt tgagtatacg ggaaactaaa tgttcataga ggtctttggg 8520
ctatatgtta ttaaataaaa taattgacca gtgaacaatt tgtttaatgt tagtttattc 8580
aatgcattgg ttgcaaatat tcattacttc tccaatccca ggtcattctt tagcgagatg 8640
atgttatgac attgctgtga aaattactac aggatatatt tttaagatgc aggagtaaca 8700
atgtgcatag taggcgtagt tatcgcagac gtgcaacgct tcgcatttga gttaccgaag 8760
tgcccaacag tgctgcggtt atggtttatg cgcacagaat ccatgcatgt cctaattgaa 8820
ccatccgatt tttcttttaa tcgcgatcgt tgtttgggca actgcgttat ttcagatcta 8880
aaaaatttac cctttatgac catcacatct ctctggctca taccccgctt ggataagata 8940
tcatgtagat tccgccctaa gaaatgcaaa ctaacattat tgtcggttcc atatacactt 9000
ccatcttgtc cttcgaaaat aacaaactcg cgcaatagac cgtccgtaca tgcatggccg 9060
atgtgtgtca acatcattgg tctgctagat cccgatggga cgaatcgtac agtcgtcgct 9120
ccagcattgg caaaaatccc cagataccct ccatgcggca aatctaaatt gcgaccccga 9180
agagactgca ccaaagtctt atcgacgcac gctgattttt ttgaacagcg ggagcccatt 9240
atcttcagtg gagcgtagac gggcgaggct aattatgtga catagcaaca ctgcatgtat 9300
gtttttataa atcaataaga gtacataatt tattacgtat catttccgtt tgtaatatac 9360
tgtatacatc atccacacta ttagtcagca ctagcgcgcg ggcgcacgtt acaatagcag 9420
cgtgcccgtt atctatattg tccgatattt acacataaca tttcatcgac atgattaaat 9480
acctaagtac tgcacacaga tgtttaatgt atatcgtcat ataaattata tcgctaggac 9540
agacccaaac gacctttatc ccaaacagtc agatcctctt ctcaagtgtc gatttctgtt 9600
atggaatatg catacctgg cccagaaatt gcacgcacga gcgtagtgaa tgcgtcattg 9660
gttttacatt taaaggctaa atgcacaaat tctttagacg acagcacatc gttaaatagc 9720
atctctagcg ttcttatgaa tgctaagcat tggagtcctc ctggtcggcc acaataacag 9780
ctgagtatca taccctgagc tccggggttg tcgcacatag cggattcgta taaacatagg 9840
attttccgcg aatccatcag ttgcaaaaat ctgttaggct ccatcaacaa cgctggattt 9900
acttcagatc cacgcgtaaa gtaatggtgc tcgaataccg tttttagagt tgtcggcatt 9960
tcaaggaaca aagaattcat ttcttcattg caacgacgcg ccagaaatcc caagacctct 10020
ttgggtagta tgttcttgcc tataaaacac ggcgttccaa gtgccaggaa ccacgcatgt 10080
gttactgttg gggcgtattc agaaataaag cggggtttat gcggcttttg aagctcggat 10140
atccaaagta tcgcttgctg atgaacgagc gatgtagctg ttacaaaacc tcctttccat 10200
cctccagtca acataatatt tatcggccta cctatgtccg taataagtat tggtcgggca 10260
attattccgt atgaggtctt gcaggaataa gctcttaggg acagccagct tggatatggt 10320
gcgaaacaga ccttctcggc ttcagaatgt cgctccgcag tctcttcgtg tcggtgcatc 10380
ttagatccac catcaatgtg tgcagcattg actcccgccc gtcgaatatt ccttttgtta 10440
cgatgcagta atgagcacga tcatgggcgg ggcgatgacg ttctatttgc atgtctgcga 10500
acaatttgcg tcagtcatac agctatggag tgggccattt ctggccgtca acttaaaaac 10560
gcgaaccgca gacatatgta tttgcatgca aagacgtatc ttcgtatttc tgggcatctt 10620
caaatgctct ggccaatatg gcaatgaatt tggattcgtt tgacgccgat ggtatgcagt 10680

```
gcaaatgtgc caatagccca catccgaaaa agttatttgt catacaagca ggtgttaagt  10740
agcaatcaca taaaggcacc agacgcctca tggcatcata atgaatagct ccttctcccc  10800
actggaacca ctgacaaaat ctgcgagtat attccgcaaa ccacatttta tttctcatag  10860
aaactaccct aaatcctttt aacgggaaga agaatcctag atagtgcttg aagtcatgac  10920
tgttactgct gcaataacac tgtatattat ttataaattc cgtttgtcta ggtatctgat  10980
gtaggcattc cgatcccttt actattgcgt cttcacgacc aaatgggaat gcgccaaaat  11040
ccccacacct catcaccctg gaggcagatt gtgtattatt aatatccgcc gattgaagca  11100
caaaacggta cggtactgtt cctaattctg gtatagattc tatggtcaaa agtctgcata  11160
tccccgacat tgccatgaga tcacacagtc caagtagcat gtttattgag tcactcagac  11220
tgtcaacgtc cctcgccgca ccaccaatcg aaaataaagt atctacgcaa gttatagctc  11280
cgcattttct atcgctagca gcaatcgcga cgcaaaacat aaaggccatg ttgggatttg  11340
aactctctgg ggggcttgtt atcttctgca ccgtcgcagt cgcagttttc cgaaatttat  11400
gtctaatata ttttccggcc gtgctccaat cggccgaaaa gaatctgcgt attaccagac  11460
tcattgacgg gccgataaag accataaaac aaaattcctg tgcactccct cctccagttt  11520
tgccatcgtc caagtcccgt aacttttttt gcgtttcgag gagcaagcgt tcgttatccc  11580
tacccacact tgttttccac cgttttctta ttataagcgg ttgtatcgcc aacgcgtcac  11640
cgcaggttgt cacatacagt gatggcatac ttgaacgtgc aacaacgcgc tcgctttgca  11700
aatctaagtc attgaccatc aaatcgcgtt gagaggatag ccaggcatct tttttcctag  11760
tatggtgacg gtgcagccac cccaactcag ttcttgtaaa aaaagctatt ggcgggaatt  11820
tatgttctga ggtgcattct atatttatga gtccatcaaa tgccattaac cagattcgta  11880
ttttttcgct cgacccggca tcactatgga tacaatacct ttctatggcc catttcagct  11940
ctcgaaccaa ccacacggac aattgactaa cataagtatg atctttatca cagtcgcacc  12000
catctgagtt atatttatgg catccgagcg ctcttactgt acggtcggat acacccatgg  12060
tttttccttt atatagtcgg gttatagtct gtcgggtttg gcggtagcac ggagtagttt  12120
gatttttaag aatcgaaaac cggcttggag agaccactgt cgaatatttg tccgtatact  12180
ctacacgtga gtgttgtcca ttcctaggta tattcatctg ttcggatacc ttcaattgct  12240
gttcaggcat aaccttaaag catatgttat gttgtacatc aaaacttggt gagttatgtt  12300
cgattgccgc gcataaagaa tcgtacatga gcgtttctgc taacatacta tctatattct  12360
cacacgcccc tgcatatact gttcctattc caaattcacg ttttgcccca tcggctatct  12420
gctcccaaaa agttgtaata taggtgccgc tgggtgcgaa attttcatca gttgtattcc  12480
tgataaactg aatcacttta cataattttt gccacatatc tgcgtgcagc catagtatcg  12540
aacccgtggg ctcggagacg acagtgcgta caatgggtat tttacctttc cccaacaaaa  12600
taatggtata caagttaggt ccgtacctag accttaatgt ttccaattct tctgaatcac  12660
tgcactctcg taggggagta acggtaataa tttcgtctct gagccccgtt ttgcgttgaa  12720
aactaatcac attagataat gtgcaatcgg tttcttttat ccggatacat ctaagtatta  12780
tgacatcggt ggtcattgtt tccatcaacg accatctttt acgatcgccc atactactca  12840
tggacgttgt cggtgttgaa aaatcaccag aattgcaacg gatctctggg taccatgctg  12900
ctgatggaat tggcggtttt aattgttgtt tcagtctatt attgctatct ttggcggggt  12960
tgaataatgt ggggggagag tgattgcagg aatccgaatg ggtcaataaa acgaccgtgc  13020
```

tccgttctgc cggcgccgat ccgattgaag ctatatactt cgcttctctc cccacttttc 13080
caatttgatc cggaaataaa acggccccgg acaacagtat cgtacgatcc ggatccggat 13140
cctgcttgcc tacagaagaa tcaacatctc gccccaatat tctggtcaaa actggctcgc 13200
tcatggcaac gcggacgttt cccccggtgg ccagtcttaa tggttaatgt tcttttcggc 13260
aatcttatac atcagcgggt tgcgtgaata ctggtcacag ttcagtcatt tactacacac 13320
cagcaatacg acgacggaca gtaccgtccc gacgaacgcg acgcccaaaa ttgctatcgc 13380
gaccgcgtcc gaggcgatgt cgtacgggcg gtgcggggtt ggatcctcgg caaagagatc 13440
ctcgtaattc ggcggtggga gcggagggta aagacgcggg tggggatctc cctccggacc 13500
gcgcgccggg cgcggttcga aaatgctttc cgcctcgctc agtgtcaacg ccaagtattc 13560
gggcgggctg ggggccggaa tatctcccgc gacttcttct atcggcgcgg aattggagtc 13620
gcggtcgtgg cgcgcttcta gcgtcgtcaa cggaagtcca ttttcggggt ctcccggtgg 13680
gcgttcagcg tccatcgtcg tatatgctct aacacacgtc tcgctatatt aaaaaaaaga 13740
agagtatcgg tcagtgtcga gtgtcgccga caatgtcgcg agttctcggc gatttaattt 13800
ttggaactgc tccctatgaa tcccgtaact gtagcgcccg cgcagaaagc cgccatcaga 13860
ccaactacgt gtctgttcga tgtttgcccg ccgatcgctt taccgattaa ggttccggcg 13920
agaaatgaca tgctcgatcc aagaacaaag tttttcgcgg taaacaacaa catagttacc 13980
gtgcgagatg gagaaaccac atctcccgaa ttagtagagg aaagcccgcg ctgtcggttt 14040
ggggacatat cgatcttttt tgtgtttttc ctaggaccct tttgccagat cgtacaaagt 14100
cgcgtcttat gagcggacgt tcttactgca gctcggtagg agtggggcag ggttagattt 14160
cgtcggcgtt tcggcccccg tatgcgccgc gccaccctct tcgccgagct ctttatgcgc 14220
ggtgggggtg agcgcttccg gagttgcgat ctccgatctc gagccgcagc ccggcggtgt 14280
ctctttcagt ggagcgttag cgccatcatg tggttcgtgg cggtggaaag gctattatgt 14340
gttaggggag agaccacgtg atcggcatgc aaatgagcaa ggcgaacgcg tcagcgttcg 14400
cactgcgaac caataatata tatattatac tattggcttt aggtgcgaac gtccggctag 14460
tccaatagcg gggtcgcgtt tcgtaccacg tgttatagac cgccctaaac tcgcactcgg 14520
gggtccggcc gcgcccagac agggcggaga cgtgccacag gggctttaaa acaccgcttc 14580
gggcaccgtt catctcgg 14598

<210> SEQ ID NO 32
<211> LENGTH: 10681
<212> TYPE: DNA
<213> ORGANISM: Artificial Sequence
<220> FEATURE:
<223> OTHER INFORMATION: Expression cassette

<400> SEQUENCE: 32
aattccagac taaatgcccc ggcccaattt gtcaagtgtg cagtcacgga ggcgtcgacc 60
gtgtccccgg cattaaacag gaaagcgtta aagtttttga atgttaggtc acaggtacaa 120
acataaatgt ttgtacaaac aggtaacagg tacaaacata aatgccccgg cataaatgtc 180
ccttacggcg gatcgaaacg acattaggca tactcgggta ccattttgca ttccgatcag 240
cacggatgaa attaggcagg aatgcggttt atattatgcg gcattggaca aacgatatgg 300
cattgattgg cagtttatga atgtcttcat gttgggcgta aacggattcc tattggttca 360
gaagacaacg acgatatatt tagagagaaa aagctaccca gcataggata aacacacatt 420
gagcattgag agacataggt atcggtatgg atgggaaaac tacacacgtg aacaccaaac 480

```
gacttatata ctcgagcggt gatactactg agcaagaatg cactgcatct gagccactga    540
atgaagactg tgatgaaaat gtgaccatcg atggaattgg agaagaatat gcgcagttct    600
tcatgtcccc gcaatgggtc ccaaatctac atcgcttgag cgaggatacc aaaaaggtat    660
accgatgtat ggtttccaac agactcaatt attttcccta ttatgaggcg ttcaggcggt    720
ctttgtttga tatgtatatg ctaggtcggt tggggcgtcg acttaagcga tctgactggg    780
agactattat gcatctgtca ccaacgcaaa gtcggcgtct acatagaact ttaagatttg    840
tggagcgtag aattatccca tctaacagtt atatacgcac atcgggccac gttccgcctt    900
cgagggcact tccgacagat acgaatttaa agatggatga ataattaaat tggaaagagt    960
aactacatta atcgagcgtc atgacggcgt cccgtgaaaa tgggaatttt ctactcgaaa   1020
caccgtgaca tttgacagac ctggaattgt tattctgata tatagtgggt gtgtctggcc   1080
ggcaacatac ataatgtgca tgcgaaacca ctttttcagt gtacgctgac attgtgcaac   1140
acggaggggt agcatctaca tacaatatat gttgattaat gattggagaa aaaactatgc   1200
agctcgccga tcatatggct aactcgcctt cgtctatatg gcggaccccg cgggaaaaat   1260
cgacgtacca tctgatttac aacaccagta atgaacatgt cgcatccctg cccagatctg   1320
tgcgcccatt ggcgcggatc gttgtgaatg ccgccgaaac acttcaggtc ggtatgagag   1380
ccgggaggcc gccatcagca ggagtttggc gagaggtgtt tgatagaatg atgacagcct   1440
tccgtgacca cgagcctact gcgacattta atgctgcaaa tcccattaga aaaatggtcg   1500
agacagttct acagaataat gaagagcccc cgcggacgca tgctgaaatg ggtaatcgcc   1560
ttatgaacat tatgtactgg tgttgcttgg gacacgcagg acaatgctcg atatggcagt   1620
tgtacgagac gaatcaggcc attttaagtt tattagatga agtggttatc ggcacaacaa   1680
atccctttg caccctcgag caatactgga agccattatg caccgcaatc gccaacaagg   1740
ggacctcatc gcttgttgag gatgccaaag tggccgagta cctggttagc atgcgcaaat   1800
tgatataaca taggcacgct ctgatgttac agaccacaat accgcataca tttattgtaa   1860
ggttgttaat aaaggtttat tctatgtaag actacaatac tttcgacatt gcttgtatac   1920
atattaaata ctttctcaag ttcctattac ataaaatggg atctatcatt acattcgtta   1980
agagtctgga taattttact gtttgccagc ttcgatcttg gaacgtactg tggatagtgc   2040
cttacttgga atcgtgaaaa tttgaaacgt ccattatttg gatatcttcc ggttgtccca   2100
tatcccgccc tggtaccgct cggatacctt gcccgtatgg attcgtattg acagtcgcgc   2160
aatcggggac caacaacgcg tgggtccaca ctcattcgga aattttccga tgattctgaa   2220
tatttattgc cgctcgttac gagtcgttgg acatatctgt aatacatttc ttcttctgaa   2280
ggatcgctgc acatttgatc tatacattgg ccaggatgtt caagtctcag atgttgcatt   2340
ctggcacagc acaactttat ggcatttccg atgtaatcgt ccggcagccc tgggggagtt   2400
ctatattcgc atattgggat ggtaaggaca atagcagatc tcgcaacctc cagggaggct   2460
ataataacgt ttttaaagga tggatttctc ataaaaatct gtcgcaaatt acactgagaa   2520
tatcctttac tagcgccgat tgagagcatc gtcgtccaat tttctaaatg gaaagaaaac   2580
aaggcgggca agagtgttcc aaacattttc attttcggcg aatctctcaa atcccatggc   2640
gtgcaattga ttgcaaaatt ggcacttccg ttcacgtttg tatctccaaa ctctaagaca   2700
cttttaattg aaaaactacg ttctagtgtg gaaagaaacc tataggcaga ccatagaact   2760
atttgacacc acatatcttt ttgtatgtca aactgaccat gatcgtatgt tgctgaatgc   2820
```

-continued

```
actagggcaa ttcgctcgcg cgactccata cattgaataa ttccacacgt cagctcatcg   2880
gttagcaagg tccagtagtt gaagtcattt atttttcccc gcggctggcc aaatctacct   2940
ctgggaatat ccaagttgtc gaatatgatc gcaccggctc tggtcatggt gaaggaactg   3000
tagcataaag acgcaggtat catagggga atattttttt attcactcac atactaaaag   3060
taacgcatat tagcaccatg tatgggctat caattgacat ttgcgtagca ctacatcacg   3120
attatgtaca acataatggg acaacatatg gcaagtagat gcaatttcct cacactagtt   3180
gggtttatct actattgaat tttcccctat ctgtgataca cttgggagcc tctacaagca   3240
tattgccatc atgtacgttt ttatctactg tcttaacgcc catgggaacg gaggcgtcgt   3300
cgtcatgtat tggacggcaa cataggcagc aacacaaatt gcgtttaggt ggggtgcatg   3360
tggactcgat accaagcccc tgcagctggg gaacgtctgg tggagagccg ataatttgat   3420
atacgcacgc catattactg tcgttgaagt acgccttatc ttctatgttt tcaaatttag   3480
gttcccaagt ggacgtgaga agtgtttgta tctcacatgg aatggcccaa ggcattccag   3540
cccaggtgcc tggtacttta atggcaaaca aacgttttgg tagaggtatt gattctattg   3600
cagttctgca gatatctgca gccccgagta tccacaggct atacgatacg ttatcggagg   3660
caagctgcgg ccgctctaga actagtggat cccccgggct gcagcccaat gtggaattcg   3720
cccttgcaca ttgttactcc tgcatcttaa aaatatatcc tgtagtaatt ttcacagcaa   3780
tgtcataaca tcatctcgct aaagaatgac ctgggattgg agaagtaatg aatatttgca   3840
accaatgcat tgaataaact aacattaaac gaattcacta gtggatcccc caactccgcc   3900
cgttttatga ctagaaccaa tagtttttaa tgccaaatgc actgaaatcc cctaatttgc   3960
aaagccaaac gccccctatg tgagtaatac ggggactttt tacccaattt cccaagcgga   4020
aagcccccta atacactcat atggcatatg aatcagcacg gtcatgcact ctaatggcgg   4080
cccataggga ctttccacat agggggcgtt caccatttcc cagcataggg gtggtgactc   4140
aatggccttt acccaagtac attgggtcaa tgggaggtaa gccaatgggt ttttcccatt   4200
actggcaagc acactgagtc aaatgggact ttccactggg ttttgcccaa gtacattggg   4260
tcaatgggag gtgagccaat gggaaaaacc cattgctgcc aagtacactg actcaatagg   4320
gactttccaa tgggtttttc cattgttggc aagcatataa ggtcaatgtg ggtgagtcaa   4380
tagggacttt ccattgtatt ctgcccagta cataaggtca atagggggtg aatcaacagg   4440
aaagtcccat tggagccaag tacactgcgt caatagggac tttccattgg gttttgccca   4500
gtacataagg tcaatagggg atgagtcaat gggaaaaacc cattggagcc aagtacactg   4560
actcaatagg gactttccat tgggttttgc ccagtacata aggtcaatag ggggtgagtc   4620
aacaggaaag tcccattgga gccaagtaca ttgagtcaat agggactttc caatgggttt   4680
tgcccagtac ataaggtcaa tgggaggtaa gccaatgggt ttttcccatt actggcacgt   4740
atactgagtc attagggact ttccaatggg ttttgcccag tacataaggt caataggggt   4800
gaatcaacag gaaagtccca ttggagccaa gtacactgag tcaataggga ctttccattg   4860
ggttttgccc agtacaaaag gtcaataggg ggtgagtcaa tgggtttttc ccattattgg   4920
cacgtacata aggtcaatag gggtgagtca ttgggttttt ccagccaatt taattaaaac   4980
gccatgtact ttcccaccat tgacgtcaat gggctattga aactaatgca acgtgacctt   5040
taaacggtac tttcccatag ctgattaatg ggaaagtacc gttctcgagc caatacacgt   5100
caatgggaag tgaaagggca gccaaaacgt aacaccgccc cggttttccc ctggaaattc   5160
catattggca cgcattctat tggctgagct gcgttctacg tgggtataag aggcgcgacc   5220
```

agcgtcggta ccgtcgcagt cttcggtctg accaccgtag aacgcagagc tcctcgctgc 5280
aggcggccgc tctagaactc gtcgatcgca gcgatgacaa acctgcaaga tcaaacccaa 5340
cagattgttc cgttcatacg gagccttctg atgccaacaa ccggaccggc gtccattccg 5400
gacgacaccc tggagaagca cactctcagg tcagagacct cgacctacaa tttgactgtg 5460
ggggacacag ggtcagggct aattgtcttt ttccctggat tccctggctc aattgtgggt 5520
gctcactaca cactgcagag caatgggaac tacaagttcg atcagatgct cctgactgcc 5580
cagaacctac cggccagcta caactactgc agactagtga gtcggagtct cacagtgagg 5640
tcaagcacac tccctggtgg cgtttatgca ctaaacggca ccataaacgc cgtgaccttc 5700
caaggaagcc tgagtgaact gacagatgtt agctacaatg ggttgatgtc tgcaacagcc 5760
aacatcaacg acaaaattgg gaatgtcctg gtaggggaag gggtcactgt cctcagccta 5820
cccacatcat atgatcttgg gtatgtgagg cttggtgacc ccattcccgc tatagggctt 5880
gacccaaaaa tggtagctac atgcgacagc agtgacaggc ccagagtcta caccataact 5940
gcagccgatg attaccaatt ctcatcacag taccaaccag gtggggtaac aatcacactg 6000
ttctcagcca acattgatgc tatcacaagc ctcagcattg gggagagagct cgtgtttcaa 6060 acaagcgtcc aaggccttgt actgggcgcc accatctacc ttataggctt tgatgggact 6120
gcggtaatca ccagagctgt agccgcagat aatgggctga cggccggcac cgacaatctt 6180
atgccattca atcttgtcat tccaaccaat gagataaccc agccaatcac atccatcaaa 6240
ctggagatag tgacctccaa aagtggtggt caggcagggg atcagatgtc atggtcggca 6300
agtgggagcc tagcagtgac gatccatggt ggcaactatc caggggccct ccgtcccgtc 6360
acactagtag cctacgaaag agtggcaaca ggatccgtcg ttacggtcgc tggggtgagt 6420
aacttcgagc tgattccaaa tcctgaacta gcaaagaacc tggttacaga atacggccga 6480
tttgacccag gagccatgaa ctacacaaaa ttgatactga gtgagaggga ccgtcttggc 6540
atcaagaccg tctggccaac aagggagtac actgattttc gtgagtactt catggaggtg 6600
gccgacctca actctcccct gaagattgca ggagcatttg gcttcaaaga cataatccgg 6660
gctataagga ggtaagcttg atctagagcg gccgcgggga tccagacatg ataagataca 6720
ttgatgagtt tggacaaacc acaactagaa tgcagtgaaa aaaatgcttt atttgtgaaa 6780
tttgtgatgc tattgcttta tttgtaacca ttataagctg caataaacaa gttaacaaca 6840
acaattgcat tcattttatg tttcaggttc agggggaggt gtgggaggtt ttttcggatc 6900
ctctagagtc gacaattatt ttatttaata acatatagcc caaagacctc tatgaacatt 6960
tagtttcccg tatactcaac ggcgcgtgta cacacaaggg cgaattccac agtggatatc 7020
aagcttagct tgcctccgat tctagcatta catagccggt cagtagatcc tgccattcgg 7080
tagcgcaacc ggctacatct tcaaacagtc tcacgataaa tgcatctctc gttcctgcca 7140
atccggaacc gggcatacca ctcccgcctg ccgatttaat tctcacaatt gggcgatgcc 7200
ggcggggcaa aacgaatgtg gatttggcaa accgacacag gtctgctgta cggactaata 7260
tgggcacacc cacatcattc ttcagatgct ccatgcattg ttctatgaga aagatccata 7320
gggtggaggc agcgtcacga gatcgcccag gcaatcgatc gcattcgtct agtaaagtga 7380
cgagagttat catgcacaca cccatgccca cgccttccga ataactggag ctgtggaaga 7440
tcggaaacgt ctttttgact gccggtctcg tactactttc gcacaggtgt atacccggac 7500
gcgtactata tattttatat catccaacgt ccgaaattac atacgtggcg gcgatggaag 7560

```
tagatgttga gtcttcgaaa gtaagtgcct cgaatatggg tattgtctgt gaaaatatcg   7620
aaagcggtac gacggttgca gaaccgtcga tgtcgccaga tactagtaac aatagcttcg   7680
ataacgaaga cttccgtggg cctgaatacg atgtggagat aaataccaga aaatctgcta   7740
atcttgatcg tatggaatct tcgtgccgtg aacaacgagc ggcgtgcgaa cttcgaaagt   7800
gttcgtgtcc tacgtctgcc gtgcgcatgc aatacagtat tctttcatct ctcgctccgg   7860
gttcagaggg tcatgtatat atatgtacta gatacgggga cgcggaccaa aaaaaatgca   7920
tagtgaaggc agtcgttgga ggaaagaatc ccgggaggga agtggatatt ttaaaaacca   7980
tctcacataa atcaattata aaattaatcc atgcctataa atggaaaaat gttgtgtgta   8040
tggcaatgcg tgtatatcgt tatgatcttt tcacatatat tgacggagtc ggccctatgc   8100
cccttcaaca gatgatctat attcaacgtg gactactaga ggcgctagca tacatacatg   8160
aaaggggcat cattcaccga gacgtaaaga cggagaatat attcttggat aatcacgaaa   8220
atgcagtttt gggtgacttc ggtgctgcat gccaactagg agattgtata gatacgcccc   8280
aatgttacgg ttggagcgga actgtggaaa caaattcgcc ggaattatct gcacttgatc   8340
cgtattgcac aaaaacagat atttggagtg ccggattggt tctatatgag atggcaatta   8400
aaaatgtacc attgtttagt aagcaggtga aaagttcggg atctcagctg agatccataa   8460
tacggtgcat gcaagtgcat gaactggagt ttccccgcaa cgattctacc aacctctgta   8520
aacatttcaa acaatatgcg gttcgtgtac gaccgcctta taccattcct cgagttataa   8580
gaaatggggg gatgccaatg gatgttgaat atgtcatttc taaaatgctt acgtttgacc   8640
aggagttcag accttctgct aaggaaatat tgaatatgcc cctatttact aaggcgccga   8700
ttaacctgct taatatcaca ccctctgaca gtgtctaacg gtatacaggc gggagcgggt   8760
cgtggcgtca tcatcaccac ttgagaattt atattttgaa ttgttgattg ataaattaac   8820
ctgattcatt gagaactgaa acgccatatt ggtttcttgg atatgtctac aacaattagt   8880
taaattgcta tgttctactg cgagtaacat ttgataagtt gtaagagacg ggcgactcat   8940
gtcgaagttg acgaatataa agtacataac gtgtttagaa tacccagaat ccgaatagtc   9000
cgcgggggcg tcttctcgcg tgagtaccaa atactgagtt gaacttgaaa atgctaaatc   9060
tgtgacactc tttgtgtgat gattattgtc accacttcga agatggcttc gacattcatg   9120
atgttctggt gtttgtttgg aatcgtaata gcgcttgttt cgtccaagtc tgacaacaaa   9180
gaaaatctga agaattatat cacggataag tcaaccaata ttagaatacc cacgccatta   9240
tttgtatcaa cggaaaactc ttatcccaca aaacatgtaa tctacgatga aaactgtggc   9300
ttcgctgtac tcaatcctat aagtgacccc aaatatgtcc ttttgagcca gcttctaatg   9360
ggaaggcgca aatatgatgc gacggtcgcg tggtttgttc tcggtaaaat gtgtgccaga   9420
ttaatatatt tgcgcgaatt ttataactgc tcgacaaatg agccttttgg cacatgttct   9480
atgagctctc ctggatggtg ggacaggcgc tacgtctcaa ccagtttcat ttctcgcgac   9540
gaattacagc tggtttttgc agcgccgtcc cgagaattag atggtttata tacgcgcgta   9600
gtagttgtca acggggactt tactacggcc gatataatgt ttaatgttaa agtggcatgt   9660
gccttttcaa agactggaat agaagatgat acattatgca aacccttca tttctttgcc   9720
aatgcaacat tgcacaattt aaccatgatt agatcggtaa ctcttcgagc gcacgaaagc   9780
catttaaagg aatgggtggc acggagaggt ggtaacgtcc ctgcagtgct acttgagtct   9840
accatgtatc atgcatccaa tctgcctaga aatttcaggg atttctacat aaagtctcca   9900
gatgattata agtataatca cctagatggg ccatctgtaa tgctcatcac tgacagacct   9960
```

-continued

```
agtgaagatt tggatgggag gctcgttcac caaagtgaca tttttactac tacaagtcct  10020

ataaaacagg tccggtatga agagcatcag tcacatacaa agcagtatcc tgtaaacaaa  10080

atacaagcta taattttttt gatagggtta ggctcgttca ttggaagcat attcgtagtt  10140

ttggtagtat ggattatacg cagatattgc aatggagcgc ggagtggggg aacgcccccc  10200

agtcctcgcc ggtatgtgta taccaggcta tgatcacgtg tgaaacttgg gcggacctgt  10260

atcatatgta caccgtccct attcgtttat agccagtacg tgttatctgc acatagagga  10320

acatgtgtca tactgggatc gcatgcatgg tatgtgtgac tctaatatta ttctgtatca  10380

taataaaaac acagtgcatg gtatatagag gatcgctggt aagcactacg gtagaccaat  10440

cggctcagat tgcattcttt ggcatcgata ccgttgttaa tttatatggc aaagtcttgt  10500

tcatgggaga tcagtatttg gaggaaatat actctggaac gatggaaata ctcaaatgga  10560

atcaagctaa ccgctgctat tctattgcgc atgcaacata ttacgccgac tgtcctataa  10620

tcagttctac ggtattcaga ggatgccggg acgccgttgt ttatactagg ccccacagca  10680

g                                                                  10681
```

RECOMBINANT NON-PATHOGENIC MAREK'S DISEASE VIRUS CONSTRUCTS ENCODING MULTIPLE HETEROLOGOUS ANTIGENS

CROSS-REFERENCE TO RELATED APPLICATIONS

This application is a Continuation application of copending U.S. patent application Ser. No. 16/753,133, filed on Apr. 2, 2020, which is a national stage entry under 35 U.S.C. § 371 of PCT/EP2018/077725, filed on Oct. 11, 2018, which claims priority to U.S. Ser. No. 62/571,524, filed on Oct. 12, 2017 and U.S. Ser. No. 62/729,673, filed on Sep. 11, 2018, the content of PCT/EP2018/077725 is hereby incorporated by reference in its entirety.

FIELD OF THE INVENTION

SEQUENCE LISTING

This application incorporates by reference in its entirety the Computer Readable Form (CRF) of a Substitute Sequence Listing in ASCII text format submitted via Patent Center. The Substitute Sequence Listing text file submitted via Patent Center is entitled "14463-317-999_SUB_SL.txt," was created on Dec. 16, 2024, and is 241,442 bytes in size.

The present invention relates to novel recombinant multivalent recombinant non-pathogenic Marek's Disease virus constructs encoding and expressing foreign antigens from three or more avian viruses and methods of employing these multivalent recombinant non-pathogenic Marek's Disease virus constructs in poultry vaccines.

BACKGROUND OF THE INVENTION

Pathogenic poultry viruses are not only debilitating to chickens, but they also are costly to chicken breeders because most of the resulting diseases are contagious and the poultry industry relies heavily on confined, large-scale breeding facilities. Vaccinating young chicks is often the only viable means to combat these viruses. Although attenuated or killed poultry viral vaccines remain important in the market place, in recent years significant resources have been expended on developing vaccines containing recombinant viral constructs which express pathogenic viral protein antigens. Furthermore, substantial efforts have been made to construct stable and efficacious multivalent recombinant non-pathogenic Marek's Disease virus (abbreviated as $rMDV_{np}$) vectors that express foreign genes from multiple viral pathogens. Such multivalent vaccines would serve to minimize the number of injections given to the chicks and thereby, reduce discomfort and stress on the vaccinated chick, as well as significantly reduce costs in labor and materials. Vaccinating with such single multivalent constructs also would be preferable to alternative multivalent $rMDV_{np}$ vaccines that contain multiple recombinant monovalent $rMDV_{np}$ constructs, because these alternative vaccines have, at least to date, resulted in protection against only a single viral pathogen. The failure of such alternative vaccines is presumably due to one of the monovalent $rMDV_{np}$ constructs overgrowing the other monovalent $rMDV_{np}$, constructs thereby, preventing these other monovalent $rMDV_{np}$ constructs from inducing a significant immune response. In any case, despite substantial efforts in the past to construct stable and efficacious multivalent $rMDV_{np}$ vectors that express foreign genes from multiple viral pathogens indeed, such vaccines had been suggested more than twenty years ago [see e.g., U.S. Pat. No. 5,965,138], it has been only recently that a multivalent vaccine that comprises a recombinant herpesvirus of turkeys (abbreviated as rHVT) encoding antigens from more than one other pathogen has been shown to be both stable and efficacious.

One poultry virus disease that can be controlled through vaccination is Marek's disease. Marek's disease is a pathogenic disease that adversely affects chickens worldwide. Marek's disease occurs predominantly in young chickens between 2 and 5 months of age. Clinical signs include: progressive paralysis of one or more of the extremities, incoordination due to paralysis of legs, drooping of the limb due to wing involvement, and a lowered head position due to involvement of the neck muscles. In acute cases, severe depression may result. Bursal and thymic atrophy may also develop.

The etiological agent for Marek's disease is Marek's disease virus serotype 1 (abbreviated as MDV1), a cell-associated virus having a double-stranded DNA genome. MDV1 is a lymphotropic avian *alphaherpesvirus* that both: (i) infects B cells, which can result in cytolysis, and (ii) latently infects T cells, which can induce T-cell lymphoma. Closely related to the virulent MDV1 strain, Marek's disease virus serotype 2 (abbreviated as MDV2), previously known as Gallid herpes virus 3, is a naturally attenuated MDV strain that has been shown to have little to no pathogenicity in chickens [Petherbridge et al., *J. Virological Methods* 158:11-17 (2009)]. SB-1 is a specific MDV2 strain that has been shown to be useful in vaccines against MDV1 [see e.g., Murthy and Calnek, Infection and Immunity 26(2) 547-553 (1979)].

Another closely related *alphaherpesvirus*, Marek's disease virus serotype 3 (abbreviated as MDV3), more widely known as herpesvirus of turkeys (abbreviated as HVT), is a nonpathogenic virus of domestic turkeys [see e.g., Kingham et al., *J. of General Virology* 82:1123-1135 (2001)]. Two commonly used strains of HVT are the PB1 strain and the FC126 strain. Whereas, HVT is also nonpathogenic in chickens, it does induce a long-lasting protective immune response in chickens against MDV1. Accordingly, HVT has been used in poultry vaccines against virulent MDV1 for many years, generally in combination with SB-1, which is more viraemic than HVT, but considered less safe. Alternatively, when flocks are challenged with particularly virulent MDV1 strains, HVT can be combined with the Rispen's vaccine. The Rispen's vaccine is an isolate that originated from a mildly virulent MDV1 strain that was subsequently further weakened by cell passaging. The Rispen's strain however, retains some virulence towards highly susceptible lines of chickens.

The sequence of the complete genome of HVT has been disclosed [Afonso et al., *J. Virology* 75(2):971-978 (2001)], and as most *alphaherpesviruses*, HVT possesses a significant number of potential nonessential insertion sites [see e.g., U.S. Pat. Nos. 5,187,087; 5,830,745; 5,834,305; 5,853,733; 5,928,648; 5,961,982; 6,121,043; 6,299,882 B1]. HVT also has been shown to be amenable to genetic modification and thus, has been used as a recombinant vector for many years [WO 87/04463]. Accordingly, recombinant HVT vectors have been reported to express foreign genes that encode antigens from e.g., Newcastle Disease Virus (NDV), [Sondermeijer et al., *Vaccine,* 11:349-358 (1993); Reddy et al., *Vaccine,* 14:469-477 (1996)], Infectious Bursal Disease Virus (IBDV), [Darteil et al., *Virology,* 211:481.490 (1995); Tsukamoto et at, *J. of Virology* 76(11):5637-5645 (2002)], and Infectious Laryngotracheitis Virus (ILTV) [Johnson et al., *Avian Disease,* 54(4):1251-1259 (2010); WO 92/03554; U.S. Pat. No. 6,875,856]. The entire genomic sequence of MDV2 is also known [see, GenBank acc. nr: AB049735.1, and Petherbridge et al., supra]. The genomic organization of the MDV2 is very similar to that of HVT, with the US region in particular, being identical to that of HVT [see, Kingham et al., supra].

In addition a recombinant chimeric virus, known as the novel avian herpesvirus (NAHV), has been constructed in which specific regions of the HVT genome have been replaced by the corresponding regions of the MDV1 genome. The NAHV also has been used to express foreign genes that encode antigens from other poultry viruses [U.S. Pat. Nos. 5,965,138; 6,913,751].

Like MDV, infectious laryngotracheitis virus (abbreviated as ILTV or ILT) is an *alphaherpesvirus* that adversely affects chickens, worldwide [Fuchs et al., *Veterinary Research* 38:261-279 (2007)]. ILTV causes acute respiratory disease in chickens, which is characterized by respiratory depression, gasping, and expectoration of bloody exudate. Viral replication is limited to cells of the respiratory tract, where in the trachea the infection gives rise to tissue erosion and hemorrhage.

Newcastle disease is another highly contagious and debilitating disease of chickens. The etiological agent for Newcastle disease is the Newcastle disease virus (NDV). NDV belongs to the order of the Mononegavirales and is in the family of Paramyxoviridae. Newcastle disease viruses have a non-segmented, negative sense, single-stranded RNA genome. NDV has been grouped into three distinct pathotypes according to their virulence. Infection of poultry by the non-pathogenic lentogenic strains of NDV is essentially asymptomatic. In direct contrast, the mesogenic (medium pathogenic) and velogenic (highly pathogenic) NDV strains cause extensive disease that can be fatal. Most types of NDV infect the respiratory system and/or the nervous system, and can result in gasping and torticollis.

Infectious bursal disease virus (abbreviated as IBDV or IBD), also called Gumboro disease virus, is the causative agent of infectious bursal disease. IBDV causes an acute, highly-contagious, viral infection of a chicken's lymphoid tissue, with its primary target being the bird's essential immunological organ: the bursa of Fabricius. The morbidity rate in susceptible flocks is high, with rapid weight loss and moderate to high mortality rates. Chicks that recover from the disease may have immune deficiencies because of destruction of (or parts of) the bursa of Fabricius. This makes them particularly vulnerable to secondary infections.

IBDV is a member of the Birnaviridae family. The viruses in this family have a genome consisting of two segments (A and B) of double-stranded RNA. Two serotypes of IBDV exist, serotype 1 and 2, which can be differentiated by virus neutralization (VN) tests. Serotype 1 viruses have been shown to be pathogenic to chickens, while serotype 2 viruses cause only sub-acute disease in turkeys. Historically, IBDV serotype 1 viruses consisted of only one type that is now known as "classic" IBD virus. More recently, so-called "variant" IBDV strains have emerged. Classic and variant strains of IBDV can be identified and distinguished by a virus neutralization test using a panel of monoclonal antibodies, or by RT-PCR [Wu et al., *Avian Diseases,* 51:515-526(2007)]. Well-known classic IBDV strains include, D78, Faragher 52/70, and STC, whereas 89/03 is a well-known variant strain. Many live or inactivated IBDV vaccines are commercially available, e.g. a live vaccine such as NOBILIS® Gumboro D78 (MSD Animal Health).

As indicated above, because HVT can act as both an antigen that provides significant protection against Marek's Disease and as a recombinant vector, it is presently used as a platform vector for such multivalent vaccines as Innovax®-ILT (sold by Merck Animal Health), which protects against ILTV; Innovax®-ND-SB (sold by Merck Animal Health) Vectormune® HVT-NDV (sold by Ceva), both of which protect against NDV; and Vaxxitek® HVT+IBD (Merial; previously named: Gallivac™ HVT-IBD), and Vectormune™ HVT-IBD (Ceva) both of which protect against IBDV. Notably, Innovax®-ILT comprises two foreign genes, i.e., ILTV gD and ILTV gI, which has proved to be safe, effective, and stable. However, these two foreign genes are from the same pathogen and moreover, they naturally overlap and need to be co-expressed in order to allow proper immunization against ILTV. More recently, a recombinant safe, effective, and stable multivalent vaccine comprising HVT-ILTV-NDV has been disclosed [U.S. Pat. Nos. 8,932,604 B2 and 9,409,954 B2, the contents of which are hereby incorporated by reference in their entireties]. An early HVT-NDV-IBDV also has been disclosed, though upon prolonged testing during the development of the corresponding product one of the main constructs, HVP309, was found neither to display adequate genetic stability nor sustained expression of the heterologous inserts [WO 2013/057,235]. Subsequently, a more stable and efficatious construct was developed [WO 2016/102647]. Other recombinant HVT constructs also have been described [see e.g., U.S. Pat. Nos. 9,114,108, 9,555,016, 9,555,096, and US 2018/0163230 A1].

However, despite the clear advantages of stable, multivalent, recombinant $MDV_{np}$ constructs that can efficaciously express heterologous antigens from three or more different pathogens, and the substantial efforts to design them, heretofore, none have been forthcoming. Indeed, prior unsuccessful attempts to construct such recombinant $MDV_{np}$ constructs has led to the general consensus in the field that the insertion of foreign antigens from three or more different viral pathogens into an $MDV_{np}$ construct overtaxes that construct, leading to the observed lack of stability. Accordingly, the suitability of any given multivalent recombinant $MDV_{np}$ as a vaccine remains at best, unpredictable when the recombinant $MDV_{np}$ comprises a combination of heterologous antigens that are obtained from a unique set of three or more poultry viruses. Therefore, there is a clear need to overcome the collective industry failures, by constructing novel, stable, recombinant $MDV_{np}$ vectors that can be used in multivalent vaccines as the sole active to protect against three or more different non-MDV1 poultry virus pathogens.

The citation of any reference herein should not be construed as an admission that such reference is available as "prior art" to the instant application.

SUMMARY OF THE INVENTION

Accordingly, the present invention provides a novel, multivalent recombinant nonpathogenic Marek's Disease virus ($rMDV_{np}$) for use as a vector to express foreign genes from multiple viral pathogens. In particular embodiments, the $rMDV_{np}$ is a recombinant herpesvirus of turkeys (rHVT). In alternative embodiments, the $rMDV_{np}$ is a recombinant Marek's disease virus serotype 2 (rMDV2). An $rMDV_{np}$, e.g., an rHVT or an rMDV2, of the present invention can be used in safe and efficacious multivalent vaccines against pathogenic poultry viruses. The present invention thus provides recombinant nonpathogenic Marek's Disease virus ($rMDV_{np}$) vectors (including HVT vectors) that encode and express antigens from three or more foreign chicken virus pathogens. In specific embodiments the $rMDV_{np}$ encodes one or more antigens from Laryngotracheitis Virus (ILTV), one or more antigens from Infectious Bursal Disease Virus (IBDV), and one or more antigens from Newcastle Disease Virus (NDV). In more specific embodiments such $rMDV_{np}$ vectors aid in the protection of the chicken vaccinate from clinical signs arising from an infection from pathogenic MDV, pathogenic IBDV, pathogenic NDV, and/or pathogenic ILTV. The vaccines are preferably effective for the vaccination of healthy animals at 18-19 day of embryonation, and for day old chicks and older.

In particular embodiments, the recombinant nonpathogenic Marek's Disease Virus ($rMDV_{np}$) comprises in one or more nonessential sites of its genome a first heterologous nucleotide sequence encoding one or more antigens from a first chicken pathogen, a second heterologous nucleotide sequence encoding one or more antigens from a second chicken pathogen, and a third heterologous nucleotide sequence encoding one or more antigens from a third chicken pathogen. In specific embodiments the first chicken pathogen, the second chicken pathogen, and the third chicken pathogen are all avian viruses. In more specific embodiments the first chicken pathogen, the second chicken pathogen, and the third chicken pathogen are all different viral species from each other and are a different viral species than Marek's Disease Virus. In certain embodiments of this type, the first chicken pathogen is Infectious Bursal Disease Virus (IBDV), the second chicken pathogen is Infectious Laryngotracheitis Virus (ILTV), and the third chicken pathogen is Newcastle Disease Virus (NDV).

In specific $rMDV_{np}$ embodiments, the first heterologous nucleotide sequence encodes an Infectious Bursal Disease Virus viral protein 2 (IBDV VP2); and/or the second heterologous nucleotide sequence encodes an Infectious Laryngotracheitis Virus glycoprotein D (ILTV gD), an Infectious Laryngotracheitis Virus glycoprotein I (ILTV gI), or both an ILTV gI and an ILTV gD; and/or the third heterologous nucleotide sequence encodes a Newcastle Disease Virus fusion protein (NDV F). In more specific $rMDV_{np}$ embodiments, the first heterologous nucleotide sequence encodes an Infectious Bursal Disease Virus viral protein 2 (IBDV VP2), the second heterologous nucleotide sequence encodes both an Infectious Laryngotracheitis Virus glycoprotein D (ILTV gD) and an Infectious Laryngotracheitis Virus glycoprotein I (ILTV gI), and the third heterologous nucleotide sequence encodes a Newcastle Disease Virus fusion protein (NDV F).

Accordingly, in particular $rMDV_{np}$ embodiments of the present invention, the first heterologous nucleotide sequence, the second heterologous nucleotide sequence and the third heterologous nucleotide sequence are located in three different nonessential sites in the $rMDV_{np}$ genome. In particular embodiments the three different sites are individually selected from the group consisting of the US2 site, the UL54.5 site, the UL7/8 site, the UL40 site, the UL43 site, the UL45/46 site, the UL55 site, the US10 site, the region between US10 and SORF3, the region between US2 and SORF3, the IG1 site, the IG2 site, and the IG3 site. In a specific embodiment of this type the first nonessential site is the US2 site, the second nonessential site is the UL54.5 site, and the third nonessential site is the UL45/46 site.

In alternative embodiments, the first heterologous nucleotide sequence, the second heterologous nucleotide sequence, and the third heterologous nucleotide sequence are located in a first nonessential site in the $rMDV_{np}$ genome or in a second nonessential site in the $rMDV_{np}$ genome. In specific embodiments of this type, the first nonessential site and the second nonessential site are the same (i.e., there is a lone nonessential insertion site). In particular embodiments of this type, the lone nonessential insertion site is the US2 site. In other embodiments of this type, the lone nonessential insertion site is the UL54.5 site. In still other embodiments of this type, the lone nonessential insertion site is the UL7/8 site. In yet other embodiments of this type, the lone nonessential insertion site is the UL40 site. In still other embodiments of this type, the lone nonessential insertion site is the UL45/46 site. In yet other embodiments of this type, the lone nonessential insertion site is the UL55 site. In still other embodiments of this type, the lone nonessential insertion site is the US10 site. In yet other embodiments of this type, lone nonessential insertion site is the region between US10 and SORF3. In still other embodiments of this type, the lone nonessential insertion site is the region between US2 and SORF3. In yet other embodiments of this type the lone nonessential insertion site is the IG1 site. In still other embodiments of this type, the lone nonessential insertion site is the IG2 site. In yet other embodiments of this type the lone nonessential insertion site Is the IG3 site. In still other embodiments of this type, the lone nonessential insertion site is the UL43 site.

In yet other types of embodiments, the first nonessential site, and the second nonessential site are different. The two different sites are individually selected from the group consisting of the US2 site, the UL54.5 site, the UL7/8 site, the UL40 site, the UL43 site, the UL45/46 site, the UL55 site, the US10 site, the region between US10 and SORF3, the region between US2 and SORF3, the IG1 site, the IG2 site, and the IG3 site. In particular embodiments, the first heterologous nucleotide sequence and the second heterologous nucleotide sequence are located in a first nonessential site and the third heterologous nucleotide sequence is located in a second nonessential site. In other embodiments, the first heterologous nucleotide sequence and the third heterologous nucleotide sequence are located in a first nonessential site and the second heterologous nucleotide sequence is located in a second nonessential site. In still other embodiments, the second heterologous nucleotide sequence and the third heterologous nucleotide sequence are located in a first nonessential site and the first heterologous nucleotide sequence is located in a second nonessential site. In preferred embodiments of this type, the first heterologous nucleotide sequence encodes an Infectious Bursal Disease Virus viral protein 2 (IBDV VP2), the second heterologous nucleotide sequence encodes an Infectious Laryngotracheitis Virus glycoprotein D (ILTV gD), an Infectious Laryngotracheitis Virus glycoprotein I (ILTV gI), or both an ILTV gI and an ILTV gD, and the third heterologous nucleotide sequence encodes a Newcastle Disease Virus fusion protein (NDV F).

In certain embodiments of this type, an $rMDV_{np}$ comprising heterologous nucleotide sequences encoding an ILTV gD protein, an ILTV gI protein, and an IBDV VP2 protein in the first nonessential site, and a heterologous nucleotide sequence that encodes a NDV F protein in the second nonessential site is constructed so that the heterologous nucleotide sequence encoding the IBDV VP2 protein is 5' to the heterologous nucleotide sequence encoding the ILTV gD protein and the ILTV gI protein. In other embodiments of this type, the $rMDV_{np}$ is constructed so that the heterologous nucleotide sequence encoding the ILTV gD protein and the ILTV gI protein are 5' to the heterologous nucleotide sequence encoding the IBDV VP2 protein.

In alternative embodiments, an $rMDV_{np}$ comprising heterologous nucleotide sequences encoding a NDV F protein and an IBDV VP2 protein in the first nonessential site and a heterologous nucleotide sequence that encodes an ILTV gD protein and an ILTV gI protein in the second nonessential site is constructed so that the heterologous nucleotide sequence encoding the NDV F protein is 5' to the heterologous nucleotide sequence encoding the IBDV VP2 protein. In other embodiments of this type, the $rMDV_{np}$ is constructed so that the heterologous nucleotide sequence encoding the IBDV VP2 protein is 5' to the heterologous nucleotide sequence encoding the NDV F protein.

In yet other alternative embodiments, an $rMDV_{np}$ comprising heterologous nucleotide sequences encoding a NDV F protein, an ILTV gD protein and an ILTV gI protein in the first nonessential site and a heterologous nucleotide sequence encoding an IBDV VP2 protein in the second nonessential site is constructed so that the heterologous nucleotide sequence encoding the NDV F protein is 5' to the heterologous nucleotide sequence encoding the ILTV gD protein and the ILTV gI protein. In alternative embodiments of this type, the $rMDV_{np}$ is constructed so that the heterologous nucleotide sequence encoding the ILTV gD protein and the ILTV gI protein is 5' to the heterologous nucleotide sequence encoding the NDV F protein.

In specific embodiments of this type, the first nonessential site is the US2 site and the second nonessential site is the UL54.5 site. In alternative embodiments, the first nonessential site is the UL54.5 site and the second nonessential site is the US2 site. In yet another embodiment of this type, the first nonessential site is the US2 site and the second nonessential site is the UL45/46 site. In still another embodiment of this type, the first nonessential site is the UL45/46 site and the second nonessential site is the US2 site. In yet another embodiment of this type, the first nonessential site is the UL54.5 site and the second nonessential site is the UL45/46 site. In still another embodiment of this type, the first nonessential site is the UL45/46 site and the second nonessential site is the UL54.5 site. In yet another embodiment of this type, the first nonessential site is the US2 site and the second nonessential site is the UL55 site. In still another embodiment of this type, the first nonessential site is the UL55 site and the second nonessential site is the US2 site.

Accordingly, the $rMDV_{np}$ vectors of the present invention can comprise heterologous nucleotide sequences that encode any combination of these foreign protein antigens. In specific embodiments, the ILTV gD protein comprises the amino acid sequence of SEQ ID NO: 2. In other embodiments, the ILTV gI protein comprises the amino acid sequence of SEQ ID NO: 4. In still other embodiments, the IBDV VP2 protein comprises the amino acid sequence of SEQ ID NO: 6. In yet other embodiments the NDV F protein comprises the amino acid sequence of SEQ ID NO: 8. In still other embodiments, the NDV F protein comprises the amino acid sequence of SEQ ID NO: 10. Moreover, the present invention also provides $rMDV_{np}$ vectors that comprise any combination of nucleotide sequences that encode one or more of these amino acid sequences, including specific embodiments that encode all of them.

In yet other embodiments of the $rMDV_{np}$, the ILTV gD protein comprises the amino acid sequence of SEQ ID NO: 2 and the ILTV gI protein comprises the amino acid sequence of SEQ ID NO: 4. In certain embodiments of this type, the ILTV gD protein comprises the amino acid sequence of SEQ ID NO: 2, the ILTV gI protein comprises the amino acid sequence of SEQ ID NO: 4, and the IBDV VP2 protein comprises the amino acid sequence of SEQ ID NO: 6. In related embodiments the ILTV gD protein comprises the amino acid sequence of SEQ ID NO: 2, the ILTV gI protein comprises the amino acid sequence of SEQ ID NO: 4, and the NDV F protein comprises the amino acid sequence of SEQ ID NO: 8. In similar embodiments the ILTV gD protein comprises the amino acid sequence of SEQ ID NO: 2, the ILTV gI protein comprises the amino acid sequence of SEQ ID NO: 4, and the NDV F protein comprises the amino acid sequence of SEQ ID NO: 10. In more specific embodiments the ILTV gD protein comprises the amino acid sequence of SEQ ID NO: 2, the ILTV gI protein comprises the amino acid sequence of SEQ ID NO: 4, the IBDV VP2 protein comprises the amino acid sequence of SEQ ID NO: 6, and the NDV F protein either comprises the amino acid sequence of SEQ ID NO: 8 or the amino acid sequence of SEQ ID NO: 10. In specific embodiments, the $rMDV_{np}$ is an rHVT. In alternative embodiments, the $rMDV_{np}$ is an rMDV2.

In related embodiments, the ILTV gD protein is encoded by the nucleotide sequence of SEQ ID NO: 1. In other embodiments, the ILTV gI protein is encoded by the nucleotide sequence of SEQ ID NO: 3. In still other embodiments, the IBDV VP2 protein Is encoded by the nucleotide sequence of SEQ ID NO: 5. In yet other embodiments, the NDV F protein is encoded by the nucleotide sequence of SEQ ID NO: 7. In still other embodiments, the NDV F protein is encoded by the nucleotide sequence of SEQ ID NO: 9.

Similarly, the $rMDV_{np}$ vectors of the present invention can comprise heterologous nucleic acids that comprise any combination of such heterologous nucleotide sequences. In certain embodiments, the $rMDV_{np}$ comprises a first heterologous nucleic acid located in the first nonessential site in the $rMDV_{np}$ genome and a second heterologous nucleic acid located in the second nonessential site in the $rMDV_{np}$ genome, with the first heterologous nucleic acid comprising both the first heterologous nucleotide sequence and the second heterologous nucleotide sequence, whereas the second heterologous nucleic acid comprises the third heterologous nucleotide sequence.

In certain embodiments of this type, the first heterologous nucleic acid comprises heterologous nucleotide sequences encoding an Infectious Laryngotracheitis Virus (ILTV) glycoprotein D (gD) protein, an Infectious Laryngotracheitis Virus (ILTV) glycoprotein I (gI) protein, and an Infectious Bursal Disease Virus (IBDV) viral protein 2 (VP2), whereas the second heterologous nucleic acid comprises a heterologous nucleotide sequence that encodes a Newcastle Disease Virus (NDV) F protein. In certain embodiments of this type, the first heterologous nucleic acid is constructed and/or inserted into the $rMDV_{np}$ genome so that the heterologous nucleotide sequence encoding the IBDV VP2 protein is 5' to the heterologous nucleotide sequence encoding the ILTV gD protein and the ILTV gI protein. In other embodiments of this type, the first heterologous nucleic acid is constructed and/or inserted into the $rMDV_{np}$ genome so that the heterologous nucleotide sequence encoding the ILTV gD protein and the ILTV gI protein is 5' to the heterologous nucleotide sequence encoding the IBDV VP2 protein.

In alternative embodiments, the first heterologous nucleic acid comprises heterologous nucleotide sequences that encode a NDV F protein and an IBDV VP2 protein, whereas the second heterologous nucleic acid comprises a heterologous nucleotide sequence encoding an ILTV gD protein and an ILTV gI protein. In certain embodiments of this type, the first heterologous nucleic acid is constructed and/or inserted into the $rMDV_{np}$ genome so that the heterologous nucleotide sequence encoding the NDV F protein is 5' to the heterologous nucleotide sequence encoding the IBDV VP2 protein.

In alternative embodiments of this type, the first heterologous nucleic acid is constructed and/or inserted into the rMDV$_{np}$ genome so that the heterologous nucleotide sequence encoding the IBDV VP2 protein is 5' to the heterologous nucleotide sequence encoding the NDV F protein.

In yet other alternative embodiments, the first heterologous nucleic acid comprises heterologous nucleotide sequences that encode a NDV F protein, an ILTV gD protein, and an ILTV gI protein, whereas the second heterologous nucleic acid comprises a heterologous nucleotide sequence encoding an IBDV VP2 protein. In certain embodiments of this type, the first heterologous nucleic acid is constructed and/or inserted into the rMDV$_{np}$ genome so that the heterologous nucleotide sequence encoding the NDV F protein is 5' to the heterologous nucleotide sequence encoding the ILTV gD protein and the ILTV gI protein. In alternative embodiments of this type, the first heterologous nucleic acid is constructed and/or inserted into the rMDV$_{np}$ genome so that the heterologous nucleotide sequence encoding the ILTV gD protein and the ILTV gI protein is 5' to the heterologous nucleotide sequence encoding the NDV F protein.

Moreover, the present invention also provides rMDV$_{np}$ vectors that encode any combination of these nucleotide sequences, including specific embodiments wherein a first heterologous nucleic acid encodes the nucleotide sequence of SEQ ID NOs: 1, 3, and 5, and the second heterologous nucleic acid comprises the nucleotide sequence of SEQ ID NO: 7. In alternative embodiments, the first heterologous nucleic acid encodes the nucleotide sequence of SEQ ID NOs: 1, 3, and 5, and the second heterologous nucleic acid comprises the nucleotide sequence of SEQ ID NO: 9. In specific embodiments, the rMDV$_{np}$ is an rHVT. In alternative embodiments, the rMDV$_{np}$ is an rMDV2.

In particular embodiments the two different nonessential sites of the rMDV$_{np}$ are individually selected from the group consisting of the US2 site, the UL54.5 site, the UL7/8 site, the UL40 site, the UL 43 site, the UL45/46 site, the UL55 site, the US10 site, the region between 1.1510 and SORF3, the region between US2 and SORF3, intergenic region 1 (IG1) site, intergenic region 2 (IG2) site and intergenic region (IG3).

In certain embodiments, the first nonessential site of the rMDV$_{np}$ is the US2 site, while the second nonessential site of the rMDV$_{np}$ is a nonessential site other than the US2 site. In other embodiments, the first nonessential site of the rMDV$_{np}$ is the UL 54.5 site, while the second nonessential site of the rMDV$_{np}$ is a nonessential site other than the UL 54.5 site. In specific embodiments of this type, the first nonessential site is the US2 site and the second nonessential site is the UL54.5 site. In alternative embodiments, the first nonessential site is the UL54.5 site and the second nonessential site is the US2 site. In yet another embodiment of this type, the first nonessential site is the US2 site and the second nonessential site is the UL45/46 site. In still another embodiment of this type, the first nonessential site is the UL45/46 site and the second nonessential site is the US2 site. In yet another embodiment of this type, the first nonessential site is the UL54.5 site and the second nonessential site is the UL45/46 site. In still another embodiment of this type, the first nonessential site is the UL45/46 site and the second nonessential site is the UL54.5 site. In yet another embodiment of this type, the first nonessential site is the US2 site and the second nonessential site is the UL55 site. In still another embodiment of this type, the first nonessential site is the UL55 site and the second nonessential site is the US2 site. In related embodiments, the first nonessential site of the rMDV$_{np}$ is the UL 54.5 and the second nonessential site of the rMDV$_{np}$ is the UL7/8 site. In yet other embodiments, the first nonessential site of the rMDV$_{np}$ is the UL 54.5 and the second nonessential site of the rMDV$_{np}$ is the US10 site. In related embodiments, the second nonessential site of the rMDV$_{np}$ is the US2 site and the first nonessential site of the rMDV$_{np}$ is the UL7/8 site. In yet other embodiments, the second nonessential site of the rMDV$_{np}$ is the US2 site and the first nonessential site of the rMDV$_{np}$ is the US10 site. In specific embodiments, the rMDV$_{np}$ is an rHVT. In alternative embodiments, the rMDV$_{np}$ is an rMDV2.

In specific embodiments of this type, the first nonessential site and the second nonessential site are the same (i.e., there is a lone nonessential insertion site). In particular embodiments of this type, the lone nonessential insertion site is the US2 site. In other embodiments of this type, the lone nonessential insertion site is the UL54.5 site. In still other embodiments of this type, the lone nonessential insertion site is the UL7/8 site. In yet other embodiments of this type, the lone nonessential insertion site is the UL40 site. In still other embodiments of this type, the lone nonessential insertion site is the UL45/46 site. In yet other embodiments of this type, the lone nonessential insertion site is the UL55 site. In still other embodiments of this type, the lone nonessential insertion site is the US10 site. In yet other embodiments of this type, lone nonessential insertion site is the region between US10 and SORF3. In still other embodiments of this type, the lone nonessential insertion site is the region between US2 and SORF3. In yet other embodiments of this type the lone nonessential insertion site is the IG1 site. In still other embodiments of this type, the lone nonessential insertion site is the 1G2 site. In yet other embodiments of this type the lone nonessential insertion site is the IG3 site. In still other embodiments of this type, the lone nonessential insertion site is the UL43 site. In specific embodiments, the rMDV$_{np}$ is an rHVT. In alternative embodiments, the rMDV$_{np}$ is an rMDV2.

The nucleotide sequences encoding the ILTV gD protein, the ILTV gI protein, and the IBDV VP2 protein can be operatively under the control of exogenous promoters, i.e., promoters that are not naturally found in the MDV$_{np}$. In certain embodiments, these three nucleotide sequences are operatively under the control of different promoters, i.e., the nucleotide sequence encoding the ILTV gD protein is operatively under the control of a first promoter, the nucleotide sequence encoding the ILTV gI protein is operatively under the control of a second promoter, and the nucleotide sequence encoding the IBDV VP2 protein is operatively under the control of a third promoter, with the first promoter, the second promoter, and the third promoter all being different. In particular embodiments, the promoter for the nucleotide sequence encoding the ILTV gD protein is the endogenous ILTV gD promoter (i.e., endogenous for ILTV). In certain embodiments, the promoter for the nucleotide sequence encoding the ILTV gI protein is the endogenous ILTV gI promoter. In particular embodiments of this type, the promoter for the nucleotide sequence encoding the ILTV gD protein is the endogenous ILTV gD promoter and the promoter for the nucleotide sequence encoding the ILTV gI protein is the endogenous ILTV gI promoter. In specific embodiments, the rMDV$_{np}$ is an rHVT. In alternative embodiments, the rMDV$_{np}$ is an rMDV2.

In certain embodiments, at least one of the promoters operably linked to a nucleotide sequence encoding the NDV F protein, the ILTV gD protein, the ILTV gI protein, or the IBDV VP2 protein is the murine cytomegalovirus immediate early (mCMV IE) promoter. In related embodiments, at least one of the promoters operably linked to a nucleotide sequence encoding the NDV F protein, the ILTV gD protein, the ILTV gI protein, or the IBDV VP2 protein is the human cytomegalovirus immediate early (hCMV IE) promoter or a derivative thereof (e.g., from strain AD169). In other embodiments, at least one of the promoters operably linked to a nucleotide sequence encoding the NDV F protein, the ILTV gD protein, the ILTV gI protein, or the IBDV VP2 protein is the guinea pig cytomegalovirus immediate early promoter. In other embodiments, at least one of the promoters operably linked to a nucleotide sequence encoding the NDV F protein, the ILTV gD protein, the ILTV gI protein, or the IBDV VP2 protein is the chicken β-actin promoter. In still other embodiments, at least one of the promoters operably linked to a nucleotide sequence encoding the NDV F protein, the ILTV gD protein, the ILTV gI protein or the IBDV VP2 protein is the pseudorabies virus (PRV) gpX promoter.

In particular embodiments, the promoter for the nucleotide sequence encoding the IBDV VP2 protein is the mCMV IE promoter. In related embodiments, the promoter for the nucleotide sequence encoding the IBDV VP2 protein is the human cytomegalovirus immediate early (hCMV IE) promoter or a derivative thereof (e.g., from strain AD169). In other embodiments, the promoter for the nucleotide sequence encoding the IBDV VP2 protein is the guinea pig cytomegalovirus immediate early promoter. In yet other embodiments, the promoter for the nucleotide sequence encoding the IBDV VP2 protein is the chicken beta-actin gene promoter.

In certain embodiments, the promoter operably linked to a nucleotide sequence encoding the NDV F protein is the human cytomegalovirus immediate early (hCMV IE) promoter. In other embodiments, the promoter operably linked to a nucleotide sequence encoding the NDV F protein is the pseudorabies virus'(PRV) gpX promoter. In related embodiments, the promoter operably linked to a nucleotide sequence encoding the NDV F protein is the chicken beta-actin gene promoter. In still other embodiments, the promoter operably linked to a nucleotide sequence encoding the NDV F protein is the Simian virus 40 (SV40) promoter.

In more specific embodiments, the promoter for the nucleotide sequence encoding the IBDV VP2 protein is the mCMV IE promoter, the promoter for the nucleotide sequence encoding the ILTV gD protein is the endogenous ILTV gD promoter, the promoter for the nucleotide sequence encoding the ILTV gI protein is the endogenous ILTV gI promoter, and the promoter for the nucleotide sequence encoding the NDV F protein is the hCMV IE promoter. In other specific embodiments, the promoter for the nucleotide sequence encoding the IBDV VP2 protein is the hCMV IE promoter (or a derivative thereof), the promoter for the nucleotide sequence encoding the ILTV gD protein is the endogenous ILTV gD promoter, the promoter for the nucleotide sequence encoding the ILTV gI protein is the endogenous ILTV gI promoter, and the promoter for the nucleotide sequence encoding the NDV F protein is the hCMV IE promoter. In yet other specific embodiments, the promoter for the nucleotide sequence encoding the IBDV VP2 protein is the chicken β-actin promoter, the promoter for the nucleotide sequence encoding the ILTV gD protein is the endogenous ILTV gD promoter, the promoter for the nucleotide sequence encoding the ILTV gI protein is the endogenous ILTV gI promoter, and the promoter for the nucleotide sequence encoding the NDV F protein is the hCMV IE promoter.

In certain embodiments, an $rMDV_{np}$ of the present invention that includes insertions of nucleotide sequences encoding the ILTV gD protein, the ILTV gI protein, and the IBDV VP2 protein also includes one or more exogenous transcription terminator sequences. In specific embodiments of this type, a transcription terminator sequence is downstream from the nucleotide sequence encoding the IBDV VP2 protein. In particular embodiments, the nucleotide sequences encoding the ILTV gD protein and the ILTV gI protein share one transcription terminator sequence and the nucleotide sequence encoding the IBDV VP2 protein has another. In more particular embodiments, at least one of the transcription terminator sequences comprises a feline herpesvirus US-9 (FHV US-9) polyadenylation sequence. In even more particular embodiments, at least one of the transcription terminator sequences comprises a Simian virus 40 (SV40) polyadenylation sequence.

In certain embodiments, the NDV F protein also includes one or more exogenous transcription terminator sequences. In specific embodiments of this type, a transcription terminator sequence is downstream from the nucleotide sequence encoding the NDV F protein. In related embodiments at least one of the transcription terminator sequences comprises a Herpes Simplex Virus thymidine kinase (HSV TK) polyadenylation sequence. In alternative embodiments at least one of the transcription terminator sequences comprises a human cytomegalovirus immediate early (hCMV IE) polyadenylation sequence. In specific embodiments, the $rMDV_{np}$ is an rHVT. In alternative embodiments, the $rMDV_{np}$ is an rMDV2.

The present invention also provides an $rMDV_{np}$ that comprises (i) an mCMV IE promoter, a chicken beta-actin gene promoter, or an hCMV promoter (ii) a coding sequence for the IBDV VP2 protein, (iii) a transcription terminator sequence (iv) an ILTV gD promoter, (v) a coding sequence for the ILTV gD protein, (vi) an ILTV gI promoter, and (vii) a coding sequence for the ILTV gI protein in the UL54.5 site of the $rMDV_{np}$ genome. In particular embodiments of this type, the nucleotide sequence of SEQ ID NO: 21 is comprised within the UL54.5 site of the $rMDV_{np}$ genome. In specific embodiments, the $rMDV_{np}$ further comprises (i) an hCMV IE promoter, (ii) a coding sequence for the NDV F protein and (iii) a hCMV IE transcription terminator sequence in the US2 site of its genome. In particular embodiments of this type, the nucleotide sequence of SEQ ID NO: 22 is comprised within the US2 site of the $rMDV_{np}$ genome.

The present invention further provides an $rMDV_{np}$ comprising (i) an mCMV IE promoter, a chicken beta-actin gene promoter, or an hCMV promoter (ii) a coding sequence for the IBDV VP2 protein, (iii) a transcription terminator sequence (iv) an ILTV gD promoter, (v) a coding sequence for the ILTV gD protein, (vi) an ILTV gI promoter, and (vii) a coding sequence for the ILTV gI protein in the US2 site of the $rMDV_{np}$ genome. In certain embodiments of this type, the nucleotide sequence of SEQ ID NO: 24 is comprised within the US2 site of the $rMDV_{np}$ genome. In yet other embodiments of this type, the nucleotide sequence of SEQ ID NO: 25 is comprised within the US2 site of the $rMDV_{np}$ genome. In more particular embodiments of this type, the nucleotide sequence of SEQ ID NO: 23 is comprised within the US2 site of the $rMDV_{np}$ genome. In specific embodiments, the $rMDV_{np}$ further comprises (i) an hCMV IE promoter, (ii) a coding sequence for the NDV F protein and (iii) a hCMV IE transcription terminator sequence in the UL54.5 site of its genome. In particular embodiments of this type, the nucleotide sequence of SEQ ID NO: 26 is comprised within the UL54.5 site of the $rMDV_{np}$ genome.

In addition, the present invention also provides an $rMDV_{np}$ comprising (i) an ILTV gD promoter, (ii) a coding sequence for the ILTV gD protein, (iii) an ILTV gI promoter, (iv) a coding sequence for the ILTV gI protein (v) an hCMV IE promoter, (vi) a coding sequence for the NDV F protein and (vii) a hCMV IE transcription terminator sequence in the UL54.5 site of the $rMDV_{np}$ genome. In particular embodiments of this type, the nucleotide sequence of SEQ ID NO: 31 is comprised within the UL54.5 site of the $rMDV_{np}$ genome. In specific embodiments, the $rMDV_{np}$ further comprises (1) a mCMV IE promoter (ii) a coding sequence for the IBDV VP2 protein, and (iii) a transcription terminator sequence within the US2 site of the $rMDV_{np}$ genome. In particular embodiments of this type, the nucleotide sequence of SEQ ID NO: 32 is comprised within the US2 site of the $rMDV_{np}$ genome.

The present invention also provides an $rMDV_{np}$ comprising (i) an ILTV gD promoter, (ii) a coding sequence for the ILTV gD protein, (iii) an ILTV gI promoter, (iv) a coding sequence for the ILTV gI protein (v) an hCMV IE promoter, (vi) a coding sequence for the NDV F protein and (vii) a hCMV IE transcription terminator sequence in the US2 site of the $rMDV_{np}$ genome. In particular embodiments of this type, the nucleotide sequence of SEQ ID NO: 28 is comprised within the US2 site of the $rMDV_{np}$ genome. In specific embodiments, the $rMDV_{np}$ further comprises (i) a mCMV IE promoter (ii) a coding sequence for the IBDV VP2 protein, and (iii) a transcription terminator sequence within the UL54.5 site of the $rMDV_{np}$ genome. In particular embodiments of this type, the nucleotide sequence of SEQ ID NO: 27 is comprised within the UL54.5 site of the $rMDV_{np}$ genome.

The present invention further provides an $rMDV_{np}$ comprising (i) an mCMV IE promoter (ii) a coding sequence for the IBDV VP2 protein, (iii) a transcription terminator sequence (iv) an hCMV IE promoter, (v) a coding sequence for the NDV F protein and (vi) a hCMV IE transcription terminator sequence in in the US2 site of the $rMDV_{np}$ genome. In particular embodiments of this type, the nucleotide sequence of SEQ ID NO: 30 is comprised within the US2 site of the $rMDV_{np}$ genome. In specific embodiments, the $rMDV_{np}$ further comprises (i) an ILTV gD promoter, (ii) a coding sequence for the ILTV gD protein, (Iii) an ILTV gI promoter, and (iv) a coding sequence for the ILTV gI protein is comprised within the UL54.5 site of its genome. In particular embodiments of this type, the nucleotide sequence of SEQ ID NO: 29 is comprised within the UL54.5 site of the $rMDV_{np}$ genome.

The present invention also provides an $rMDV_{np}$ comprising (i) an mCMV IE promoter (ii) a coding sequence for the IBDV VP2 protein, (iii) a transcription terminator sequence (iv) an hCMV IE promoter, (v) a coding sequence for the NDV F protein and (vi) a hCMV IE transcription terminator sequence in in the UL54.5 site of the $rMDV_{np}$ genome. In specific embodiments, the $rMDV_{np}$ further comprises (i) an ILTV gD promoter, (ii) a coding sequence for the ILTV gD protein, (iii) an ILTV gI promoter, and (iv) a coding sequence for the ILTV gI protein is comprised within the US2 site of its genome.

The present invention also provides an $rMDV_{np}$ comprising (i) an mCMV IE promoter (ii) a coding sequence for the IBDV VP2 protein, (iii) a transcription terminator sequence (iv) an hCMV IE promoter, (v) a coding sequence for the NDV F protein and (vi) a hCMV IE transcription terminator sequence in the US2 site of the $rMDV_{np}$ genome and (i) an ILTV gD promoter, (ii) a coding sequence for the ILTV gD protein, (iii) an ILTV gI promoter, and (iv) a coding sequence for the ILTV gI protein comprised within the UL7/8 site of its genome.

In more specific embodiments, the present invention provides an rHVT that comprises a first heterologous nucleic acid and a second heterologous nucleic acid. The first heterologous nucleic acid comprising (i) a murine cytomegalovirus immediate early (mCMV IE) promoter, (ii) a coding sequence for the IBDV VP2 protein, (iii) a transcription terminator sequence (iv) an ILTV gD promoter, (v) a coding sequence for the ILTV gD protein, (vi) an ILTV gI promoter, and (vii) a coding sequence for the ILTV gI protein. In particular embodiments of this type, the specific 5' to 3' order for the nucleotide sequences of this recombinant nucleic acid is (i)-(vii). In a more specific embodiment the transcription terminator sequence comprises an SV40 polyadenylation sequence. In an even more specific embodiment of this type, the first heterologous nucleic is located in the US2 site of the rHVT genome. The second heterologous nucleic acid comprises a recombinant nucleic acid that comprises in 5' to 3' direction in the following order (i) a human cytomegalovirus immediate early (hCMV IE) promoter, (ii) a coding sequence for the NDV F protein, and (iii) a transcription terminator sequence. In a more specific embodiment the transcription terminator sequence comprises a human cytomegalovirus immediate early (hCMV IE) polyadenylation sequence. In more specific embodiments of this type, the second heterologous nucleic acid is located in the UL54.5 site of the rHVT genome.

Accordingly the present invention includes recombinant HVTs (rHVTs) that comprises two heterologous nucleic acids, each inserted in separate nonessential sites of the HVT genome. In certain embodiments the first heterologous nucleic acid comprises (i) a murine cytomegalovirus immediate early (mCMV IE) promoter, (ii) a coding sequence for the IBDV VP2 protein, (iii) a transcription terminator sequence (iv) an ILTV gD promoter, (v) a coding sequence for the ILTV gD protein, (vi) an ILTV gI promoter, and (vii) a coding sequence for the ILTV gI protein. In particular embodiments of this type, the specific 5' to 3' order for the nucleotide sequences of this recombinant nucleic acid is (i)-(vii). The second heterologous nucleic acid comprises the following 5' to 3' order (i) a human cytomegalovirus immediate early (hCMV IE) promoter, (ii) a coding sequence for the NDV F protein, and (iii) a transcription terminator sequence. In particular embodiments the first heterologous nucleic acid is inserted into the US2 site and the second heterologous nucleic acid is inserted into the UL54.5 site. In particular embodiments of this type, the first heterologous nucleic acid comprises the nucleotide sequence of SEQ ID NO: 23 and the second heterologous nucleic acid comprises the nucleotide sequence of SEQ ID NO: 26. In alternative embodiments the second heterologous nucleic acid is inserted into the US2 site and the first heterologous nucleic acid is inserted into the UL54.5 site. In certain embodiments of this type, the first heterologous nucleic acid comprises the nucleotide sequence of SEQ ID NO: 21 and the second heterologous nucleic acid comprises the nucleotide sequence of SEQ ID NO: 22.

In other embodiments, the first heterologous nucleic acid comprises (i) a murine cytomegalovirus immediate early (mCMV IE) promoter, (ii) a coding sequence for the IBDV VP2 protein, (iii) a transcription terminator sequence (iv) a human cytomegalovirus immediate early (hCMV IE) promoter, (v) a coding sequence for the NDV F protein, and (vi) a transcription terminator sequence. In particular embodiments of this type, the specific 5' to 3' order for the nucleotide sequences of this recombinant nucleic acid is (i)-(vi). The second heterologous nucleic acid comprises the following 5' to 3' order (i) an ILTV gD promoter, (ii) a coding sequence for the ILTV gD protein, (iii) an ILTV gI promoter, and (iv) a coding sequence for the ILTV gI protein. In particular embodiments the first heterologous nucleic acid is inserted into the US2 site and the second heterologous nucleic acid is inserted into the UL54.5 site. In particular embodiments, the first heterologous nucleic acid comprises the nucleotide sequence of SEQ ID NO: 30 and the second heterologous nucleic acid comprises the nucleotide sequence of SEQ ID NO: 29. In alternative embodiments the second heterologous nucleic acid is inserted into the US2 site and the first heterologous nucleic acid is inserted into the UL54.5 site.

In still other embodiments, the first heterologous nucleic acid comprises (i) an ILTV gD promoter, (ii) a coding sequence for the ILTV gD protein, (iii) an ILTV gI promoter, (iv) a coding sequence for the ILTV gI protein (v) a human cytomegalovirus immediate early (hCMV IE) promoter, (vi) a coding sequence for the NDV F protein, and (vii) a transcription terminator sequence. In particular embodiments of this type, the specific 5' to 3' order for the nucleotide sequences of this recombinant nucleic acid is (i)-(vii). The second heterologous nucleic acid comprises the following 5' to 3' order (i) a murine cytomegalovirus immediate early (mCMV IE) promoter, (ii) a coding sequence for the IBDV VP2 protein, (iii) a transcription terminator sequence. In particular embodiments the first heterologous nucleic acid is inserted into the US2 site and the second heterologous nucleic acid is inserted into the UL54.5 site. In particular embodiments of this type the first heterologous nucleic acid comprises the nucleotide sequence of SEQ ID NO: 28 and the second heterologous nucleic acid comprises the nucleotide sequence of SEQ ID NO: 27. In alternative embodiments the second heterologous nucleic acid is inserted into the US2 site and the first heterologous nucleic acid is inserted into the UL54.5 site. In particular embodiments of this type the first heterologous nucleic acid comprises the nucleotide sequence of SEQ ID NO: 31 and the second heterologous nucleic acid comprises the nucleotide sequence of SEQ ID NO: 32.

The present invention further provides methods for making any $rMDV_{np}$ of the present invention (e.g., a rHVT). In certain embodiments, a first heterologous nucleic acid is constructed to comprise a nucleotide sequence that encodes an ILTV gD protein, a nucleotide sequence that encodes an ILTV gI protein, and a nucleotide sequence that encodes an IBDV VP2 protein. In particular embodiments of this type, the promoters for the nucleotide sequences that encode the ILTV gD protein and the ILTV gI protein respectively, are their respective endogenous promoters. In related embodiments, the promoter for the nucleotide sequence that encodes an IBDV VP2 protein is the mCMV IE promoter, the chicken beta-actin gene promoter, or the hCMV promoter.

The first heterologous nucleic acid is then inserted into a nonessential site of an $rMDV_{np}$ of the present invention. In certain embodiments, the first heterologous nucleic acid is an expression cassette. In particular embodiments of this type, the expression cassette comprises the nucleotide sequence of SEQ ID NO: 21.

The process can further comprises a second heterologous nucleic acid being constructed that is also inserted into a nonessential site of the $rMDV_{np}$. In particular embodiments, the second heterologous nucleic acid comprises a human cytomegalovirus immediate early (hCMV IE) promoter, a coding sequence for the NDV F protein, and a transcription terminator sequence. In certain embodiments, the second heterologous nucleic acid is an expression cassette. In particular embodiments of this type, the expression cassette comprises the nucleotide sequence of SEQ ID NO: 22. In specific embodiments the first heterologous nucleic acid is inserted into a first nonessential site of the $rMDV_{np}$, and the second heterologous nucleic acid is inserted into second nonessential site of the $rMDV_{np}$. In certain embodiments, the first nonessential site of the $rMDV_{np}$ is the UL 54.5 site. In related embodiments, the second nonessential site of the $rMDV_{np}$ is the US2 site. In alternative embodiments, the first nonessential site of the $rMDV_{np}$ is the US2 site and the second nonessential site of the $rMDV_{np}$ is the UL 54.5 site. In specific embodiments of this type, the first heterologous nucleic acid comprises the nucleotide sequence of SEQ ID NO: 23 and the second heterologous nucleic acid comprises the nucleotide sequence of SEQ ID NO: 26. In other embodiments of this type, the first heterologous nucleic acid comprises the nucleotide sequence of SEQ ID NO: 24 and the second heterologous nucleic acid comprises the nucleotide sequence of SEQ ID NO: 26. In still other embodiments of this type the the first heterologous nucleic acid comprises the nucleotide sequence of SEQ ID NO: 25 and the second heterologous nucleic acid comprises the nucleotide sequence of SEQ ID NO: 26. In certain embodiments, the method of making an $rMDV_{np}$ is a method of making an rHVT. In alternative embodiments, the method of making an $rMDV_{np}$ is a method of making an rMDV2.

Accordingly in one aspect, the present invention provides immunogenic compositions and/or vaccines that comprise an $rMDV_{np}$ of the present invention (e.g., a rHVT). In particular embodiments these immunogenic compositions and/or vaccines are stable, safe, and have relatively strong antigen expression and/or efficacy. Alternatively, or in addition, the immunogenic compositions and/or vaccines that comprise an $rMDV_{np}$ of the present invention aid in the protection of a chicken against a disease caused by ILTV and/or IBDV and/or NDV and/or MDV1, following the administration of the immunogenic compositions and/or vaccines to the chicken.

The present invention further provides immunogenic compositions and/or vaccines that comprise any $rMDV_{np}$ of the present invention (e.g., a rHVT) that are further combined with an additional IBDV, ILTV, NDV, and/or MDV antigen(s) to improve and expand the immunogenicity provided. In a particular embodiment of this type, the antigen is an attenuated or mild live variant IBDV (e.g., IBDV 89/03). In another particular embodiment of this type, the antigen is an attenuated (or mild live) Newcastle Disease Virus (NDV), e.g., NDV C2. In yet another particular embodiment of this type, the antigen is an attenuated Marek's disease virus e.g., SB1. In addition, the present invention also provides immunogenic compositions and/or vaccines that comprise any $rMDV_{np}$ of the present invention that is further encodes an antigen for a pathogen other than MDV, ILTV, or NDV.

The present invention also provides methods for aiding in the protection of poultry against a disease caused by ILTV and/or IBDV and/or NDV and/or MDV1 by administering such vaccines and/or immunogenic compositions to a poultry subject (e.g., to a chicken). In particular embodiments of this type, a vaccine of the present invention is administered subcutaneously. In other embodiments, a vaccine of the present invention is administered in ovo.

These and other aspects of the present invention will be better appreciated by reference to the following Figures and the Detailed Description.

DETAILED DESCRIPTION OF THE INVENTION

Figure 1:
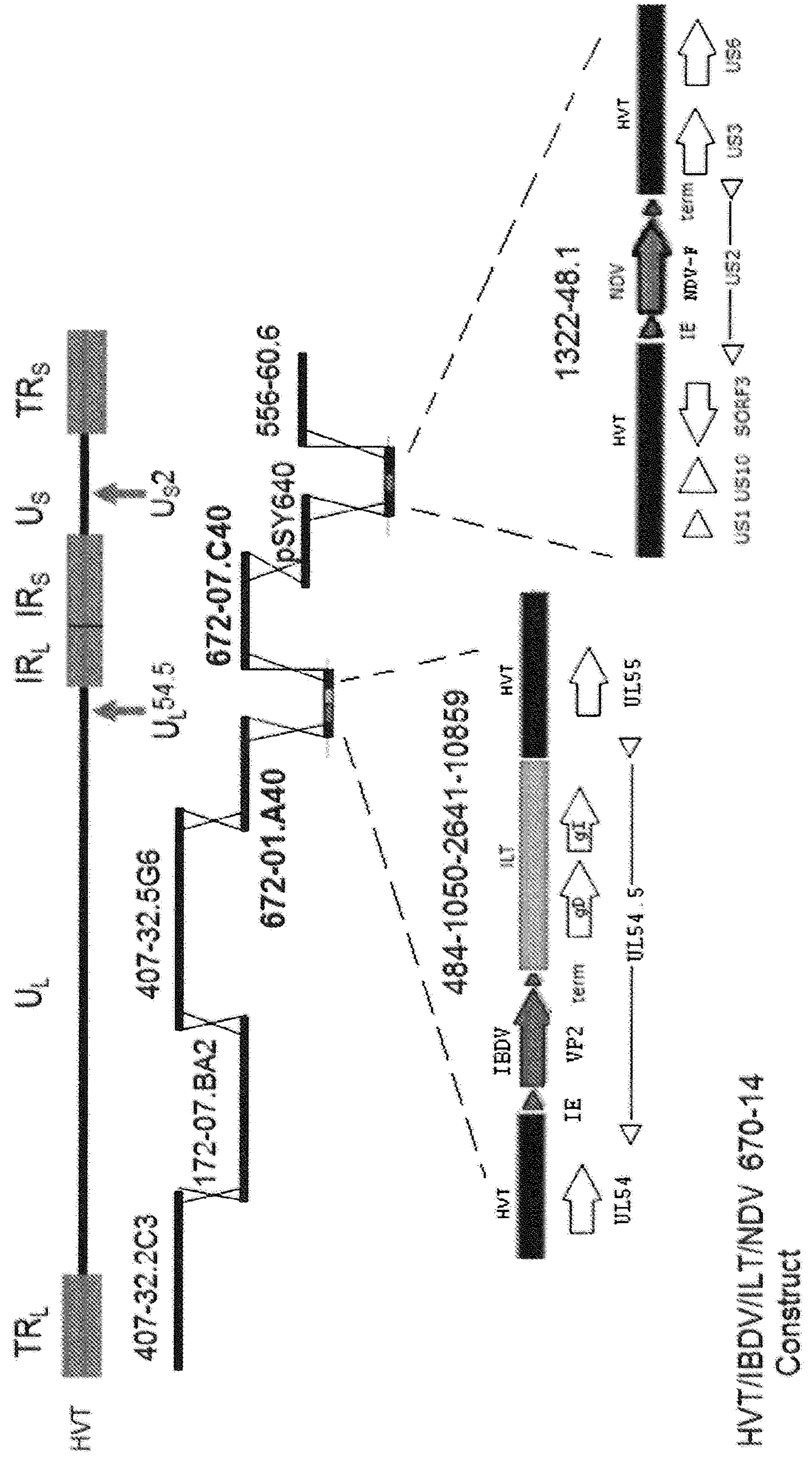
FIG. 1 is a schematic drawing of insertion fragments for generating HVT/IBDV/ILTV/NDV constructs as described in Example 2, below. In short, this is a schematic view of the HVT genome, consisting of two unique regions, each flanked by repeat regions, and the cloned fragments required to reconstruct the HVT/IBDV/ILTV/NDV 670-14 virus. The orientation of the inserted gene cassettes (mIE-IBDV-vp2 and ILTV-gD/gI or hIE-NDV-F), relative to the interrupted genes (UL54.5 or US2), and the flanking genes are shown in the blow-up regions. Legend: TRL: Terminal Repeat Long region, UL: Unique Long region; IRL: Internal Repeat Long region, IRS: Internal Repeat Short region; US: Unique Short region; TRS: Terminal Repeat Short region.

The present invention overcomes the prior failure to be able to construct a single rMDV$_{np}$ vector that encodes and expresses antigens from three or more foreign pathogenic chicken viruses. In particular embodiments, an rMDV$_{np}$ of the present invention encodes and expresses foreign antigen proteins from three or more of the avian viruses. In particular embodiments the avian viruses are Newcastle Disease Virus (NDV), Infectious Laryngotraceitis virus (ILTV), and Infectious Bursal Disease (IBDV). Such rMDV$_{np}$ vectors can be employed in vaccines and/or immunogenic compositions that aid in the protection against Marek's disease, Infectious Bursal Disease (Gumboro disease), Infectious Laryngotraceitis virus, and/or Newcastle Disease Virus. In specific embodiments, the rMDV$_{np}$ is an rHVT. In alternative embodiments, the rMDV$_{np}$ is an rMDV2. The present invention further provides immunogenic compositions and/or vaccines that comprise any rMDV$_{np}$ of the present invention combined with an additional IBDV, ILTV, NDV, and/or MDV antigen, and/or one or more antigens from a chicken pathogen other than MDV, ILTV, NDV, or IBDV. In a completely different aspect, the recombinant vector that encodes and expresses the foreign antigens from NDV, ILTV, IBDV is not an rMDV$_{np}$, but rather a chimeric Marek's Disease virus that contains specified genomic sequences from KM replacing their counterparts in an HVT vector, e.g., the novel avian herpes virus (NAHV) [see e.g., U.S. Pat. No. 6,913,751].

Prior to the present invention, an HVT vector already had been constructed containing an NDV gene inserted'into the US10 region. This HVT-NDV vector was shown to be stable and to express sufficient levels of the corresponding NDV gene product, the NDV F protein, to protect vaccinated chickens against a virulent NDV challenge. In addition, an HVT vector already had been constructed containing a pair of ILTV genes inserted in the HVT UL54.5 region. This HVT-ILTV vector was shown to be stable and to express sufficient levels of the corresponding ILTV gene products, the ILTV gI and gD proteins, to protect vaccinated chickens against a virulent ILTV challenge virus. More recently, other multivalent constructs also have been reported.

More particularly, a multivalent HVT construct to protect against both NDV and ILTV was designed based on the successful constructs comprising the insertion of the NDV-F gene in the US10 site and the insertion of the ILTV gD and gI genes in UL54.5 site in individual constructs [see, U.S. Pat. No. 8,932,604 B2]. Unexpectedly however, following the passaging of this multivalent construct in tissue culture the recombinant virus lost its ability to express the ILTVgD, ILTVgI, and NDV F proteins. This proved to be true with a number of duplicate recombinant HVT constructs. Indeed, these recombinant viruses were unstable and unsuitable for further development as vaccines. These findings demonstrate that the design of a single multivalent rHVT vector that can stably express both the NDV F protein and the ILTVgD and ILTVgI proteins was not a simple process that can be extrapolated from existing information. Indeed, if such stable and efficacious multivalent rHVT vectors were possible at all, their design needed to be premised on an unpredictable set of complex interactions minimally involving the relationship between the insertion sites used and the foreign nucleotide sequences to be inserted. Accordingly, the design of rHVT constructs remains unpredictable from the known art. This would appear to be even a bigger issue for an rMDV$_{np}$ that encodes heterologous antigens from three or more avian virus pathogens.

Despite the clear difficulties outlined above, and the general consensus in the field that the insertion of foreign antigens from three or more different viral pathogens into an MDV$_{np}$ construct overtaxes that construct, leading to a lack of stability, the present invention surprisingly provides stable recombinant MDV$_{np}$ vectors in which two genes from ILTV, one gene from IBDV, and one gene from NDV have been inserted into a single MDV$_{np}$. Accordingly, such a single rMDV$_{np}$ construct can be employed as the sole active in a vaccine that aids in the protection against four major pathogenic poultry viruses.

In particular embodiments of the present invention nucleotide sequences encoding four foreign antigens are inserted into one or more nonessential regions of the genome of a single HVT. Accordingly, such a recombinant HVT vector should be capable of being used to provide protection against MDV, NDV, IBDV, and ILTV infections. Previously, multiple different rHVT vectors were necessary to protect against these four viruses, which can interfere with the antigenicity of each other.

The present invention therefore, is advantageous over current methods because it should be able to provide simultaneous protection against MDV, NDV, IBDV, and ILTV infections by inoculation of poultry and/or poultry eggs with only a single recombinant MDV$_{np}$. In particular, this allows for additional vaccines to be administered via the in ovo route, because there is a limit on how much volume can be injected into an egg, and further saves on manufacturing costs because only one rather than two vectors is needed.

Furthermore, the present invention includes embodiments that comprise different $rMDV_{np}$ constructs in the same vaccine and/or immunogenic compositions. In certain embodiments of this type, the vaccine and/or immunogenic composition comprise both an rMDV2 and an rHVT, each of which encode one or more foreign antigens. Indeed, unlike the combination of two rHVTs, which inevitably lead to one construct significantly overgrowing the other, combining an rHVT with an rMDV2 has been reported not to lead to significant overgrowth.

Therefore, in specific embodiments, a vaccine of the present invention comprises an rHVT that encodes an ILTV gD protein, an ILTV gI protein, an IBDV VP2 protein, and an NDV F protein, with an rMDV2 that encodes yet another poultry viral antigen. Heretofore, no $rMDV_{np}$ had been shown to encode and express foreign antigens from three different poultry viruses, and still remain stable, as well as capable of expressing sufficient levels of the corresponding antigens for protecting vaccinated chickens against a virulent challenge with the corresponding three viruses, as well as against virulent MDV.

Accordingly, the present invention provides immunogenic compositions and/or vaccines that comprise any $rMDV_{np}$ of the present invention. In specific embodiments, the $rMDV_{np}$ is an rHVT. In alternative embodiments, the $rMDV_{np}$ is an rMDV2. In addition, the present invention provides methods for aiding in the protection of poultry (and in certain embodiments protects) against a disease caused by ILTV and/or IBDV and/or NDV and/or MDV1 by administering such a vaccine and/or immunogenic composition of the present invention. In specific embodiments, the poultry subject is a chicken. In particular embodiments of this type, a vaccine of the present invention is administered subcutaneously. In other embodiments, a vaccine of the present invention is administered in ovo. In preferred embodiments, the $rMDV_{np}$ vaccine of the present invention is both safe, stable, and efficacious.

In order to more fully appreciate the instant Invention, the following definitions are provided.

The use of singular terms for convenience in description is in no way intended to be so limiting. Thus, for example, reference to a composition comprising "a polypeptide" includes reference to one or more of such polypeptides.

As used herein a "nonpathogenic Marek's Disease Virus" or "$MDV_{np}$" or "npMDV" is a virus in the MDV family that shows little to no pathogenicity in poultry. The term "$MDV_{np}$" includes naturally occurring MDVs that have been passaged or otherwise similarly manipulated, but does not include viral constructs in which a specific region of the genome of one MDV serotype is replaced by the corresponding region of a different MDV serotype to form a chimeric virus, such as the novel avian herpesvirus (NAHV). In certain embodiments, the $MDV_{np}$ is an HVT. In other embodiments, the $MDV_{np}$ is an MDV2. In particular embodiments of this type, the MDV2 is SB1. *As used herein, an $MDV_{np}$* that has been genetically modified to encode a heterologous nucleotide sequence (e.g., a foreign gene) is defined as a "recombinant $MDV_{np}$" or "$rMDV_{np}$". The term "$rMDV_{np}$" includes naturally occurring $MDV_{np}$'s that have been genetically modified to encode a heterologous nucleotide sequence, but does not include viral constructs in which a specific region of the genome of one MDV serotype is replaced by the corresponding region of a different MDV serotype to form a chimeric virus, such as the novel avian herpesvirus (NAHV).

As used herein a "novel avian herpesvirus" ("NAHV") is a recombinant chimeric virus comprising a unique long viral genomic region which naturally occurs in herpesvirus of turkeys virus (HVT) and a unique short viral genomic region which naturally occurs in Marek's disease 1 (MDV1) [see, U.S. Pat. Nos. 5,965,138, 6,183,753, 6,913,751 B2]. In a preferred embodiment the NAHV comprises a unique long viral genomic region which naturally occurs in herpesvirus of turkeys virus (HVT), a unique short viral genomic region which naturally occurs in Marek's disease 1 (MDV1), and the repeat viral regions of the HVT [see, U.S. Pat. No. 6,913,751 B2].

As used herein, a "nonessential site" is a site in the $MDV_{np}$ genome (or alternatively in the NAVH genome) in which an insertion of a heterologous nucleotide sequence into that site does not prevent the $MDV_{np}$ (or NAVH) from replicating in a host cell. Nonessential sites are generally identified by the open reading frame in which they reside, e.g., the US2 site, or a region between two open reading frames, e.g., the UL7/8 site. The use of the term "nonessential site" is in no way intended to even suggest that there is only a single unique nucleotide position in the nucleotide sequence of a given open reading frames (or in the region between two open reading frames) where an insertion of a heterologous nucleic acid must be made in order for the $MDV_{np}$ (or NAVH) to maintain its ability to replicate in a host cell.

As used herein, when an $rMDV_{np}$ (or NAHV) is said to comprise a given nucleic acid "inserted" in a nonessential site in the $rMDV_{np}$ genome (or NAHV genome), it means that the given nucleic acid is a heterologous nucleic acid that is located in that nonessential site of the $MDV_{np}$ (or NAHV). Accordingly, an $rMDV_{np}$ comprising a first nucleic acid inserted in a first nonessential site in the $rMDV_{np}$ genome and a second nucleic acid inserted in a second nonessential site in the $rMDV_{np}$ genome is equivalent to an $rMDV_{np}$ comprising a first heterologous nucleic acid located in a first nonessential site in the $rMDV_{np}$ genome and a second heterologous nucleic acid located in a second nonessential site in the $rMDV_{np}$ genome, and vice versa.

As used herein the term "poultry" can Include chickens, turkeys, ducks, geese, quail, and pheasants.

As used herein, a "vaccine" is a composition that is suitable for application to an animal (including, in certain embodiments, humans, while in other embodiments being specifically not for humans) comprising one or more antigens typically combined with a pharmaceutically acceptable carrier such as a liquid containing water, which upon administration to the animal induces an immune response strong enough to minimally aid in the protection from a disease arising from an infection with a wild-type micro-organism, i.e., strong enough for aiding in the prevention of the disease, and/or preventing, ameliorating or curing the disease.

As used herein, the term "aids in the protection" does not require complete protection from any indication of infection. For example, "aids in the protection" can mean that the protection is sufficient such that, after challenge, symptoms of the underlying infection are at least reduced, and/or that one or more of the underlying cellular, physiological, or biochemical causes or mechanisms causing the symptoms are reduced and/or eliminated. It is understood that "reduced," as used in this context, means relative to the state of the infection, including the molecular state of the infection, not just the physiological state of the infection.

The vaccines of the present invention comprise at least one stable $rMDV_{np}$ of the present invention. A $rMDV_{np}$ is considered phenotypically stable when at least 90% of the viral plaques examined are positive for expression of the inserted foreign antigen, as demonstrated by binding of antibodies specific for the expressed protein in an immunofluorescent assay, following at least 10 tissue culture passages from the original stock, or following reisolation of the virus from vaccinated birds.

The vaccines of the present invention also are efficacious and preferably minimally provide at least 70% protection against NDV, and/or at least 70% protection against IBDV, and/or at least 70% protection against ILTV, and/or at least 60% protection against MDV from clinical signs or lesions associated with the disease. More preferably, the vaccine minimally provides at least 80% protection against NDV, at least 80% protection against IBDV, at least 80% protection against ILTV, and at least 70% protection against MDV from clinical signs or lesions associated with the disease. Even more preferably the vaccines follow the guidelines established by the USDA and codified in the Title 9 Code of Federal Regulations, part 113 (9CFR 113) «Standard requirements for Animal Products» live virus vaccines must provide at least 90% protection, in the case of NDV, IBDV and ILTV, and at least 80% in the case of MDV, from clinical signs or lesions associated with the disease to obtain a license.

As used herein, a "multivalent vaccine" is a vaccine that comprises two or more different antigens. In a particular embodiment of this type, the multivalent vaccine stimulates the immune system of the recipient against two or more different pathogens.

As used herein, an "adjuvant" is a substance that is able to favor or amplify the cascade of immunological events, ultimately leading to a better immunological response, i.e., the integrated bodily response to an antigen. An adjuvant is in general not required for the immunological response to occur, but favors or amplifies this response.

As used herein, the term "pharmaceutically acceptable" is used adjectivally to mean that the modified noun is appropriate for use in a pharmaceutical product. When it is used, for example, to describe an excipient in a pharmaceutical vaccine, it characterizes the excipient as being compatible with the other ingredients of the composition and not disadvantageously deleterious to the intended recipient.

As used herein, "systemic administration" is administration into the circulatory system of the body (comprising the cardiovascular and lymphatic system), thus affecting the body as a whole rather than a specific locus such as the gastro-intestinal tract (via e.g., oral or rectal administration) and the respiratory system (via e.g., intranasal administration). Systemic administration can be performed e.g., by administering into muscle tissue (intramuscular), into the dermis (intradermal or transdermal), underneath the skin (subcutaneous), underneath the mucosa (submucosal), in the veins (intravenous) etc.

As used herein the term "parenteral administration" includes subcutaneous injections, submucosal injections, intravenous injections, intramuscular injections, intradermal injections, and infusion.

The term "approximately" is used interchangeably with the term "about" and signifies that a value is within twenty-five percent of the indicated value i.e., a peptide containing "approximately" 100 amino acid residues can contain between 75 and 125 amino acid residues.

As used herein, the term, "polypeptide" is used interchangeably with the terms "protein" and "peptide" and denotes a polymer comprising two or more amino acids connected by peptide bonds. The term "polypeptide" as used herein includes a significant fragment or segment, and encompasses a stretch of amino acid residues of at least about 8 amino acids, generally at least about 12 amino acids, typically at least about 16 amino acids, preferably at least about 20 amino acids, and, in particularly preferred embodiments, at least about 30 or more amino acids, e.g., 35, 40, 45, 50, etc. Such fragments may have ends which begin and/or end at virtually all positions, e.g., beginning at residues 1, 2, 3, etc., and ending at, e.g., 155, 154, 153, etc., in all practical combinations.

Optionally, a polypeptide may lack certain amino acid residues that are encoded by a gene or by an mRNA. For example, a gene or mRNA molecule may encode a sequence of amino acid residues on the N-terminus of a polypeptide (i.e., a signal sequence) that is cleaved from, and therefore, may not be part of the final protein.

As used herein the term "antigenic fragment" in regard to a particular protein (e.g., a protein antigen) is a fragment of that protein (including large fragments that are missing as little as a single amino acid from the full-length protein) that is antigenic, i.e., capable of specifically interacting with an antigen recognition molecule of the immune system, such as an immunoglobulin (antibody) or T cell antigen receptor. For example, an antigenic fragment of an IBDV VP2 protein is a fragment of the VP2 protein that is antigenic. Preferably, an antigenic fragment of the present invention is immunodominant for antibody and/or T cell receptor recognition. In particular embodiments, an antigenic fragment with respect to a given protein antigen Is a fragment of that protein that retains at least 25% of the antigenicity of the full length protein. In preferred embodiments an antigenic fragment retains at least 50% of the antigenicity of the full length protein. More preferred embodiments it retains at least 75% of the antigenicity of the full length protein. Antigenic fragments can be as small as 5-10 amino acids or at the other extreme, be large fragments that are missing as little as a single amino acid from the full-length protein. In particular embodiments the antigenic fragment comprises 25 to 100 amino acid residues.

As used herein an amino acid sequence is 100% "homologous" to a second amino acid sequence if the two amino acid sequences are identical, and/or differ only by neutral or conservative substitutions as defined below. Accordingly, an amino acid sequence is about 80% "homologous" to a second amino acid sequence if about 80% of the two amino acid sequences are identical, and/or differ only by neutral or conservative substitutions.

Functionally equivalent amino acid residues often can be substituted for residues within the sequence resulting in a conservative amino acid substitution. Such alterations define the term "a conservative substitution" as used herein. For example, one or more amino acid residues within the sequence can be substituted by another amino acid of a similar polarity, which acts as a functional equivalent, resulting in a silent alteration. Substitutions for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids Include aspartic acid and glutamic acid. Such alterations will not be expected to affect apparent molecular weight as determined by polyacrylamide gel electrophoresis, or isoelectric point.

Particularly preferred conservative substitutions are: Lys for Arg and vice versa such that a positive charge may be maintained; Glu for Asp and vice versa such that a negative charge may be maintained; Ser for Thr such that a free —OH can be maintained; and Gln for Asn such that a free $NH_2$ can be maintained. The amino acids also can be placed in the following similarity groups: (1) proline, alanine, glycine, serine, and threonine; (2) glutamine, asparagine, glutamic acid, and aspartic acid; (3) histidine, lysine, and arginine; (4) cysteine; (5) valine, leucine, isoleucine, methionine; and (6) phenylalanine, tyrosine, and tryptophan.

In a related embodiment, two highly homologous DNA sequences can be identified by their own homology, or the homology of the amino acids they encode. Such comparison of the sequences can be performed using standard software available in sequence data banks. In a particular embodiment two highly homologous DNA sequences encode amino acid sequences having about 80% identity, more preferably about 90% identity and even more preferably about 95% identity. More particularly, two highly homologous amino acid sequences have about 80% identity, even more preferably about 90% identity and even more preferably about 95% identity.

As used herein, protein and DNA sequence percent identity can be determined using software such as MacVector v9, commercially available from Accelrys (Burlington, Mass.) and the ClustalW algorithm with the alignment default parameters, and default parameters for identity. See, e.g., Thompson, et al., 1994. *Nucleic Acids Res.* 22:4673-4680. ClustalW is freely downloadable for Dos, Macintosh and Unix platforms from, e.g., EMBLI, the European Bioinformatics Institute. The present download link is found at www.ebiec.uk/clustalw/. These and other available programs can also be used to determine sequence similarity using the same or analogous default parameters.

As used herein the terms "polynucleotide", or a "nucleic acid" or a "nucleic acid molecule" are used interchangeably and denote a molecule comprising nucleotides including, but is not limited to, RNA, cDNA, genomic DNA and even synthetic DNA sequences. The terms are also contemplated to encompass nucleic acid molecules that include any of the art-known base analogs of DNA and RNA.

A nucleic acid "coding sequence" or a "sequence encoding" a particular protein or peptide, is a nucleotide sequence which is transcribed and translated into a polypeptide in vitro or in vivo when placed under the control of appropriate regulatory elements.

The boundaries of the coding sequence are determined by a start codon at the 5'-terminus and a translation stop codon at the 3'-terminus. A coding sequence can Include, but is not limited to, prokaryotic sequences, cDNA from eukaryotic mRNA, genomic DNA sequences from eukaryotic (e.g., avian) DNA, and even synthetic DNA sequences. A transcription termination sequence can be located 3' to the coding sequence.

"Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter and the coding sequence and the promoter can still be considered "operably linked" to the coding sequence.

As used herein, the term "transcription terminator sequence" is used interchangeably with the term "polyadenylation regulatory element" and is a sequence that is generally downstream from a DNA coding region and that may be required for the complete termination of the transcription of that DNA coding sequence. A transcription terminator is a regulatory DNA element involved in the termination of the transcription of a coding region into RNA. Generally, such an element encodes a section, e.g. a hairpin structure, which has a secondary structure that can cause the RNA polymerase complex to stop transcription. A transcription terminator is therefore always situated downstream of the stop codon from the region to be translated, the 3' untranslated region.

As used herein an "expression cassette" is a recombinant nucleic acid that minimally comprises a promoter and a heterologous coding sequence operably linked to that promoter. In many such embodiments, the expression cassette further comprises a transcription terminator sequence. Accordingly, the insertion of an expression cassette into a nonessential site of the $rMDV_{np}$ genome can lead to the expression of the heterologous coding sequence by the $rMDV_{np}$. In specific embodiments, the $rMDV_{np}$ is an rHVT. In alternative embodiments, the $rMDV_{np}$ is an rMDV2.

A "heterologous nucleotide sequence" as used herein is a nucleotide sequence that is added to a nucleotide sequence of the present invention by recombinant methods to form a nucleic acid that is not naturally formed in nature. In specific embodiments, a "heterologous nucleotide sequence" of the present invention can encode a protein antigen, (e.g., encoded by a "foreign gene" relative to the $rMDV_{np}$ vectors of the present invention) such as an IBDV VP2 protein, an ILTV gI protein, an ILTV gD protein, and/or an NDV F protein. In this case, such protein antigens can be termed "foreign antigens" or more specifically "foreign protein antigens".

Heterologous nucleotide sequences can also encode fusion (e.g., chimeric) proteins. In addition, a heterologous nucleotide sequence can encode peptides and/or proteins that contain regulatory and/or structural properties. In other such embodiments, a heterologous nucleotide sequence can encode a protein or peptide that functions as a means of detecting the protein or peptide encoded by the nucleotide sequence of the present invention after the recombinant nucleic acid is expressed. In still another embodiment, the heterologous nucleotide sequence can function as a means of detecting a nucleotide sequence of the present invention. A heterologous nucleotide sequence can comprise non-coding sequences including restriction sites, regulatory sites, promoters and the like. A "heterologous nucleic acid" comprises a heterologous nucleotide sequence.

Insertion of a nucleic acid encoding an antigen of the present invention into an $rMDV_{np}$ vector is easily accomplished when the termini of both the nucleic acid and the vector comprise compatible restriction sites. If this cannot be done, it may be necessary to modify the termini of the nucleotide sequence and/or vector by digesting back single-stranded nucleic acid overhangs (e.g., DNA overhangs) generated by restriction endonuclease cleavage to produce blunt ends, or to achieve the same result by filling in the single-stranded termini with an appropriate polymerase. Alternatively, desired sites may be produced, e.g., by ligating nucleotide sequences (linkers) onto the termini. Such linkers may comprise specific oligonucleotide sequences that define desired restriction sites. Restriction sites can also be generated through the use of the polymerase chain reaction (PCR). [See, e.g., Saiki et al., *Science* 239:487-491

(1988)]. The cleaved vector and the DNA fragments may also be modified, if required, by homopolymeric tailing. Alternatively, a recombinant nucleotide sequence can be synthesized de novo.

Protein Antigens and Nucleic Acids Encoding the Protein Antigens

The ILTV gD gene appears to encode a glycoprotein of 434 amino acids In length having a molecular weight of 48,477 daltons, although others have suggested that a downstream start codon, which leads to an ILTV gD protein comprising only 377 amino acid residues, is the actual start codon [Wild et al., *Virus Genes* 12:104-116 (1996)]. The ILTV gI gene encodes a glycoprotein of 362 amino acids in length having a molecular weight of 39,753 daltons [U.S. Pat. No. 6,875,856, hereby incorporated by reference]. Nucleic acids encoding natural and/or laboratory derived variants of the ILTV gD and ILTV gI may be substituted for those presently exemplified.

In particular embodiments of the present invention, an $rMDV_{np}$ comprises a recombinant nucleic acid (e.g., an expression cassette) that encodes an ILTV gD protein comprising the amino acid sequence of SEQ ID NO: 2 or an antigenic fragment thereof. In related embodiments the $rMDV_{np}$ comprises a recombinant nucleic acid that encodes an ILTV gD protein comprising an amino acid sequence that has greater than 90%, and/or greater than 95%, and/or greater than 98%, and/or greater than 99% identity to the amino acid sequence of SEQ ID NO: 2. In particular embodiments, the ILTV gD protein is encoded by the nucleotide sequence of SEQ ID NO: 1. In specific embodiments, the $rMDV_{np}$ is an rHVT. In alternative embodiments, the $rMDV_{np}$ is an rMDV2.

In certain embodiments of the present invention, an $rMDV_{np}$ comprises a recombinant nucleic acid (e.g., an expression cassette) that encodes an ILTV gI protein comprising the amino acid sequence of SEQ ID NO: 4 or an antigenic fragment thereof. In related embodiments, the $rMDV_{np}$ comprises a recombinant nucleic acid that encodes an ILTV gI protein comprising an amino acid sequence that has greater than 90%, and/or greater than 95%, and/or greater than 98%, and/or greater than 99% identity to the amino acid sequence of SEQ ID NO: 4. In particular embodiments, the ILTV gI protein is encoded by the nucleotide sequence of SEQ ID NO: 3. In specific embodiments, the $rMDV_{np}$ is an rHVT. In alternative embodiments, the $rMDV_{np}$ is an rMDV2.

As mentioned earlier, IBDV is a member of the Bimaviridae family, which has a genome consisting of two segments (A and B) of double-stranded RNA. The larger segment A encodes a polyprotein of 110 kDa, which is subsequently cleaved by autoproteolysis to form mature viral proteins VP2, VP3 and VP4. Of these, VP2 and VP3 are the structural capsid proteins for the virion, with VP2 protein being the major host-protective immunogen. In the case of IBDV, two serotypes exist, serotype 1 and 2 which can be distinguished by virus neutralization (VN) tests. Serotype 1 viruses have been shown to be pathogenic to chickens, while serotype 2 IBDV only causes sub-acute disease in turkeys. Historically, IBDV serotype 1 viruses consisted of only one type that is known as “classic” IBD virus, but subsequently, so-called “variant” IBDV strains have emerged. In particular embodiments of the present invention the IBDV VP2 gene encodes a VP2 protein from an IBDV that is of the classic type. Such genes are well known and their sequence information is readily available, [see e.g., GenBank acc.nr. 000869 (F52/70), 000499 (STC), or AF499929 (D78)]. Alternatively, this gene can be obtained from the genome of a classic IBDV isolated from nature, using routine techniques for manipulating a Birnavirus. Classic type IBDV’s can be readily identified using serology, or molecular biology.

In particular embodiments of the present invention, an $rMDV_{np}$ comprises a recombinant nucleic acid (e.g., an expression cassette) that encodes an IBDV VP2 protein comprising the amino acid sequence of SEQ ID NO: 6 or an antigenic fragment thereof. In related embodiments, the $rMDV_{np}$ comprises a recombinant nucleic acid that encodes an IBDV VP2 protein comprising an amino acid sequence that has greater than 90%, and/or greater than 95%, and/or greater than 98%, and/or greater than 99% identity to the amino acid sequence of SEQ ID NO: 6. In specific embodiments, the IBDV VP2 protein is encoded by the nucleotide sequence of SEQ ID NO: 5. In specific embodiments, the $rMDV_{np}$ is an rHVT. In alternative embodiments, the $rMDV_{np}$ is an rMDV2.

Routine vaccinations against IBDV are performed as early as possible in the life of poultry using attenuated IBDV strains, but these can only be applied when the level of MDA against IBDV has decreased enough, which commonly is somewhere between 15 and 20 days post hatch. Many ‘live’ or inactivated IBDV vaccines are commercially available, e.g., a ‘live’ vaccine such as Nobilis™ Gumboro D78 (Merck Animal Health).

NDV has a non-segmented, negative sense, single stranded RNA genome, which is about 15 kb in size, and contains six genes, amongst which is the NDV F protein gene which encodes the so-called “fusion” glycoprotein (F protein). The F protein is involved in NDV’s attachment of and entry into host cells, and as the immunodominant protein it can be the basis of an effective immune response against NDV. The NDV F protein is expressed as a native F0 protein, which is activated upon cleavage by extra-cellular peptidases.

An NDV F protein gene, for example, can be derived from NDV Clone 30, a common lentogenic NDV vaccine strain. In certain embodiments of the present invention, an $rMDV_{np}$ comprises a recombinant nucleic acid (e.g., an expression cassette) that encodes an NDV F protein comprising the amino acid sequence of SEQ ID NO: 8 or an antigenic fragment thereof. In related embodiments, the $rMDV_{np}$ comprises a recombinant nucleic acid that encodes an NDV F protein comprising an amino acid sequence that has greater than 90%, and/or greater than 95%, and/or greater than 98%, and/or greater than 99% identity to the amino acid sequence of SEQ ID NO: 8. In particular embodiments, the NDV F protein is encoded by the nucleotide sequence of SEQ ID NO: 7. In specific embodiments, the $rMDV_{np}$ is an rHVT. In alternative embodiments, the $rMDV_{np}$ is an rMDV2.

In related embodiments of the present invention, an $rMDV_{np}$ comprises a recombinant nucleic acid (e.g., an expression cassette) that encodes an NDV F protein comprising the amino acid sequence of SEQ ID NO: 10 or an antigenic fragment thereof. In other embodiments, the $rMDV_{np}$ comprises a recombinant nucleic acid that encodes an NDV F protein comprising an amino acid sequence that has greater than 90%, and/or greater than 95%, and/or greater than 98%, and/or greater than 99% identity to the amino acid sequence of SEQ ID NO: 10. In particular embodiments, the NDV F protein is encoded by the nucleotide sequence of SEQ ID NO: 9. In specific embodiments, the $rMDV_{np}$ is an rHVT. In alternative embodiments, the $rMDV_{np}$ is an rMDV2.

Nucleic acids encoding natural and/or laboratory derived variants of the F protein gene would equally be applicable, either from lentogenic, mesogenic or velogenic NDV, as the F protein gene sequence itself is highly conserved in these different NDV pathotypes.

Nucleotide and/or protein sequences for the chicken pathogen protein antigens encoded by the $rMDV_{np}$'s of the present invention also can be found in publicly available databases such as GenBank or the Protein Information Resource.

Promoters and Polyadenylation Regulatory Elements

A promoter is a functional region on the genome of an organism that directs the transcription of a downstream coding region. A promoter is therefore situated upstream of the coding region of a gene. The mRNA synthesis directed by the promoter starts from the 'transcription start site' (TSS). The mRNA produced is in turn translated into protein starting from the gene's start codon, which is the first ATG sequence in the open reading frame (the first AUG in the mRNA). Typically the TSS is located at 30-40 nucleotides upstream of the start codon. A TSS can be determined by sequencing the 5' end of the mRNA of a gene, e.g. by the RACE technique. In general promoters are comprised within about 1000 nucleotides upstream of the position of the A of the start codon, which is generally denoted as A+1, and most promoters are situated between nucleotides −500 and A+1.

The nomenclature for a promoter is commonly based on the name of gene that it controls the expression of. For example, the murine cytomegalovirus immediate early 1 gene (mCMV-IE1) promoter "mCMV-IE1 gene promoter", refers to the promoter that naturally drives the expression of the early 1 gene (IE1 gene) for mCMV and accordingly, is situated immediately upstream of that gene. Because the IE1-gene is such a well-documented and clearly recognizable gene, and because the genomes of several mCMVs have been sequenced (in whole or in part), such a promoter readily can be identified by routine techniques. For example, in a basic protocol a promoter can be obtained by roughly sub-cloning the region in between two consecutive genes, e.g. from the poly A signal of an upstream gene to the TSS of a downstream gene. The promoter then can be identified by standard tests, e.g., by the expression of a marker gene by progressively smaller sections of a suspected promoter.

Generally, promoters contain a number of recognizable regulatory regions, such as an enhancer region, which is involved in binding regulatory factors that influence the time, the duration, the conditions, and the level of transcription. Whereas the enhancer region is normally situated upstream, a promoter also contains a region more downstream that is involved in the binding of transcription factors and directing RNA polymerase itself. This downstream region generally contains a number of conserved promoter sequence elements such as the TATA box, the CAAT box, and the GC box.

A promoter comprising both the enhancer- and the downstream region is termed a "complete" promoter, whereas a promoter comprising only the downstream region, is termed a "core" promoter.

A promoter for the expression of a (heterologous) gene in a (virus) vector needs to be able to effectively drive the transcription of that downstream coding sequence. This is generally referred to as the promoter being "operatively linked" to the coding sequence, such that the gene is 'under the control' of the promoter, or is 'driven by' the promoter. This generally means that in an expression cassette the promoter and the coding sequence of the gene are found on the same nucleic acid, in effective proximity, and with no signals or sequences between them that would intervene with effective transcription of the coding sequence.

The mCMV-IE1 gene promoter is well known in the art, and can be readily obtained from a variety of commercial sources, such as from suppliers of commercial plasmids for cloning and expression. The IE1 gene is also called the 'major IE gene'. The mCMV-IE1 protein has also been referred to as pp89. Dörsch-Häsler et al. [*Proc. Nat. Acad. Sci.,* 82:8325-8329 (1985)] described the mCMV IE1 gene promoter in 1985, and the use of this promoter in heterologous expression is also described in WO 87/03.905 and EP 728,842. The nucleotide sequence of the complete mCMV IE locus is available from GenBank under acc. nr. L06816.1 (from March 2004). The mCMV itself is available from the ATCC: initially under acc. nr. VR-194, and more recently this has been continued under acc. nr. VR-1399.

In one embodiment of the invention, the mCMV-IE1 gene promoter is a complete promoter, comprising both the core promoter region, as well as the enhancer region for the mCMV-IE1 gene. The complete mCMV-IE1 gene promoter is about 1.4 kb in size. However, the present invention also allows for some variance in length of not only the mCMV IE1-gene promoter, but also of the other elements that make up the recombinant DNA expression cassette employed in the present invention. This can result from differences in the exact conditions that are used for cloning and construction. For example, this variance may arise from using different restriction enzyme sites, PCR cloning primers, or different conditions for adapting the ends of the cloning molecules used. Consequently, some variation in length—smaller or larger—of the constituting elements may occur, without affecting the stability, and relatively strong antigen expression and/or efficacy of the overall expression cassette. In that case these length differences are Immaterial, and are within the scope of the invention. Therefore, an mCMV-IE1 gene promoter of "about 1.4 kb" is: 1.4 kb±about 25%. In particular embodiments the promoter is 1.4 kb±about 20%. In still other embodiments the variance can be 1.4 kb t about 15%, 1.4 kb±about 12%, 1.4 kb±about 10%, 1.4 kb±about 8%, 1.4 kb±about 6%, 1.4 kb±about 5%, 1.4 kb±about 4%, 1.4 kb±about 3%, 1.4 kb±about 2%, or even 1.4 kb±about 1%.

Similarly, homologs or variants of the promoter element may be used that are equally effective and stable. Therefore, in certain embodiments the mCMV-IE1 gene promoter of the present invention can be a DNA molecule of about 1.4 kb that comprises a nucleotide sequence with at least 95%, 96%, 97%, 98%, or even 99% nucleotide sequence identity to the nucleotide sequence of SEQ ID NO: 13. In a particular embodiment the mCMV-IE1 gene promoter consists of nucleotide sequence of SEQ ID NO: 13.

Many alternative promoters can be used to drive the expression of a heterologous gene encoding a protein antigen or antigenic fragment thereof in an $rMDV_{np}$ of the present invention. Examples include the pseudorabies virus (PRV) gpX promoter [see, WO 87/04463], the Rous sarcoma virus LTR promoter, the SV40 early gene promoter, the chicken beta-actin gene promoter comprising the nucleotide sequence of SEQ ID NO: 17, the Towne Strain hCMV IE promoter SEQ ID NO: 16, a derivative of the hCMV IE promoter (from strain AD169) comprising the nucleotide sequence of SEQ ID NO: 14, an ILTV gD promoter comprising the nucleotide sequence of SEQ ID NO: 11, and an ILTV gI promoter comprising the nucleotide sequence of SEQ ID NO: 12, [see e.g., U.S. Pat. No. 6,183,753 B1], the human cytomegalovirus immediate early1 (hCMV IE1) gene promoter [U.S. Pat. Nos. 5,830,745; 5,980,906], and the chicken beta-actin gene promoter [EP 1 298 139 B1]. A particular heterologous promoter for the IBDV VP2 gene is the murine (mCMV IE1) cytomegalovirus promoter. In a particular embodiment of this type the mCMV IE1 comprises the nucleotide sequence of SEQ ID NO: 13 [see e.g., EP 728,842; PCT/EP2015/081121].

The inclusion of a polyadenylation regulatory element downstream from a DNA coding region is oftentimes required to terminate the transcription of the coding DNA sequence. Accordingly, many genes comprise a polyadenylation regulatory element at the downstream end of their coding sequence. Many such regulatory elements have been identified and can be used in an $rMDV_{np}$ of the present invention. Specific examples of polyadenylation regulatory elements as exemplified herein, include a Feline Herpesvirus (FHV) US-9 polyadenylation signal comprising the nucleotide sequence of SEQ ID NO: 18, and the human Herpes Simplex Virus (HSV) thymidine kinase polyadenylation signal comprising the nucleotide sequence of SEQ ID NO: 19. The terminator and polyadenylation sequence also may come from the glycoprotein B (gB) gene of Feline Herpesvirus (FHV), from the immediate early (IE) gene of human cytomegalovirus (hCMV), strain AD 169, or from simian virus 40 (SV40).

Vaccines and Immunogenic Compositions

The present invention relates to the use of the recombinant $MDV_{np}$, the nucleic acid molecules used to construct the $MDV_{np}$, or the host cells to grow them, or any combination thereof, all according to the present invention for the manufacture of a vaccine for poultry. Accordingly, the present invention provides vaccines and/or immunogenic compositions that include a multivalent recombinant $MDV_{np}$ of the present invention. Such vaccines can be used to aid in the prevention and/or prevent Infectious Bursal Disease (Gumboro disease), and/or Marek's disease, and/or maladies associated with ILTV infections and/or maladies associated with NDV infections. A vaccine according to the present invention can be used for prophylactic and/or for therapeutic treatment, and thus can interfere with the establishment and/or with the progression of an infection and/or its clinical signs of disease.

A recombinant $MDV_{np}$ of the present invention can be grown by any number of means currently practiced in the field. For example, a recombinant $MDV_{np}$ of the present invention can be grown through the use of in vitro cultures of primary chicken cells, see e.g., the Examples below where chicken embryo fibroblast cells (CEFs) were used. The CEFs can be prepared by trypsinization of chicken embryos. The CEFs also can be plated in monolayers and then infected with the $MDV_{np}$. This particular process can be readily scaled up to industrial-sized production.

Therefore, a further aspect of the invention relates to a method for the preparation of the vaccine according to the invention comprising the steps of infecting host cells with a recombinant $MDV_{np}$ of the present invention, harvesting the infected host cells, and then mixing the harvested infected host cells with a pharmaceutically acceptable carrier. Suitable methods for infection, culture and harvesting are well known in the art and are described and exemplified herein.

Typically, the infected host cells are harvested while still intact to obtain the recombinant $MDV_{np}$ in its cell-associated form. These cells can be taken up in an appropriate carrier composition to provide stabilization for storage and freezing. The infected cells can be filled Into glass ampoules, which are sealed, frozen and stored in liquid nitrogen. Accordingly, in certain embodiments of the present invention, the vaccines and/or immunogenic compositions of the present invention are stored frozen and accordingly, comprise a cryopreservative, such as dimethyl sulfoxide (DMSO), to preserve the frozen infected cells.

Alternatively, when the recombinant $MDV_{np}$ is a recombinant HVT, it can be isolated from its host cell, for instance through sonication at the end of culturing, and then taken up into a stabilizer, and freeze-dried (lyophilized) for stable storage or otherwise reduced in liquid volume, for storage, and then reconstituted in a liquid diluent before or at the time of administration. Such reconstitution may be achieved using, for example, vaccine-grade water. In certain embodiments, a lyophilized portion of a multivalent vaccine can comprise one or more antigens and the diluent can comprise one or more other antigens.

In particular embodiments a vaccine of the present invention (or a portion thereof) can be in a freeze-dried form, e.g., as tablets and/or spheres that are produced by a method described in WO 2010/125084, hereby incorporated by reference in its entirety. In particular, reference is made to the examples, from page 15, line 28 to page 27, line 9 of WO 2010/125084, describing a method to produce such fast disintegrating tablets/spheres. Such freeze-dried forms can be readily dissolved in a diluent, to enable systemic administration of the vaccine.

Vaccines and immunogenic compositions can, but do not necessarily include, physiologically compatible buffers and saline and the like, as well as pharmaceutically acceptable adjuvants. Adjuvants can be useful for improving the immune response and/or increasing the stability of vaccine preparations. Adjuvants are typically described as non-specific stimulators of the immune system, but also can be useful for targeting specific arms of the immune system. One or more compounds which have this activity may be added to the vaccine. Therefore, particular vaccines of the present invention can further comprise an adjuvant. Examples of chemical compounds that can be used as adjuvants include, but are not limited to aluminum compounds (e.g., aluminum hydroxide), metabolizable and non-metabolizable oils, mineral oils including mannide oleate derivatives in mineral oil solution (e.g., MONTANIDE ISA 70 from Seppic SA, France), and light mineral oils such as DRAKEOL 6VR, block polymers, ISCOM's (immune stimulating complexes), vitamins and minerals (including but not limited to: vitamin E, vitamin A, selenium, and vitamin B12) and CARBOPOL®.

Other suitable adjuvants, which sometimes have been referred to as immune stimulants, include, but are not limited to: cytokines, growth factors, chemokines, supernatants from cell cultures of lymphocytes, monocytes, cells from lymphoid organs, cell preparations and/or extracts from plants, bacteria or parasites (*Staphylococcus aureus* or lipopolysaccharide preparations) or mitogens. Generally, an adjuvant is administered at the same time as an antigen of the present invention. However, adjuvants can also or alternatively be administered within a two-week period prior to the vaccination, and/or for a period of time after vaccination, i.e., so long as the antigen, e.g., a recombinant $MDV_{np}$ of the present invention persists in the tissues.

The vaccines and/or immunogenic compositions of the present invention may be administered by any route such as in ovo, by parenteral administration, Including intramuscular injection, subcutaneous injection, intravenous injection, intradermal injection, by scarification, by oral administration, or by any combination thereof.

Furthermore, the multivalent recombinant $MDV_{np}$ of the present invention can be used and/or combined with additional IBDV, ILTV, NDV, and/or MDV antigens to improve and expand the immunogenicity provided, and/or antigens for other pathogens in order to provide immune protection against such other pathogens. These additional antigens can be either live or killed whole microorganisms, other recombinant vectors, cell homogenates, extracts, proteins, or any other such derivative, provided that they do not negatively interfere with the safety, and stability with relatively strong antigen expression and/or efficacy of the vaccine according to the present invention.

The combination of a multivalent recombinant $MDV_{np}$ of the present invention with an additional MDV, IBDV, NDV, and/or ILTV antigen can be advantageous in those cases in which very virulent field strains of MDV, IBDV, NDV, or ILTV are prevalent, e.g., in a particular geographic region. In this regard, the combination of a multivalent recombinant $MDV_{np}$ of the present invention with an MDV1, MDV2, or HVT includes the Rispens (MDV1) strain, the SB1 (MDV2) strain, the FC-126 (HVT) strain and/or PB1 (HVT) strain. To improve the response against IBDV, multivalent recombinant $MDV_{np}$ may be combined with an IBDV vaccine strain, such as a mild live IBDV vaccine strain, e.g., D78 (cloned intermediate strain), PBG98, Cu-1, ST-12 (an intermediate strain), or 89/03 (a live Delaware variant strain) in a multivalent vaccine.

Examples of other microorganisms that can be used as antigens together with the multivalent recombinant $MDV_{np}$ of the present invention include: (i) viruses such as infectious bronchitis virus, avian influenza virus, adenovirus, egg drop syndrome virus, infectious bursal disease virus, chicken anaemia virus, avian encephalo-myelitis virus, fowl pox virus, turkey rhinotracheitis virus, duck plague virus (duck viral enteritis), pigeon pox virus, avian leucosis virus, avian pneumovirus, and reovirus, (ii) bacteria, such as *Escherichia coli, Salmonella* spec., *Ornitobacterium rhinotracheale, Haemophilis paragallinarum, Pasteurella multocida, Erysipelothrix rhusiopathiae, Erysipelas* spec., *Mycoplasma* spec., and *Clostridium* spec., (iii) parasites such as *Eimeria* spec., and (iv) fungi, such as *Aspergillus* spec. In particular embodiments of the present invention, a recombinant $MDV_{np}$ of the present invention can be combined with a mild live NDV vaccine strain such as vaccine strain C2. Many of such strains are used in commercial vaccines.

The combination vaccine can be made in a variety of ways including by combining the recombinant $MDV_{np}$ of the present invention with preparations of virus, or bacteria, or fungi, or parasites, or host cells, or a mixture of any and/or all of these. In particular embodiments, the components for such a combination vaccine are conveniently produced separately and then combined and filled into the same vaccine container.

As described above, a vaccine according to the invention can be used advantageously to provide safe and effective immune protection to a chicken, for example, from one or more poultry diseases by a single inoculation at very young age or in ovo. Alternatively, as would be apparent to anyone skilled in the art of poultry vaccines, the combinations described above also could include vaccination schedules in which the multivalent recombinant $MDV_{np}$ of the present invention and an additional antigen are not applied simultaneously; e.g., the recombinant $MDV_{np}$ may be applied in ovo, and the NDV C2 and/or the IBDV strain (e.g., 89/03) could be applied at a subsequent time/date.

Accordingly, the vaccines of the present invention can be administered to the avian subject in a single dose or in multiple doses. For example, a vaccine of the present invention may be applied at the day of hatch and/or in ovo at day 16-18 (Embryonation Day) ED. When multiple doses are administered, they may be given either at the same time or sequentially, in a manner and time compatible with the formulation of the vaccine, and in such an amount as will be immunologically effective. Therefore, a vaccine of the present invention may effectively serve as a priming vaccination, which later can be followed and amplified by a booster vaccination of the identical vaccine, or with a different vaccine preparation e.g., a classical inactivated, adjuvanted whole-virus vaccine. Alternatively, a vaccine of the present invention can be administered to the avian subject solely as a booster vaccination.

The volume per dose of a vaccine of the present invention can be optimized according to the intended route of application: in ova inoculation is commonly applied with a volume between 0.05 and 0.5 ml/egg, and parenteral injection is commonly done with a volume between 0.1 and 1 ml/avian. In any case, optimization of the vaccine dose volume is well within the capabilities of the skilled artisan.

SEQUENCE TABLE

| SEQ ID NO: | Description | Type |
|---|---|---|
| 1 | ILTV gD Glycoprotein | nucleic acid |
| 2 | ILTV gD Glycoprotein | amino acid |
| 3 | ILTV gI Glycoprotein | nucleic acid |
| 4 | ILTV gI Glycoprotein | amino acid |
| 5 | IBDV VP2 | nucleic acid |
| 6 | IBDV VP2 | amino acid |
| 7 | NDV F Protein (Clone 30) | nucleic acid |
| 8 | NDV F Protein (Clone 30) | amino acid |
| 9 | NDV F Protein (B1 Hitchner) | nucleic acid |
| 10 | NDV F Protein (B1 Hitchner) | amino acid |
| 11 | ILTV gD promoter | nucleic acid |
| 12 | ILTV gI promoter | nucleic acid |
| 13 | mCMV IE promoter | nucleic acid |
| 14 | hCMV IE promoter (from strain AD169) | nucleic acid |
| 15 | hCMV IE promoter (Truncated) | nucleic acid |
| 16 | hCMV IE promoter (Towne Strain) | nucleic acid |
| 17 | chicken β-actin promoter | nucleic acid |
| 18 | FHV US-9 polyadenylation signal | nucleic acid |
| 19 | HSV TK polyadenylation signal | nucleic acid |
| 20 | SV40 polyadenylation signal | nucleic acid |
| 21 | 484-1050-2641-10859 (HVT/IBDV/ILTV/NDV 670-14) mCMV IEpro-VP2-SV40pA/ILTV/HVT UL54.5 | nucleic acid |

-continued

SEQUENCE TABLE

| SEQ ID NO: | Description | Type |
|---|---|---|
| 22 | (HVT/IBDV/ILTV/NDV 670-14)<br>hCMV IEpro-F-IE(term)/HVT US2 1322-48.1 | nucleic acid |
| 23 | (HVT/IBDV/ILTV/NDV #2)<br>228509-ILT-435Vec6 (mCMV IEpro-VP2-SV40pA/ILTV/HVT) | nucleic acid |
| 24 | 1333-85.B6 (ILTV/Chicken β-actin pro-VP2-FHV US9pA/HVT) | nucleic acid |
| 25 | 1386-04.4#1 (ILTV/hCMV IEpro-VP2-HSV TKpA/HVT) | nucleic acid |
| 26 | 654-45: 325341 IE-F/1C1 (HVT/IBDV/ILT/NDV # 2)<br>hCMV IEpro-F-IE(term)/HVT UL54.5 | nucleic acid |
| 27 | VP2/1C1#8<br>(HVT/IBDV/ILT/NDV # 3)<br>mCMV IEpro-VP2-SV40pA/HVT UL54.5 | nucleic acid |
| 28 | 1332-47.A2<br>(HVT/IBDV/ILT/NDV # 3)<br>ILT/hCMV IEpro-F-IE(term)/HVT US2 | nucleic acid |
| 29 | 1332-23.7<br>(HVT/IBDV/ILT/NDV # 4)<br>ILT/HVT UL54.5 | nucleic acid |
| 30 | 435Vec60<br>(HVT/IBDV/ILT/NDV # 4)<br>mCMV IEpro-VP2-SV40pA/<br>hCMV IEpro-F-IE(term)/HVT US2 | nucleic acid |
| 31 | 1332-29.4<br>(HVT/IBDV/ILT/NDV # 5)<br>ILT/hCMV IEpro-F-IE(term)/HVT UL54.5 | nucleic acid |
| 32 | 435Vec6<br>(HVT/IBDV/ILT/NDV # 5)<br>mCMV IEDro-VP2-SV40DA/HVT US2 | nucleic acid |

The present invention may be better understood by reference to the following non-limiting examples, which are provided as exemplary of the invention. The following examples are presented in order to more fully illustrate embodiments of the invention and should in no way be construed as limiting the broad scope of the invention.

EXAMPLES

Example 1

Construction of Recombinant HVT/ILTV/IBDV/NDV Viral Vectors

Recombinant multivalent non-pathogenic Marek's Disease virus constructs were prepared that encode and express (i) two Infectious Laryngotracheitis Virus protein antigens, (ii) an Infectious Bursal Disease Virus protein antigen, and (iii) a Newcastle Disease Virus protein antigen. The present invention overcomes the problem of vaccine interference encountered when two recombinant HVT vaccines, such as Innovax®-ILT (sold by Merck Animal Health) and Vaxxitek® (sold by Merial) are given to the same animal. Moreover, the present invention uniquely provides the first recombinant nonpathogenic Marek's Disease Virus ($rMDV_{np}$) that encodes antigens from three different viral pathogens other than MDV.

Recombinant Herpesvirus of Turkey (HVT) constructs were created in which antigenic donor material from three poultry pathogens, Infectious Laryngotracheitis Virus (ILTV), Newcastle Disease Virus (NDV) and Infectious Bursal Disease virus (IBDV) were inserted into the HVT vector [see also, U.S. Pat. No. 8,932,604 B2, WO 2013/057,235, WO 2016/102647, and U.S. Ser. No. 62/351,471 filed Jun. 17, 2016, the contents of all of which are hereby incorporated by reference in its entireties]. The donor materials include a 3.563 kb SalI-HindIII fragment from ILTV, NVSL Challenge Strain, Lot #83-2 [nucleotide positions 10532-14094; Wild et al., *Virus Genes* 12:104-116 (1996): Acc. #U28832], encoding the full length genes for glycoprotein D (gD) and glycoprotein I (gI), plus partial coding regions from glycoprotein E (amino acids 1-101), and ORF5 (amino acids 734-985); an expression cassette consisting of the coding region for NDV, Clone 30 strain, fusion protein (F) gene (nucleotide positions 4544-6205; Romer-Oberdorfer et al., (1999): Acc. #Y18898), driven by a viral promoter and followed by a terminator sequence; and an expression cassette consisting of the coding region for IBDV, Faragher, type F52/70 strain, viral protein 2 (vp2) gene, driven by a viral promoter and followed by a terminator sequence. In the exemplified embodiment, the promoter driving IBDV VP2 expression comes from the immediate early (IE) of mouse cytomegalovirus (mCMV) strain ATCC VR-194, whereas that for NDV F expression comes from the immediate early (IE) gene of human cytomegalovirus (hCMV), strain AD 169. The terminator and polyadenylation sequence for IBDV VP2 comes from Simian virus 40 (SV40), whereas the terminator and polyadenylation sequence for NDV F comes from the immediate early (IE) gene of human cytomegalovirus (hCMV). The donor material for the first heterologous nucleic acid was inserted into the UL54.5 site (pos. 111240/111241, Afonso et al., *J. Virology* 75(2):971-978 (2001); Acc. #AF291866, between amino acids residues 21 and 22), whereas the donor material for the second heterologous nucleic acid was inserted into the US2 site (position 140540/140541, Afonso et al., (2001) supra; Acc. #AF291866, between amino acids residues 124 and 125) [see, FIG. 1].

Genetic and phenotypic stability is a major component of the safety and relatively strong antigen expression and/or efficacy profile of any new recombinant viral vaccine candidate. The IBDV/ILTV and NDV expression cassettes inserted into the HVT backbone are not intrinsically required for viral replication and therefore may be lost due to mutation during amplification of the virus stock in tissue culture passages. A satisfactory vaccine candidate must not easily mutate to lose expression of the foreign gene insert. A vaccine candidate is considered stable if it can be demonstrated that at least 90% of the viral plaques express the inserted foreign antigenic protein following greater than or equal to 10 passages in tissue culture.

The ability to generate herpesviruses by the cosmid reconstruction method previously had been demonstrated for pseudorabies virus [van Zijl et al., *J. Virology* 62:2191-2195 (1988)]. This procedure subsequently was employed to construct recombinant HVT vectors [see, U.S. Pat. No. 5,853,733, hereby incorporated by references with respect to the methodology disclosed regarding the construction of recombinant HVT vectors] and was used to construct the recombinant HVT/IBDV/ILTV/NDV vectors of the present invention. In this method, the entire HVT genome is cloned into bacterial vectors as several large overlapping subgenomic fragments constructed utilizing standard recombinant DNA techniques [Maniatis et al., *Molecular Cloning, Cold Spring Harbor Laboratory press*, Cold Spring Harbor, New York (1982); and Sambrook et al., *Molecular Cloning, Cold Spring Harbor Laboratory press*, Cold Spring Harbor, New York (1989)]. An HVT strain FC126 cosmid library was derived from sheared viral DNA cloned into the cosmid vector pWE15 (Stratagene, now Agilent Technologies of Santa Clara, Calif.). In addition, several large genomic DNA fragments were isolated by restriction digestion with the enzyme, BamHI, and cloned into either pWE15 or the plasmid vector pSP64 (Promega Corporation, Madison Wis.). As described in U.S. Pat. No. 5,853,733, cotransfection of these fragments into chicken embryo fibroblast (CEF) cells results in the regeneration of the HVT genome mediated by homologous recombination across the overlapping regions of the fragments. If an insertion is engineered directly into one or more of the subgenomic fragments prior to the cotransfection, this procedure results in a high frequency of viruses containing the insertion. Five overlapping subgenomic clones are required to generate the complete genome of FC126 HVT, and served as the basis for creating all HVT/IBDV/ILTV/NDV recombinant viruses.

Construction of HVT/IBDV/ILTV/NDV 670-14.1-1A1 or A2

The triple recombinant HVT vector virus, HVT/IBDV/ILTV/NDV 670-14.1-1 contains an IBDV/ILTV expression cassette inserted into the HVT UL54.5 site, and an NDV expression cassette inserted into the HVT US2 site. The cosmid regeneration of HVT/IBDV/ILTV/NDV 670-14.1-1 was performed essentially as described in U.S. Pat. No. 5,853,733 [e.g., FIG. 8 of U.S. Pat. No. 5,853,733]. To allow integration into the UL54.5 region of the FC126 HVT genome, the region covered by the cosmid nr. 407-31.1C1 in U.S. Pat. No. 5,853,733, was now provided from three smaller plasmids: 672-01.A40 and 672-07.C40, and one transfer plasmid (484-1050-2641-10859), overlapping these two, and containing the IBDV/ILTV expression cassettes in the UL54.5 gene locus. To allow integration into the US region of the FC126 HVT genome, the region covered by the cosmid nr. 378-50 In U.S. Pat. No. 5,853,733, was now provided from three smaller plasmids: pSY640 and 556-60.6, and one transfer plasmid (1322-48.1), overlapping these two, and containing the NDV expression cassettes in the US2 gene locus.

The set of nine linearized constructs: 2 cosmids and 7 plasmids are transfected all together into chicken embryo fibroblasts (CEFs), using a standard $CaCl_2$ transfection protocol and the resulting virus stock was plaque purified two times.

Description of Subgenomic Fragments for Generating FC126 HVT

Subgenomic Clone 407-32.2C3

Cosmid 407-32.2C3 contains an approximately 40,170 base pair region of genomic HVT DNA [Left terminus—pos. 39,754; Afonso et al., (2001), supra; Acc. #AF291866]. This region includes HVT BamHI fragments F', L, P, N1, E, D, and 2,092 base pairs of fragment B.

Subgenomic Clone 172-07.8A2

Plasmid 172-07.BA2 contains a 25,931 base pair region of genomic HVT DNA. It was constructed by cloning the HVT BamHI B fragment [pos. 37,663 to 63,593; Afonso et al., 2001, supra; Acc. #AF291866], into the plasmid pSP64 (Promega Corporation, Madison Wis.).

Subgenomic Clone 407-32.5G6

Cosmid 407-32.5G6 contains a 39,404 base pair region of genomic HVT DNA [pos. 61,852-101,255; Afonso et al., (2001), supra; Acc. #AF291866]. This region includes HVT BamHI fragments H, C, Q, K1, M, K2, plus 1,742 base pairs of fragment B, and 3,880 base pairs of fragment J.

Subgenomic Clone 407-31.1C1

Cosmid 407-31.1C1 contains a 37,444 base pair region of genomic HVT DNA [pos. 96,095-133,538; Afonso et al., (2001), supra; Acc. #AF291866]. This region includes HVT BamHI fragments J, G, I, F, O, plus 1,281 base pairs of fragment K2, and 6,691 base pairs of fragment A.

Subgenomic Clone 378-50

Cosmid 378-50 contains a 28,897 base pair region of genomic HVT DNA [see, FIG. 8 of U.S. Pat. No. 5,853,733]. This region includes the HVT BamHI fragment A. It was constructed by cloning the HVT BamHI A fragment [position 126,848-155,744; Afonso et al., (2001), supra; Acc. #AF291866] into cosmid pWE15.

Additional Insertion Fragments for Generating HVT/IBDV/ILTV/NDV 87044.1-1A1 or A2 (see, FIG. 1)

Subgenomic Clone 484-1050-2641-10859

The insertion plasmid 484-1050-2641-10859 contains an 8636 base pair region of genomic HVT unique long region [pos. 109489-118124; Afonso et al., 2001, supra; Acc. #AF291866], cloned into a derivative of plasmid pNEB193 (deleted AatII-PvuII). It is flanked by AscI sites and includes HVT BamHI fragments I, S, plus 1337 base pairs of fragment G and 1177 base pairs of fragment F. Inserted into an XhoI site within the HVT UL54.5 open reading frame [pos. 111240/111241; Afonso et al., 2001, supra; Acc. #AF291866, between amino acid residues 21 and 22] are 2 elements: an expression cassette consisting of the MCMV IE promoter, the IBDV classic type F52/70, Faragher strain, virus protein 2 gene (VP2), and the SV40 polyadenylation signal, followed by a 3563 base pair SalI-HindIII fragment from ILTV, NVSL Challenge Strain, Lot #83-2 [pos. 10532-14094; Wild et al., *Virus Genes* 12:104-116 (1996); Acc. #U28832], encoding the full length genes for glycoprotein D (gD) and glycoprotein I (gI), plus partial coding regions from glycoprotein E (amino adds 1-101), and ORF5 (amino acids 734985). The IBDV VP2, ILTV gD and ILTV gI genes are transcribed in the opposite direction relative to the HVT UL54.5 gene.

Subgenomic Clone 672-01.A40

Plasmid 672-01.A40 contains a 14,731 base pair region of genomic HVT DNA derived from the unique long region [pos. 96095-110825; Afonso et al., 2001, supra; Acc. #AF291866], cloned into a derivative of plasmid pNEB193. This region includes HVT BamHI fragments G, J and 1281 base pairs of K2.

Subgenomic clone 672-07.C40

Plasmid 672-07.C40 contains a 12,520 base pair region of genomic HVT DNA derived from the unique long region [pos. 116948-129467; Afonso et al., 2001, supra; Acc. #AF291866], cloned into a derivative of plasmid pNEB193. This region includes HVT BamHI fragments F, O and 2620 base pairs of A.

Subgenomic Clone 1322-48.1

The insertion plasmid 1322-48.1 contains a 7311 base pair EcoRI fragment of the HVT unique short regions [pos. 126880-144190; Afonso et al., 2001, supra; Acc. #AF291866], cloned into the plasmid pSP64 (Promega Corporation, Madison, WI.). Inserted into a unique StuI site within the HVT US2 gene [pos. 140540/140541; Afonso et al., 2001, supra; Acc. #AF291866, between amino acid residues 124 and 125] is an expression cassette consisting of the HCMV IE promoter, the NDV, Clone 30 strain, fusion gene (F), and the transcription terminator from the HCMV IE gene. The NDV F gene is transcribed in the opposite direction relative to the HVT US2 gene.

Subgenomic Clone pSY640

Plasmid pSY640 contains an approximately 13,600 base pair region of genomic HVT DNA (pos. 126848-140540; Afonso et al., 2001, supra; Acc. #AF291866] derived from BamHI fragment A. To generate this plasmid the region of DNA located upstream of the US2 gene, beginning at the StuI site located in the US2 gene and continuing to the end of the BamHI A fragment, was cloned into the plasmid pSP64 (Promega Corporation, Madison WI.).

Subgenomic Clone 556-60.6

Plasmid 556-60.6 contains an approximately 12,500 base pair region of genomic HVT DNA derived from BamHI fragment A (approximate pos. 143300-155744; Afonso et al., 2001, supra; Acc. #AF291866]. To generate this plasmid, the region of DNA located downstream of the US2 gene (beginning at the StuI site located in the US2 gene and continuing to the end of the BamHI A fragment) was cloned into pSP64 (Promega Corporation, Madison WI.), and then treated with exonuclease to "chewed back" from StuI site ~150 bp, and re-cloned into pBR322 plasmid vector.

Standard $CaCl_2$ Transfection Protocol

Secondary CEF's are seeded on 6 well culture plates and incubated at 38° C. with 5% $CO_2$ for 24 hours and confluent monolayers form. For each well a total amount of 0.5 μg DNA of cosmids and plasmids were mixed in Hepes buffer and 125 mM $CaCl_2$ was added dropwise until precipitation was imminent. This mixture was added to the CEF cell monolayer, and incubated for 2 to 3 hours. The supernatant was removed and an overlay of 15% glycerol was added, and kept on the cells for one minute. Then this was removed, washed with phosphate buffered saline (PBS), and fresh culture medium was added and the cells were incubated for two days. Next, the infection was expanded twice by harvesting cells by trypsinization and seeding onto larger plates, 6 cm plates first, then 10 cm plates 3 days later, until 50-90% CPE was achieved. Next, the amplified transfected cells were harvested by trypsinization, and dilutions of $10^{-3}$ to $10^{-4}$ were plated on 6 cm plates with CEF monolayers and incubated. The following day, the plates were covered with agar, and a number of individual plaques of HVT/IBDV/ILTV/NDV were isolated and amplified on CEFs. Each virus stock was plaque purified a second time by infecting confluent monolayers of CEFs on 6 cm plates with first round purified stocks diluted to $10^{-4}$ to $10^{-5}$ and incubating cells. The following day, the plates were covered with agar, and a number of individual plaques of HVT/IBDV/ILTV/NDV were isolated and amplified on CEFs.

Example 2

Recombinant HVT/IBDV/ILTV/NDV Virus Stocks are Phenotypically Stable for Expression of the IBDV, ILTV, and NDV Proteins Following Serial Passage in Tissue Culture Two plaque purified isolates of HVT/IBDV/ILTV/NDV, each from a separate cotransfection stock were serial passaged 15 times on secondary CEF cells and evaluated for expression of the inserted ILTV, NDV and IBDV genes in an Immunofluorescence Assay.

Generation of Tissue Culture Passage Stocks

For each tissue culture passage, confluent secondary CEF monolayers were inoculated with 50-100 μL of virus stock, and incubated at 38° C., 5% $CO_2$ for 2-5 days until CPE was evident. Next, cells were harvested by trypsinization, passage 1 (P1). The process was repeated to prepare further passage stocks (P2-P15).

Phenotypic Stability Analysis

Six well plates were planted with secondary CEF monolayers. The cells were inoculated with virus stocks harvested at various passage levels: P0-P15, or diluent alone. The plates were inoculated at multiple dilutions to achieve a countable number of plaques per well, and incubated at 38° C., 5% $CO_2$. After a five-day incubation, the supernatant was decanted and CEF monolayers were fixed with 70% acetone for approximately 20 minutes at 15-30° C. The acetone solution was decanted and the cells were allowed to air dry prior to staining with ILTV gD (polyclonal Rabbit anti-ILTV gD), ILTV gI (polyclonal rabbit anti-ILTV gI), NDV F (Mab #57), and IBDV VP2 (MCA GDV-R63) primary antibodies. Following an approximately 1.5 hour blocking step, 5% goat sera in PBS+0.5% TRITON™ X-100, 2 mL per well, is added to the dishes, and then incubated at 36°-39° C. in a humidified incubator. The primary antibodies were diluted as appropriate, added at 2 mL per well, and then incubated at 36°-39° C. for 1.3 hours in a humidified incubator.

Following the antibody incubation, the plates were washed three times with PBS+0.5% TRITON™ X-100. The FITC-labeled secondary antibody solution (rabbit anti-mouse or goat anti-rabbit) was prepared at 1:50 and 2 mL was added to each well. Following incubation, plates were washed three times with PBS+0.5% TRITON™ X-100, and examined under a fluorescent scope, and the plaques were scored as positive or negative for fluorescent staining. Plates were then examined under a white light microscope and the plaques were re-counted. The percentage of fluorescing plaques at each passage level is described in the Table 1 below. Both isolates maintain an acceptable expression level for all four antigens (greater than 90%) at passage level 15.

TABLE 1

STABILITY OF EXPRESSION FOLLOWING PASSAGE IN TISSUE CULTURE

| Virus | Passage | Percent Expression | | | |
|---|---|---|---|---|---|
| Number | Level | ILT-gD | ILT-gI | IBDV-VP2 | NDV-F |
| 640-14.1-1A1 | P0 | 100% | 100% | 100% | 100% |
| | P5 | 100% | 100% | 100% | 100% |
| | P10 | 100% | 100% | 100% | 100% |
| | P15 | 100% | 100% | 93% | 99% |

TABLE 1-continued

| STABILITY OF EXPRESSION FOLLOWING PASSAGE IN TISSUE CULTURE | | | | | |
|---|---|---|---|---|---|
| Virus | Passage | Percent Expression | | | |
| Number | Level | ILT-gD | ILT-gI | IBDV-VP2 | NDV-F |
| 640-14.1-1A2 | P0 | 100% | 100% | 100% | 100% |
| | P5 | 100% | 100% | 100% | 100% |
| | P10 | 100% | 100% | 100% | 100% |
| | P15 | 100% | 100% | 96% | 100% |

Example 3

Recombinant HVT/IBDV/ILTV/NDV Virus Stocks are Phenotypically Stable for Expression of the ILTV, NDV, And IBDV Proteins Following Vaccination and Recovery from Birds Vaccines were prepared from the two isolates of HVT/IBDV/ILTV/NDV 670-14.1-1, isolate A1 and isolate A2, and used to inoculate two groups of twenty-one (21) day-of-age chickens by the subcutaneous route. A third group of birds were vaccinated with diluent alone to serve as a negative control group. Pooled spleen samples from three birds were collected twice weekly for four weeks post vaccination, and processed for virus isolation on chicken embryo fibroblast cells (CEFs). When a cytopathic effect was clearly visible, monolayers were fixed, and the plaques were analyzed for the expression of the IBDV VP2, ILTV gD, and ILTV gI, and NDV F proteins by immunofluorescence assay (IFA), with antibodies that are specific for each protein.

Phenotypic Stability Analysis

Six well plates were planted with secondary CEF monolayers. The cells were inoculated with 5×106 spleen cells, and incubated at 38° C., 5% CO2. After five days of incubation, the supernatant was decanted and the CEF monolayers were fixed with 70% acetone for approximately 20 minutes at 15-30° C. The acetone solution was decanted and the cells were allowed to air dry prior to staining with ILTV gD (polyclonal rabbit anti-ILTV gD), ILTV gI (polyclonal rabbit anti-ILTV gI), NDV F (Mab #57) and IBDV VP2 (MCA GDV-R63) primary antibodies. Following an approximately 0.5 hour blocking step, 5% goat sera in PBS+0.5% TRITON™ X-100, 2 mL per well, is added to the dishes, and then incubated at 36°-39° C. in a humidified incubator. The primary antibodies were diluted as appropriate, added at 2 mL per well, and then incubated at 36°-39° C. for 1 hour in a humidified incubator. After the antibody incubation, the plates were washed three times with PBS+0.5% TRITON™ X-100. The FITC-labeled secondary antibody solution (rabbit anti-mouse or goat anti-rabbit) was prepared at 1:50, and 2 mL was added to each well. The plates were incubated for 1 hour at 36°-39° C. in a humidified incubator. Following incubation, the plates were washed three times with PBS+0.5% TRITON™ X-100, and examined under a fluorescent scope and the plaques were scored for positive (+) or negative (−) fluorescence staining. The plates were then examined under a white light microscope and the plaques were re-counted. The percentage of fluorescing plaques at each passage level is provided in Table 2 below.

TABLE 2

| STABILITY OF EXPRESSION FOLLOWING PASSAGE IN BIRDS (D 18) | | | | | |
|---|---|---|---|---|---|
| | Vaccine | Percent Expressing | | | |
| Vaccine | Dose (PFU) | NDV F | ILTVgI | ILTV gD | IBDV VP2 |
| HVT/IBDV/ILTV/NDV 670-14.1-1A1 (p10) | 1660 | 100% | 100% | 100% | 100% |
| HVT/IBDV/ILTV/NDV 670-14.1-1A2 (p10) | 4800 | 100% | 100% | 100% | 100% |
| Diluent | NA | 0 | 0 | 0 | 0 |

Example 4

HVT/IBDV/ILTV/NDV Efficacy Data for Two Isolates of a Particular Construct

The following four studies were conducted to demonstrate the effectiveness of a single construct HVT/IBDV/ILTV/NDV 670-14 as a vaccine candidate for protecting against a challenge with virulent Infectious Laryngotracheitis virus (ILTV), or virulent Infectious Bursal Disease Virus (IBDV), or virulent Marek's disease virus (MDV).

In the first study, one-day-old specific pathogen free (SPF) chicks were vaccinated with an HVT/IBDV/ILTV/NDV 670-14.1-1A2 vaccine candidate. Controls included a second group that remained unvaccinated. At 28 days post-vaccination, the vaccinated chicks and the non-vaccinated control chicks were challenged with virulent ILTV/USDA lot LT 96-3 via the intracheal (IT) route. Birds were then observed for clinical signs of disease for 10 days. In Table 3, the results show the 670-14.1-1A2 vaccine provided partial protection from challenge. A second study was conducted using a second clone of the vaccine, 670-14.1-1A1. In Table 4, the results show a marked improvement in protection. Accordingly, the next two studies were performed with the 670-14.1-1A1 vaccine candidate. These results provide evidence that an HVT/IBDV/ILTV/NDV can be both stable and efficacious.

TABLE 3

ILTV Challenge Following Vaccination with Isolate 670-14.1-1A2

| | | Vaccination | | | Challenge at 4 weeks | | |
|---|---|---|---|---|---|---|---|
| Group | Vaccine Identification | Age | Actual Dose | Route | # Affected/ Total | % Affected | % Protected |
| 5 | Challenged controls | 1 day | NA | SC | 15/15 | 100% | 0% |
| 6 | Non-challenged controls | 1 day | NA | SC | 0/10 | 0% | NA |
| 7 | HVT/IBDV/ ILTV/NDV | 1 day | 2394 | SC | 14/22 | 64% | 36% |

TABLE 4

ILTV CHALLENGE FOLLOWING VACCINATION WITH ISOLATE 670-14.1-1A1

| | | Vaccination | | | Challenge at 4 weeks | | |
|---|---|---|---|---|---|---|---|
| Group | Vaccine Identification | Age | Actual Dose | Route | # Affected/ Total | % Affected | % Protected |
| 5 | HVT/IBDV/ ILTV/NDV | 1 day | 1359 | SC | 9/20 | 45% | 55% |
| 6 | Challenged controls | 1 day | NA | SC | 10/10 | 100% | NA |
| 7 | Non-challenged controls | 1 day | NA | SC | 0/10 | 0% | NA |

In the third study, one-day-old specific pathogen free (SPF) chicks were vaccinated with the HVT/IBDV/ILTV/NDV 670-14.1-1A1 vaccine. Controls included a second unvaccinated group. At 28 days post-vaccination, vaccinated chicks and non-vaccinated control chicks were challenged with virulent IBDV/CS89 strain via the intraocular (10) route. Birds were then observed for clinical signs of disease for 10 days, and bursa collected and examined histologically for gross lesions consistent with IBDV and scored as per the European Pharmacopoeia 9.0 (04/2013:0587). The results, in Table 5, show the 670-14.1-1A1 vaccine provided 100% protection from challenge.

TABLE 5

IBDV CHALLENGE FOLLOWING VACCINATION WITH ISOLATE 670-14.1-1A1#

| | | Vaccination | | | Virulent CS89 IBDV Challenge at 4 weeks | |
|---|---|---|---|---|---|---|
| Group | Vaccine Identification | Age | Route | Dose (0.2 mL) | # Affected/ Total | % Protection |
| 3 | Placebo (Marek's Diluent) | 1 day | SC | N/A | 0/15 | 0 |
| 4 | Negative Controls (Non-Challenged) | 1 day | N/A | N/A | 10/10 | NA |
| 5 | HVT/IBD/ ILTV/NDV | 1 day | SC | 1,810 | 21/21 | 100 |

#P10

In a fourth study, one-day-old specific pathogen free (SPF) chicks were vaccinated with the HVT/IBD/ILTV/NDV 670-14.1-1A1 vaccine. Controls included a second group of unvaccinated chicks. At 5 days post-vaccination, the vaccinated chicks and the non-vaccinated control chicks were challenged with virulent MDV/GA strain via the intra-abdominal (IA) route. Birds were then observed for clinical signs of disease for 50 days, and following death or euthanasia examined for gross lesions consistent with MDV. The results, in Table 6, show that the 670-14.1-1A1 vaccine provided 95% protection from challenge. In sum, these results indicate that an HVT/IBD/ILTV/NDV vaccine can be both stable and efficacious. It also leads credence for the upper limit of foreign antigens encoded in a multivalent HVT construct has not been reached for stable and efficacious multivalent HVT vaccines.

TABLE 6

MDV CHALLENGE FOLLOWING VACCINATION WITH ISOLATE 670-14.1-1A1

| Group | Vaccine Identification | Vaccination SC Age | Vaccination SC Dose | Challenge MDV GA5 Age at Challenge | Results Day 50 Necropsy # Affected/ Total | % Affected | % Protection |
|---|---|---|---|---|---|---|---|
| 3 | HVT/IBDV/ ILTV/NDV | 1 day | 3328 | Day 5 | 1/22 | 5% | 95% |
| 4 | HVT | 1 day | 2372 | Day 5 | 0/22 | 0% | 100% |
| 5 | Diluent | 1 day | NA | Day 5 | 15/22 | 68% | NA |
| 6 | Diluent | 1 day | NA | — | 0/12 | 0% | NA |

Example 5

Additional HVT/IBDV/ILTV/NDV Constructs

Construction of HVT/IBDV/ILTV/NDV #2

The triple recombinant HVT vector virus, HVT/IBDV/ILTV/NDV #2 contains an NDV expression cassette inserted into the HVT UL54.5 site, and an IBDV/ILTV expression cassette inserted into the HVT US2 site. The cosmid regeneration of HVT/IBDV/ILTV/NDV #2 was performed essentially as described in U.S. Pat. No. 5,853,733 [e.g., FIG. 8 of U.S. Pat. No. 5,853,733]. To allow integration into the UL54.5 region of the FC126 HVT genome, the region covered by the cosmid nr. 407-32.1C1 in U.S. Pat. No. 5,853,733, was now provided from three smaller plasmids: 672-01.A40 and 672-07.C40, and one transfer plasmid (654-45:325341_IE-F/1C1), overlapping these two, and containing the NDV expression cassette in the UL54.5 gene locus. To allow integration into the US region of the FC126 HVT genome, the region covered by the cosmid nr. 378-50 in U.S. Pat. No. 5,853,733, was now provided from three smaller plasmids: pSY640 and 556-60.6, and one transfer plasmid (228509-ILT-435Vec6), overlapping these two, and containing the IBDV/ILTV expression cassettes in the US2 gene locus.

The set of nine linearized constructs: 2 cosmids and 7 plasmids are transfected all together into chicken embryo fibroblasts (CEFs), using a standard $CaCl_2$ transfection protocol and the resulting virus stock was plaque purified two times.

Construction of HVT/IBDV/ILTV/NDV #3

The triple recombinant HVT vector virus, HVT/IBDV/ILTV/NDV #3 contains an IBDV expression cassette inserted into the HVT UL54.5 site, and an ILTV/NDV expression cassette inserted into the HVT US2 site. The cosmid regeneration of HVT/IBDV/ILTV/NDV #3 was performed essentially as described in U.S. Pat. No. 5,853,733 [e.g., FIG. 8 of U.S. Pat. No. 5,853,733]. To allow integration into the UL54.5 region of the FC126 HVT genome, the region covered by the cosmid nr. 407-32.1C1 in U.S. Pat. No. 5,853,733, was now provided from three smaller plasmids: 672-01.A40 and 672-07.C40, and one transfer plasmid (VP2/1C1#8), overlapping these two, and containing the IBDV expression cassette in the UL54.5 gene locus. To allow integration into the US region of the FC126 HVT genome, the region covered by the cosmid nr. 378-50 in U.S. Pat. No. 5,853,733, was now provided from three smaller plasmids: pSY640 and 556-60.6, and one transfer plasmid (1332-47.A2), overlapping these two, and containing the ILTV/NDV expression cassettes in the US2 gene locus.

The set of nine linearized constructs: 2 cosmids and 7 plasmids are transfected all together into chicken embryo fibroblasts (CEFs), using a standard $CaCl_2$ transfection protocol and the resulting virus stock was plaque purified two times.

Construction of HVT/IBDV/ILTV/NDV #4

The triple recombinant HVT vector virus, HVT/IBDV/ILTV/NDV #4 contains an ILTV expression cassette inserted into the HVT UL54.5 site, and an IBDV/NDV expression cassette inserted into the HVT US2 site. The cosmid regeneration of HVT/IBDV/ILTV/NDV #4 was performed essentially as described in U.S. Pat. No. 5,853,733 [e.g., FIG. 8 of U.S. Pat. No. 5,853,733]. To allow integration into the UL54.5 region of the FC126 HVT genome, the region covered by the cosmid nr. 407-32.1C1 in U.S. Pat. No. 5,853,733, was now provided from three smaller plasmids: 672-01.A40 and 672-07.C40, and one transfer plasmid (1332-23.7), overlapping these two, and containing the ILTV expression cassette in the UL54.5 gene locus. To allow integration into the US region of the FC126 HVT genome, the region covered by the cosmid nr. 378-50 in U.S. Pat. No. 5,853,733, was now provided from three smaller plasmids: pSY640 and 556-60.6, and one transfer plasmid (435Vec60), overlapping these two, and containing the IBDV/NDV expression cassettes in the US2 gene locus. The set of nine linearized constructs: 2 cosmids and 7 plasmids are transfected all together into chicken embryo fibroblasts (CEFs), using a standard $CaCl_2$ transfection protocol and the resulting virus stock was plaque purified two times.

Construction of HVT/IBDV/ILTV/NDV #5

The triple recombinant HVT vector virus, HVT/IBDV/ILTV/NDV #5 contains an ILTV/NDV expression cassettes inserted into the HVT UL54.5 site, and an IBDV expression cassette inserted into the HVT US2 site. The cosmid regeneration of HVT/IBDV/ILTV/NDV #5 was performed essentially as described in U.S. Pat. No. 5,853,733 [e.g., FIG. 8 of U.S. Pat. No. 5,853,733]. To allow integration into the UL54.5 region of the FC126 HVT genome, the region covered by the cosmid nr. 407-32.1C1 in U.S. Pat. No. 5,853,733, was now provided from three smaller plasmids: 672-01.A40 and 672-07.C40, and one transfer plasmid (1332-29.4), overlapping these two, and containing the ILTV/NDV expression cassettes in the UL54.5 gene locus. To allow integration into the US region of the FC126 HVT genome, the region covered by the cosmid nr. 378-50 in U.S.

Pat. No. 5,853,733, was now provided from three smaller plasmids: pSY640 and 556-60.6, and one transfer plasmid (435Vec6), overlapping these two, and containing the IBDV expression cassette in the US2 gene locus.

The set of nine linearized constructs: 2 cosmids and 7 plasmids are transfected all together into chicken embryo fibroblasts (CEFs), using a standard $CaCl_2$ transfection protocol and the resulting virus stock was plaque purified two times.

Figure 2:
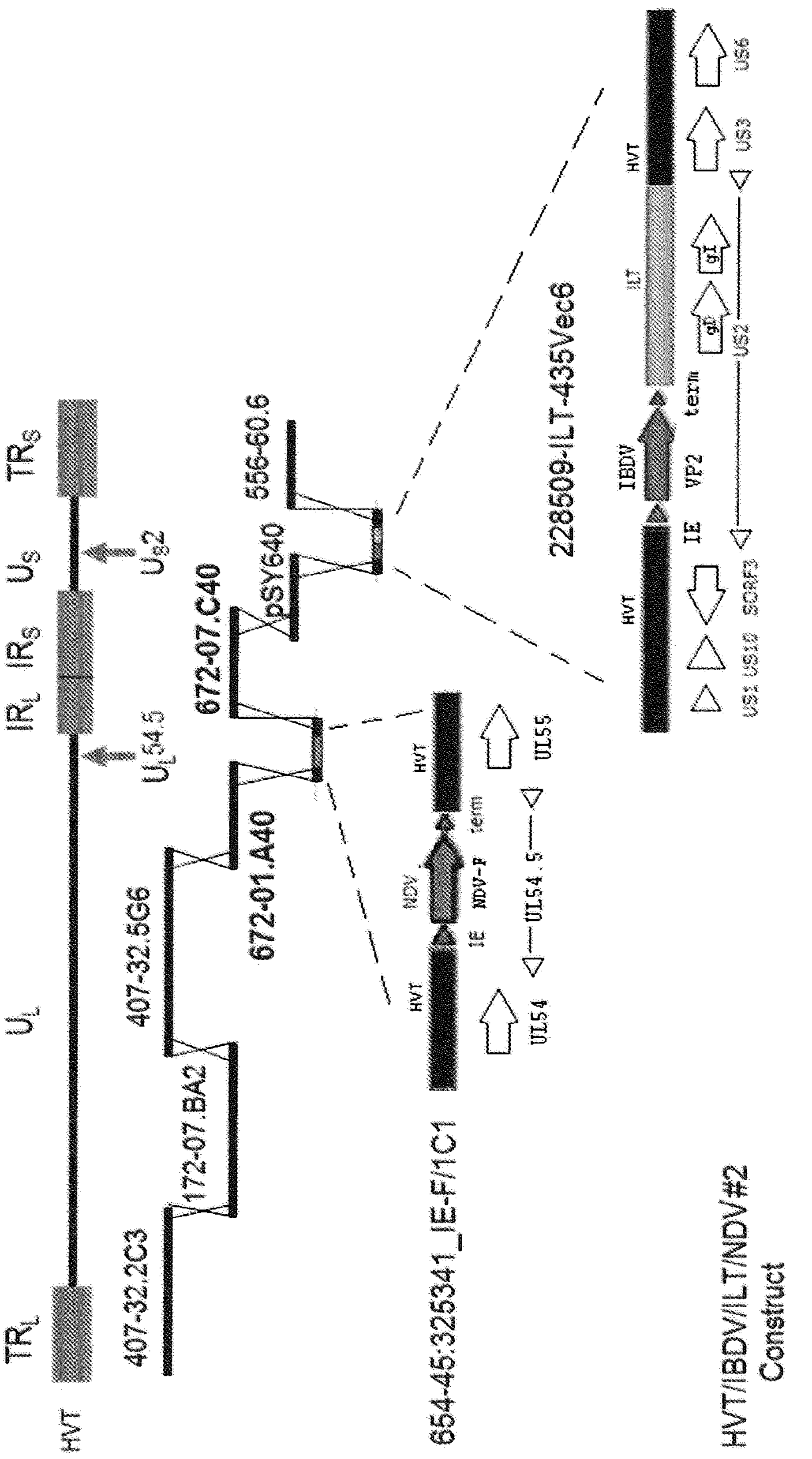
FIG. 2 is a schematic drawing of insertion fragments for generating HVT/IBDV/ILT/NDV construct #2. The two HVT insertion sites are UL54.5 and US2. [See also description for FIG. 1 above].

Additional Insertion Fragments for Generating HVT/IBDV/ILTV/NDV #2 (see, FIG. 2)

Subgenomic Clone 654-45:325341_IE-F/1C1

The insertion plasmid 654-45:325341_IE-F/1C1 contains an 8636 base pair region of genomic HVT unique long region [pos. 109489-118124; Afonso et al., 2001, supra; Acc. #AF291866], cloned into a derivative of plasmid pNEB193 (deleted AatII-PvuII). It is flanked by AscI sites and includes HVT BamHI fragments I, S, plus 1337 base pairs of fragment G and 1177 base pairs of fragment F. Inserted into an XhoI site within the HVT UL54.5 open reading frame [pos. 111240/111241; Afonso et al., 2001, supra; Acc. #AF291866, between amino acid residues 21 and 22] is an expression cassette consisting of the HCMV IE promoter, the NDV, Clone 30 strain, fusion gene (F), and the transcription terminator from the HCMV IE gene. The NDV F gene is transcribed in the opposite direction relative to the HVT UL54.5 gene.

Subgenomic Clone 228509-ILT-435Vec6 [see, International Application PCT/EP2017/064662]

The insertion plasmid 228509-ILT-435Vec6 contains a 7311 base pair EcoRI fragment of the HVT unique short regions [pos. 126880-144190; Afonso et al., 2001, supra; Acc. #AF291866], cloned into the plasmid pSP64 (Promega Corporation, Madison, WI.). Inserted into a unique StuI site within the HVT US2 gene [pos. 140540/140541; Afonso et al., 2001, supra; Acc. #AF291866, between amino acid residues 124 and 125] are two elements: an expression cassette consisting of the MCMV IE promoter, the IBDV classic type F52/70, Faragher strain, virus protein 2 gene (VP2), and the SV40 polyadenylation signal; followed by a 3563 base pair SalI-HindIII fragment from ILTV, NVSL Challenge Strain, Lot #83-2 [pos. 10532-14094; Wild et al., *Virus Genes* 12:104-116 (1996); Acc. #U28832], encoding the full length genes for glycoprotein D (gD) and glycoprotein I (gI), plus partial coding regions from glycoprotein E (amino acids 1-101), and ORF5 (amino acids 734-985). The IBDV VP2, ILTV gD and ILTV gI genes are transcribed in the opposite direction relative to the HVT US2 gene.

Figure 3:
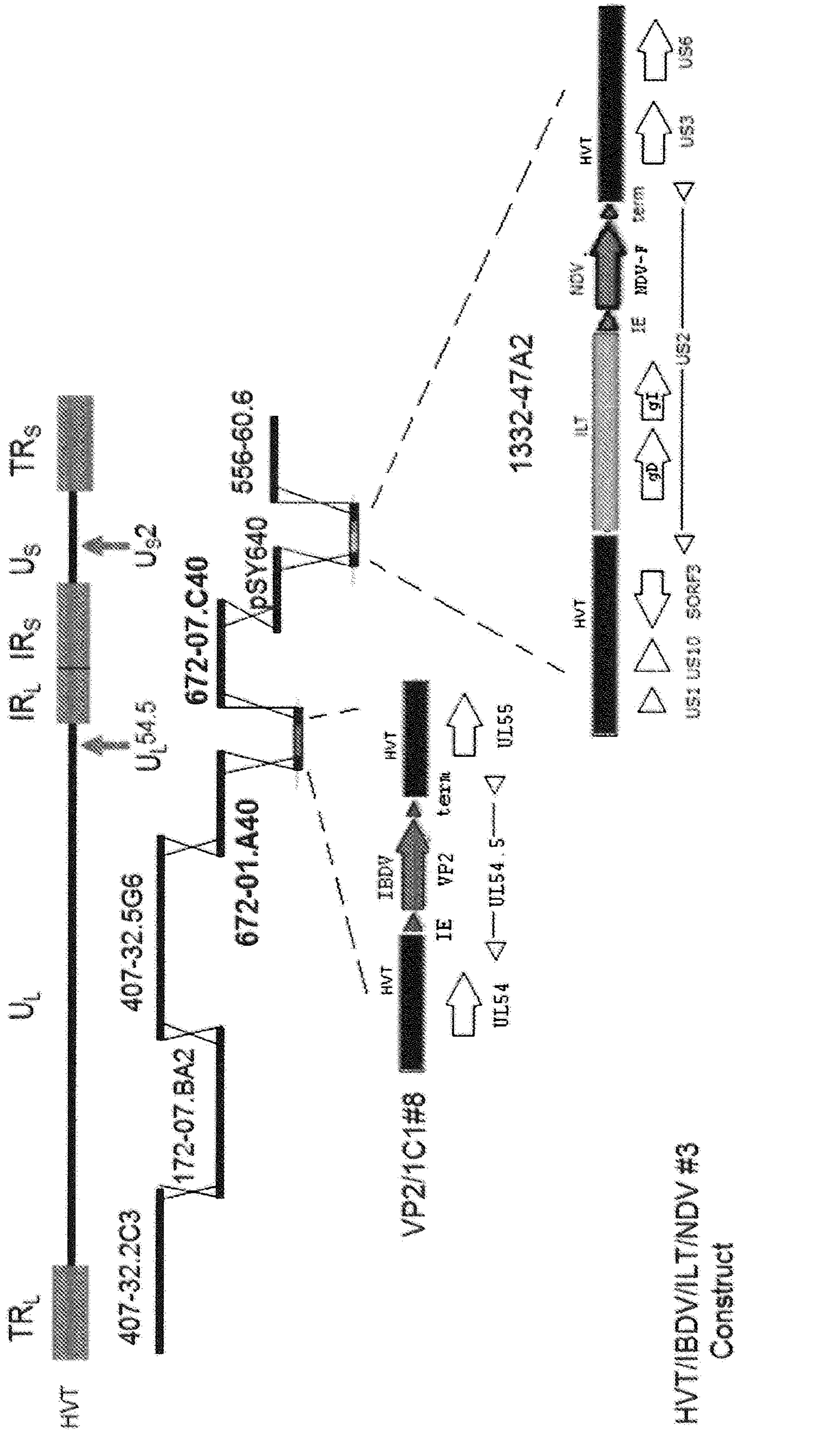
FIG. 3 is a schematic drawing of insertion fragments for generating HVT/IBDV/ILT/NDV construct #3. The two HVT insertion sites are UL54.5 and US2. [See also description for FIG. 1 above].

Additional Insertion Fragments for Generating HVT/IBDV/ILTV/NDV #3 (see, FIG. 3)

Subgenomic Clone VP2/1C1#8

The insertion plasmid VP2/1C1#8 contains an 8636 base pair region of genomic HVT unique long region [pos. 109489-118124; Afonso et al., 2001, supra; Acc. #AF291866], cloned into a derivative of plasmid pNEB193 (deleted AatII-PvuII). It is flanked by AscI sites and includes HVT BamHI fragments I, S, plus 1337 base pairs of fragment G and 1177 base pairs of fragment F. Inserted into an XhoI site within the HVT UL54.5 open reading frame [pos. 111240/111241; Afonso et al., 2001, supra; Acc. #AF291866, between amino acid residues 21 and 22] is an expression cassette consisting of the MCMV IE promoter, the IBDV classic type F52/70, Faragher strain, virus protein 2 gene (VP2), and the SV40 polyadenylation signal. The IBDV VP2 gene is transcribed in the opposite direction relative to the HVT UL54.5 gene.

Subgenomic Clone 1332-47.A2

The insertion plasmid 1332-47.A2 contains a 7311 base pair EcoRI fragment of the HVT unique short regions [pos. 126880-144190; Afonso et al., 2001, supra; Acc. #AF291866], cloned into the plasmid pSP64 (Promega Corporation, Madison, WI.). Inserted into a unique StuI site within the HVT US2 gene [pos. 140540/140541; Afonso et al., 2001, supra; Acc. #AF291866, between amino acid residues 124 and 125] are two elements: a 3563 base pair SalI-HindIII fragment from ILTV, NVSL Challenge Strain, Lot #83-2 [pos. 10532-14094; Wild et al., *Virus Genes* 12:104-116 (1996); Acc. #U28832], encoding the full length genes for glycoprotein D (gD) and glycoprotein I (gI), plus partial coding regions from glycoprotein E (amino acids 1-101), and ORF5 (amino acids 734-985); followed by an expression cassette consisting of the HCMV IE promoter, the NDV, Clone 30 strain, fusion gene (F), and the transcription terminator from the HCMV IE gene. The ILTV gD, the ILTV gI, and the NDV F genes are transcribed in the opposite direction relative to the HVT US2 gene.

Figure 4:
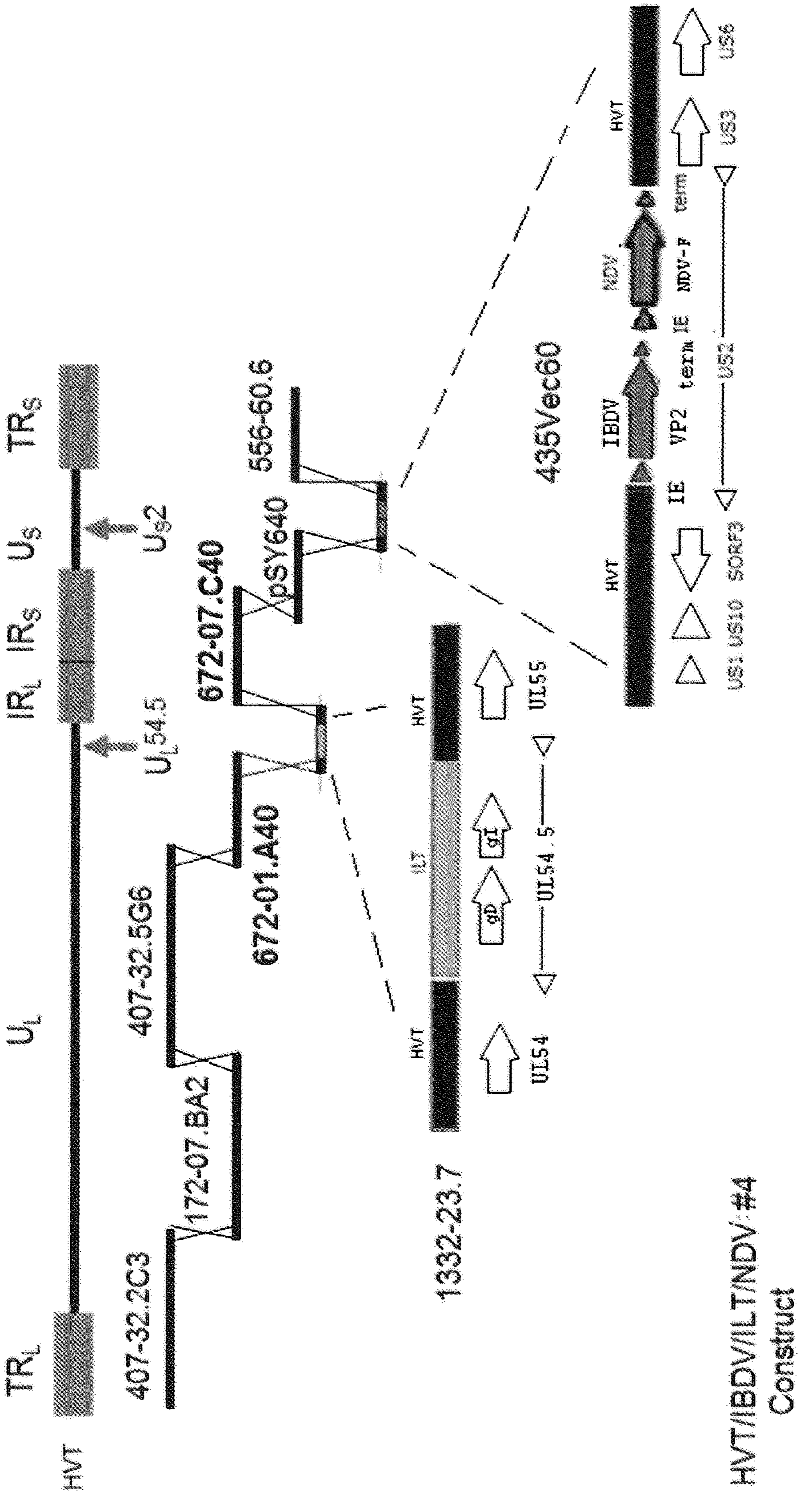
FIG. 4 is a schematic drawing of insertion fragments for generating HVT/IBDV/ILT/NDV construct: #4. The two HVT insertion sites are UL54.5 and US2. [See also description for FIG. 1 above].

Additional Insertion Fragments for Generating HVT/IBDV/ILTV/NDV #4 (see, FIG. 4)

Subgenomic Clone 1332-23.7

The insertion plasmid 1332-23.7 contains an 8636 base pair region of genomic HVT unique long region [pos. 109489-118124; Afonso et al., 2001, supra; Acc. #AF291866], cloned into a derivative of plasmid pNEB193 (deleted AatII-PvuII). It is flanked by AscI sites and includes HVT BamHI fragments I, S, plus 1337 base pairs of fragment G and 1177 base pairs of fragment F. Inserted into an XhoI site within the HVT UL54.5 open reading frame [pos. 111240/111241; Afonso et al., 2001, supra; Acc. #AF291866, between amino acid residues 21 and 22] is a 3563 base pair SalI-HindIII fragment from ILTV, NVSL Challenge Strain, Lot #83-2 [pos. 10532-14094; Wild et al., *Virus Genes* 12:104-116 (1996); Acc. #U28832], encoding the full length genes for glycoprotein D (gD) and glycoprotein I (gI), plus partial coding regions from glycoprotein E (amino acids 1-101), and ORF5 (amino acids 734-985). The ILTV gD and the ILTV gI genes are transcribed in the opposite direction relative to the HVT UL54.5 gene.

Subgenomic Clone 435Vec60

The insertion plasmid 435Vec60 contains a 7311 base pair EcoRI fragment of the HVT unique short regions [pos. 126880-144190; Afonso et al., 2001, supra; Acc. #AF291866], cloned into the plasmid pSP64 (Promega Corporation, Madison, WI.). Inserted into a unique StuI site within the HVT US2 gene [pos. 140540/140541; Afonso et al., 2001, supra; Acc. #AF291866, between amino acid residues 124 and 125] are two elements: an expression cassette consisting of the MCMV IE promoter, the IBDV classic type F52/70, Faragher strain, virus protein 2 gene (VP2), and the SV40 polyadenylation signal; followed by an expression cassette consisting of the HCMV IE promoter, the NDV, Clone 30 strain, fusion gene (F), and the transcription terminator from the HCMV IE gene. Both the IBDV VP2 and NDV F genes are transcribed in in the opposite direction relative to the HVT US2 gene.

Figure 5:
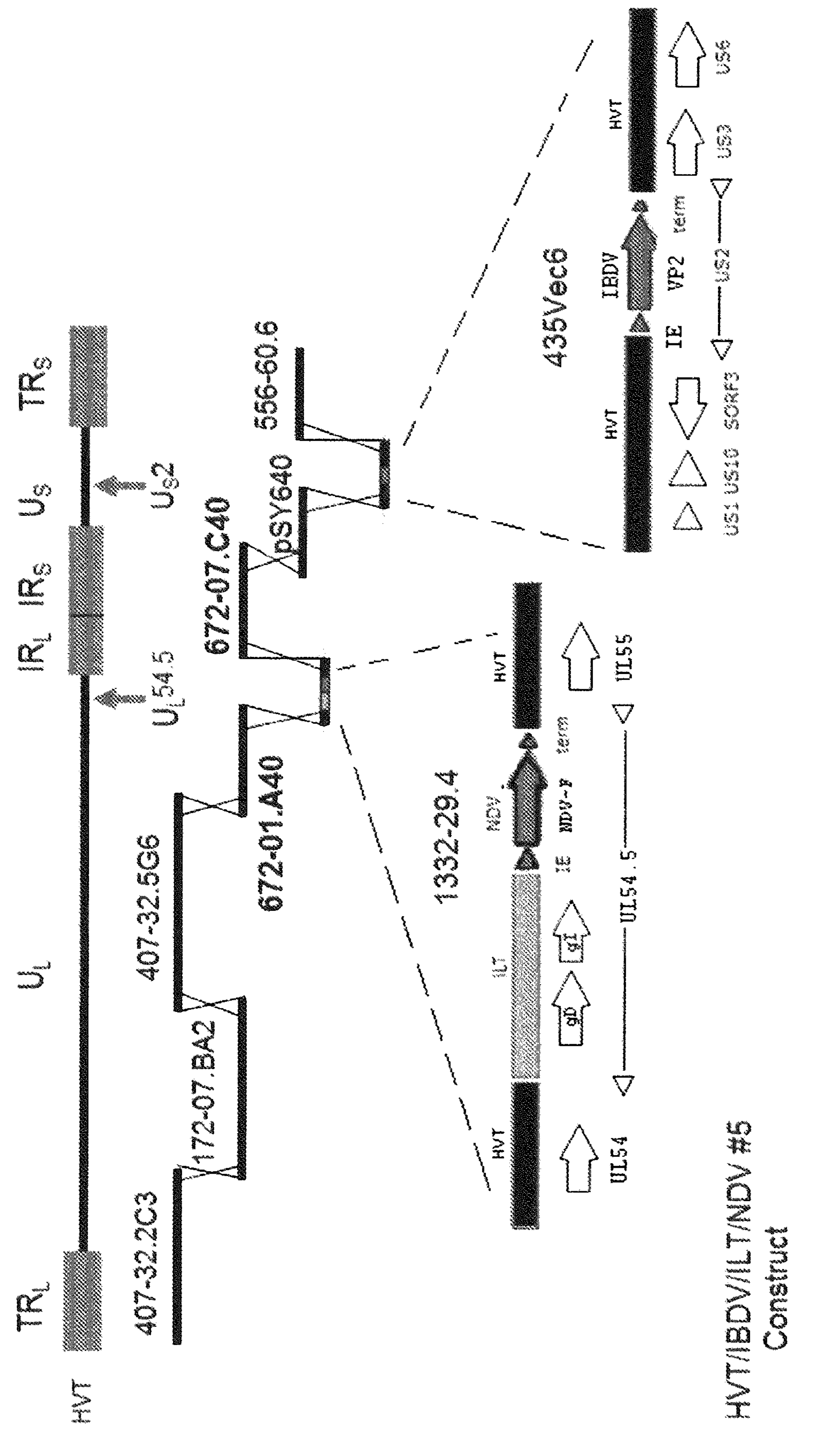
FIG. 5 is a schematic drawing of insertion fragments for generating HVT/IBDV/ILT/NDV construct #5. The two HVT insertion sites are UL54.5 and US2. [See also description for FIG. 1 above].

Additional Insertion Fragments for Generating HVT/IBDV/ILTV/NDV #5 (see, FIG. 5)

Subgenomic Clone 1332-29.4 [see, U.S. Pat. No. 9,409,954 B2]

The insertion plasmid 1332-29.4 contains an 8636 base pair region of genomic HVT unique long region [pos. 109489-118124; Afonso et al., 2001, supra; Acc. #AF291866], cloned into a derivative of plasmid pNEB193 (deleted AatII-PvuII). It is flanked by AscI sites and includes HVT BamHI fragments I, S, plus 1337 base pairs of fragment G and 1177 base pairs of fragment F. Inserted into an XhoI site within the HVT UL54.5 open reading frame [pos. 111240/111241; Afonso et al., 2001, supra; Acc. #AF291866, between amino acid residues 21 and 22] are two elements: a 3563 base pair SalI-HindIII fragment from ILTV, NVSL Challenge Strain, Lot #83-2 [pos. 10532-14094; Wild et al., *Virus Genes* 12:104-116 (1996); Acc. #U28832], encoding the full length genes for glycoprotein D (gD) and glycoprotein I (gI), plus partial coding regions from glycoprotein E (amino acids 1-101), and ORF5 (amino acids 734-985); followed by an expression cassette consisting of the HCMV IE promoter, the NDV, Clone 30 strain, fusion gene (F), and the transcription terminator from the HCMV IE gene. The ILTV gD, the ILTV 91, and the NDV F genes are transcribed in the opposite direction relative to the HVT UL54.5 gene.

Subgenomic Clone 435Vec6

The insertion plasmid 435Vec6 contains a 7311 base pair EcoRI fragment of the HVT unique short regions [pos. 126880-144190; Afonso et al., 2001, supra; Acc. #AF291866], cloned into the plasmid pSP64 (Promega Corporation, Madison, WI.). Inserted into a unique StuI site within the HVT US2 gene [pos. 140540/140541; Afonso et al., 2001, supra; Acc. #AF291866, between amino acid residues 124 and 125] is an expression cassette consisting of the MCMV IE promoter, the IBDV classic type F52/70, Faragher strain, virus protein 2 gene (VP2), and the SV40 polyadenylation signal. The IBDV VP2 gene is transcribed in in the opposite direction relative to the HVT US2 gene.

The sequences used in the HVT/ILTV/IBDV/NDV viral vectors disclosed in this example are provided in Example 7 below as SEQ ID NOs: 23 and 26-32.

Example 6

Unsuccessful Constructs

The recombinant vector vaccine viruses, by definition are engineered to carry and express foreign genes. Should transcription and expression of these foreign genes provide a growth disadvantage to the recombinant virus relative to the parental virus, it is possible for these genes to be lost during production of the vaccine. For this reason, vaccine candidates must be tested for both genetic and phenotypic stability.

In addition, the protection criteria used is that which has been established by the USDA and codified in the Title 9 Code of Federal Regulations, part 113 (9CFR 113) «Standard requirements for Animal Products». Live virus vaccines must provide at least 90% protection, in the case of NDV, IBDV and ILTV, and at least 80% in the case of MDV, from clinical signs or lesions associated with the disease to obtain a license.

Genetic stability of the viral constructs was determined by Southern blot analysis after a defined number of passages in tissue culture, the highest anticipated vaccine production level, and compared with DNA from the original isolate. DNA extracted from viral stocks would be digested with restriction enzymes, transferred to a membrane and hybridized with probes designed to detect the presence of the inserted foreign genes. Genetic stability may also be determined by PCR analysis. PCR primers designed to anneal to DNA within or flanking the foreign DNA could be used to amplify fragments of a known size from the viral DNA templates both before and after passage in tissue culture.

Phenotypic stability of the viral constructs was determined by immunological staining of individual viral plaques with antibodies directed against the protein products of these inserted foreign genes. Protection provided by these recombinant vaccines relies on expression of these protein products in order to stimulate the animals immune system. In most cases, if the percent of viruses staining positive for the foreign protein expression dropped below 90%, it was likely detrimental to the viruses ability to be grown in tissue culture, and therefore unsuitable as a vaccine candidate.

As is readily apparent from Tables 7A and 7B below, most rMDV$_{np}$ constructs do not meet these two criteria, namely stability with relatively strong antigen expression and/or efficacy. Table 7A provides a series of recombinant HVT constructs with multiple heterologous inserts in which one of the heterologous inserts encodes an IBDV antigen. As the results show, all of the constructs in Table 7A failed to meet the stability with relatively strong antigen expression and/or efficacy criteria.

TABLE 7A

DOUBLE RECOMBINANT HVT AND IBDV VIRUS CONSTRUCTS:

| Name/ Designation | Insertion site | Insert | IBDV Promoter | IBDV Expression | Stability |
|---|---|---|---|---|---|
| HVT 003 | UL43 | [IBDV] polyprotein [*Ecoli*] Bgal | PRV gX | Poor | stable |
| HVT 016 | UL43 | [IBDV] VP2 [*Ecoli*] Bgal | hCMV IE | Strong | unstable |
| HVT 056 | US2 | [MDV] gA, gB [IBDV] VP2 | hCMV IE | Strong | Unstable |
| HVT 060 | US2 | [MDV] gA, gB [IBDV] VP2, 16 kD ORF | IE-VP2, gX-16dk ORF | Strong | unstable |
| HVT 137 | US2 UL54.5 | [MDV] gA, gB, gC [IBDV] VP2 | [BHV] VP8 (tegument) | Poor | stable |
| HVT 143 | US2 US2 UL54.5 | [MDV] gA, gB, gD [NDV] HN, F [IBDV] VP2 | [BHV] VP8 (tegument) | Poor | Unstable |
| HVT/NDV/IBDV 1312-92 | US2 UL7/UL8 | [IBDV] VP2 [NDV] F | hCMV IE | Strong | Unstable |
| HVT/NDV/IBDV 1312-94 | US2 UL7/UL8 | [IBDV] VP2 [NDV] F | hCMV IE | Strong | Unstable |
| HVT/NDV/IBDV 1312-95 | US2 UL7/UL8 | [IBDV] VP2 [NDV] F | hCMV IE | Strong | Unstable |
| HVT/NDV/IBDV 1329-54 | US2 | [IBDV] VP2 [NDV] F | FHV gB | Strong | Unstable |

Table 7B below, provides a series of eleven recombinant HVT constructs and one lone NAHV construct each of which comprise multiple heterologous inserts in which at least one of the heterologous inserts encodes either an NDV or an LTV antigen.[1] As the results show, all of the constructs in Table 7B failed to meet the stability with relatively strong antigen expression and/or efficacy criteria.

[1] The data in Table 7B was submitted to the U.S. Patent Office during the prosecution of U.S. Pat. No. 8,932,604 B2 in a Declaration signed by one of the co-Inventors of the present application.

TABLE 7B

DOUBLE RECOMBINANT HVT AND NAHV VIRUS CONSTRUCTS:

| Name | Insertion site | Insert | Stability | NDV Protection | MDV Protection | ILTV Protection |
|---|---|---|---|---|---|---|
| HVT 048 | US2 | [MDV] gA, gB<br>[NDV] F | Stable | Good | *Protective | — |
| HVT 049 | US2 | [MDV] gA, gB<br>[NDV] HN | Stable | Poor (<20%) | Not tested | — |
| HVT 050 | US2 | [MDV] gA, gB<br>[NDV] F, HN | Stable | Good | *Protective | — |
| HVT 053 | US2 | [MDV] gA, gB<br>[ILTV] gB, gD | Unstable | — | Not tested | None |
| HVT 078 | US2 | [MDV] gA, gB, gD<br>[NDV]HN, F | Unstable | Not tested | Not tested | — |
| HVT 079 | US2 | [MDV] gA, gB, gD<br>[ILTV] gB, gD | Unstable | — | Not tested | (71-100%) |
| HVT 106 | US2 | [MDV]gA, gB, gD<br>[NDV]HN, F | Stable | **Unknown | Not tested | — |
| HVT 123 | UL54.5 + US2 | [ILTV] gD, gB/UL54.5<br>[MDV] gA, gD, gB/US2 | Unstable | — | Not tested | Not tested |
| HVT 125 | UL54.5 + US2 | [ILTV] gDgI, gB/UL54.5<br>[MDV] gA, gD, gB/US2 | Unstable | — | Not tested | Not tested |
| HVT 128 | UL54.5 + US2 | [NDV] HN, F/UL54.5<br>[MDV] gA, gD, gB/US2 | Unstable | Not tested | Not tested | — |
| HVT139 | UL54.5 + US2 | [ILTV] gDgI /UL54.5<br>[MDV] gA, gD, gB/US2 | Unstable | — | Not tested | Not tested |
| HVY-198 (NAHV) | US2* (MDV) | [NDV] F +<br>[ILTV] gD, gI | Unstable | | | |

*Protective, but subsequently failed in field studies
**Only 75% birds seroconverted to NDV F

Example 7

Sequences

The following sequences have been used in the exemplary rHVT constructs. The coding sequences provided below include individual stop codons, which can be readily replaced with alternative stop codons without modifying the properties of the protein antigens that the coding sequences encode.

```
SEQ ID NO 1: ILTV gD Glycoprotein (1134 bp)
atggaccgccatttatttttgaggaatgctttttggactatcgtactgctttcttccttcgctagcca

gagcaccgccgccgtcacgtacgactacattttaggccgtcgcgcgctcgacgcgctaaccataccgg

cggttggcccgtataacagatacctcactagggtatcaagaggctgcgacgttgtcgagctcaacccg

atttctaacgtggacgacatgatatcggcggccaaagaaaaagagaagggggccctttcgaggcctc

cgtcgtctggttctacgtgattaagggcgacgacggcgaggacaagtactgtccaatctatagaaaag

agtacagggaatgtggcgacgtacaactgctatctgaatgcgccgttcaatctgcacagatgtgggca

gtggactatgttcctagcacccttgtatcgcgaaatggcgcgggactgactatattctcccccactgc

tgcgctctctggccaatacttgctgaccctgaaaatcgggagatttgcgcaaacagctctcgtaactc

tagaagttaacgatcgctgtttaaagatcgggtcgcagcttaactttttaccgtcgaaatgctggaca

acagaacagtatcagactggatttcaaggcgaacacctttatccgatcgcagacaccaatacacgaca

cgcggacgacgtatatcggggatacgaagatattctgcagcgctggaataatttgctgaggaaaaaga

atcctagcgcgccagaccctcgtccagatagcgtcccgcaagaaattcccgctgtaaccaagaaagcg

gaagggcgcaccccggacgcagaaagcagcgaaaagaaggcccctccagaagactcggaggacgacat
```

-continued gcaggcagaggcttctggagaaaatcctgccgccctccccgaagacgacgaagtccccgaggacaccg agcacgatgatccaaactcggatcctgactattacaatgacatgcccgccgtgatcccggtggaggag actactaaaagttctaatgccgtctccatgcccatattcgcggcgttcgtagcctgcgcggtcgcgct cgtggggctactggtttggagcatcgtaaaatgcgcgcgtagctaa SEQ ID NO 2: ILTV gD Glycoprotein (377 amino acids)
MDRHLFLRNAFWTIVLLSSFASQSTAAVTYDYILGRRALDALTIPAVGPYNRYLTRVSRGCDVVELNP

ISNVDDMISAAKEKEKGGPFEASVVWFYVIKGDDGEDKYCPIYRKEYRECGDVQLLSECAVQSAQMWA

VDYVPSTLVSRNGAGLTIFSPTAALSGQYLLTLKIGRFAQTALVTLEVNDRCLKIGSQLNFLPSKCWT

TEQYQTGFQGEHLYPIADTNTRHADDVYRGYEDILQRWNNLLRKKNPSAPDPRPDSVPQEIPAVTKKA

EGRTPDAESSEKKAPPEDSEDDMQAEASGENPAALPEDDEVPEDTEHDDPNSDPDYYNDMPAVIPVEE

TTKSSNAVSMPIFAAFVACAVALVGLLVWSIVKCARS

SEQ ID NO 3: ILTV gI Glycoprotein (1089 bp)
atggcatcgctacttggaactctggctctccttgccgcgacgctcgcacccttcggcgcgatgggaat cgtgatcactggaaatcacgtctccgccaggattgacgacgatcacatcgtgatcgtcgcgcctcgcc ccgaagctacaattcaactgcagctatttttcatgcctggccagagaccccacaaaccctactcagga accgtccgcgtcgcgtttcggtctgatataacaaaccagtgctaccaggaacttagcgaggagcgctt tgaaaattgcactcatcgatcgtcttctgtttttgtcggctgtaaagtgaccgagtacacgttctccg cctcgaacagactaaccggacctccacacccgtttaagctcactatacgaaatcctcgtccgaacgac agcgggatgttctacgtaattgttcggctagacgacaccaaagaacccattgacgtcttcgcgatcca actatcggtgtatcaattcgcgaacaccgccgcgactcgcggactctattccaaggcttcgtgtcgca ccttcggattacctaccgtccaacttgaggcctatctcaggaccgaggaaagttggcgcaactggcaa gcgtacgttgccacggaggccacgacgaccagcgccgaggcgacaaccccgacgcccgtcactgcaac cagcgcctccgaacttgaagcggaacactttacctttccctggctagaaaatggcgtggatcattacg aaccgacacccgcaaacgaaaattcaaacgttactgtccgtctcgggacaatgagccctacgctaatt ggggtaaccgtggctgccgtcgtgagcgcaacgatcggcctcgtcattgtaatttccatcgtcaccag aaacatgtgcaccccgcaccgaaaattagacacggtctcgcaagacgacgaagaacgttcccaaacta gaagggaatcgcgaaaatttggacccatggttgcgtgcgaaataaacaaggggggctgaccaggatagt gaacttgtggaactggttgcgattgttaacccgtctgcgctaagctcgcccgactcaataaaaatgtg a SEQ ID NO 4: ILTV gI Glycoprotein (362 amino acids)
MASLLGTLALLAATLAPFGAMGIVITGNHVSARIDDDHIVIVAPRPEATIQLQLFFMPGQRPHKPYSG

TVRVAFRSDITNQCYQELSEERFENCTHRSSSVFVGCKVTEYTFSASNRLTGPPHPFKLTIRNPRPND

SGMFYVIVRLDDTKEPIDVFAIQLSVYQFANTAATRGLYSKASCRTFGLPTVQLEAYLRTEESWRNWQ

AYVATEATTTSAEATTPTPVTATSASELEAEHFTFPWLENGVDHYEPTPANENSNVTVRLGTMSPTLI

GVTVAAVVSATIGLVIVISIVTRNMCTPHRKLDTVSQDDEERSQTRRESRKFGPMVACEINKGADQDS

ELVELVAIVNPSALSSPDSIKM

SEQ ID NO 5: IBDV VP2 (1362 bp)
atgacaaacctgcaagatcaaacccaacagattgttccgttcatacggagccttctgatgccaacaac cggaccggcgtccattccggacgacaccctggagaagcacactctcaggtcagagacctcgacctaca atttgactgtgggggacacagggtcagggctaattgtctttttccctggattccctggctcaattgtg ggtgctcactacacactgcagagcaatgggaactacaagttcgatcagatgctcctgactgcccagaa cttaccggccagctacaactactgcagactagtgagtcggagtctcatagtgaggtcaagcacactcc -continued ctggtggcgtttatgcactaaacggcaccataaacgccgtgaccttccaaggaagcctgagtgaactg acagatgttagctacaatgggttgatgtctgcaacagccaacatcaacgacaaaattgggaatgtcct ggtaggggaaggggtcactgtcctcagcctacccacatcatatgatcttgggtatgtgaggcttggtg accccattcccgctatagggcttgacccaaaaatggtagctacatgcgacagcagtgacaggcccaga gtctacaccataactgcagccgatgattaccaattctcatcacagtaccaaccaggtggggtaacaat cacactgttctcagccaacattgatgctatcacaagcctcagcattgggggagagctcgtgtttcaaa caagcgtccaaggccttgtactgggcgccaccatctaccttataggctttgatgggactgcggtaatc accagagctgtggccgcagataatgggctgacggccggcaccgacaatcttatgccattcaatcttgt cattccaaccaatgagataacccagccaatcacatccatcaaactggagatagtgacctccaaaagtg gtggtcaggcaggggatcagatgtcatggtcggcaagtgggagcctagcagtgacgatccatggtggc aactatccaggggccctccgtcccgtcacactagtagcctacgaaagagtggcaacaggatccgtcgt tacggtcgctggggtgagtaacttcgagctgattccaaatcctgaactagcaaagaacctggttacag aatacggccgatttgacccaggagccatgaactacacaaaattgatactgagtgagagggaccgtctt ggcatcaagaccgtctggccaacaagggagtacactgattttcgtgagtacttcatggaggtggccga cctcaactctcccctgaagattgcaggagcatttggcttcaaagacataatccgggctataaggaggt aa SEQ ID NO 6: IBDV VP2 (453 amino acids)
MTNLQDQTQQIVPFIRSLLMPTTGPASIPDDTLEKHTLRSETSTYNLTVGDTGSGLIVFFPGFPGSIV

GAHYTLQSNGNYKFDQMLLTAQNLPASYNYCRLVSRSLTVRSSTLPGGVYALNGTINAVTFQGSLSEL

TDVSYNGLMSATANINDKIGNVLVGEGVTVLSLPTSYDLGYVRLGDPIPAIGLDPKMVATCDSSDRPR

VYTITAADDYQFSSQYQPGGVTITLFSANIDAITSLSIGGELVFQTSVQGLVLGATIYLIGFDGTAVI

TRAVAADNGLTAGTDNLMPFNLVIPTNEITQPITSIKLEIVTSKSGGQAGDQMSWSASGSLAVTIHGG

NYPGALRPVTLVAYERVATGSVVTVAGVSNFELIPNPELAKNLVTEYGRFDPGAMNYTKLILSERDRL

GIKTVWPTREYTDFREYFMEVADLNSPLKIAGAFGFKDIIRAIRR

SEQ ID NO: 7: NDV F Protein, coding sequence (Clone 30; 1662 bp)
atgggccccagaccttctaccaagaacccagtacctatgatgctgactgtccgagtcgcgctggtact gagttgcatctgtccggcaaactccattgatggcaggcctcttgcggctgcaggaattgtggttacag gagacaaagccgtcaacatatacacctcatcccagacaggatcaatcatagttaagctcctcccgaat ctgcccaaggataaggaggcatgtgcgaaagccccccttggatgcatacaacaggacattgaccacttt gctcaccccccttggtgactctatccgtaggatacaagagtctgtgactacatctggagggggggagac aggggcgccttataggcgccattattggcggtgtggctcttggggttgcaactgccgcacaaataaca gaggccgcagctctgatacaagccaaacaaaatgctgccaacatcctccgacttaaagagagcattgc cgcaaccaatgaggctgtgcatgaggtcactgacggattatcgcaactagcagtggcagttgggaaga tgcagcagtttgttaatgaccaatttaataaaacagctcaggaattagactgcatcaaaattgcacag caagttggtgtagagctcaacctgtacctaaccgaattgactacagtattcggaccacaaatcacttc acctgctttaaacaagctgactattcaggcactttacaatctagctggtggaaatatggattacttat tgactaagttaggtgtagggaacaatcaactcagctcattaatcggtagcggcttaatcaccggtaac cctattctatacgactcacagactcaactcttgggtatacaggtaactctaccttcagtcgggaagct aaataatatgcgtgccacctacttggaaaccttatccgtaagcacaaccaggggatttgcctcggcac ttgtcccaaaagtggtgacacaggtcggttctgtgatagaagaacttgacacctcatactgtatagaa actgacttacatttatattgtacaagaatagtaacgttccctatgtcccctggtatttattcctgctt gagcggcaatacgtcggcctgtatgtactcaaagaccgaaggcgcacttactacaccatacatgacta -continued tcaaaggttcagtcatcgccaactgcaagatgacaacatgtagatgtgtaaaccccccgggtatcata tcgcaaaactatggagaagccgtgtctctaatagataaacaatcatgcaatgttttatccttaggcgg gataactttaaggctcagtggggaattcgatgtaacttatcagaagaatatctcaatacaagattctc aagtaataataacaggcaatcttgatatctcaactgagcttgggaatgtcaacaactcgatcagtaat gctttgaataagttagaggaaagcaacagaaaactagacaaagtcaatgtcaaactgactagcacatc tgctctcattacctatatcgtgttgactatcatatctcttgtttttggtatacttagcctgattctag catgctacctaatgtacaagcaaaaggcgcaacaaaagaccttattatggcttgggaataatactcta gatcagatgagagccactacaaaaatgtga SEQ ID NO: 8: NDV F Protein (Clone 30; 553 amino acids)
MGPRPSTKNPVPMMLTVRVALVLSCICPANSIDGRPLAAAGIVVTGDKAVNIYTSSQTGSIIVKLLPN

LPKDKEACAKAPLDAYNRTLTTLLTPLGDSIRRIQESVTTSGGGRQGRLIGAIIGGVALGVATAAQIT

AAAALIQAKQNAANILRLKESIAATNEAVHEVTDGLSQLAVAVGKMQQFVNDQFNKTAQELDCIKIAQ

QVGVELNLYLTELTTVFGPQITSPALNKLTIQALYNLAGGNMDYLLTKLGVGNNQLSSLIGSGLITGN

PILYDSQTQLLGIQVTLPSVGKLNNMRATYLETLSVSTTRGFASALVPKVVTQVGSVIEELDTSYCIE

TDLHLYCTRIVTFPMSPGIYSCLSGNTSACMYSKTEGALTTPYMTIKGSVIANCKMTTCRCVNPPGII

SQNYGEAVSLIDKQSCNVLSLGGITLRLSGEFDVTYQKNISIQDSQVIITGNLDISTELGNVNNSISN

ALNKLEESNRKLDKVNVKLTSTSALITYIVLTIISLVFGILSLILACYLMYKQKAQQKTLLWLGNNTL

DQMRATTKM

SEQ ID NO: 9: NDV F Protein, coding sequence: (B1 Hitchner; 1698 bp)
atggatcgatcccggttggcgccctccaggtgcaggatgggctccagaccttctaccaagaacccagc acctatgatgctgactatccgggtcgcgctggtactgagttgcatctgtccggcaaactccattgatg gcaggcctcttgcagctgcaggaattgtggttacaggagacaaagcagtcaacatatacacctcatcc cagacaggatcaatcatagttaagctcctcccgaatctgccaaaggataaggaggcatgtgcgaaagc ccccttggatgcatacaacaggacattgaccactttgctcaccccccttggtgactctatccgtagga tacaagagtctgtgactacatctggagggggagacaggggcgccttataggcgccattattggcggt gtggctcttggggttgcaactgccgcacaaataacagcggccgcagctctgatacaagccaaacaaaa tgctgccaacatcctccgacttaaagagagcattgccgcaaccaatgaggctgtgcatgaggtcactg acggattatcgcaactagcagtggcagttgggaagatgcagcagttcgttaatgaccaatttaataaa acagctcaggaattagactgcatcaaaattgcacagcaagttggtgtagagctcaacctgtacctaac cgaatcgactacagtattcggaccacaaatcacttcacctgccttaaacaagctgactattcaggcac tttacaatctagctggtgggaatatggattacttattgactaagttaggtatagggaacaatcaactc agctcattaatcggtagcggcttaatcaccggtaaccctattctatacgactcacagactcaactctt gggtatacaggtaactctaccttcagtcgggaacctaaataatatgcgtgccacctacttggaaacct tatccgtaagcacaaccaggggatttgcctcggcacttgtcccaaaagtggtgacacgggtcggttct gtgatagaagaacttgacacctcatactgtatagaaactgacttagatttatattgtacaagaatagt aacgttccctatgtcccctggtatttactcctgcttgagcggcaatacatcggcctgtatgtactcaa agaccgaaggcgcacttactacaccatatatgactatcaaaggctcagtcatcgctaactgcaagatg acaacatgtagatgtgtaaaccccccgggtatcatatcgcaaaactatggagaagccgtgtctctaat agataaacaatcatgcaatgttttatccttaggcgggataactttaaggctcagtggggaattcgatg taacttatcagaagaatatctcaatacaagattctcaagtaataataacaggcaatcttgatatctca actgagcttgggaatgtcaacaactcgatcagtaatgccttgaataagttagaggaaagcaacagaaa -continued actagacaaagtcaatgtcaaactgaccagcacatctgctctcattacctatatcgttttgactatca tatctcttgtttttggtatacttagcctgattctagcatgctacctaatgtacaagcaaaaggcgcaa caaaagaccttattatggcttgggaataataccctagatcagatgagagccactacaaaaatgtga SEQ ID NO: 10: NDV F Protein (B1 Hitchner; 565 amino acids)
MDRSRLAPSRCRMGSRPSTKNPAPMMLTIRVALVLSCICPANSIDGRPLAAAGIVVTGDKAVNIYTSS

QTGSIIVKLLPNLPKDKEACAKAPLDAYNRTLTTLLTPLGDSIRRIQESVTTSGGGRQGRLIGAIIGG

VALGVATAAQITAAAALIQAKQNAANILRLKESIAATNEAVHEVTDGLSQLAVAVGKMQQFVNDQFNK

TAQELDCIKIAQQVGVELNLYLTESTTVFGPQITSPALNKLTIQALYNLAGGNMDYLLTKLGIGNNQL

SSLIGSGLITGNPILYDSQTQLLGIQVTLPSVGNLNNMRATYLETLSVSTTRGFASALVPKVVTRVGS

VIEELDTSYCIETDLDLYCTRIVTFPMSPGIYSCLSGNTSACMYSKTEGALTTPYMTIKGSVIANCKM

TTCRCVNPPGIISQNYGEAVSLIDKQSCNVLSLGGITLRLSGEFDVTYQKNISIQDSQVIITGNLDIS

TELGNVNNSISNALNKLEESNRKLDKVNVKLTSTSALITYIVLTIISLVFGILSLILACYLMYKQKAQ

QKTLLWLGNNTLDQMRATTKM

SEQ ID NO 11: ILTV gD promoter (527 bp)
aaacagctgtactacagagtaaccgatggaagaacatcggtccagctaatgtgcctgtcgtgcacgag ccattctccggaaccttactgtcttttcgacacgtctcttatagcgagggaaaaagatatcgcgccag agttatactttacctctgatccgcaaacggcatactgcacaataactctgccgtccggcgttgttccg agattcgaatggagccttaataatgtttcactgccggaatatttgacggccacgaccgttgtttcgca taccgctggccaaagtacagtgtggaagagcagcgcgagagcaggcgaggcgtggatttctggccggg gaggcaatatatacgaatgcaccgtcctcatctcagacggcactcgcgttactacgcgaaaggagagg tgcttaacaaacacatggattgcggtggaaaacggtgctgctcaggcgcagctgtattcactcttttc tggacttgtgtcaggattatgcgggagcatatctgctttgtacgcaacgct SEQ ID NO 12: ILTV gI promoter (264 bp)
tgactattacaatgacatgcccgccgtgatcccggtggaggagactactaaaagttctaatgccgtct ccatgcccatattcgcggcgttcgtagcctgcgcggtcgcgctcgtggggctactggtttggagcatc gtaaaatgcgcgcgtagctaatcgagcctagaataggtggtttcttcctacatgccacgcctcacgct cataatataaatcacatggaatagcataccaatgcctattcattgggacgttcgaaaagc SEQ ID NO 13: mCMV IE promoter (1391 bp)
aactccgcccgttttatgactagaaccaatagtttttaatgccaaatgcactgaaatcccctaatttg caaagccaaacgcccccctatgtgagtaatacggggactttttacccaatttcccacgcggaaagcccc ctaatacactcatatggcatatgaatcagcacggtcatgcactctaatggcggcccatagggactttc cacatagggggcgttcaccatttcccagcataggggtggtgactcaatggcctttacccaagtacatt gggtcaatgggaggtaagccaatgggtttttcccattactggcaagcacactgagtcaaatgggactt tccactgggttttgcccaagtacattgggtcaatgggaggtgagccaatgggaaaaacccattgctgc caagtacactgactcaatagggactttccaatgggtttttccattgttggcaagcatataaggtcaat gtgggtgagtcaatagggactttccattgtattctgcccagtacataaggtcaatagggggtgaatca acaggaaagtcccattggagccaagtacactgcgtcaatagggactttccattgggttttgcccagta cataaggtcaataggggatgagtcaatgggaaaaacccattggagccaagtacactgactcaataggg actttccattgggttttgcccagtacataaggtcaatagggggtgagtcaacaggaaagttccattgg agccaagtacattgagtcaatagggactttccaatgggttttgcccagtacataaggtcaatgggagg taagccaatgggtttttcccattactggcacgtatactgagtcattagggactttccaatgggttttg cccagtacataaggtcaataggggtgaatcaacaggaaagtcccattggagccaagtacactgagtca atagggactttccattgggttttgcccagtacaaaaggtcaatagggggtgagtcaatgggtttttcc -continued cattattggcacgtacataaggtcaataggggtgagtcattgggtttttccagccaatttaattaaaa cgccatgtactttcccaccattgacgtcaatgggctattgaaactaatgcaacgtgacctttaaacgg tactttcccatagctgattaatgggaaagtaccgttctcgagccaatacacgtcaatgggaagtgaaa gggcagccaaaacgtaacaccgccccggttttcccctggaaattccatattggcacgcattctattgg ctgagctgcgttctacgtgggtataagaggcgcgaccagcgtcggtaccgtcgcagtcttcggtctga ccaccgtagaacgcagagctcctcgctgcag SEQ ID NO 14: hCMV IE promoter, from strain AD169 (301 bp)
ggcagtacatctacgtattagtcatcgctattaccatggtgatgcggttttggcagtacatcaatggg cgtggatagcggtttgactcacggggatttccaagtctccaccccattgacgtcaatgggagtttgtt ttggcaccaaaatcaacgggactttccaaaatgtcgtaacaactccgccccattgacgcaaatgggcg gtaggcgtgtacggtgggaggtctatataagcagagctcgtttagtgaaccgtcagatcgcctggaga cgccatccacgctgttttgacctccatag SEQ ID NO: 15: hCMV IE Promoter (Truncated; 360 bp)
cgcgccaggtcaattccctggcattatgcccagtacatgaccttatgggactttcctacttggcagta catctacgtattagtcatcgctattaccatggtgatgcggttttggcagtacatcaatgggcgtggat agcggtttgactcacggggatttccaagtctccaccccattgacgtcaatgggagtttgttttggcac caaaatcaacgggactttccaaaatgtcgtaacaactccgccccattgacgcaaatgggcggtagcgt gtacggtgggaggtctatataagcagagctcgtttagtgaaccgtcagatcgcctggagacgccatcc acgctgttttgacctccata SEQ ID NO: 16: hCMV IE Promoter (Towne Strain; 1191 bp)
gtgaataataaaatgtgtgtttgtccgaaatacgcgtttgagatttctgtcccgactaaattcatgtc gcgcgatagtggtgtttatcgccgatagagatggcgatattggaaaaatcgatatttgaaaatatggc atattgaaaatgtcgccgatgtgagtttctgtgtaactgatatcgccatttttccaaaagttgatttt tgggcatacgcgatatctggcgatacgcttatatcgtttacgggggatggcgatagacgcctttggtg acttgggcgattctgtgtgtcgcaaatatcgcagtttcgatataggtgacagacgatatgaggctata tcgccgatagaggcgacatcaagctggcacatggccaatgcatatcgatctatacattgaatcaatat tggccattagccatattattcattggttatatagcataaatcaatattggctattggccattgcatac gttgtatccatatcataatatgtacatttatattggctcatgtccaacattaccgccatgttgacatt gattattgactagttattaatagtaatcaattacggggtcattagttcatagcccatatatggagttc cgcgttacataacttacggtaaatggcccgcctggctgaccgcccaacgacccccgcccattgacgtc aataatgacgtatgttcccatagtaacgccaatagggactttccattgacgtcaatgggtggagtatt tacggtaaactgcccacttggcagtacatcaagtgtatcatatgccaagtacgccccctattgacgtc aatgacggtaaatggcccgcctggcattatgcccagtacatgaccttatgggactttcctacttggca gtacatctacgtattagtcatcgctattaccatggtgatgcggttttggcagtacatcaatgggcgtg gatagcggtttgactcacggggatttccaagtctccaccccattgacgtcaatgggagtttgttttgg caccaaaatcaacgggactttccaaaatgtcgtaacaactccgccccattgacgcaaatgggcggtag gcgtgtacggtgggaggtctatataagcagagctcgtttagtgaaccgtcagatcgcctggagacgcc atccacgctgttttgacctccatagaagacaccgg SEQ ID NO 17: chicken β-actin promoter (692 bp)
(Note: “nnn” denotes an ambiguous sequence in highly GC-rich region. Could be 3-5 “g’s”)
cgcgccggatcagatctccatggtcgaggtgagccccacgttctgcttcactctccccatctcccccc cctccccacccccaattttgtatttatttattttttaattattttgtgcagcgatgggggcgggggg -continued ggggnnncgcgcgccaggcggggcggggcggggcgaggggcggggcggggcgaggcggagaggtgcgg cggcagccaatcagagcggcgcgctccgaaagtttccttttatggcgaggcggcggcggcggcggccc tataaaaagcgaagcgcgcggcgggcgggagtcgctgcgcgctgccttcgccccgtgccccgctccgc cgccgcctcgcgccgcccgccccggctctgactgaccgcgttactcccacaggtgagcgggcgggacg gcccttctcctccgggctgtaattagcggcaggaaggaaatgggcggggagggccttcgtgcgtcgcc gcgccgccgtccccttctccctctccagcctcggggctgtccgcgggggggacggctgccttcgggggg gacggggcagggcggggttcggcttctggcgtgtgaccggcggctctagagcctctgctaaccatgtt catgccttcttctttttcctacagctcctgggcaacgtgctggttattgtgctgtctcatcattttgg caaagaattgca SEQ ID NO 18: FHV US-9 polyadenylation signal (55 bp)
caataaacatagcatacgttatgacatggtctaccgcgtcttatatggggacgac SEQ ID NO 19: HSV TK polyadenylation signal (370 bp)
gatccataattgattgacgggagatgggggaggctaactgaaacacggaaggagacaataccggaagg aacccgcgctatgacggcaataaaaagacagaataaaacgcacgggtgttgggtcgtttgttcataaa cgcggggttcggtcccagggctggcactctgtcgataccccaccgagaccccattggggccaatacgc ccgcgtttcttccttttccccaccccaccccccaagttcgggtgaaggcccagggctcgcagccaacg tcggggcggcaggccctgccatagccactggccccgtgggttagggacggggtcccccatggggaatg gtttatggttcgtgggggttattattttga SEQ ID NO 20: SV40 polyadenylation signal (199 bp)
agcttcagacatgataagatacattgatgagtttggacaaaccacaactagaatgcagtgaaaaaaat gctttatttgtgaaatttgtgatgctattgctttatttgtaaccattataagctgcaataaacaagtt aacaacaacaattgcattcattttatgtttcaggttcagggggaggtgtgggaggttttttcg SEQ ID NO 21: 484-1050-2641-10859(mCMV IEpro-VP2-SV40pA/ILTV/HVT UL54.5 region (15,252 bp) (HVT/IBDV/ILTV/NDV 670-14 Virus)
ggcgcgccactggagaacggcatgaccgcaaaaggcgttgtagagatcgatcccacgaactctcaggc gatcgtgtcagtcgccataaacagcgacgatcgtctccaggatctgaacggttttcttctcaacgatc atcagtatatgaggaactgaacctgatatttagccgagggaaacgcaggttaaaaaccctatcaagcg attgcgattttcgcgtatctagtaaaaatagatgggcttcggtactagccttcgccgccaactctgaa tatgcccttcgtggacctcatataacatggcattgtttgttggatgcggggccggaattaagaagaac attcgaaatacgagcaaaaatttcggccctggcatgtgctgcgcgagaatcggtacttcggggagaaa gttttatcggagctttgggtagtgcagaggaaactctatcttggttgaaaatgcatgcgaccctgcac ttgattctggttaaccacgatccaattttaagacggctggcgcggtcctagataacctccgcttaaa actagccccaatattgatgtgcagatataacacagaaaaacgatcaatggaagacatgctacggcggt catctcccgaagacatcaccgattccctaacaatgtgcctgattatgttatcgcgcattcgtcgtacc atgcgcaccgcaggaaataaatatagctatatgatagatccaatgaatcgtatgtctaattacactcc aggcgaatgtatgacaggtatattgcgatatattgacgaacatgctagaaggtgtcctgatcacatat gtaatttgtatatcacatgtacacttatgccgatgtatgtgcacgggcgatatttctattgtaattca tttttttgttagtaaactaccacaggctgtccggaaatctaagttaatgaataaagtagatggttaat actcattgcttagaattggactacttttaattctctttaatgttcgtattaaataaaaacatctttaa taaacttcagcctcttcgcttattgtagaaattgagtattcaaaatcatgttcaaagccgtcttcgga gagtgtactcgccacggtggttggaacatcactatgtctacacgtcaaatttaagcacgtcaggtctg tcgaggacaagaaatggttaactagtgtttcaattattcttataaacgttaagcattgtaagcccccc ggccgtccgcagcaacaatttactagtatgccgtgggctccgggactatcacggatgtccaattcgca -continued catgcatataatttttctagggtctctcatttcgagaaatcttcggggatccatcagcaatgcgggct gtagtcccgattcccgtttcaaatgaaggtgctccaacacggtcttcaaagcaaccggcataccagca aacacagactgcaactccccgctgcaatgattggttataaacagtaatctgtcttctggaagtatatt tcgcccgacaatccacggcgcccccaaagttaaaaaccatccatgtgtatttgcgtcttctctgttaa aagaatattgactggcattttcccgttgaccgccagatatccaaagtacagcacgatgttgcacggac gactttgcagtcaccagccttcctttccacccccccaccaacaaaatgtttatcgtaggacccatatc cgtaataaggatgggtctggcagcaaccccataggcgcctcggcgtggtagttctcgaggccttaagc ttaaggatcccccaactccgcccgttttatgactagaaccaatagtttttaatgccaaatgcactgaa atcccctaatttgcaaagccaaacgcccccctatgtgagtaatacggggactttttacccaatttccca cgcggaaagcccccctaatacactcatatggcatatgaatcagcacggtcatgcactctaatggcggcc catagggactttccacatagggggcgttcaccatttcccagcataggggtggtgactcaatggccttt acccaagtacattgggtcaatgggaggtaagccaatgggtttttcccattactggcaagcacactgag tcaaatgggactttccactgggttttgcccaagtacattgggtcaatgggaggtgagccaatgggaaa aacccattgctgccaagtacactgactcaatagggactttccaatgggtttttccattgttggcaagc atataaggtcaatgtgggtgagtcaatagggactttccattgtattctgcccagtacataaggtcaat agggggtgaatcaacaggaaagtcccattggagccaagtacactgcgtcaatagggactttccattgg gttttgcccagtacataaggtcaataggggatgagtcaatgggaaaaacccattggagccaagtacac tgactcaatagggactttccattgggttttgcccagtacataaggtcaatagggggtgagtcaacagg aaagttccattggagccaagtacattgagtcaatagggactttccaatgggttttgcccagtacataa ggtcaatgggaggtaagccaatgggtttttcccattactggcacgtatactgagtcattagggacttt ccaatgggttttgcccagtacataaggtcaataggggtgaatcaacaggaaagtcccattggagccaa gtacactgagtcaatagggactttccattgggttttgcccagtacaaaaggtcaatagggggtgagtc aatgggtttttcccattattggcacgtacataaggtcaataggggtgagtcattgggtttttccagcc aatttaattaaaacgccatgtactttcccaccattgacgtcaatgggctattgaaactaatgcaacgt gacctttaaacggtactttcccatagctgattaatgggaaagtaccgttctcgagccaatacacgtca atgggaagtgaaagggcagccaaaacgtaacaccgccccggttttcccctggaaattccatattggca cgcattctattggctgagctgcgttctacgtgggtataagaggcgcgaccagcgtcggtaccgtcgca gtcttcggtctgaccaccgtagaacgcagagctcctcgctgcaggcggccgctctagaactcgtcgat cgcagcgatgacaaacctgcaagatcaaacccaacagattgttccgttcatacggagccttctgatgc caacaaccggaccggcgtccattccggacgacaccctggagaagcacactctcaggtcagagacctcg acctacaatttgactgtgggggacacagggtcagggctaattgtctttttccctggattccctggctc aattgtgggtgctcactacacactgcagagcaatgggaactacaagttcgatcagatgctcctgactg cccagaacctaccggccagctacaactactgcagactagtgagtcggagtctcacagtgaggtcaagc acactccctggtggcgtttatgcactaaacggcaccataaacgccgtgaccttccaaggaagcctgag tgaactgacagatgttagctacaatgggttgatgtctgcaacagccaacatcaacgacaaaattggga atgtcctggtaggggaaggggtcactgtcctcagcctacccacatcatatgatcttgggtatgtgagg cttggtgaccccattcccgctatagggcttgacccaaaaatggtagctacatgcgacagcagtgacag gcccagagtctacaccataactgcagccgatgattaccaattctcatcacagtaccaaccaggtgggg taacaatcacactgttctcagccaacattgatgctatcacaagcctcagcattgggggagagctcgtg tttcaaacaagcgtccaaggccttgtactgggcgccaccatctaccttataggctttgatgggactgc ggtaatcaccagagctgtggccgcagataatgggctgacggccggcaccgacaatcttatgccattca -continued atcttgtcattccaaccaatgagataacccagccaatcacatccatcaaactggagatagtgacctcc aaaagtggtggtcaggcaggggatcagatgtcatggtcggcaagtgggagcctagcagtgacgatcca tggtggcaactatccaggggccctccgtcccgtcacactagtagcctacgaaagagtggcaacaggat ccgtcgttacggtcgctggggtgagtaacttcgagctgattccaaatcctgaactagcaaagaacctg gttacagaatacggccgatttgacccaggagccatgaactacacaaaattgatactgagtgagaggga ccgtcttggcatcaagaccgtctggccaacaagggagtacactgattttcgtgagtacttcatggagg tggccgacctcaactctcccctgaagattgcaggagcatttggcttcaaagacataatccgggctata aggaggtagatccagacatgataagatacattgatgagtttggacaaaccacaactagaatgcagtga aaaaaatgctttatttgtgaaatttgtgatgctattgctttatttgtaaccattataagctgcaataa acaagttaacaacaacaattgcattcattttatgtttcaggttcagggggaggtgtgggaggtttttt cggatcctctagagtcgacggcagagtcgcagacgcccctattggacgtcaaaattgtagaggtgaag ttttcaaacgatggcgaagtaacggcgacttgcgtttccaccgtcaaatctccctatagggtagaaac taattggaaagtagacctcgtagatgtaatggatgaaatttctgggaacagtcccgccggggtttta acagtaatgagaaatggcagaaacagctgtactacagagtaaccgatggaagaacatcggtccagcta atgtgcctgtcgtgcacgagccattctccggaaccttactgtcttttcgacacgtctcttatagcgag ggaaaaagatatcgcgccagagttatactttacctctgatccgcaaacggcatactgcacaataactc tgccgtccggcgttgttccgagattcgaatggagccttaataatgtttcactgccggaatatttgacg gccacgaccgttgtttcgcataccgctggccaaagtacagtgtggaagagcagcgcgagagcaggcga ggcgtggatttctggccggggaggcaatatatacgaatgcaccgtcctcatctcagacggcactcgcg ttactacgcgaaaggagaggtgcttaacaaacacatggattgcggtggaaaacggtgctgctcaggcg cagctgtattcactcttttctggacttgtgtcaggattatgcgggagcatatctgctttgtacgcaac gctatggaccgccatttatttttgaggaatgctttttggactatcgtactgctttcttccttcgctag ccagagcaccgccgccgtcacgtacgactacattttaggccgtcgcgcgctcgacgcgctaaccatac cggcggttggcccgtataacagatacctcactagggtatcaagaggctgcgacgttgtcgagctcaac ccgatttctaacgtggacgacatgatatcggcggccaaagaaaaagagaagggggccctttcgaggc ctccgtcgtctggttctacgtgattaagggcgacgacggcgaggacaagtactgtccaatctatagaa aagagtacagggaatgtggcgacgtacaactgctatctgaatgcgccgttcaatctgcacagatgtgg gcagtggactatgttcctagcacccttgtatcgcgaaatggcgcgggactgactatattctcccccac tgctgcgctctctggccaatacttgctgaccctgaaaatcgggagatttgcgcaaacagctctcgtaa ctctagaagttaacgatcgctgtttaaagatcgggtcgcagcttaactttttaccgtcgaaatgctgg acaacagaacagtatcagactggatttcaaggcgaacacctttatccgatcgcagacaccaatacacg acacgcggacgacgtatatcggggatacgaagatattctgcagcgctggaataatttgctgaggaaaa agaatcctagcgcgccagaccctcgtccagatagcgtcccgcaagaaattcccgctgtaaccaagaaa gcggaagggcgcaccccggacgcagaaagcagcgaaaagaaggcccctccagaagactcggaggacga catgcaggcagaggcttctggagaaaatcctgccgccctccccgaagacgacgaagtccccgaggaca ccgagcacgatgatccaaactcggatcctgactattacaatgacatgcccgccgtgatcccggtggag gagactactaaaagttctaatgccgtctccatgcccatattcgcggcgttcgtagcctgcgcggtcgc gctcgtggggctactggtttggagcatcgtaaaatgcgcgcgtagctaatcgagcctagaataggtgg tttcttcctacatgccacgcctcacgctcataatataaatcacatggaatagcataccaatgcctatt cattgggacgttcgaaaagcatggcatcgctacttggaactctggctctccttgccgcgacgctcgca -continued cccttcggcgcgatgggaatcgtgatcactggaaatcacgtctccgccaggattgacgacgatcacat cgtgatcgtcgcgcctcgccccgaagctacaattcaactgcagctatttttcatgcctggccagagac cccacaaaccctactcaggaaccgtccgcgtcgcgtttcggtctgatataacaaaccagtgctaccag gaacttagcgaggagcgctttgaaaattgcactcatcgatcgtcttctgtttttgtcggctgtaaagt gaccgagtacacgttctccgcctcgaacagactaaccggacctccacacccgtttaagctcactatac gaaatcctcgtccgaacgacagcgggatgttctacgtaattgttcggctagacgacaccaaagaaccc attgacgtcttcgcgatccaactatcggtgtatcaattcgcgaacaccgccgcgactcgcggactcta ttccaaggcttcgtgtcgcaccttcggattacctaccgtccaacttgaggcctatctcaggaccgagg aaagttggcgcaactggcaagcgtacgttgccacggaggccacgacgaccagcgccgaggcgacaacc ccgacgcccgtcactgcaaccagcgcctccgaacttgaagcggaacactttacctttccctggctaga aaatggcgtggatcattacgaaccgacacccgcaaacgaaaattcaaacgttactgtccgtctcggga caatgagccctacgctaattggggtaaccgtggctgccgtcgtgagcgcaacgatcggcctcgtcatt gtaatttccatcgtcaccagaaacatgtgcaccccgcaccgaaaattagacacggtctcgcaagacga cgaagaacgttcccaaactagaagggaatcgcgaaaatttggacccatggttgcgtgcgaaataaaca agggggctgaccaggatagtgaacttgtggaactggttgcgattgttaacccgtctgcgctaagctcg cccgactcaataaaaatgtgattaagtctgaatgtggctctccaatcatttcgattctctaatctccc aatcctctcaaaaggggcagtatcggacacggactgggaggggcgtacacgatagttatatggtacag cagaggcctctgaacacttaggaggagaattcagccggggagagcccctgttgagtaggcttgggagc atattgcaggatgaacatgttagtgatagttctcgcctcttgtcttgcgcgcctaacttttgcgacgc gacacgtcctctttttggaaggcactcaggctgtcctcggggaagatgatcccagaaacgttccggaa gggactgtaatcaaatggacaaaagtcctgcggaacgcgtgcaagatgaaggcggccgatgtctgctc ttcgcctaactattgctttcatgatttaatttacgacggaggaaagaaagactgcccgcccgcgggac ccctgtctgcaaacctggtaattttactaaagcgcggcgaaagcttcccgggttaattaaggccctcg aggatacatccaaagaggttgagtattctctctacacttcttgttaaatggaaagtgcatttgcttgt tcttacaatcggcccgagtctcgttcacagcgcctcgttcacacttaaaccacaaatagtctacaggc tatatgggagccagactgaaactcacatatgactaatattcgggggtgttagtcacgtgtagcccatt gtgtgcatataacgatgttggacgcgtccttattcgcggtgtacttgatactatggcagcgagcatgg gatattcatcctcgtcatcgttaacatctctacgggttcagaatgtttggcatgtcgtcgatcctttg cccatcgttgcaaattacaagtccgatcgccatgaccgcgataagcctgtaccatgtggcattagggt gacatctcgatcatacattataagaccaacgtgcgagtcttccaaagacctgcacgccttcttcttcg gattgtcaacgggttcttcagaatctatgcccatatctggcgttgagaccattgtgcgtttaatgaac aataaagcggcatgccatggaaaggagggctgcagatctccattttctcacgccactatcctggacgc tgtagacgataattataccatgaatatagaggggggtatgtttccactgccactgtgatgataagtttt ctccagattgttggatatctgcattttctgctgccgaacaaacttcatcgctatgcaaagagatgcgt gtgtacacgcgccggtggagtatacgggaaactaaatgttcatagaggtctttgggctatatgttatt aaataaaataattgaccagtgaacaatttgtttaatgttagtttattcaatgcattggttgcaaatat tcattacttctccaatcccaggtcattctttagcgagatgatgttatgacattgctgtgaaaattact acaggatatatttttaagatgcaggagtaacaatgtgcatagtaggcgtagttatcgcagacgtgcaa cgcttcgcatttgagttaccgaagtgcccaacagtgctgcggttatggtttatgcgcacagaatccat gcatgtcctaattgaaccatccgatttttcttttaatcgcgatcgatgtttgggcaactgcgttattt cagatctaaaaaatttaccctttatgaccatcacatctctctggctcataccccgcttggataagata -continued tcatgtagattccgccctaagaaatgcaaactaacattattgtcggttccatatacacttccatcttg tccttcgaaaataacaaactcgcgcaatagaccgtccgtacatgcatggccgatgtgtgtcaacatca ttggtctgctagatcccgatgggacgaatcgtacagtcgtcgctccagcattggcaaaaatccccaga taccctccatgcggcaaatctaaattgcgaccccgaagagactgcaccaaagtcttatcgacgcacgc tgatttttttgaacagcgggagcccattatcttcagtggagcgtagacgggcgaggctaattatgtga catagcaacactgcatgtatgtttttataaatcaataagagtacataatttattacgtatcatttccg tttgtaatatactgtatacatcatccacactattagtcagcactagcgcgcgggcgcacgttacaata gcagcgtgcccgttatctatattgtccgatatttacacataacatttcatcgacatgattaaatacct aagtactgcacacagatgtttaatgtatatcgtcatataaattatatcgctaggacagacccaaacga cctttatcccaaacagtcagatcctcttctcaagtgtcgatttctgttatggaatatgcatacccctgg cccagaaattgcacgcacgagcgtagtgaatgcgtcattggttttacatttaaaggctaaatgcacaa attctttagacgacagcacatcgttaaatagcatctctagcgttcttatgaatgctaagcattggagt cctcctggtcggccacaataacagctgagtatcataccctgagctccggggttgtcgcacatagcgga ttcgtataaacataggattttccgcgaatccatcagttgcaaaaatctgttaggctccatcaacaacg ctggatttacttcagatccacgcgtaaagtaatggtgctcgaataccgtttttagagttgtcggcatt tcaaggaacaaagaattcatttcttcattgcaacgacgcgccagaaatcccaagacctctttgggtag tatgttcttgcctataaaacacggcgttccaagtgccaggaaccacgcatgtgttactgttggggcgt attcagaaataaagcggggtttatgcggcttttgaagctcggatatccaaagtatcgcttgctgatga acgagcgatgtagctgttacaaaacctcctttccatcctccagtcaacataatatttatcggcctacc tatgtccgtaataagtattggtcgggcaattattccgtatgaggtcttgcaggaataagctcttaggg acagccagcttggatatggtgcgaaacagaccttctcggcttcagaatgtcgctccgcagtctcttcg tgtcggtgcatcttagatccaccatcaatgtgtgcagcattgactcccgcccgtcgaatattcctttt gttacgatgcagtaatgagcacgatcatgggcggggcgatgacgttctatttgcatgtctgcgaacaa tttgcgtcagtcatacagctatggagtgggccatttctggccgtcaacttaaaaacgcgaaccgcaga catatgtatttgcatgcaaagacgtatcttcgtatttctgggcatcttcaaatgctctggccaatatg gcaatgaatttggattcgtttgacgccgatggtatgcagtgcaaatgtgccaatagcccacatccgaa aaagttatttgtcatacaagcaggtgttaagtagcaatcacataaaggcaccagacgcctcatggcat cataatgaatagctccttctccccactggaaccactgacaaaatctgcgagtatattccgcaaaccac attttatttctcatagaaactaccctaaatccttttaacgggaagaagaatcctagatagtgcttgaa gtcatgactgttactgctgcaataacactgtatattatttataaattccgtttgtctaggtatctgat gtaggcattccgatccctttactattgcgtcttcacgaccaaatgggaatgcgccaaaatccccacac ctcatcaccctggaggcagattgtgtattattaatatccgccgattgaagcacaaaacggtacggtac tgttcctaattctggtatagattctatggtcaaaagtctgcatatccccgacattgccatgagatcac acagtccaagtagcatgtttattgagtcactcagactgtcaacgtccctcgccgcaccaccaatcgaa aataaagtatctacgcaagttatagctccgcattttctatcgctagcagcaatcgcgacgcaaaacat aaaggccatgttgggatttgaactctctgggggggcttgttatcttctgcaccgtcgcagtcgcagttt tccgaaatttatgtctaatatattttccggccgtgctccaatcggccgaaaagaatctgcgtattacc agactcattgacgggccgataaagaccataaaacaaaattcctgtgcactccctcctccagttttgcc atcgtccaagtcccgtaactttttttgcgtttcgaggagcaagcgttcgttatccctacccacacttg ttttccaccgttttcttattataagcggttgtatcgccaacgcgtcaccgcaggttgtcacatacagt -continued gatggcatacttgaacgtgcaacaacgcgctcgctttgcaaatctaagtcattgaccatcaaatcgcg ttgagaggatagccaggcatctttttttcctagtatggtgacggtgcagccaccccaactcagttcttg taaaaaaagctattggcgggaatttatgttctgaggtgcattctatatttatgagtccatcaaatgcc attaaccagattcgtatttttttcgctcgacccggcatcactatggatacaatacctttctatggccca tttcagctctcgaaccaaccacacggacaattgactaacataagtatgatctttatcacagtcgcacc catctgagttatatttatggcatccgagcgctcttactgtacggtcggatacacccatggtttttcct ttatatagtcgggttatagtctgtcgggtttggcggtagcacggagtagtttgatttttaagaatcga aaaccggcttggagagaccactgtcgaatatttgtccgtatactctacacgtgagtgttgtccattcc taggtatattcatctgttcggataccttcaattgctgttcaggcataaccttaaagcatatgttatgt tgtacatcaaaacttggtgagttatgttcgattgccgcgcataaagaatcgtacatgagcgtttctgc taacatactatctatattctcacacgcccctgcatatactgttcctattccaaattcacgttttgccc catcggctatctgctcccaaaaagttgtaatataggtgccgctgggtgcgaaattttcatcagttgta ttcctgataaactgaatcactttacataatttttgccacatatctgcgtgcagccatagtatcgaacc cgtgggctcggagacgacagtgcgtacaatgggtatttacctttccccaacaaaataatggtataca agttaggtccgtacctagaccttaatgtttccaattcttctgaatcactgcactctcgtaggggagta acggtaataatttcgtctctgagccccgttttgcgttgaaaactaatcacattagataatgtgcaatc ggtttcttttatccggatacatctaagtattatgacatcggtggtcattgtttccatcaacgaccatc ttttacgatcgcccatactactcatggacgttgtcggtgttgaaaaatcaccagaattgcaacggatc tctgggtaccatgctgctgatggaattggcggttttaattgttgtttcagtctattattgctatcttt ggcggggttgaataatgtgggggagagtgattgcaggaatccgaatgggtcaataaaacgaccgtgc tccgttctgccggcgccgatccgattgaagctatatacttcgcttctctccccacttttccaatttga tccggaaataaaacggccccggacaacagtatcgtacgatccggatccggatcctgcttgcctacaga agaatcaacatctcgccccaatattctggtcaaaactggctcgctcatggcaacgcggacgtttcccc cggtggccagtcttaatggttaatgttcttttcggcaatcttatacatcagcgggttgcgtgaatact ggtcacagttcagtcatttactacacaccagcaatacgacgacggacagtaccgtcccgacgaacgcg acgcccaaaattgctatcgcgaccgcgtccgaggcgatgtcgtacgggcggtgcggggttggatcctc ggcaaagagatcctcgtaattcggcggtgggagcggagggtaaagacgcgggtggggatctccctccg gaccgcgcgccgggcgcggttcgaaaatgctttccgcctcgctcagtgtcaacgccaagtattcgggc gggctgggggccggaatatctcccgcgacttcttctatcggcgcggaattggagtcgcggtcgtggcg cgcttctagcgtcgtcaacggaagtccattttcggggtctcccggtgggcgttcagcgtccatcgtcg tatatgctctaacacacgtctcgctatattaaaaaaaagaagagtatcggtcagtgtcgagtgtcgcc gacaatgtcgcgagttctcggcgatttaatttttggaactgctccctatgaatcccgtaactgtagcg cccgcgcagaaagccgccatcagaccaactacgtgtctgttcgatgtttgcccgccgatcgctttacc gattaaggttccggcgagaaatgacatgctcgatccaagaacaaagtttttcgcggtaaacaacaaca tagttaccgtgcgagatggagaaaccacatctcccgaattagtagaggaaagcccgcgctgtcggttt ggggacatatcgatctttttttgtgtttttcctaggacccttttgccagatcgtacaaagtcgcgtctt atgagcggacgttcttactgcagctcggtaggagtggggcagggttagatttcgtcggcgtttcggcc cccgtatgcgccgcgccaccctcttcgccgagctctttatgcgcggtgggggtgagcgcttccggagt tgcgatctccgatctcgagccgcagcccggcggtgtctctttcagtggagcgttagcgccatcatgtg gttcgtggcggtggaaaggctattatgtgttaggggagagaccacgtgatcggcatgcaaatgagcaa ggcgaacgcgtcagcgttcgcactgcgaaccaataatatatatattatactattggctttaggtgcga -continued acgtccggctagtccaatagcggggtcgcgtttcgtaccacgtgttatagaccgccctaaactcgcac tcgggggtccggccgcgcccagacagggcggagacgtgccacaggggctttaaaacaccgcttcgggc accgttcatctcggcgcgcc SEQ ID NO 22: 1322-48.1 hCMV IEpro-F-IE(term)/HVT US2 region
(12,692 bp) (HVT/IBDV/ILTV/NDV 670-14 Virus)

ctcgcgcgtttcggtgatgacggtgaaaacctctgacacatgcagctcccggagacggtcacagcttg tctgtaagcggatgccgggagcagacaagcccgtcagggcgcgtcagcgggtgttggcgggtgtcggg gctggcttaactatgcggcatcagagcagattgtactgagagtgcaccatatcgacgctctcccttat gcgactcctgcattaggaagcagcccagtagtaggttgaggccgttgagcaccgccgccgcaaggaat ggtgcatgcaaggagatggcgcccaacagtcccccggccacggggcctgccaccatacccacgccgaa acaagcgctcatgagcccgaagtggcgagcccgatcttccccatcggtgatgtcggcgatataggcgc cagcaaccgcacctgtggcgccggtgatgccggccacgatgcgtccggcgtagaggatctggctagcg atgaccctgctgattggttcgctgaccatttccggggtgcggaacggcgttaccagaaactcagaagg ttcgtccaaccaaaccgactctgacggcagtttacgagagagatgatagggtctgcttcagtaagcca gatgctacacaattaggcttgtacatattgtcgttagaacgcggctacaattaatacataaccttatg tatcatacacatacgatttaggtgacactatagaatacaagctagcttgggctgcaggtcgactctag aggatcgttaattaacgatccccgggcgagctcgaattccagactaaatgccccggcccaatttgtca agtgtgcagtcacggaggcgtcgaccgtgtccccggcattaaacaggaaagcgttaaagtttttgaat gttaggtcacaggtacaaacataaatgtttgtacaaacaggtaacaggtacaaacataaatgccccgg cataaatgtcccttacggcggatcgaaacgacattaggcatactcgggtaccattttgcattccgatc agcacggatgaaattaggcaggaatgcggtttatattatgcggcattggacaaacgatatggcattga ttggcagtttatgaatgtcttcatgttgggcgtaaacggattcctattggttcagaagacaacgacga tatatttagagagaaaaagctacccagcataggataaacacacattgagcattgagagacataggtat cggtatggatgggaaaactacacacgtgaacaccaaacgacttatatactcgagcggtgatactactg agcaagaatgcactgcatctgagccactgaatgaagactgtgatgaaaatgtgaccatcgatggaatt ggagaagaatatgcgcagttcttcatgtccccgcaatgggtcccaaatctacatcgcttgagcgagga taccaaaaaggtataccgatgtatggtttccaacagactcaattattttccctattatgaggcgttca ggcggtctttgtttgatatgtatatgctaggtcggttggggcgtcgacttaagcgatctgactgggag actattatgcatctgtcaccaacgcaaagtcggcgtctacatagaactttaagatttgtggagcgtag aattatcccatctaacagttatatacgcacatcgggccacgttccgccttcgagggcacttccgacag atacgaatttaaagatggatgaataattaaattggaaagagtaactacattaatcgagcgtcatgacg gcgtcccgtgaaaatgggaattttctactcgaaacaccgtgacatttgacagacctggaattgttatt ctgatatatagtgggtgtgtctggccggcaacatacataatgtgcatgcgaaaccactttttcagtgt acgctgacattgtgcaacacggaggggtagcatctacatacaatatatgttgattaatgattggagaa aaaactatgcagctcgccgatcatatggctaactcgccttcgtctatatggcggaccccgcgggaaaa atcgacgtaccatctgatttacaacaccaataatgaacatgtcgcatccctgcccagatctgtgcgcc cattggcgcggatcgttgtgaatgccgccgaaacacttcaggtcggtatgagagccgggaggccgcca tcagcaggagtttggcgagaggtgtttgatagaatgatgacagccttccgtgaccacgagcctactgc gacatttaatgctgcaaatcccattagaaaaatggtcgagacagttctacagaataatgaagagcccc cgcggacgcatgctgaaatgggtaatcgccttatgaacattatgtactggtgttgcttgggacacgca ggacaatgctcgatatggcagttgtacgagacgaatcaggccattttaagtttattagatgaagtggt -continued tatcggcacaacaaatcccttttgcaccctcgagcaatactggaagccattatgcaccgcaatcgcca acaaggggacctcatcgcttgttgaggatgccaaagtggccgagtacctggttagcatgcgcaaattg atataacataggcacgctctgatgttacagaccacaataccgcatacatttattgtaaggttgttaat aaaggtttattctatgtaagactacaatactttcgacattgcttgtatacatattaaatactttctca agttcctattacataaaatgggatctatcattacattcgttaagagtctggataattttactgtttgc cagcttcgatcttggaacgtactgtggatagtgccttacttggaatcgtgaaaatttgaaacgtccat tatttggatatcttccggttgtcccatatcccgccctggtaccgctcggataccttgcccgtatggat tcgtattgacagtcgcgcaatcggggaccaacaacgcgtgggtccacactcattcggaaattttccga tgattctgaatatttattgccgctcgttacgagtcgttggacatatctgtaatacatttcttcttctg aaggatcgctgcacatttgatctatacattggccaggatgttcaagtctcagatgttgcattctggca cagcacaactttatggcatttccgatgtaatcgtccggcagccctgggggagttctatattcgcatat tgggatggtaaggacaatagcagatctcgcaacctccagggaggctataataacgtttttaaaggatg gatttctcataaaaatctgtcgcaaattacactgagaatatcctttactagcgccgattgagagcatc gtcgtccaattttctaaatggaaagaaaacaaggcgggcaagagtgttccaaacattttcattttcgg cgaatctctcaaatcccatggcgtgcaattgattgcaaaattggcacttccgttcacgtttgtatctc caaactctaagacacttttaattgaaaaactacgttctagtgtggaaagaaacctataggcagaccat agaactatttgacaccacatatctttttgtatgtcaaactgaccatgatcgtatgttgctgaatgcac tagggcaattcgctcgcgcgactccatacattgaataattccacacgtcagctcatcggttagcaagg tccagtagttgaagtcatttattttccccgcggctggccaaatctacctctgggaatatccaagttg tcgaatatgatcgcaccggctctggtcatggtgaaggaactgtagcataaagacgcaggtatcatagg ggtaatatttttttattcactcacatactaaaagtaacgcatattagcaccatgtatgggctatcaat tgacatttgcgtagcactacatcacgattatgtacaacataatgggacaacatatggcaagtagatgc aatttcctcacactagttgggtttatctactattgaattttcccctatctgtgatacacttgggagcc tctacaagcatattgccatcatgtacgtttttatctactgtcttaacgcccatgggaacggaggcgtc gtcgtcatgtattggacggcaacataggcagcaacacaaattgcgtttaggtggggtgcatgtggact cgataccaagcccctgcagctggggaacgtctggtggagagccgataatttgatatacgcacgccata ttactgtcgttgaagtacgccttatcttctatgttttcaaatttaggttcccaagtggacgtgagaag tgtttgtatctcacatggaatggcccaaggcattccagcccaggtgcctggtactttaatggcaaaca aacgttttggtagaggtattgattctattgcagttctgcagatatctgcagccccgagtatccacagg ctatacgatacgttatcggaggcaagcttcgcgccaggtcaattccctggcattatgcccagtacatg accttatgggactttcctacttggcagtacatctacgtattagtcatcgctattaccatggtgatgcg gttttggcagtacatcaatgggcgtggatagcggtttgactcacggggatttccaagtctccacccca ttgacgtcaatgggagtttgttttggcaccaaaatcaacgggactttccaaaatgtcgtaacaactcc gccccattgacgcaaatgggcggtagcgtgtacggtgggaggtctatataagcagagctcgtttagtg aaccgtcagatcgcctggagacgccatccacgctgttttgacctccatagaagacaccggttgcgccg ccaccatgggccccagaccttctaccaagaacccagtacctatgatgctgactgtccgagtcgcgctg gtactgagttgcatctgtccggcaaactccattgatggcaggcctcttgcggctgcaggaattgtggt tacaggagacaaagccgtcaacatatacacctcatcccagacaggatcaatcatagttaagctcctcc cgaatctgcccaaggataaggaggcatgtgcgaaagccccccttggatgcatacaacaggacattgacc actttgctcacccccccttggtgactctatccgtaggatacaagagtctgtgactacatctggaggggg gagacaggggcgccttataggcgccattattggcggtgtggctcttggggttgcaactgccgcacaaa -continued taacagcggccgcagctctgatacaagccaaacaaaatgctgccaacatcctccgacttaaagagagc
attgccgcaaccaatgaggctgtgcatgaggtcactgacggattatcgcaactagcagtggcagttgg
gaagatgcagcagtttgttaatgaccaatttaataaaacagctcaggaattagactgcatcaaaattg
cacagcaagttggtgtagagctcaacctgtacctaaccgaattgactacagtattcggaccacaaatc
acttcacctgctttaaacaagctgactattcaggcactttacaatctagctggtggaaatatggatta
cttattgactaagttaggtgtagggaacaatcaactcagctcattaatcggtagcggcttaatcaccg
gtaaccctattctatacgactcacagactcaactcttgggtatacaggtaactctaccttcagtcggg
aagctaaataatatgcgtgccacctacttggaaaccttatccgtaagcacaaccaggggatttgcctc
ggcacttgtcccaaaagtggtgacacaggtcggttctgtgatagaagaacttgacacctcatactgta
tagaaactgacttacatttatattgtacaagaatagtaacgttccctatgtcccctggtatttattcc
tgcttgagcggcaatacgtcggcctgtatgtactcaaagaccgaaggcgcacttactacaccatacat
gactatcaaaggttcagtcatcgccaactgcaagatgacaacatgtagatgtgtaaaccccccgggta
tcatatcgcaaaactatggagaagccgtgtctctaatagataaacaatcatgcaatgttttatcctta
ggcgggataactttaaggctcagtggggaattcgatgtaacttatcagaagaatatctcaatacaaga
ttctcaagtaataataacaggcaatcttgatatctcaactgagcttgggaatgtcaacaactcgatca
gtaatgctttgaataagttagaggaaagcaacagaaaactagacaaagtcaatgtcaaactgactagc
acatctgctctcattacctatatcgtgttgactatcatatctcttgtttttggtatacttagcctgat
tctagcatgctacctaatgtacaagcaaaaggcgcaacaaaagaccttattatggcttgggaataata
ctctagatcagatgagagccactacaaaaatgtgaggatctctcgaggaattctagatcccacgtcac
tattgtatactctatattatactctatgttatactctgtaatcctactcaataaacgtgtcacgcctg
tgaaaccgtactaagtctcccgtgtcttcttatcaccatcaggtgacatcctcgcccaggctgtcaat
catgccggtatcgattccagtagcaccggccccacgctgacaacccactcttgcagcgttagcagcgc
ccctcttaacaagccgaccccccaccagcgtcgcggttactaacactcctctccccgacctgcaactag
taagcttgcctccgattctagcattacatagccggtcagtagatcctgccattcggtagcgcaaccgg
ctacatcttcaaacagtctcacaataaatgcatctctcgttcctgccaatccggaaccgggcatacca
ctcccgcctgccgatttaattctcacaattgggcgatgccggcggggcaaaacgaatgtggatttggc
aaaccgacacaggtctgctgtacggactaatatgggcacacccacatcattcttcagatgctccatgc
attgttctatgagaaagatccatagggtggaggcagcgtcacgagatcgcccaggcaatcgatcgcat
tcgtctagtaaagtgacgagagttatcatgcacacacccatgcccacgccttccgaataactggagct
gtggaagatcggaaacgtctttttgactgccggtctcgtactactttcgcacaggtgtatacccggac
gcgtactatatatttatatcatccaacgtccgaaattacatacgtggcggcgatggaagtagatgtt
gagtcttcgaaagtaagtgcctcgaatatgggtattgtctgtgaaaatatcgaaagcggtacgacggt
tgcagaaccgtcgatgtcgccagatactagtaacaatagcttcgataacgaagacttccgtgggcctg
aatacgatgtggagataaataccagaaaatctgctaatcttgatcgtatggaatcttcgtgccgtgaa
caacgagcggcgtgcgaacttcgaaagtgttcgtgtcctacgtctgccgtgcgcatgcaatacagtat
tctttcatctctcgctccgggttcagagggtcatgtatatatatgtactagatacggggacgcggacc
aaaaaaaatgcatagtgaaggcagtcgttggaggaaagaatcccgggagggaagtggatattttaaaa
accatctcacataaatcaattataaaattaatccatgcctataaatggaaaaatgttgtgtgtatggc
aatgcgtgtatatcgttatgatcttttcacatatattgacggagtcggccctatgccccttcaacaga
tgatctatattcaacgtggactactagaggcgctagcatacatacatgaaaggggcatcattcaccga -continued gacgtaaagacggagaatatattcttggataatcacgaaaatgcagttttgggtgacttcggtgctgc atgccaactaggagattgtatagatacgccccaatgttacggttggagcggaactgtggaaacaaatt cgccggaattatctgcacttgatccgtattgcacaaaaacagatatttggagtgccggattggttcta tatgagatggcaattaaaaatgtaccattgtttagtaagcaggtgaaaagttcgggatctcagctgag atccataatacggtgcatgcaagtgcatgaactggagtttccccgcaacgattctaccaacctctgta aacatttcaaacaatatgcggttcgtgtacgaccgccttataccattcctcgagttataagaaatggg gggatgccaatggatgttgaatatgtcatttctaaaatgcttacgtttgaccaggagttcagaccttc tgctaaggaaatattgaatatgcccctatttactaaggcgccgattaacctgcttaatatcacaccct ctgacagtgtctaacggtatacaggcgggagcgggtcgtggcgtcatcatcaccacttgagaatttat attttgaattgttgattgataaattaacctgattcattgagaactgaaacgccatattggtttcttgg atatgtctacaacaattagttaaattgctatgttctactgcgagtaacatttgataagttgtaagaga cgggcgactcatgtcgaagttgacgaatataaagtacataacgtgtttagaatacccagaatccgaat agtccgcgggggcgtcttctcgcgtgagtaccaaatactgagttgaacttgaaaatgctaaatctgtg acactctttgtgtgatgattattgtcaccacttcgaagatggcttcgacattcatgatgttctggtgt ttgtttggaatcgtaatagcgcttgtttcgtccaagtctgacaacaaagaaaatctgaagaattatat cacggataagtcaaccaatattagaatacccacgccattatttgtatcaacggaaaactcttatccca caaaacatgtaatctacgatgaaaactgtggcttcgctgtactcaatcctataagtgaccccaaatat gtccttttgagccagcttctaatgggaaggcgcaaatatgatgcgacggtcgcgtggtttgttctcgg taaaatgtgtgccagattaatatatttgcgcgaattttataactgctcgacaaatgagccttttggca catgttctatgagctctcctggatggtgggacaggcgctacgtctcaaccagtttcatttctcgcgac gaattacagctggtttttgcagcgccgtcccgagaattagatggtttatatacgcgcgtagtagttgt caacggggactttactacggccgatataatgtttaatgttaaagtggcatgtgccttttcaaagactg gaatagaagatgatacattatgcaaaccctttcatttctttgccaatgcaacattgcacaatttaacc atgattagatcggtaactcttcgagcgcacgaaagccatttaaaggaatgggtggcacggagaggtgg taacgtccctgcagtgctacttgagtctaccatgtatcatgcatccaatctgcctagaaatttcaggg atttctacataaagtctccagatgattataagtataatcacctagatgggccatctgtaatgctcatc actgacagacctagtgaagatttggatgggaggctcgttcaccaaagtgacatttttactactacaag tcctataaaacaggtccggtatgaagagcatcagtcacatacaaagcagtatcctgtaaacaaaatac aagctataatttttttgatagggttaggctcgttcattggaagcatattcgtagttttggtagtatgg attatacgcagatattgcaatggagcgcggagtgggggaacgcccccccagtcctcgccggtatgtgta taccaggctatgatcacgtgtgaaacttgggcggacctgtatcatatgtacaccgtccctattcgttt atagccagtacgtgttatctgcacatagaggaacatgtgtcatactgggatcgcatgcatggtatgtg tgactctaatattattctgtatcataataaaaacacagtgcatggtatatagaggatcgctggtaagc actacggtagaccaatcggctcagattgcattctttggcatcgataccgttgttaatttatatggcaa agtcttgttcatgggagatcagtatttggaggaaatatactctggaacgatggaaatactcaaatgga atcaagctaaccgctgctattctattgcgcatgcaacatattacgccgactgtcctataatcagttct acggtattcagaggatgccgggacgccgttgtttatactaggccccacagcagaattcgtaatcatgg tcatagctgtttcctgtgtgaaattgttatccgctcacaattccacacaacatacgagccggaagcat aaagtgtaaagcctggggtgcctaatgagtgagctaactcacattaattgcgttgcgctcactgcccg ctttccagtcgggaaacctgtcgtgccagctgcattaatgaatcggccaacgcgcggggagaggcggt ttgcgtattgggcgctcttccgcttcctcgctcactgactcgctgcgctcggtcgttcggctgcggcg -continued agcggtatcagctcactcaaaggcggtaatacggttatccacagaatcaggggataacgcaggaaaga acatgtgagcaaaaggccagcaaaaggccaggaaccgtaaaaaggccgcgttgctggcgtttttccat aggctccgcccccctgacgagcatcacaaaaatcgacgctcaagtcagaggtggcgaaacccgacagg actataaagataccaggcgtttccccctggaagctccctcgtgcgctctcctgttccgaccctgccgc ttaccggatacctgtccgcctttctcccttcgggaagcgtggcgctttctcaatgctcacgctgtagg tatctcagttcggtgtaggtcgttcgctccaagctgggctgtgtgcacgaaccccccgttcagcccga ccgctgcgccttatccggtaactatcgtcttgagtccaacccggtaagacacgacttatcgccactgg cagcagccactggtaacaggattagcagagcgaggtatgtaggcggtgctacagagttcttgaagtgg tggcctaactacggctacactagaaggacagtatttggtatctgcgctctgctgaagccagttacctt cggaaaaagagttggtagctcttgatccggcaaacaaaccaccgctggtagcggtggtttttttgttt gcaagcagcagattacgcgcagaaaaaaaggatctcaagaagatcctttgatcttttctacggggtct gacgctcagtggaacgaaaactcacgttaagggattttggtcatgagattatcaaaaaggatcttcac ctagatccttttaaattaaaaatgaagttttaaatcaatctaaagtatatatgagtaaacttggtctg acagttaccaatgcttaatcagtgaggcacctatctcagcgatctgtctatttcgttcatccatagtt gcctgactccccgtcgtgtagataactacgatacgggagggcttaccatctggccccagtgctgcaat gataccgcgagacccacgctcaccggctccagatttatcagcaataaaccagccagccggaagggccg agcgcagaagtggtcctgcaactttatccgcctccatccagtctattaattgttgccgggaagctaga gtaagtagttcgccagttaatagtttgcgcaacgttgttgccattgctacaggcatcgtggtgtcacg ctcgtcgtttggtatggcttcattcagctccggttcccaacgatcaaggcgagttacatgatccccca tgttgtgcaaaaaagcggttagctccttcggtcctccgatcgttgtcagaagtaagttggccgcagtg ttatcactcatggttatggcagcactgcataattctcttactgtcatgccatccgtaagatgcttttc tgtgactggtgagtactcaaccaagtcattctgagaatagtgtatgcggcgaccgagttgctcttgcc cggcgtcaatacgggataataccgcgccacatagcagaactttaaaagtgctcatcattggaaaacgt tcttcggggcgaaaactctcaaggatcttaccgctgttgagatccagttcgatgtaacccactcgtgc acccaactgatcttcagcatcttttactttcaccagcgtttctgggtgagcaaaaacaggaaggcaaa atgccgcaaaaaagggaataagggcgacacggaaatgttgaatactcatactcttcctttttcaatat tattgaagcatttatcagggttattgtctcatgagcggatacatatttgaatgtatttagaaaaataa acaaataggggttccgcgcacatttccccgaaaagtgccacctgacgtctaagaaaccattattatca tgacattaacctataaaaataggcgtatcacgaggccctttcgt SEQ ID NO 23: 228509-ILT-435Vec6 (mCMV IEpro-VP2-SV40pA/ILTV/HVT US2 region)(14113 bp)(HVT/IBDV/ILTV/NDV #2 Virus)
gaattccagactaaatgccccggcccaatttgtcaagtgtgcagtcacggaggcgtcgaccgtgtccc cggcattaaacaggaaagcgttaaagtttttgaatgttaggtcacaggtacaaacataaatgtttgta caaacaggtaacaggtacaaacataaatgccccggcataaatgtcccttacggcggatcgaaacgaca ttaggcatactcgggtaccattttgcattccgatcagcacggatgaaattaggcaggaatgcggttta tattatgcggcattggacaaacgatatggcattgattggcagtttatgaatgtcttcatgttgggcgt aaacggattcctattggttcagaagacaacgacgatatatttagagagaaaaagctacccagcatagg ataaacacacattgagcattgagagacataggtatcggtatggatgggaaaactacacacgtgaacac caaacgacttatatactcgagcggtgatactactgagcaagaatgcactgcatctgagccactgaatg aagactgtgatgaaaatgtgaccatcgatggaattggagaagaatatgcgcagttcttcatgtccccg caatgggtcccaaatctacatcgcttgagcgaggataccaaaaaggtataccgatgtatggtttccaa -continued cagactcaattattttccctattatgaggcgttcaggcggtctttgtttgatatgtatatgctaggtc ggttggggcgtcgacttaagcgatctgactgggagactattatgcatctgtcaccaacgcaaagtcgg cgtctacatagaactttaagatttgtggagcgtagaattatcccatctaacagttatatacgcacatc gggccacgttccgccttcgagggcacttccgacagatacgaatttaaagatggatgaataattaaatt ggaaagagtaactacattaatcgagcgtcatgacggcgtcccgtgaaaatgggaattttctactcgaa acaccgtgacatttgacagacctggaattgttattctgatatatagtgggtgtgtctggccggcaaca tacataatgtgcatgcgaaaccactttttcagtgtacgctgacattgtgcaacacggaggggtagcat ctacatacaatatatgttgattaatgattggagaaaaaactatgcagctcgccgatcatatggctaac tcgccttcgtctatatggcggaccccgcgggaaaaatcgacgtaccatctgatttacaacaccagtaa tgaacatgtcgcatccctgcccagatctgtgcgcccattggcgcggatcgttgtgaatgccgccgaaa cacttcaggtcggtatgagagccgggaggccgccatcagcaggagtttggcgagaggtgtttgataga atgatgacagccttccgtgaccacgagcctactgcgacatttaatgctacaaatcccattagaaaaat ggtcgagacagttctacagaataatgaagagcccccgcggacgcatgctgaaatgggtaatcgcctta tgaacattatgtactggtgttgcttgggacacgcaggacaatgctcgatatggcagttgtacgagacg aatcaggccattttaagtttattagatgaagtggttatcggcacaacaaatccctttttgcaccctcga gcaatactggaagccattatgcaccgcaatcgccaacaaggggacctcatcgcttgttgaggatgcca aagtggccgagtacctggttagcatgcgcaaattgatataacataggcacgctctgatgttacagacc acaataccgcatacatttattgtaaggttgttaataaaggtttattctatgtaagactacaatacttt cgacattgcttgtatacatattaaatactttctcaagttcctattacataaaatgggatctatcatta cattcgttaagagtctggataattttactgtttgccagcttcgatcttggaacgtactgtggatagtg ccttacttggaatcgtgaaaatttgaaacgtccattatttggatatcttccggttgtcccatatcccg ccctggtaccgctcggataccttgcccgtatggattcgtattgacagtcgcgcaatcggggaccaaca acgcgtgggtccacactcattcggaaattttccgatgattctgaatatttattgccgctcgttacgag tcgttggacatatctgtaatacatttcttcttctgaaggatcgctgcacatttgatctatacattggc caggatgttcaagtctcagatgttgcattctggcacagcacaactttatggcatttccgatgtaatcg tccggcagccctgggggagttctatattcgcatattgggatggtaaggacaatagcagatctcgcaac ctccagggaggctataataacgtttttaaaggatggatttctcataaaaatctgtcgcaaattacact gagaatatcctttactagcgccgattgagagcatcgtcgtccaattttctaaatggaaagaaaacaag gcgggcaagagtgttccaaacattttcattttcggcgaatctctcaaatcccatggcgtgcaattgat tgcaaaattggcacttccgttcacgtttgtatctccaaactctaagacacttttaattgaaaaactac gttctagtgtggaaagaaacctataggcagaccatagaactatttgacaccacatatctttttgtatg tcaaactgaccatgatcgtatgttgctgaatgcactagggcaattcgctcgcgcgactccatacattg aataattccacacgtcagctcatcggttagcaaggtccagtagttgaagtcatttatttttccccgcg gctggccaaatctacctctgggaatatccaagttgtcgaatatgatcgcaccggctctggtcatggtg aaggaactgtagcataaagacgcaggtatcataggggtaatatttttttattcactcacatactaaaa gtaacgcatattagcaccatgtatgggctatcaattgacatttgcgtagcactacatcacgattatgt acaacataatgggacaacatatggcaagtagatgcaatttcctcacactagttgggtttatctactat tgaattttcccctatctgtgatacacttgggagcctctacaagcatattgccatcatgtacgtttta tctactgtcttaacgcccatgggaacggaggcgtcgtcgtcatgtattggacggcaacataggcagca acacaaattgcgtttaggtggggtgcatgtggactcgataccaagcccctgcagctggggaacgtctg gtggagagccgataatttgatatacgcacgccatattactgtcgttgaagtacgccttatcttctatg -continued

```
ttttcaaatttaggttcccaagtggacgtgagaagtgtttgtatctcacatggaatggcccaaggcat
tccagcccaggtgcctggtactttaatggcaaacaaacgttttggtagaggtattgattctattgcag
ttctgcagatatctgcagccccgagtatccacaggctatacgatacgttatcggaggcaagctgcggc
cgctctagaactagtggatcccccgggctgcagcccaatgtggaattcgcccttgcacattgttactc
ctgcatcttaaaaatatatcctgtagtaattttcacagcaatgtcataacatcatctcgctaaagaat
gacctgggattggagaagtaatgaatatttgcaaccaatgcattgaataaactaacattaaacgaatt
cactagtggatcccccaactccgcccgttttatgactagaaccaatagtttttaatgccaaatgcact
gaaatcccctaatttgcaaagccaaacgcccctatgtgagtaatacggggactttttacccaatttc
ccacgcggaaagcccctaatacactcatatggcatataaatcagcacggtcatgcactctaatggcg
gcccatagggactttccacatagggggcgttcaccatttcccagcataggggtggtgactcaatggcc
tttacccaagtacattgggtcaatgggaggtaagccaatgggtttttcccattactggcaagcacact
gagtcaaatgggactttccactgggttttgcccaagtacattgggtcaatgggaggtgagccaatggg
aaaaacccattgctgccaagtacactgactcaatagggactttccaatgggtttttccattgttggca
agcatataaggtcaatgtgggtgagtcaatagggactttccattgtattctgcccagtacataaggtc
aataggggtgaatcaacaggaaagtcccattggagccaagtacactgcgtcaatagggactttccat
tgggttttgcccagtacataaggtcaataggggatgagtcaatgggaaaaacccattggagccaagta
cactgactcaatagggactttccattgggttttgcccagtacataaggtcaataggggtgagtcaac
aggaaagttccattggagccaagtacattgagtcaatagggactttccaatgggttttgcccagtaca
taaggtcaatgggaggtaagccaatgggtttttcccattactggcacgtatactgagtcattagggac
tttccaatgggttttgcccagtacataaggtcaataggggtgaatcaacaggaaagtcccattggagc
caagtacactgagtcaatagggactttccattgggttttgcccagtacaaaaggtcaataggggtga
gtaaatgggtttttcccattattggcacgtacataaggtcaataggggtgagtcattgggtttttcca
gccaatttaattaaaacgccatgtactttcccaccattgacgtcaatgggctattgaaactaatgcaa
cgtgacctttaaacggtactttcccatagctgattaatgggaaagtaccgttctcgagccaatacacg
tcaatgggaagtgaaagggcagccaaaacgtaacaccgccccggttttcccctggaaattccatattg
gcacgcattctattggctgagctgcgttctacgtgggtataagaggcgcgaccagcgtcggtaccgtc
gcagtcttcggtctgaccaccgtagaacgcagagctcctcgctgcaggcggccgctctagaactcgtc
gatcgcagcgatgacaaacctgcaagatcaaacccaacagattgttccgttcatacggagccttctga
tgccaacaaccggaccggcgtccattccggacgacaccctggagaagcacactctcaggtcagagacc
tcgacctacaatttgactgtgggggacacagggtcagggctaattgtctttttccctggattccctgg
ctcaattgtgggtgctcactacacactgcagagcaatgggaactacaagttcgatcagatgctcctga
ctgcccagaacctaccggccagctacaactactgcagactagtgagtcggagtctcacagtgaggtca
agcacactccctggtggcgtttatgcactaaacggcaccataaacgccgtgaccttccaaggaagcct
gagtgaactgacagatgttagctacaatgggttgatgtctgcaacagccaacatcaacgacaaaattg
ggaatgtcctggtaggggaaggggtcactgtcctcagcctacccacatcatatgatcttgggtatgtg
aggcttggtgaccccattcccgctatagggcttgacccaaaaatggtagctacatgcgacagcagtga
caggcccagagtctacaccataactgcagccgatgattaccaattctcatcacagtaccaaccaggtg
gggtaacaatcacactgttctcagccaacattgatgctatcacaagcctcagcattgggggagagctc
gtgtttcaaacaagcgtccaaggccttgtactgggcgccaccatctaccttataggctttgatgggac
tgcggtaatcaccagagctgtggccgcagataatgggctgacggccggcaccgacaatcttatgccat
```

-continued tcaatcttgtcattccaaccaatgagataacccagccaatcacatccatcaaactggagatagtgacc tccaaaagtggtggtcaggcaggggatcagatgtcatggtcggcaagtgggagcctagcagtgacgat ccatggtggcaactatccaggggccctccgtcccgtcacactagtagcctacgaaagagtggcaacag gatccgtcgttacggtcgctggggtgagtaacttcgagctgattccaaatcctgaactagcaaagaac ctggttacagaatacggccgatttgacccaggagccatgaactacacaaaattgatactgagtgagag ggaccgtcttggcatcaagaccgtctggccaacaagggagtacactgattttcgtgagtacttcatgg aggtggccgacctcaactctcccctgaagattgcaggagcatttggcttcaaagacataatccgggct ataaggaggtaagcttcagacatgataagatacattgatgagtttggacaaaccacaactagaatgca gtgaaaaaaatgctttatttgtgaaatttgtgatgctattgctttatttgtaaccattataagctgca ataaacaagttaacaacaacaattgcattcattttatgtttcaggttcagggggaggtgtgggaggtt ttttcggatcctctagagtcgacggcagagtcgcagacgcccctattggacgtcaaaattgtagaggt gaagttttcaaacgatggcgaagtaacggcgacttgcgtttccaccgtcaaatctccctatagggtag aaactaattggaaagtagacctcgtagatgtaatggatgaaatttctgggaacagtcccgccggggtt tttaacagtaatgagaaatggcagaaacagctgtactacagagtaaccgatggaagaacatcggtcca gctaatgtgcctgtcgtgcacgagccattctccggaaccttactgtcttttcgacacgtctcttatag cgagggaaaaagatatcgcgccagagttatactttacctctgatccgcaaacggcatactgcacaata actctgccgtccggcgttgttccgagattcgaatggagccttaataatgtttcactgccggaatattt gacggccacgaccgttgtttcgcataccgctggccaaagtacagtgtggaagagcagcgcgagagcag gcgaggcgtggatttctggccggggaggcaatatatacgaatgcaccgtcctcatctcagacggcact cgcgttactacgcgaaaggagaggtgcttaacaaacacatggattgcggtggaaaacggtgctgctca ggcgcagctgtattcactcttttctggacttgtgtcaggattatgcgggagcatatctgctttgtacg caacgctatggaccgccatttattttttgaggaatgctttttggactatcgtactgctttcttccttcg ctagccagagcaccgccgccgtcacgtacgactacattttaggccgtcgcgcgctcgacgcgctaacc ataccggcggttggcccgtataacagatacctcactagggtatcaagaggctgcgacgttgtcgagct caacccgatttctaacgtggacgacatgatatcggcggccaaagaaaaagagaagggggggccctttcg aggcctccgtcgtctggttctacgtgattaagggcgacgacggcgaggacaagtactgtccaatctat agaaaagagtacagggaatgtggcgacgtacaactgctatctgaatgcgccgttcaatctgcacagat gtgggcagtggactatgttcctagcacccttgtatcgcgaaatggcgcgggactgactatattctccc ccactgctgcgctctctggccaatacttgctgaccctgaaaatcgggagatttgcgcaaacagctctc gtaactctagaagttaacgatcgctgtttaaagatcgggtcgcagcttaactttttaccgtcgaaatg ctggacaacagaacagtatcagactggatttcaaggcgaacacctttatccgatcgcagacaccaata cacgacacgcggacgacgtatatcggggatacgaagatattctgcagcgctggaataatttgctgagg aaaaagaatcctagcgcgccagaccctcgtccagatagcgtcccgcaagaaattccccgctgtaaccaa gaaagcggaagggcgcaccccggacgcagaaagcagcgaaaagaaggcccctccagaagactcggagg acgacatgcaggcagaggcttctggagaaaatcctgccgccctccccgaagacgacgaagtccccgag gacaccgagcacgatgatccaaactcggatcctgactattacaatgacatgcccgccgtgatcccggt ggaggagactactaaaagttctaatgccgtctccatgcccatattcgcggcgttcgtagcctgcgcgg tcgcgctcgtggggctactggtttggagcatcgtaaaatgcgcgcgtagctaatcgagcctagaatag gtggtttcttcctacatgccacgcctcacgctcataatataaatcacatggaatagcataccaatgcc tattcattgggacgttcgaaaagcatggcatcgctacttggaactctggctctccttgccgcgacgct cgcacccttcggcgcgatgggaatcgtgatcactggaaatcacgtctccgccaggattgacgacgatc -continued acatcgtgatcgtcgcgcctcgccccgaagctacaattcaactgcagctatttttcatgcctggccag agaccccacaaaccctactcaggaaccgtccgcgtcgcgtttcggtctgatataacaaaccagtgcta ccaggaacttagcgaggagcgctttgaaaattgcactcatcgatcgtcttctgtttttgtcggctgta aagtgaccgagtacacgttctccgcctcgaacagactaaccggacctccacacccgtttaagctcact atacgaaatcctcgtccgaacgacagcgggatgttctacgtaattgttcggctagacgacaccaaaga acccattgacgtcttcgcgatccaactatcggtgtatcaattcgcgaacaccgccgcgactcgcggac tctattccaaggcttcgtgtcgcaccttcggattacctaccgtccaacttgaggcctatctcaggacc gaggaaagttggcgcaactggcaagcgtacgttgccacggaggccacgacgaccagcgccgaggcgac aaccccgacgcccgtcactgcaaccagcgcctccgaacttgaagcggaacactttacctttccctggc tagaaaatggcgtggatcattacgaaccgacacccgcaaacgaaaattcaaacgttactgtccgtctc gggacaatgagccctacgctaattggggtaaccgtggctgccgtcgtgagcgcaacgatcggcctcgt cattgtaatttccatcgtcaccagaaacatgtgcaccccgcaccgaaaattagacacggtctcgcaag acgacgaagaacgttcccaaactagaagggaatcgcgaaaatttggacccatggttgcgtgcgaaata aacaaggggggctgaccaggatagtgaacttgtggaactggttgcgattgttaacccgtctgcgctaag ctcgcccgactcaataaaaatgtgattaagtctgaatgtggctctccaatcatttcgattctctaatc tcccaatcctctcaaaaggggcagtatcggacacggactgggaggggcgtacacgatagttatatggt acagcagaggcctctgaacacttaggaggagaattcagccggggagagcccctgttgagtaggcttgg gagcatattgcaggatgaacatgttagtgatagttctcgcctcttgtcttgcgcgcctaacttttgcg acgcgacacgtcctctttttggaaggcactcaggctgtcctcggggaagatgatcccagaaacgttcc ggaagggactgtaatcaaatggacaaaagtcctgcggaacgcgtgcaagatgaaggcggccgatgtct gctcttcgcctaactattgctttcatgatttaatttacgacggaggaaagaaagactgcccgcccgcg ggacccctgtctgcaaacctggtaattttactaaagcgcggcgaagcttagcttgcctccgattctag cattacatagccggtcagtagatcctgccattcggtagcgcaaccggctacatcttcaaacagtctca cgataaatgcatctctcgttcctgccaatccggaaccgggcataccactcccgcctgccgatttaatt ctcacaattgggcgatgccggcggggcaaaacgaatgtggatttggcaaaccgacacaggtctgctgt acggactaatatgggcacacccacatcattcttcagatgctccatgcattgttctatgagaaagatcc atagggtggaggcagcgtcacgagatcgcccaggcaatcgatcgcattcgtctagtaaagtgacgaga gttatcatgcacacacccatgcccacgccttccgaataactggagctgtggaagatcggaaacgtctt tttgactgccggtctcgtactactttcgcacaggtgtatacccggacgcgtactatatattttatatc atccaacgtccgaaattacatacgtggcggcgatggaagtagatgttgagtcttcgaaagtaagtgcc tcgaatatgggtattgtctgtgaaaatatcgaaagcggtacgacggttgcagaaccgtcgatgtcgcc agatactagtaacaatagcttcgataacgaagacttccgtgggcctgaatacgatgtggagataaata ccagaaaatctgctaatcttgatcgtatggaatcttcgtgccgtgaacaacgagcggcgtgcgaactt cgaaagtgttcgtgtcctacgtctgccgtgcgcatgcaatacagtattctttcatctctcgctccggg ttcagagggtcatgtatatatatgtactagatacggggacgcggaccaaaaaaaatgcatagtgaagg cagtcgttggaggaaagaatcccgggagggaagtggatattttaaaaaccatctcacataaatcaatt ataaaattaatccatgcctataaatggaaaaatgttgtgtgtatggcaatgcgtgtatatcgttatga tcttttcacatatattgacggagtcggccctatgccccttcaacagatgatctatattcaacgtggac tactagaggcgctagcatacatacatgaaaggggcatcattcaccgagacgtaaagacggagaatata ttcttggataatcacgaaaatgcagttttgggtgacttcggtgctgcatgccaactaggagattgtat -continued
agatacgccccaatgttacggttggagcggaactgtggaaacaaattcgccggaattatctgcacttg
atccgtattgcacaaaaacagatatttggagtgccggattggttctatatgagatggcaattaaaaat
gtaccattgtttagtaagcaggtgaaaagttcgggatctcagctgagatccataatacggtgcatgca
agtgcatgaactggagtttccccgcaacgattctaccaacctctgtaaacatttcaaacaatatgcgg
ttcgtgtacgaccgccttataccattcctcgagttataagaaatggggggatgccaatggatgttgaa
tatgtcatttctaaaatgcttacgtttgaccaggagttcagaccttctgctaaggaaatattgaatat
gcccctatttactaaggcgccgattaacctgcttaatatcacaccctctgacagtgtctaacggtata
caggcgggagcgggtcgtggcgtcatcatcaccacttgagaatttatatttgaattgttgattgata
aattaacctgattcattgagaactgaaacgccatattggtttcttggatatgtctacaacaattagtt
aaattgctatgttctactgcgagtaacatttgataagttgtaagagacgggcgactcatgtcgaagtt
gacgaatataaagtacataacgtgtttagaatacccagaatccgaatagtccgcgggggcgtcttctc
gcgtgagtaccaaatactgagttgaacttgaaaatgctaaatctgtgacactctttgtgtgatgatta
ttgtcaccacttcgaagatggcttcgacattcatgatgttctggtgtttgtttggaatcgtaatagcg
cttgtttcgtccaagtctgacaacaaagaaaatctgaagaattatatcacggataagtcaaccaatat
tagaatacccacgccattatttgtatcaacggaaaactcttatcccacaaaacatgtaatctacgatg
aaaactgtggcttcgctgtactcaatcctataagtgaccccaaatatgtccttttgagccagcttcta
atgggaaggcgcaaatatgatgcgacggtcgcgtggtttgttctcggtaaaatgtgtgccagattaat
atatttgcgcgaattttataactgctcgacaaatgagccttttggcacatgttctatgagctctcctg
gatggtgggacaggcgctacgtctcaaccagtttcatttctcgcgacgaattacagctggtttttgca
gcgccgtcccgagaattagatggtttatatacgcgcgtagtagttgtcaacggggactttactacggc
cgatataatgtttaatgttaaagtggcatgtgccttttcaaagactggaatagaagatgatacattat
gcaaaccctttcatttctttgccaatgcaacattgcacaatttaaccatgattagatcggtaactctt
cgagcgcacgaaagccatttaaaggaatgggtggcacggagaggtggtaacgtccctgcagtgctact
tgagtctaccatgtatcatgcatccaatctgcctagaaatttcagggatttctacataaagtctccag
atgattataagtataatcacctagatgggccatctgtaatgctcatcactgacagacctagtgaagat
ttggatgggaggctcgttcaccaaagtgacatttttactactacaagtcctataaaacaggtccggta
tgaagagcatcagtcacatacaaagcagtatcctgtaaacaaaatacaagctataatttttttgatag
ggttaggctcgttcattggaagcatattcgtagttttggtagtatggattatacgcagatattgcaat
ggagcgcggagtgggggaacgcccccccagtcctcgccggtatgtgtataccaggctatgatcacgtgt
gaaacttgggcggacctgtatcatatgtacaccgtccctattcgtttatagccagtacgtgttatctg
cacatagaggaacatgtgtcatactgggatcgcatgcatggtatgtgtgactctaatattattctgta
tcataataaaaacacagtgcatggtatatagaggatcgctggtaagcactacggtagaccaatcggct
cagattgcattctttggcatcgataccgttgttaatttatatggcaaagtcttgttcatgggagatca
gtatttggaggaaatatactctggaacgatggaaatactcaaatggaatcaagctaaccgctgctatt
ctattgcgcatgcaacatattacgccgactgtcctataatcagttctacggtattcagaggatgccgg
gacgccgttgtttatactaggccccacagcagaattc SEQ ID NO 24: 1333-85.B6 (ILTV/Chicken β-actin pro-VP2-FHV US9pA/
HVT US2 region)(13064 bp)
gaattccagactaaatgccccggcccaatttgtcaagtgtgcagtcacggaggcgtcgaccgtgtccc
cggcattaaacaggaaagcgttaaagtttttgaatgttaggtcacaggtacaaacataaatgtttgta
caaacaggtaacaggtacaaacataaatgccccggcataaatgtcccttacggcggatcgaaacgaca
ttaggcatactcgggtaccattttgcattccgatcagcacggatgaaattaggcaggaatgcggttta -continued tattatgcggcattggacaaacgatatggcattgattggcagtttatgaatgtcttcatgttgggcgt aaacggattcctattggttcagaagacaacgacgatatatttagagagaaaaagctacccagcatagg ataaacacacattgagcattgagagacataggtatcggtatggatgggaaaactacacacgtgaacac caaacgacttatatactcgagcggtgatactactgagcaagaatgcactgcatctgagccactgaatg aagactgtgatgaaaatgtgaccatcgatggaattggagaagaatatgcgcagttcttcatgtccccg caatgggtcccaaatctacatcgcttgagcgaggataccaaaaaggtataccgatgtatggtttccaa cagactcaattattttccctattatgaggcgttcaggcggtctttgtttgatatgtatatgctaggtc ggttggggcgtcgacttaagcgatctgactgggagactattatgcatctgtcaccaacgcaaagtcgg cgtctacatagaactttaagatttgtggagcgtagaattatcccatctaacagttatatacgcacatc gggccacgttccgccttcgagggcacttccgacagatacgaatttaaagatggatgaataattaaatt ggaaagagtaactacattaatcgagcgtcatgacggcgtcccgtgaaaatgggaattttctactcgaa acaccgtgacatttgacagacctggaattgttattctgatatatagtgggtgtgtctggccggcaaca tacataatgtgcatgcgaaaccactttttcagtgtacgctgacattgtgcaacacggaggggtagcat ctacatacaatatatgttgattaatgattggagaaaaaactatgcagctcgccgatcatatggctaac tcgccttcgtctatatggcggaccccgcgggaaaaatcgacgtaccatctgatttacaacaccagtaa tgaacatgtcgcatccctgcccagatctgtgcgcccattggcgcggatcgttgtgaatgccgccgaaa caattcaggtcggtatgagagccgggaggccgccatcagcaggagtttggcgagaggtgtttgataga atgatgacagccttccgtgaccacgagcctactgcgacatttaatgctgcaaatcccattagaaaaat ggtcgagacagttctacagaataatgaagagcccccgcggacgcatgctgaaatgggtaatcgcctta tgaacattatgtactggtgttgcttgggacacgcaggacaatgctcgatatggcagttgtacgagacg aatcaggccattttaagtttattagatgaagtggttatcggcacaacaaatcccttttgcaccctcga gcaatactggaagccattatgcaccgcaatcgccaacaaggggacctcatcgcttgttgaggatgcca aagtggccgagtacctggttagcatgcgcaaattgatataacataggcacgctctgatgttacagacc acaataccgcatacatttattgtaaggttgttaataaaggtttattctatgtaagactacaatacttt cgacattgcttgtatacatattaaatactttctcaagttcctattacataaaatgggatctatcatta cattcgttaagagtctggataattttactgtttgccagcttcgatcttggaacgtactgtggatagtg ccttacttggaatcgtgaaaatttgaaacgtccattatttggatatcttccggttgtcccatatcccg ccctggtaccgctcggataccttgcccgtatggattcgtattgacagtcgcgcaatcggggaccaaca acgcgtgggtccacactcattcggaaattttccgatgattctgaatatttattgccgctcgttacgag tcgttggacatatctgtaatacatttcttcttctgaaggatcgctgcacatttgatctatacattggc caggatgttcaagtctcagatgttgcattctggcacagcacaactttatggcatttccgatgtaatcg tccggcagccctgggggagttctatattcgcatattgggatggtaaggacaatagcagatctcgcaac ctccagggaggctataataacgtttttaaaggatggatttctcataaaaatctgtcgcaaattacact gagaatatcctttactagcgccgattgagagcatcgtcgtccaattttctaaatggaaagaaaacaag gcgggcaagagtgttccaaacattttcattttcggcgaatctctcaaatcccatggcgtgcaattgat tgcaaaattggcacttccgttcacgtttgtatctccaaactctaagacacttttaattgaaaaactac gttctagtgtggaaagaaacctataggcagaccatagaactatttgacaccacatatctttttgtatg tcaaactgaccatgatcgtatgttgctgaatgcactagggcaattcgctcgcgcgactccatacattg aataattccacacgtcagctcatcggttagcaaggtccagtagttgaagtcatttatttttccccgcg gctggccaaatctacctctgggaatatccaagttgtcgaatatgatcgcaccggctctggtcatggtg -continued aaggaactgtagcataaagacgcaggtatcataggggtaatatttttttattcactcacatactaaaa gtaacgcatattagcaccatgtatgggctatcaattgacatttgcgtagcactacatcacgattatgt acaacataatgggacaacatatggcaagtagatgcaatttcctcacactagttgggtttatctactat tgaattttcccctatctgtgatacacttgggagcctctacaagcatattgccatcatgtacgtttttta tctactgtcttaacgcccatgggaacggaggcgtcgtcgtcatgtattggacggcaacataggcagca acacaaattgcgtttaggtggggtgcatgtggactcgataccaagcccctgcagctggggaacgtctg gtggagagccgataatttgatatacgcacgccatattactgtcgttgaagtacgccttatcttctatg ttttcaaatttaggttcccaagtggacgtgagaagtgtttgtatctcacatggaatggcccaaggcat tccagcccaggtgcctggtactttaatggcaaacaaacgttttggtagaggtattgattctattgcag ttctgcagatatctgcagccccgagtatccacaggctatacgatacgttatcggaggcaagcttaatt aagtaccgagctcgaattggcgcgcccgacggcagagtcgcagacgcccctattggacgtcaaaattg tagaggtgaagttttcaaacgatggcgaagtaacggcgacttgcgtttccaccgtcaaatctccctat agggtagaaactaattggaaagtagacctcgtagatgtaatggatgaaatttctgggaacagtcccgc cggggtttttaacagtaatgagaaatggcagaaacagctgtactacagagtaaccgatggaagaacat cggtccagctaatgtgcctgtcgtgcacgagccattctccggaaccttactgtcttttcgacacgtct cttatagcgagggaaaaagatatcgcgccagagttatactttacctctgatccgcaaacggcatactg cacaataactctgccgtccggcgttgttccgagattcgaatggagccttaataatgtttcactgccgg aatatttgacggccacgaccgttgtttcgcataccgctggccaaagtacagtgtggaagagcagcgcg agagcaggcgaggcgtggatttctggccggggaggcaatatatacgaatgcaccgtcctcatctcaga cggcactcgcgttactacgcgaaaggagaggtgcttaacaaacacatggattgcggtggaaaacggtg ctgctcaggcgcagctgtattcactcttttctggacttgtgtcaggattatgcgggagcatatctgct ttgtacgcaacgctatggaccgccatttatttttgaggaatgctttttggactatcgtactgctttct tccttcgctagccagagcaccgccgccgtcacgtacgactacattttaggccgtcgcgcgctcgacgc gctaaccataccggcggttggcccgtataacagatacctcactagggtatcaagaggctgcgacgttg tcgaactcaacccgatttctaacgtggacgacatgatatcggcgaccaaagaaaaagagaagggggc cctttcgaggcctccgtcgtctggttctacgtgattaagggcgacgacggcgaggacaagtactgtcc aatctatagaaaagagtacagggaatgtggcgacgtacaactgctatctgaatgcgccgttcaatctg cacagatgtgggcagtggactatgttcctagcacccttgtatcgcgaaatggcgcgggactgactata ttctcccccactgctgcgctctctggccaatacttgctgaccctgaaaatcgggagatttgcgcaaac agctctcgtaactctagaagttaacgatcgctgtttaaagatcgggtcgcagcttaactttttaccgt cgaaatgctggacaacagaacagtatcagactggatttcaaggcgaacacctttatccgatcgcagac accaatacacgacacgcggacgacgtatatcggggatacgaagatattctgcagcgctggaataattt gctgaggaaaaagaatcctagcgcgccagaccctcgtccagatagcgtcccgcaagaaattcccgctg taaccaagaaagcggaagggcgcaccccggacgcagaaagcagcgaaaagaaggcccctccagaagac tcggaggacgacatgcaggcagaggcttctggagaaaatcctgccgccctccccgaagacgacgaagt ccccgaggacaccgagcacgatgatccaaactcggatcctgactattacaatgacatgcccgccgtga tcccggtggaggagactactaaaagttctaatgccgtctccatgcccatattcgcggcgttcgtagcc tgcgcggtcgcgctcgtggggctactggtttggagcatcgtaaaatgcgcgcgtagctaatcgagcct agaataggtggtttcttcctacatgccacgcctcacgctcataatataaatcacatggaatagcatac caatgcctattcattgggacgttcgaaaagcatggcatcgctacttggaactctggctctccttgccg cgacgctcgcacccttcggcgcgatgggaatcgtgatcactggaaatcacgtctccgccaggattgac -continued gacgatcacatcgtgatcgtcgcgcctcgccccgaagctacaattcaactgcagctatttttcatgcc
tggccagagaccccacaaaccctactcaggaaccgtccgcgtcgcgtttcggtctgatataacaaacc
agtgctaccaggaacttagcgaggagcgctttgaaaattgcactcatcgatcgtcttctgtttttgtc
ggctgtaaagtgaccgagtacacgttctccgcctcgaacagactaaccggacctccacacccgtttaa
gctcactatacgaaatcctcgtccgaacgacagcgggatgttctacgtaattgttcggctagacgaca
ccaaagaacccattgacgtcttcgcgatccaactatcggtgtatcaattcgcgaacaccgccgcgact
cgcggactctattccaaggcttcgtgtcgcaccttcggattacctaccgtccaacttgaggcctatct
caggaccgaggaaagttggcgcaactggcaagcgtacgttgccacggaggccacgacgaccagcgccg
aggcgacaaccccgacgcccgtcactgcaaccagcgcctccgaacttgaagcggaacactttaccttt
ccctggctagaaaatggcgtggatcattacgaaccgacacccgcaaacgaaaattcaaacgttactgt
ccgtctcgggacaatgagccctacgctaattggggtaaccgtggctgccgtcgtgagcgcaacgatcg
gcctcgtcattgtaatttccatcgtcaccagaaacatgtgcaccccgcaccgaaaattagacacggtc
tcgcaagacgacgaagaacgttcccaaactagaagggaatcgcgaaaatttggacccatggttgcgtg
cgaaataaacaaggggggctgaccaggatagtgaacttgtggaactggttgcgattgttaacccgtctg
cgctaagctcgcccgactcaataaaaatgtgattaagtctgaatgtggctctccaatcatttcgattc
tctaatctcccaatcctctcaaaaggggcagtatcggacacggactgggaggggcgtacacgatagtt
atatggtacagcagaggcctctgaacacttaggaggagaattcagccggggagagcccctgttgagta
ggcttgggagcatattgcaggatgaacatgttagtgatagttctcgcctcttgtcttgcgcgcctaac
ttttgcgacgcgacacgtcctctttttggaaggcactcaggctgtcctcggggaagatgatcccagaa
acgttccggaagggactgtaatcaaatggacaaaagtcctgcggaacgcgtgcaagatgaaggcggcc
gatgtctgctcttcgcctaactattgctttcatgatttaatttacgacggaggaaagaaagactgccc
gcccgcgggacccctgtctgcaaacctggtaattttactaaagcgcggcgggcgcgccggatcagatc
tccatggtcgaggtgagccccacgttctgcttcactctccccatctcccccccctccccacccccaat
tttgtatttatttattttttaattattttgtgcagcgatgggggcgggggggggggnnncgcgcgcca
ggcggggcggggcggggcgaggggcggggcggggcgaggcggagaggtgcggcggcagccaatcagag
cggcgcgctccgaaagtttccttttatggcgaggcggcggcggcggcggccctataaaaagcgaagcg
cgcggcgggcgggagtcgctgcgcgctgccttcgccccgtgccccgctccgccgccgcctcgcgccgc
ccgccccggctctgactgaccgcgttactcccacaggtgagcgggcgggacggcccttctcctccggg
ctgtaattagcggcaggaaggaaatgggcggggagggccttcgtgcgtcgccgcgccgccgtcccctt
ctccctctccagcctcggggctgtccgcggggggacggctgccttcgggggggacggggcagggcggg
gttcggcttctggcgtgtgaccggcggctctagagcctctgctaaccatgttcatgccttcttctttt
tcctacagctcctgggcaacgtgctggttattgtgctgtctcatcattttggcaaagaattgcagatc
tggatctatgacaaacctgcaagatcaaacccaacagattgttccgttcatacggagccttctgatgc
caacaaccggaccggcgtccattccggacgacaccctggagaagcacactctcaggtcagagacctcg
acctacaatttgactgtgggggacacagggtcagggctaattgtctttttccctggattccctggctc
aattgtgggtgctcactacacactgcagagcaatgggaactacaagttcgatcagatgctcctgactg
cccagaacctaccggccagctacaactactgcagactagtgagtcggagtctcacagtgaggtcaagc
acactccctggtggcgtttatgcactaaacggcaccataaacgccgtgaccttccaaggaagcctgag
tgaactgacagatgttaactacaatgggttgatgtctgcaacagccaacatcaacgacaaagttggga
atgtcctggtaggggaaggggtcactgtcctcagcctacccacatcatatgatcttgggtatgtgagg -continued cttggtgaccccattcccgctatagggcttgacccaaaaatggtagctacatgcgacagcagtgacag gcccagagtctacaccataactggagccgatgattaccaattctcatcacagtaccaaccaggtgggg taacaatcacactgttctcagccaacattgatgctatcacaagcctcagcattgggggagagctcgtg tttcaaacaagcgtccaaggccttgtactgggcgccaccatctaccttataggctttgatgggactgc ggtaatcaccagagctgtggccgcagataatgggctgacggccggcaccgacaatcttatgccattca atcttgtcattccaaccaatgagataacccagccgatcacatccatcaaactggagatagtgacctcc aaaagtggtggtcaggcaggggatcagatgtcatggtcggcaagtgggagcctagcagtgacgatcca tggtggcaactatccaggggccctccgtcccgtcacactagtagcctacgaaagagtggcaacaggat ccgtcgttacggtcgctggggtgagtaacttcgagctgatcccaaatcctgaactagcaaagaacctg gttacagaatacggccgatttgacccaggagccatgaactacacaaaattgatactgagtgagaggga ccgtcttggcatcaagaccgtctggccaacaagggagtacactgattttcgtgagtacttcatggagg tggccgacctcaactctcccctgaagattgcaggagcatttggcttcaaagacataatccgggctata aggaggtaagatccgatctctcgattaattaacaataaacatagcatacgttatgacatggtctaccg cgtcttatatggggacgacaagcttgcctccgattctagcattacatagccggtcagtagatcctgcc attcggtagcgcaaccggctacatcttcaaacagtctcacgataaatgcatctctcgttcctgccaat ccggaaccgggcataccactcccgcctgccgatttaattctcacaattgggcgatgccggcggggcaa aacgaatgtggatttggcaaaccgacacaggtctgctgtacggactaatatgggcacacccacatcat tcttcagatgctccatgcattgttctatgagaaagatccatagggtggaggcagcgtcacgagatcgc ccaggcaatcgatcgcattcgtctagtaaagtgacgagagttatcatgcacacacccatgcccacgcc ttccgaataactggagctgtggaagatcggaaacgtctttttgactgccggtctcgtactactttcgc acaggtgtatacccggacgcgtactatatattttatatcatccaacgtccgaaattacatacgtggcg gcgatggaagtagatgttgagtcttcgaaagtaagtgcctcgaatatgggtattgtctgtgaaaatat cgaaagcggtacgacggttgcagaaccgtcgatgtcgccagatactagtaacaatagcttcgataacg aagacttccgtgggcctgaatacgatgtggagataaataccagaaaatctgctaatcttgatcgtatg gaatcttcgtgccgtgaacaacgagcggcgtgcgaacttcgaaagtgttcgtgtcctacgtctgccgt gcgcatgcaatacagtattctttcatctctcgctccgggttcagagggtcatgtatatatatgtacta gatacggggacgcggaccaaaaaaaatgcatagtgaaggcagtcgttggaggaaagaatcccgggagg gaagtggatattttaaaaaccatctcacataaatcaattataaaattaatccatgcctataaatggaa aaatgttgtgtgtatggcaatgcgtgtatatcgttatgatcttttcacatatattgacggagtcggcc ctatgccgcttcaagagatgatctatattcaacgtggactactagaggcgctagcatacatacatgaa aggggcatcattcaccgagacgtaaagacggagaatatattcttggataatcacgaaaatgcagtttt gggtgacttcggtgctgcatgccaactaggagattgtatagatacgccccaatgttacggttggagcg gaactgtggaaacaaattcgccggaattatctgcacttgatccgtattgcacaaaaacagatatttgg agtgccggattggttctatatgagatggcaattaaaaatgtaccattgtttagtaagcaggtgaaaag ttcgggatctcagctgagatccataatacggtgcatgcaagtgcatgaactggagtttccccgcaacg attctaccaacctctgtaaacatttcaaacaatatgcggttcgtgtacgaccgccttataccattcct cgagttataagaaatgggggatgccaatggatgttgaatatgtcatttctaaaatgcttacgtttga ccaggagttcagaccttctgctaaggaaatattgaatatgcccctatttactaaggcgccgattaacc tgcttaatatcacaccctctgacagtgtctaacggtatacaggcgggagcgggtcgtggcgtcatcat caccacttgagaatttatattttgaattgttgattgataaattaacctgattcattgagaactgaaac gccatattggtttcttggatatgtctacaacaattagttaaattgctatgttctactgcgagtaacat -continued ttgataagttgtaagagacgggcgactcatgtcgaagttgacgaatataaagtacataacgtgtttag aatacccagaatccgaatagtccgcgggggcgtcttctcgcgtgagtaccaaatactgagttgaactt gaaaatgctaaatctgtgacactctttgtgtgatgattattgtcaccacttcgaagatggcttcgaca ttcatgatgttctggtgtttgtttggaatcgtaatagcgcttgtttcgtccaagtctgacaacaaaga aaatctgaagaattatatcacggataagtcaaccaatattagaatacccacgccattatttgtatcaa cggaaaactcttatcgcacaaaacatgtaatctacgatgaaaactgtggcttcgctgtactcaatcct ataagtgaccccaaatatgtccttttgagccagcttctaatgggaaggcgcaaatatgatgcgacggt cgcgtggtttgttctcggtaaaatgtgtgccagattaatatatttgcgcgaattttataactgctcga caaatgagccttttggcacatgttctatgagctctcctggatggtgggacaggcgctacgtctcaacc agtttcatttctcgcgacgaattacagctggtttttgcagcgccgtcccgagaattagatggtttata tacgcgcgtagtagttgtcaacggggactttactacggccgatataatgtttaatgttaaagtggcat gtgccttttcaaagactggaatagaagatgatacattatgcaaaccctttcatttctttgccaatgca acattgcacaatttaaccatgattagatcggtaactcttcgagcgcacgaaagccatttaaaggaatg ggtggcacggagaggtggtaacgtccctgcagtgctacttgagtctaccatgtatcatgcatccaatc tgcctagaaatttcagggatttctacataaagtctccagatgattataagtataatcacctagatggg ccatctgtaatgctcatcactgacagacctagtgaagatttggatgggaggctcgttcaccaaagtga catttttactactacaagtcctataaaacaggtccggtatgaagagcatcagtcacatacaaagcagt atcctgtaaacaaaatacaagctataatttttttgatagggttaggctcgttcattggaagcatattc gtagttttggtagtatggattatacgcagatattgcaatggagcgcggagtgggggaacgccccccag tcctcgccggtatgtgtataccaggctatgatcacgtgtgaaacttgggcggacctgtatcatatgta caccgtccctattcgtttatagccagtacgtgttatctgcacatagaggaacatgtgtcatactggga tcgcatgcatggtatgtgtgactctaatattattctgtatcataataaaaacacagtgcatggtatat agaggatcgctggtaagcactacggtagaccaatcggctcagattgcattctttggcatcgataccgt tgttaatttatatggcaaagtcttgttcatgggagatcagtatttggaggaaatatactctggaacga tggaaatactcaaatggaatcaagctaaccgctgctattctattgcgcatgcaacatattacgccgac tgtcctataatcagttctacggtattcagaggatgccgggacgccgttgtttatactaggccccacag cagaattc SEQ ID NO 25: 1386-04.4#1 (ILTV/hCMV IEpro-VP2-HSV TKpA/HVT US2 region)(13017 bp)

gaattccagactaaatgccccggcccaatttgtcaagtgtgcagtcacggaggcgtcgaccgtgtccc cggcattaaacaggaaagcgttaaagtttttgaatgttaggtcacaggtacaaacataaatgtttgta caaacaggtaacaggtacaaacataaatgccccggcataaatgtcccttacggcggatcgaaacgaca ttaggcatactcgggtaccattttgcattccgatcagcacggatgaaattaggcaggaatgcggttta tattatgcggcattggacaaacgatatggcattgattggcagtttatgaatgtcttcatgttgggcgt aaacggattcctattggttcagaagacaacgacgatatatttagagagaaaaagctacccagcatagg ataaacacacattgagcattgagagacataggtatcggtatggatgggaaaactacacacgtgaacac caaacgacttatatactcgagcggtgatactactgagcaagaatgcactgcatctgagccactgaatg aagactgtgatgaaaatgtgaccatcgatggaattggagaagaatatgcgcagttcttcatgtccccg caatgggtcccaaatctacatcgcttgagcgaggataccaaaaaaggtataccgatgtatggtttccaa cagactcaattattttccctattatgaggcgttcaggcggtctttgtttgatatgtatatgctaggtc ggttggggcgtcgacttaagcgatctgactgggagactattatgcatctgtcaccaacgcaaagtcgg -continued cgtctacatagaactttaagatttgtggagcgtagaattatcccatctaacagttatatacgcacatc gggccacgttccgccttcgagggcacttccgacagatacgaatttaaagatggatgaataattaaatt ggaaagagtaactacattaatcgagcgtcatgacggcgtcccgtgaaaatgggaattttctactcgaa acaccgtgacatttgacagacctggaattgttattctgatatatagtgggtgtgtctggccggcaaca tacataatgtgcatgcgaaaccactttttcagtgtacgctgacattgtgcaacacggaggggtagcat ctacatacaatatatgttgattaatgattggagagaaaaaactatgcagctcgccgatcatatggctaac tcgccttcgtctatatggcggaccccgcgggaaaaatcgacgtaccatctgatttacaacaccagtaa tgaacatgtcgcatccctgcccagatctgtgcgcccattggcgcggatcgttgtgaatgccgccgaaa cacttcaggtcggtatgagagccgggaggccgccatcagcaggagtttggcgagaggtgtttgataga atgatgacagccttccgtgaccacgagcctactgcgacatttaatgctgcaaatcccattagaaaaat ggtcgagacagttctacagaataatgaagagcccccgcggacgcatgctgaaatgggtaatcgcctta tgaacattatgtactggtgttgcttgggacacgcaggacaatgctcgatatggcagttgtacgagacg aatcaggccatttaagtttattagatgaagtggttatcggcacaacaaatccccttttgcaccctcga gcaatactggaagccattatgcaccgcaatcgccaacaaggggacctcatcgcttgttgaggatgcca aagtggccgagtacctggttagcatgcgcaaattgatataacataggcacgctctgatgttacagacc acaataccgcatacatttattgtaaggttgttaataaaggtttattctatgtaagactacaatacttt cgacattgcttgtatacatattaaatactttctcaagttcctattacataaaatgggatctatcatta cattcgttaagagtctggataattttactgtttgccagcttcgatcttggaacgtactgtggatagtg ccttacttggaatcgtgaaaatttgaaacgtccattatttggatatcttccggttgtcccatatcccg ccctggtaccgctcggataccttgcccgtatggattcgtattgacagtcgcgcaatcggggaccaaca acgcgtgggtccacactcattcggaaattttccgatgattctgaatatttattgccgctcgttacgag tcgttggacatatctgtaatacatttcttcttctgaaggatcgctgcacatttgatctatacattggc caggatgttcaagtctcagatgttgcattctggcacagcacaactttatggcatttccgatgtaatcg tccggcagccctgggggagttctatattcgcatattgggatggtaaggacaatagcagatctcgcaac ctccagggaggctataataacgtttttaaaggatggatttctcataaaaatctgtcgcaaattacact gagaatatcctttactagcgccgattgagagcatcgtcgtccaattttctaaatggaaagaaaacaag gcgggcaagagtgttccaaacattttcattttcggcgaatctctcaaatcccatggcgtgcaattgat tgcaaaattggcacttccgttcacgtttgtatctccaaactctaagacacttttaattgaaaaactac gttctagtgtggaaagaaacctataggcagaccatagaactatttgacaccacatatctttttgtatg tcaaactgaccatgatcgtatgttgctgaatgcactagggcaattcgctcgcgcgactccatacattg aataattccacacgtcagctcatcggttagcaaggtccagtagttgaagtcatttatttttccccgcg gctggccaaatctacctctgggaatatccaagttgtcgaatatgatcgcaccggctctggtcatggtg aaggaactgtagcataaagacgcaggtatcatagggggtaatatttttttattcactcacatactaaaa gtaacgcatattagcaccatgtatgggctatcaattgacatttgcgtagcactacatcacgattatgt acaacataatgggacaacatatggcaagtagatgcaatttcctcacactagttgggtttatctactat tgaattttcccctatctgtgatacacttgggagcctctacaagcatattgccatcatgtacgtttttta tctactgtcttaacgcccatgggaacggaggcgtcgtcgtcatgtattggacggcaacataggcagca acacaaattgcgtttaggtggggtgcatgtggactcgataccaagcccctgcagctggggaacgtctg gtggagagccgataatttgatatacgcacgccatattactgtcgttgaagtacgccttatcttctatg ttttcaaatttaggttcccaagtggacgtgagaagtgtttgtatctcacatggaatggcccaaggcat tccagcccaggtgcctggtactttaatggcaaacaaacgttttggtagaggtattgattctattgcag -continued ttctgcagatatatgcagccccgagtatccacaggctatacgatacgttatcggaggcaagcttgtta attaagtcgacggcagagtcgcagacgcccctattggacgtcaaaattgtagaggtgaagttttcaaa cgatggcgaagtaacggcgacttgcgtttccaccgtcaaatctccctatagggtagaaactaattgga aagtagacctcgtagatgtaatggatgaaatttctgggaacagtcccgccggggtttttaacagtaat gagaaatggcagaaacagctgtactacagagtaaccgatggaagaacatcggtccagctaatgtgcct gtcgtgcacgagccattctccggaaccttactgtcttttcgacacgtctcttatagcgagggaaaaag atatcgcgccagagttatactttacctctgatccgcaaacggcatactgcacaataactctgccgtcc ggcgttgttccgagattcgaatggagccttaataatgtttcactgccggaatatttgacggccacgac cgttgtttcgcataccgctggccaaagtacagtgtggaagagcagcgcgagagcaggcgaggcgtgga tttctggccggggaggcaatatatacgaatgcaccgtcctcatctcagacggcactcgcgttactacg cgaaaggagaggtgcttaacaaacacatggattgcggtggaaaacggtgctgctcaggcgcagctgta ttcactcttttctggacttgtgtcaggattatgcgggagcatatctgctttgtacgcaacgctatgga ccgccatttattttgaggaatgctttttggactatcgtactgctttcttccttcgctagccagagca ccgccgccgtcacgtacgactacattttaggccgtcgcgcgctcgacgcgctaaccataccggcggtt ggcccgtataacagatacctcactagggtatcaagaggctgcgacgttgtcgagctcaacccgatttc taacgtggacgacatgatatcggcggccaaagaaaaagagaagggggccctttcgaggcctccgtcg tctggttctacgtgattaagggcgacgacggcgaggacaagtactgtccaatctatagaaaagagtac agggaatgtggcgacgtacaactgctatctgaatgcgccgttcaatctgcacagatgtgggcagtgga ctatgttcctagcacccttgtatcgcgaaatggcgcgggactgactatattctcccccactgctgcgc tctctggccaatacttgctgaccctgaaaatcgggagatttgcgcaaacagctctcgtaactctagaa gttaacgatcgctgtttaaagatcgggtcgcagcttaacttttaccgtcgaaatgctggacaacaga acagtatcagactggatttcaaggcgaacacctttatccgatcgcagacaccaatacacgacacgcgg acgacgtatatcggggatacgaagatattctgcagcgctggaataatttgctgaggaaaaagaatcct agcgcgccagaccctcgtccagatagcgtcccgcaagaaattcccgctgtaaccaagaaagcggaagg gcgcaccccggacgcagaaagcagcgaaaagaaggcccctccagaagactcggaggacgacatgcagg cagaggcttctggagaaaatcctgccgccctccccgaagacgacgaagtccccgaggacaccgagcac gatgatccaaactcggatcctgactattacaatgacatgcccgccgtgatcccggtggaggagactac taaaagttctaatgccgtctccatgcccatattcgcggcgttcgtagcctgcgcggtcgcgctcgtgg ggctactggtttggagcatcgtaaaatgcgcgcgtagctaatcgagcctagaataggtggtttcttcc tacatgccacgcctcacgctcataatataaatcacatggaatagcataccaatgcctattcattggga cgttcgaaaagcatggcatcgctacttggaactctggctctccttgccgcgacgctcgcaccattcgg cgcgatgggaatcgtgatcactggaaatcacgtctccgccaggattgacgacgatcacatcgtgatcg tcgcgcctcgccccgaagctacaattcaactgcagctatttttcatgcctggccagagaccccacaaa ccctactcaggaaccgtccgcgtcgcgtttcggtctgatataacaaaccagtgctaccaggaacttag cgaggagcgctttgaaaattgcactcatcgatcgtcttctgtttttgtcggctgtaaagtgaccgagt acacgttctccgcctcgaacagactaaccggacctccacacccgtttaagctcactatacgaaatcct cgtccgaacgacagcgggatgttctacgtaattgttcggctagacgacaccaaagaacccattgacgt cttcgcgatccaactatcggtgtatcaattcgcgaacaccgccgcgactcgcggactctattccaagg cttcgtgtcgcaccttcggattacctaccgtccaacttgaggcctatctcaggaccgaggaaagttgg cgcaactggcaagcgtacgttgccacggaggccacgacgaccagcgccgaggcgacaaccccgacgcc -continued cgtcactgcaaccagcgcctccgaacttgaagcggaacactttacctttccctggctagaaaatggcg tggatcattacgaaccgacacccgcaaacgaaaattcaaacgttactgtccgtctcgggacaatgagc cctacgctaattggggtaaccgtggctgccgtcgtgagcgcaacgatcggcctcgtcattgtaatttc catcgtcaccagaaacatgtgcaccccgcaccgaaaattagacacggtctcgcaagacgacgaagaac gttcccaaactagaagggaatcgcgaaaatttggacccatggttgcgtgcgaaataaacaaggggggct gaccaggatagtgaacttgtggaactggttgcgattgttaacccgtctgcgctaagctcgcccgactc aataaaaatgtgattaagtctgaatgtggctctccaatcatttcgattctctaatctcccaatcctct caaaaggggcagtatcggacacggactgggaggggcgtacacgatagttatatggtacagcagaggcc tctgaacacttaggaggagaattcagccggggagagcccctgttgagtaggcttgggagcatattgca ggatgaacatgttagtgatagttctcgcctcttgtcttgcgcgcctaacttttgcgacgcgacacgtc ctctttttggaaggcactcaggctgtcctcggggaagatgatcccagaaacgttccggaagggactgt aatcaaatggacaaaagtcctgcggaacgcgtgcaagatgaaggcggccgatgtctgctcttcgccta actattgctttcatgatttaatttacgacggaggaaagaaagactgcccgcccgcgggacccctgtct gcaaacctggtaattttactaaagcgcggcgaaagcttaggtcaattccctggcattatgcccagtac atgaccttatgggactttcctacttggcagtacatctacgtattagtcatcgctattaccatggtgat gcggttttggcagtacatcaatgggcgtggatagcggtttgactcacggggatttccaagtctccacc ccattgacgtcaatgggagtttgttttggcaccaaaatcaacgggactttccaaaatgtcgtaacaac tccgccccattgacgcaaatgggcggtaggcgtgtacggtgggaggtctatataagcagagctcgttt agtgaaccgtcagatcgcctggagacgccatccacgctgttttgacctccatagaagacaccgggcgc gccggatctatgacaaacctgcaagatcaaacccaacagattgttccgttcatacggagccttctgat gccaacaaccggaccggcgtccattccggacgacaccctggagaagcacactctcaggtcagagacct cgacctacaatttgactgtgggggacacagggtcagggctaattgtctttttccctggattccctggc tcaattgtgggtgctcactacacactgcagagcaatgggaactacaagttcgatcagatgctcctgac tgcccagaacctaccggccagctacaactactgcagactagtgagtcggagtctcacagtgaggtcaa gcacactccctggtggcgtttatgcactaaacggcaccataaacgacgtgaccttccaaggaagcctg agtgaactgacagatgttagctacaatgggttgatgtctgcaacagccaacatcaacgacaaagttgg gaatgtcctggtaggggaaggggtcactgtcctcagcctacccacatcatatgatcttgggtatgtga ggcttggtgaccccattcccgctatagggcttgacccaaaaatggtagctacatgcgacagcagtgac aggcccagagtctacaccataactgcagccgatgattaccaattctcatcacagtaccaaccaggtgg ggtaacaatcacactgttctcagccaacattgatgctatcacaagcctcagcattggggggagagctcg tgtttcaaacaagcgtccaaggccttgtactgggcgccaccatctaccttataggctttgatgggact gcggtaatcaccagagctgtggccgcagataatgggctgacggccggcaccgacaatcttatgccatt caatcttgtcattccaaccaatgagataacccagccgatcacatccatcaaactggagatagtgacct ccaaaagtggtggtcaggcaggggatcagatgtcatggtcggcaagtgggagcctagcagtgacgatc catggtggcaactatccaggggccctccgtcccgtcacactagtagcctacgaaagagtggcaacagg atccgtcgttacggtcgctggggtgagtaacttcgagctgatcccaaatcctgaactagcaaagaacc tggttacagaatacggccgatttgacccaggagccatgaactacacaaaattgatactgagtgagagg gaccgtcttggcatcaagaccgtctggccaacaagggagtacactgattttcgtgagtacttcatgga ggtggccgacctcaactctcccctgaagattgcaggagcatttggcttcaaagacataatccgggcta taaggaggtaagatccataattgattgacgggagatgggggaggctaactgaaacacggaaggagaca ataccggaaggaacccgcgctatgacggcaataaaaagacagaataaaacgcacgggtgttgggtcgt -continued ttgttcataaacgcggggttcggtcccagggctggcactctgtcgataccccaccgagaccccattgg ggccaatacgcccgcgtttcttccttttccccaccccaccccccaagttcgggtgaaggcccagggct cgcagccaacgtcggggcggcaggccctgccatagccactggccccgtgggttagggacggggtcccc catggggaatggtttatggttcgtgggggttattattttgaagcttgcctccgattctagcattacat agccggtcagtagatcctgccattcggtagcgcaaccggctacatcttcaaacagtctcacaataaat gcatctctcgttcctgccaatccggaaccgggcataccactcccgcctgccgatttaattctcacaat tgggcgatgccggcggggcaaaacgaatgtggatttggcaaaccgacacaggtctgctgtacggacta atatgggcacacccacatcattcttcagatgctccatgcattgttctatgagaaagatccatagggtg gaggcagcgtcacgagatcgcccaggcaatcgatcgcattcgtctagtaaagtgacgagagttatcat gcacacacccatgcccacgccttccgaataactggagctgtggaagatcggaaacgtctttttgactg ccggtctcgtactactttcgcacaggtgtatacccggacgcgtactatatattttatatcatccaacg tccgaaattacatacgtggcggcgatggaagtagatgttgagtcttcgaaagtaagtgcctcgaatat gggtattgtctgtgaaaatatcgaaagcggtacgacggttgcagaaccgtcgatgtcgccagatacta gtaacaatagcttcgataacgaagacttccgtgggcctgaatacgatgtggagataaataccagaaaa tctgctaatcttgatcgtatggaatcttcgtgccgtgaacaacgagcggcgtgcgaacttcgaaagtg ttcgtgtcctacgtctgccgtgcgcatgcaatacagtattctttcatctctcgctccgggttcagagg gtcatgtatatatatgtactagatacggggacgcggaccaaaaaaaatgcatagtgaaggcagtcgtt ggaggaaagaatcccgggagggaagtggatattttaaaaaccatctcacataaatcaattataaaatt aatccatgcctataaatggaaaaatgttgtgtgtatggcaatgcgtgtatatcgttatgatcttttca catatattgacggagtcggccctatgccccttcaacagatgatctatattcaacgtggactactagag gcgctagcatacatacatgaaaggggcatcattcaccgagacgtaaagacggagaatatattcttgga taatcacgaaaatgcagttttgggtgacttcggtgctgcatgccaactaggagattgtatagatacgc cccaatgttacggttggagcggaactgtggaaacaaattcgccggaattatctgcacttgatccgtat tgcacaaaaacagatatttggagtgccggattggttctatatgagatggcaattaaaaatgtaccatt gtttagtaagcaggtgaaaagttcgggatctcagctgagatccataatacggtgcatgcaagtgcatg aactggagtttccccgcaacgattctaccaacctctgtaaacatttcaaacaatatgcggttcgtgta cgaccgccttataccattcctcgagttataagaaatggggggatgccaatggatgttgaatatgtcat ttctaaaatgcttacgtttgaccaggagttcagaccttctgctaaggaaatattgaatatgcccctat ttactaaggcgccgattaacctgcttaatatcacaccctctgacagtgtctaacggtatacaggcggg agcgggtcgtggcgtcatcatcaccacttgagaatttatattttgaattgttgattgataaattaacc tgattcattgagaactgaaacgccatattggtttcttggatatgtctacaacaattagttaaattgct atgttctactgcgagtaacatttgataagttgtaagagacgggcgactcatgtcgaagttgacgaata taaagtacataacgtgtttagaatacccagaatccgaatagtccgcgggggcgtcttctcgcgtgagt accaaatactgagttgaacttgaaaatgctaaatctgtgacactctttgtgtgatgattattgtcacc acttcgaagatggcttcgacattcatgatgttctggtgtttgtttggaatcgtaatagcgcttgtttc gtccaagtctgacaacaaagaaaatctgaagaattatatcacggataagtcaaccaatattagaatac ccacgccattatttgtatcaacggaaaactcttatcccacaaaacatgtaatctacgatgaaaactgt ggcttcgctgtactcaatcctataagtgaccccaaatatgtccttttgagccagcttctaatgggaag gcgcaaatatgatgcgacggtcgcgtggtttgttctcggtaaaatgtgtgccagattaatatatttgc gcgaattttataactgctcgacaaatgagccttttggcacatgttctatgagctctcctggatggtgg -continued gacaggcgctacgtctcaaccagtttcatttctcgcgacgaattacagctggtttttgcagcgccgtc ccgagaattagatggtttatatacgcgcgtagtagttgtcaacggggactttactacggccgatataa tgtttaatgttaaagtggcatgtgccttttcaaagactggaatagaagatgatacattatgcaaaccc tttcatttctttgccaatgcaacattgcacaatttaaccatgattagatcggtaactcttcgagcgca cgaaagccatttaaaggaatgggtggcacggagaggtggtaacgtccctgcagtgctacttgagtcta ccatgtatcatgcatccaatctgcctagaaatttcagggatttctacataaagtctccagatgattat aagtataatcacctagatgggccatctgtaatgctcatcactgacagacctagtgaagatttggatgg gaggctcgttcaccaaagtgacatttttactactacaagtcctataaaacaggtccggtatgaagagc atcagtcacatacaaagcagtatcctgtaaacaaaatacaagctataatttttttgatagggttaggc tcgttcattggaagcatattcgtagttttggtagtatggattatacgcagatattgcaatggagcgcg gagtgggggaacgccccccagtcctcgccggtatgtgtataccaggctatgatcacgtgtgaaacttg ggcggacctgtatcatatgtacaccgtccctattcgtttatagccagtacgtgttatctgcacataga ggaacatgtgtcatactgggatcgcatgcatggtatgtgtgactctaatattattctgtatcataata aaaacacagtgcatggtatatagaggatcgctggtaagcactacggtagaccaatcggctcagattgc attctttggcatcgataccgttgttaatttatatggcaaagtcttgttcatgggagatcagtatttgg aggaaatatactctggaacgatggaaatactcaaatggaatcaagctaaccgctgctattctattgcg catgcaacatattacgccgactgtcctataatcagttctacggtattcagaggatgccgggacgccgt tgtttatactaggccccacagcagaattc SEQ ID NO 26: 654-45:325341_IE-F/1C1 (HVT/IBDV/ILT/NDV #2 virus)
HCMV IEpro-F-IEpA/HVT UL54.5 region (11,017 bp)

ggcgcgccactggagaacggcatgaccgcaaaaggcgttgtagagatcgatcccacgaactctcaggc gatcgtgtcagtcgccataaacagcgacgatcgtctccaggatctgaacggttttcttctcaacgatc atcagtatatgaggaactgaacctgatatttagccgagggaaacgcaggttaaaaaccctatcaagcg attgcgattttcgcgtatctagtaaaaatagatgggcttcggtactagccttcgccgccaactctgaa tatgcccttcgtggacctcatataacatggcattgtttgttggatgcggggccggaattaagaagaac attcgaaatacgagcaaaaatttcggccctggcatgtgctgcgcgagaatcggtacttcggggagaaa gttttatcggagctttgggtagtgcagaggaaactctatcttggttgaaaatgcatgcgaccctgcac ttgattctggttaaccacgatccaatttttaagacggctggcgcggtcctagataacctccgcttaaa actagccccaatattgatgtgcagatataacacagaaaaacgatcaatggaagacatgctacggcggt catctcccgaagacatcaccgattccctaacaatgtgcctgattatgttatcgcgcattcgtcgtacc atgcgcaccgcaggaaataaatatagctatatgatagatccaatgaatcgtatgtctaattacactcc aggcgaatgtatgacaggtatattgcgatatattgacgaacatgctagaaggtgtcctgatcacatat gtaatttgtatatcacatgtacacttatgccgatgtatgtgcacgggcgatatttctattgtaattca tttttttgttagtaaactaccacaggctgtccggaaatctaagttaatgaataaagtagatggttaat actcattgcttagaattggactacttttaattctctttaatgttcgtattaaataaaaacatctttaa taaacttcagcctcttcgcttattgtagaaattgagtattcaaaatcatgttcaaagccgtcttcgga gagtgtactcgccacggtggttggaacatcactatgtctacacgtcaaatttaagcacgtcaggtctg tcgaggacaagaaatggttaactagtgtttcaattattcttataaacgttaagcattgtaagcccccc ggccgtccgcagcaacaatttactagtatgccgtgggctccgggactatcacggatgtccaattcgca catgcatataatttttctagggtctctcatttcgagaaatcttcggggatccatcagcaatgcgggct gtagtcccgattcccgtttcaaatgaaggtgctccaacacggtcttcaaagcaaccggcataccagca aacacagactgcaactccccgctgcaatgattggttataaacagtaatctgtcttctggaagtatatt -continued tcgcccgacaatccacggcgcccccaaagttaaaaaccatccatgtgtatttgcgtcttctctgttaa aagaatattgactggcattttcccgttgaccgccagatatccaaagtacagcacgatgttgcacggac gactttgcagtcaccagccttcctttccacccccccaccaacaaaatgtttatcgtaggacccatatc cgtaataaggatgggtctggcagcaaccccataggcgcctcggcgtggtagttctcgaggccttaatt aagtaccgagctcgaattggcgcgccaggtcaattccctggcattatgcccagtacatgaccttatgg gactttcctacttggcagtacatctacgtattagtcatcgctattaccatggtgatgcggttttggca gtacatcaatgggcgtggatagcggtttgactcacggggatttccaagtctccaccccattgacgtca atgggagtttgttttggcaccaaaatcaacgggactttccaaaatgtcgtaacaactccgccccattg acgcaaatgggcggtaggcgtgtacggtgggaggtctatataagcagagctcgtttagtgaaccgtca gatcgcctggagacgccatccacgctgttttgacctccatagaagacaccgggcgcgccggatccatg ggccccagaccttctaccaagaacccagtacctatgatgctgactgtccgagtcgcgctggtactgag ttgcatctgtccggcaaactccattgatggcaggcctcttgcggctgcaggaattgtggttacaggag acaaagccgtcaacatatacacctcatcccagacaggatcaatcatagttaagctcctcccgaatctg cccaaggataaggaggcatgtgcgaaagccccccttggatgcatacaacaggacattgaccactttgct cacccccccttggtgactctatccgtaggatacaagagtctgtgactacatctggaggggggagacagg ggcgccttataggcgccattattggcggtgtggctcttggggttgcaactgccgcacaaataacagcg gccgcagctctgatacaagccaaacaaaatgctgccaacatcctccgacttaaagagagcattgccgc aaccaatgaggctgtgcatgaggtcactgacggattatcgcaactagcagtggcagttgggaagatgc agcagtttgttaatgaccaatttaataaaacagctcaggaattagactgcatcaaaattgcacagcaa gttggtgtagagctcaacctgtacctaaccgaattgactacagtattcggaccacaaatcacttcacc tgctttaaacaagctgactattcaggcactttacaatctagctggtggaaatatggattacttattga ctaagttaggtgtagggaacaatcaactcagctcattaatcggtagcggcttaatcaccggtaaccct attctatacgactcacagactcaactcttgggtatacaggtaactctaccttcagtcgggaacctaaa taatatgcgtgccacctacttggaaaccttatccgtaagcacaaccaggggatttgcctcggcacttg tcccaaaagtggtgacacaggtcggttctgtgatagaagaacttgacacctcatactgtatagaaact gacttagatttatattgtacaagaatagtaacgttccctatgtcccctggtatttattcctgcttgag cggcaatacgtcggcctgtatgtactcaaagaccgaaggcgcacttactacaccatacatgactatca aaggttcagtcatcgccaactgcaagatgacaacatgtagatgtgtaaaccccccgggtatcatatcg caaaactatggagaagccgtgtctctaatagataaacaatcatgcaatgttttatccttaggcgggat aactttaaggctcagtggggaattcgatgtaacttatcagaagaatatctcaatacaagattctcaag taataataacaggcaatcttgatatctcaactgagcttgggaatgtcaacaactcgatcagtaatgct ttgaataagttagaggaaagcaacagaaaactagacaaagtcaatgtcaaactgactagcacatctgc tctcattacctatatcgttttgactatcatatctcttgtttttggtatacttagcccgattctagcat gctacctaatgtacaagcaaaaggcgcaacaaaagaccttattatggcttgggaataatactctagat cagatgagagccactacaaaaatgtgaggatctctcgaggaattctagatcccacgtcactattgtat actctatattatactctatgttatactctgtaatcctactcaataaacgtgtcacgcctgtgaaaccg tactaagtctcccgtgtcttcttatcaccatcaggtgacatcctcgcccaggctgtcaatcatgccgg tatcgattccagtagcaccggccccacgctgacaacccactcttgcagcgttagcagcgcccctctta acaagccgacccccaccagcgtcgcggttactaacactcctctcccctcgaggatacatccaaagagg ttgagtattctctctacacttcttgttaaatggaaagtgcatttgcttgttcttacaatcggcccgag -continued tctcgttcacagcgcctcgttcacacttaaaccacaaatagtctacaggctatatgggagccagactg aaactcacatatgactaatattcgggggtgttagtcacgtgtagcccattgtgtgcatataacgatgt tggacgcgtccttattcgcggtgtacttgatactatggcagcgagcatgggatattcatcctcgtcat cattaacatctctacgggttcagaatgtttggcatgtcgtcgatcctttgcccatcgttgcaaattac aagtccgatcgccatgaccgcgataagcctgtaccatgtggcattagggtgacatctcgatcatacat tataagaccaacgtgcgagtcttccaaagacctgcacgccttcttcttcggattgtcaacgggttctt cagaatctatgcccatatctggcgttgagaccattgtgcgtttaatgaacaataaagcggcatgccat ggaaaggagggctgcagatctccattttctcacgccactatcctggacgctgtagacgataattatac catgaatatagagggggtatgtttccactgccactgtgatgataagttttctccagattgttggatat ctgcattttctgctgccgaacaaacttcatcgctatgcaaagagatgcgtgtgtacacgcgccgttga gtatacgggaaactaaatgttcatagaggtctttgggctatatgttattaaataaaataattgaccag tgaacaatttgtttaatgttagtttattcaatgcattggttgcaaatattcattacttctccaatccc aggtcattctttagcgagatgatgttatgacattgctgtgaaaattactacaggatatatttttaaga tgcaggagtaacaatgtgcatagtaggcgtagttatcgcagacgtgcaacgcttcgcatttgagttac cgaagtgcccaacagtgctgcggttatggtttatgcgcacagaatccatgcatgtcctaattgaacca tccgatttttcttttaatcgcgatcgttgtttgggcaactgcgttatttcagatctaaaaaatttacc ctttatgaccatcacatctctctggctcataccccgcttggataagatatcatgtagattccgcccta agaaatgcaaactaacattattgtcggttccatatacacttccatcttgtccttcgaaaataacaaac tcgcgcaatagaccgtccgtacatgcatggccgatgtgtgtcaacatcattggtctgctagatcccga tgggacgaatcgtacagtcgtcgctccagcattggcaaaaatccccagataccctccatgcggcaaat ctaaattgcgaccccgaagagactgcaccaaagtcttatcgacgcacgctgatttttttgaacagcgg gagcccattatcttcagtggagcgtagacgggcgaggctaattatgtgacatagcaacactgcatgta tgtttttataaatcaataagagtacataatttattacgtatcatttccgtttgtaatatactgtatac atcatccacactattagtcagcactagcgcgcgggcgcacgttacaatagcagcgtgcccgttatcta tattgtccgatatttacacataacatttcatcgacatgattaaatacctaagtactgcacacagatgt ttaatgtatatcgtcatataaattatatcgctaggacagacccaaacgacctttatcccaaacagtca gatcctcttctcaagtgtcgatttctgttatggaatatgcataccctggcccagaaattgcacgcacg agcgtagtgaatgcgtcattggttttacatttaaaggctaaatgcacaaattctttagacgacagcac atcgttaaatagcatctctagcgttcttatgaatgctaagcattggagtcctcctggtcggccacaat aacagctgagtatcataccctgagctccggggttgtcgcacatagcggattcgtataaacataggatt ttccgcgaatccatcagttgcaaaaatctgttaggctccatcaacaacgctggatttacttcagatcc acgcgtaaagtaatggtgctcgaataccgtttttagagttgtcggcatttcaaggaacaaagaattca tttcttcattgcaacgacgcgccagaaatcccaagacctctttgggtagtatgttcttgcctataaaa cacggcgttccaagtgccaggaaccacgcatgtgttactgttggggcgtattcagaaataaagcgggg tttatgcggcttttgaagctcggatatccaaagtatcgcttgctgatgaacgagcgatgtagctgtta caaaacctcctttccatcctccagtcaacataatatttatcggcctacctatgtccgtaataagtatt ggtcgggcaattattccgtatgaggtcttgcaggaataagctcttagggacagccagcttggatatgg tgcgaaacagaccttctcggcttcagaatgtcgctccgcagtctcttcgtgtcggtgcatcttagatc caccatcaatgtgtgcagcattgactcccgcccgtcgaatattccttttgttacgatgcagtaatgag cacgatcatgggcggggcgatgacgttctatttgcatgtctgcgaacaatttgcgtcagtcatacagc tatggagtgggccatttctggccgtcaacttaaaaacgcgaaccgcagacatatgtatttgcatgcaa -continued agacgtatcttcgtatttctgggcatcttcaaatgctctggccaatatggcaatgaatttggattcgt ttgacgccgatggtatgcagtgcaaatgtgccaatagcccacatccgaaaaagttatttgtcatacaa gcaggtgttaagtagcaatcacataaaggcaccagacgcctcatggcatcataatgaatagctccttc tccccactggaaccactgacaaaatctgcgagtatattccgcaaaccacattttatttctcatagaaa ctaccctaaatccttttaacgggaagaagaatcctagatagtgcttgaagtcatgactgttactgctg caataacactgtatattatttataaattccgtttgtctaggtatctgatgtaggcattccgatccctt tactattgcgtcttcacgaccaaatgggaatgcgccaaaatccccacacctcatcaccctggaggcag attgtgtattattaatatccgccgattgaagcacaaaacggtacggtactgttcctaattctggtata gattctatggtcaaaagtctgcatatccccgacattgccatgagatcacacagtccaagtagcatgtt tattgagtcactcagactgtcaacgtccctcgccgcaccaccaatcgaaaataaagtatctacgcaag ttatagctccgcattttctatcgctagcagcaatcgcgacgcaaaacataaaggccatgttgggattt gaactctctgggggcttgttatcttctgcaccgtcgcagtcgcagttttccgaaatttatgtctaat atattttccggccgtgctccaatcggccgaaaagaatctgcgtattaccagactcattgacgggccga taaagaccataaaacaaaattcctgtgcactccctcctccagttttgccatcgtccaagtcccgtaac tttttttgcgtttcgaggagcaagcgttcgttatccctacccacacttgttttccaccgttttcttat tataagcggttgtatcgccaacgcgtcaccgcaggttgtcacatacagtgatggcatacttgaacgtg caacaacgcgctcgctttgcaaatctaagtcattgaccatcaaatcgcgttgagaggatagccaggca tctttttttcctagtatggtgacggtgcagccaccccaactcagttcttgtaaaaaaagctattggcgg gaatttatgttctgaggtgcattctatatttatgagtccatcaaatgccattaaccagattcgtattt tttcgctcgacccggcatcactatggatacaatacctttctatggcccatttcagctctcgaaccaac cacacggacaattgactaacataagtatgatctttatcacagtcgcacccatctgagttatatttatg gcatccgagcgctcttactgtacggtcggatacacccatggtttttcctttatatagtcgggttatag tctgtcgggtttggcggtagcacggagtagtttgatttttaagaatcgaaaaccggcttggagagacc actgtcgaatatttgtccgtatactctacacgtgagtgttgtccattcctaggtatattcatctgttc ggataccttcaattgctgttcaggcataaccttaaagcatatgttatgttgtacatcaaaacttggtg agttatgttcgattgccgcgcataaagaatcgtacatgagcgtttctgctaacatactatctatattc tcacacgcccctgcatatactgttcctattccaaattcacgttttgccccatcggctatctgctccca aaaagttgtaatataggtgccgctgggtgcgaaattttcatcagttgtattcctgataaactgaatca ctttacataatttttgccacatatctgcgtgcagccatagtatcgaacccgtgggctcggagacgaca gtgcgtacaatgggtattttacctttccccaacaaaataatggtatacaagttaggtccgtacctaga ccttaatgtttccaattcttctgaatcactgcactctcgtaggggagtaacggtaataatttcgtctc tgagccccgttttgcgttgaaaactaatcacattagataatgtgcaatcggtttcttttatccggata catctaagtattatgacatcggtggtcattgtttccatcaacgaccatcttttacgatcgcccatact actcatggacgttgtcggtgttgaaaaatcaccagaattgcaacggatctctgggtaccatgctgctg atggaattggcggttttaattgttgtttcagtctattattgctatctttggcggggttgaataatgtg gggggagagtgattgcaggaatccgaatgggtcaataaaacgaccgtgctccgttctgccggcgccga tccgattgaagctatatacttcgcttctctccccacttttccaatttgatccggaaataaaacggccc cggacaacagtatcgtacgatccggatccggatcctgcttgcctacagaagaatcaacatctcgcccc aatattctggtcaaaactggctcgctcatggcaacgcggacgtttcccccggtggccagtcttaatgg ttaatgttcttttcggcaatcttatacatcagcgggttgcgtgaatactggtcacagttcagtcattt -continued actacacaccagcaatacgacgacggacagtaccgtcccgacgaacgcgacgcccaaaattgctatcg cgaccgcgtccgaggcgatgtcgtacgggcggtgcggggttggatcctcggcaaagagatcctcgtaa ttcggcggtgggagcggagggtaaagacgcgggtggggatctccctccggaccgcgcgccgggcgcgg ttcgaaaatgctttccgcctcgctcagtgtcaacgccaagtattcgggcgggctgggggccggaatat ctcccgcgacttcttctatcggcgcggaattggagtcgcggtcgtggcgcgcttctagcgtcgtcaac ggaagtccattttcggggtctcccggtgggcgttcagcgtccatcgtcgtatatgctctaacacacgt ctcgctatattaaaaaaaagaagagtatcggtcagtgtcgagtgtcgccgacaatgtcgcgagttctc ggcgatttaatttttggaactgctccctatgaatcccgtaactgtagcgcccgcgcagaaagccgcca tcagaccaactacgtgtctgttcgatgtttgcccgccgatcgctttaccgattaaggttccggcgaga aatgacatgctcgatccaagaacaaagtttttcgcggtaaacaacaacatagttaccgtgcgagatgg agaaaccacatctcccgaattagtagaggaaagcccgcgctgtcggtttggggacatatcgatctttt ttgtgtttttcctaggacccttttgccagatcgtacaaagtcgcgtcttatgagcggacgttcttact gcagctcggtaggagtggggcagggttagatttcgtcggcgtttcggcccccgtatgcgccgcgccac cctcttcgccgagctctttatgcgcggtgggggtgagcgcttccggagttgcgatctccgatctcgag ccgcagcccggcggtgtctctttcagtggagcgttagcgccatcatgtggttcgtggcggtggaaagg ctattatgtgttaggggagagaccacgtgatcggcatgcaaatgagcaaggcgaacgcgtcagcgttc gcactgcgaaccaataatatatatattatactattggctttaggtgcgaacgtccggctagtccaata gcggggtcgcgtttcgtaccacgtgttatagaccgccctaaactcgcactcgggggtccggccgcgcc cagacagggcggagacgtgccacaggggctttaaaacaccgcttcgggcaccgttcatctcggcgcgc c SEQ ID NO 27: VP2/1C1#8 (HVT/IBDV/ILT/NDV # 3 virus)
MCMV IEpro-VP2-SV40pA/HVT UL54.5 region (11,665 bp)
ggcgcgccactggagaacggcatgaccgcaaaaggcgttgtagagatcgatcccacgaactctcaggc gatcgtgtcagtcgccataaacagcgacgatcgtctccaggatctgaacggttttcttctcaacgatc atcagtatatgaggaactgaacctgatatttagccgagggaaacgcaggttaaaaaccctatcaagcg attgcgattttcgcgtatctagtaaaaatagatgggcttcggtactagccttcgccgccaactctgaa tatgcccttcgtggacctcatataacatggcattgtttgttggatgcggggccggaattaagaagaac attcgaaatacgagcaaaaatttcggccctggcatgtgctgcgcgagaatcggtacttcggggagaaa gttttatcggagctttgggtagtgcagaggaaactctatcttggttgaaaatgcatgcgaccctgcac ttgattctggttaaccacgatccaatttttaagacggctggcgcggtcctagataacctccgcttaaa actagccccaatattgatgtgcagatataacacagaaaaacgatcaatggaagacatgctacggcggt catctcccgaagacatcaccgattccctaacaatgtgcctgattatgttatcgcgcattcgtcgtacc atgcgcaccgcaggaaataaatatagctatatgatagatccaatgaatcgtatgtctaattacactcc aggcgaatgtatgacaggtatattgcgatatattgacgaacatgctagaaggtgtcctgatcacatat gtaatttgtatatcacatgtacacttatgccgatgtatgtgcacgggcgatatttctattgtaattca tttttttgttagtaaactaccacaggctgtccggaaatctaagttaatgaataaagtagatggttaat actcattgcttagaattggactacttttaattctctttaatgttcgtattaaataaaaacatctttaa taaacttcagcctcttcgcttattgtagaaattgagtattcaaaatcatgttcaaagccgtcttcgga gagtgtactcgccacggtggttggaacatcactatgtctacacgtcaaatttaagcacgtcaggtctg tcgaggacaagaaatggttaactagtgtttcaattattcttataaacgttaagcattgtaagcccccc ggccgtccgcagcaacaatttactagtatgccgtgggctccgggactatcacggatgtccaattcgca catgcatataatttttctagggtctctcatttcgagaaatcttcggggatccatcagcaatgcgggct -continued gtagtcccgattcccgtttcaaatgaaggtgctccaacacggtcttcaaagcaaccggcataccagca aacacagactgcaactccccgctgcaatgattggttataaacagtaatctgtcttctggaagtatatt tcgcccgacaatccacggcgcccccaaagttaaaaaccatccatgtgtatttgcgtcttctctgttaa aagaatattgactggcattttcccgttgaccgccagatatccaaagtacagcacgatgttgcacggac gactttgcagtcaccagccttcctttccacccccccaccaacaaaatgtttatcgtaggacccatatc cgtaataaggatgggtctggcagcaaccccataggcgcctcggcgtggtagttctcgaggccttaagc ttaaggatcccccaactccgcccgttttatgactagaaccaatagtttttaatgccaaatgcactgaa atcccctaatttgcaaagccaaacgcccccctatgtgagtaatacggggactttttacccaatttccca cgcggaaagcccccctaatacactcatatggcatatgaatcagcacggtcatgcactctaatggcggcc catagggactttccacatagggggcgttcaccatttcccagcataggggtggtgactcaatggccttt acccaagtacattgggtcaatgggaggtaagccaatgggtttttcccattactggcaagcacactgag tcaaatgggactttccactgggttttgcccaagtacattgggtcaatgggaggtgagccaatgggaaa aacccattgctgccaagtacactgactcaatagggactttccaatgggtttttccattgttggcaagc atataaggtcaatgtgggtgagtcaatagggactttccattgtattctgcccagtacataaggtcaat agggggtgaatcaacaggaaagtcccattggagccaagtacactgcgtcaatagggactttccattgg gttttgcccagtacataaggtcaataggggatgagtcaatgggaaaaacccattggagccaagtacac tgactcaatagggactttccattgggttttgcccagtacataaggtcaatagggggtgagtcaacagg aaagttccattggagccaagtacattgagtcaatagggactttccaatgggttttgcccagtacataa ggtcaatgggaggtaagccaatgggtttttcccattactggcacgtatactgagtcattagggacttt ccaatgggttttgcccagtacataaggtcaataggggtgaatcaacaggaaagtcccattggagccaa gtacactgagtcaatagggactttccattgggttttgcccagtacaaaaggtcaatagggggtgagtc aatgggtttttcccattattggcacgtacataaggtcaataggggtgagtcattgggtttttccagcc aatttaattaaaacgccatgtactttcccaccattgacgtcaatgggctattgaaactaatgcaacgt gacctttaaacggtactttcccatagctgattaatgggaaagtaccgttctcgagccaatacacgtca atgggaagtgaaagggcagccaaaacgtaacaccgccccggttttcccctggaaattccatattggca cgcattctattggctgagctgcgttctacgtgggtataagaggcgcgaccagcgtcggtaccgtcgca gtcttcggtctgaccaccgtagaacgcagagctcctcgctgcaggcggccgctctagaactcgtcgat cgcagcgatgacaaacctgcaagatcaaacccaacagattgttccgttcatacggagccttctgatgc caacaaccggaccggcgtccattccggacgacaccctggagaagcacactctcaggtcagagacctcg acctacaatttgactgtgggggacacagggtcagggctaattgtctttttccctggattccctggctc aattgtgggtgctcactacacactgcagagcaatgggaactacaagttcgatcagatgctcctgactg cccagaacctaccggccagctacaactactgcagactagtgagtcggagtctcacagtgaggtcaagc acactccctggtggcgtttatgcactaaacggcaccataaacgccgtgaccttccaaggaagcctgag tgaactgacagatgttagctacaatgggttgatgtctgcaacagccaacatcaacgacaaaattggga atgtcctggtaggggaaggggtcactgtcctcagcctacccacatcatatgatcttgggtatgtgagg cttggtgaccccattcccgctatagggcttgacccaaaaatggtagctacatgcgacagcagtgacag gcccagagtctacaccataactgcagccgatgattaccaattctcatcacagtaccaaccaggtgggg taacaatcacactgttctcagccaacattgatgctatcacaagcctcagcattgggggagagctcgtg tttcaaacaagcgtccaaggccttgtactgggcgccaccatctaccttataggctttgatgggactgc ggtaatcaccagagctgtggccgcagataatgggctgacggccggcaccgacaatcttatgccattca -continued atcttgtcattccaaccaatgagataacccagccaatcacatccatcaaactggagatagtgacctcc
aaaagtggtggtcaggcaggggatcagatgtcatggtcggcaagtgggagcctagcagtgacgatcca
tggtggcaactatccaggggccctccgtcccgtcacactagtagcctacgaaagagtggcaacaggat
ccgtcgttacggtcgctggggtgagtaacttcgagctgattccaaatcctgaactagcaaagaacctg
gttacagaatacggccgatttgacccaggagccatgaactacacaaaattgatactgagtgagaggga
ccgtcttggcatcaagaccgtctggccaacaagggagtacactgattttcgtgagtacttcatggagg
tggccgacctcaactctcccctgaagattgcaggagcatttggcttcaaagacataatccgggctata
aggaggtagatccagacatgataagatacattgatgagtttggacaaaccacaactagaatgcagtga
aaaaaatgctttatttgtgaaatttgtgatgctattgctttatttgtaaccattataagctgcaataa
acaagttaacaacaacaattgcattcattttatgtttcaggttcagggggaggtgtgggaggtttttt
cggatcctctagagtcgaggatacatccaaagaggttgagtattctctctacacttcttgttaaatgg
aaagtgcatttgcttgttcttacaatcggcccgagtctcgttcacagcgcctcgttcacacttaaacc
acaaatagtctacaggctatatgggagccagactgaaactcacatatgactaatattcgggggtgtta
gtcacgtgtagcccattgtgtgcatataacgatgttggacgcgtccttattcgcggtgtacttgatac
tatggcagcgagcatgggatattcatcctcgtcatcgttaacatctctacgggttcagaatgtttggc
atgtcgtcgatcctttgcccatcgttgcaaattacaagtccgatcgccatgaccgcgataagcctgta
ccatgtggcattagggtgacatctcgatcatacattataagaccaacgtgcgagtcttccaaagacct
gcacgccttcttcttcggattgtcaacgggttcttcagaatctatgcccatatctggcgttgagacca
ttgtgcgtttaatgaacaataaagcggcatgccatggaaaggagggctgcagatctccattttctcac
gccactatcctggacgctgtagacgataattataccatgaatatagagggggtatgtttccactgcca
ctgtgatgataagttttctccagattgttggatatctgcattttctgctgccgaacaaacttcatcgc
tatgcaaagagatgcgtgtgtacacgcgccggtggagtatacgggaaactaaatgttcatagaggtct
ttgggctatatgttattaaataaaataattgaccagtgaacaatttgtttaatgttagtttattcaat
gcattggttgcaaatattcattacttctccaatcccaggtcattctttagcgagatgatgttatgaca
ttgctgtgaaaattactacaggatatatttttaagatgcaggagtaacaatgtgcatagtaggcgtag
ttatcgcagacgtgcaacgcttcgcatttgagttaccgaagtgcccaacagtgctgcggttatggttt
atgcgcacagaatccatgcatgtcctaattgaaccatccgattttttcttttaatcgcgatcgatgttt
gggcaactgcgttatttcagatctaaaaaatttaccctttatgaccatcacatctctctggctcatac
cccgcttggataagatatcatgtagattccgccctaagaaatgcaaactaacattattgtcggttcca
tatacacttccatcttgtccttcgaaaataacaaactcgcgcaatagaccgtccgtacatgcatggcc
gatgtgtgtcaacatcattggtctgctagatcccgatgggacgaatcgtacagtcgtcgctccagcat
tggcaaaaatccccagataccctccatgcggcaaatctaaattgcgaccccgaagagactgcaccaaa
gtcttatcgacgcacgctgatttttttgaacagcgggagcccattatcttcagtggagcgtagacggg
cgaggctaattatgtgacatagcaacactgcatgtatgtttttataaatcaataagagtacataattt
attacgtatcatttccgtttgtaatatactgtatacatcatccacactattagtcagcactagcgcgc
gggcgcacgttacaatagcagcgtgcccgttatctatattgtccgatatttacacataacatttcatc
gacatgattaaatacctaagtactgcacacagatgtttaatgtatatcgtcatataaattatatcgct
aggacagacccaaacgacctttatcccaaacagtcagatcctcttctcaagtgtcgatttctgttatg
gaatatgcataccctggcccagaaattgcacgcacgagcgtagtgaatgcgtcattggttttacattt
aaaggctaaatgcacaaattctttagacgacagcacatcgttaaatagcatctctagcgttcttatga
atgctaagcattggagtcctcctggtcggccacaataacagctgagtatcatacccctgagctccgggg -continued ttgtcgcacatagcggattcgtataaacataggattttccgcgaatccatcagttgcaaaaatctgtt aggctccatcaacaacgctggatttacttcagatccacgcgtaaagtaatggtgctcgaataccgttt ttagagttgtcggcatttcaaggaacaaagaattcatttcttcattgcaacgacgcgccagaaatccc aagacctctttgggtagtatgttcttgcctataaaacacggcgttccaagtgccaggaaccacgcatg tgttactgttggggcgtattcagaaataaagcggggtttatgcggcttttgaagctcggatatccaaa gtatcgcttgctgatgaacgagcgatgtagctgttacaaaacctcctttccatcctccagtcaacata atatttatcggcctacctatgtccgtaataagtattggtcgggcaattattccgtatgaggtcttgca ggaataagctcttagggacagccagcttggatatggtgcgaaacagaccttctcggcttcagaatgtc gctccgcagtctcttcgtgtcggtgcatcttagatccaccatcaatgtgtgcagcattgactcccgcc cgtcgaatattcctttttgttacgatgcagtaatgagcacgatcatgggcggggcgatgacgttctatt tgcatgtctgcgaacaatttgcgtcagtcatacagctatggagtgggccatttctggccgtcaactta aaaacgcgaaccgcagacatatgtatttgcatgcaaagacgtatcttcgtatttctgggcatcttcaa atgctctggccaatatggcaatgaatttggattcgtttgacgccgatggtatgcagtgcaaatgtgcc aatagcccacatccgaaaaagttatttgtcatacaagcaggtgttaagtagcaatcacataaaggcac cagacgcctcatggcatcataatgaatagctccttctccccactggaaccactgacaaaatctgcgag tatattccgcaaaccacattttatttctcatagaaactaccctaaatccttttaacgggaagaagaat cctagatagtgcttgaagtcatgactgttactgctgcaataacactgtatattatttataaattccgt ttgtctaggtatctgatgtaggcattccgatccctttactattgcgtcttcacgaccaaatgggaatg cgccaaaatccccacacctcatcaccctggaggcagattgtgtattattaatatccgccgattgaagc acaaaacggtacggtactgttcctaattctggtatagattctatggtcaaaagtctgcatatccccga cattgccatgagatcacacagtccaagtagcatgtttattgagtcactcagactgtcaacgtccctcg ccgcaccaccaatcgaaaataaagtatctacgcaagttatagctccgcattttctatcgctagcagca atcgcgacgcaaaacataaaggccatgttgggatttgaactctctggggggcttgttatcttctgcac cgtcgcagtcgcagttttccgaaatttatgtctaatatattttccggccgtgctccaatcggccgaaa agaatctgcgtattaccagactcattgacgggccgataaagaccataaaacaaaattcctgtgcactc cctcctccagttttgccatcgtccaagtcccgtaactttttttgcgtttcgaggagcaagcgttcgtt atccctacccacacttgttttccaccgttttcttattataagcggttgtatcgccaacgcgtcaccgc aggttgtcacatacagtgatggcatacttgaacgtgcaacaacgcgctcgctttgcaaatctaagtca ttgaccatcaaatcgcgttgagaggatagccaggcatctttttttcctagtatggtgacggtgcagcca ccccaactcagttcttgtaaaaaaagctattggcgggaatttatgttctgaggtgcattctatattta tgagtccatcaaatgccattaaccagattcgtatttttttcgctcgacccggcatcactatggataca tacctttctatggcccatttcagctctcgaaccaaccacacggacaattgactaacataagtatgatc tttatcacagtcgcacccatctgagttatatttatggcatccgagcgctcttactgtacggtcggata cacccatggtttttcctttatatagtcgggttatagtctgtcgggtttggcggtagcacggagtagtt tgatttttaagaatcgaaaaccggcttggagagaccactgtcgaatatttgtccgtatactctacacg tgagtgttgtccattcctaggtatattcatctgttcggataccttcaattgctgttcaggcataacct taaagcatatgttatgttgtacatcaaaacttggtgagttatgttcgattgccgcgcataaagaatcg tacatgagcgtttctgctaacatactatctatattctcacacgcccctgcatatactgttcctattcc aaattcacgttttgccccatcggctatctgctcccaaaaagttgtaatataggtgccgctgggtgcga aattttcatcagttgtattcctgataaactgaatcactttacataattttgccacatatctgcgtgc -continued agccatagtatcgaacccgtgggctcggagacgacagtgcgtacaatgggtattttacctttccccaa caaaataatggtatacaagttaggtccgtacctagaccttaatgtttccaattcttctgaatcactgc actctcgtaggggagtaacggtaataatttcgtctctgagccccgttttgcgttgaaaactaatcaca ttagataatgtgcaatcggtttcttttatccggatacatctaagtattatgacatcggtggtcattgt ttccatcaacgaccatcttttacgatcgcccatactactcatggacgttgtcggtgttgaaaaatcac cagaattgcaacggatctctgggtaccatgctgctgatggaattggcggttttaattgttgtttcagt ctattattgctatctttggcggggttgaataatgtgggggggagagtgattgcaggaatccgaatgggt caataaaacgaccgtgctccgttctgccggcgccgatccgattgaagctatatacttcgcttctctcc ccacttttccaatttgatccggaaataaaacggccccggacaacagtatcgtacgatccggatccgga tcctgcttgcctacagaagaatcaacatctcgccccaatattctggtcaaaactggctcgctcatggc aacgcggacgtttcccccggtggccagtcttaatggttaatgttcttttcggcaatcttatacatcag cgggttgcgtgaatactggtcacagttcagtcatttactacacaccagcaatacgacgacggacagta ccgtcccgacgaacgcgacgcccaaaattgctatcgcgaccgcgtccgaggcgatgtcgtacgggcgg tgcggggttggatcctcggcaaagagatcctcgtaattcggcggtgggagcggagggtaaagacgcgg gtggggatctccctccggaccgcgcgccggcgcggttcgaaaatgctttccgcctcgctcagtgtca acgccaagtattcgggcgggctgggggccggaatatctcccgcgacttcttctatcggcgcggaattg gagtcgcggtcgtggcgcgcttctagcgtcgtcaacggaagtccattttcggggtctcccggtgggcg ttcagcgtccatcgtcgtatatgctctaacacacgtctcgctatattaaaaaaaagaagagtatcggt cagtgtcgagtgtcgccgacaatgtcgcgagttctcggcgatttaattttggaactgctccctatga atcccgtaactgtagcgcccgcgcagaaagccgccatcagaccaactacgtgtctgttcgatgtttgc ccgccgatcgctttaccgattaaggttccggcgagaaatgacatgctcgatccaagaacaaagttttt cgcggtaaacaacaacatagttaccgtgcgagatggagaaaccacatctcccgaattagtagaggaaa gcccgcgctgtcggtttggggacatatcgatctttttttgtgtttttcctaggacccttttgccagatc gtacaaagtcgcgtcttatgagcggacgttcttactgcagctcggtaggagtggggcagggttagatt tcgtcggcgtttcggcccccgtatgcgccgcgccaccctcttcgccgagctctttatgcgcggtgggg gtgagcgcttccggagttgcgatctccgatctcgagccgcagcccggcggtgtctctttcagtggagc gttagcgccatcatgtggttcgtggcggtggaaaggctattatgtgttaggggagagaccacgtgatc ggcatgcaaatgagcaaggcgaacgcgtcagcgttcgcactgcgaaccaataatatatatattatact attggctttaggtgcgaacgtccggctagtccaatagcggggtcgcgtttcgtaccacgtgttataga ccgccctaaactcgcactcgggggtccggccgcgcccagacagggcggagacgtgccacaggggcttt aaaacaccgcttcgggcaccgttcatctcggcgcgcc SEQ ID NO 28: 1332-47.A2 (HVT/IBDV/ILT/NDV # 3 virus)
ILT/hCMV IEpro-F-IE(term)/HVT US2 region (13,253 bp)
aattccagactaaatgccccggcccaatttgtcaagtgtgcagtcacggaggcgtcgaccgtgtcccc ggcattaaacaggaaagcgttaaagtttttgaatgttaggtcacaggtacaaacataaatgtttgtac aaacaggtaacaggtacaaacataaatgccccggcataaatgtcccttacggcggatcgaaacgacat taggcatactcgggtaccattttgcattccgatcagcacggatgaaattaggcaggaatgcggtttat attatgcggcattggacaaacgatatggcattgattggcagtttatgaatgtcttcatgttgggcgta aacggattcctattggttcagaagacaacgacgatatatttagagagaaaaagctacccagcatagga taaacacacattgagcattgagagacataggtatcggtatggatgggaaaactacacacgtgaacacc aaacgacttatatactcgagcggtgatactactgagcaagaatgcactgcatctgagccactgaatga agactgtgatgaaaatgtgaccatcgatggaattggagaagaatatgcgcagttcttcatgtccccgc -continued aatgggtcccaaatctacatcgcttgagcgaggataccaaaaaggtataccgatgtatggtttccaac
agactcaattattttccctattatgaggcgttcaggcggtctttgtttgatatgtatatgctaggtcg
gttggggcgtcgacttaagcgatctgactgggagactattatgcatctgtcaccaacgcaaagtcggc
gtctacatagaactttaagatttgtggagcgtagaattatcccatctaacagttatatacgcacatcg
ggccacgttccgccttcgagggcacttccgacagatacgaatttaaagatggatgaataattaaattg
gaaagagtaactacattaatcgagcgtcatgacggcgtcccgtgaaaatgggaattttctactcgaaa
caccgtgacatttgacagacctggaattgttattctgatatatagtgggtgtgtctggccggcaacat
acataatgtgcatgcgaaaccactttttcagtgtacgctgacattgtgcaacacggaggggtagcatc
tacatacaatatatgttgattaatgattggagaaaaaactatgcagctcgccgatcatatggctaact
cgccttcgtctatatggcggaccccgcgggaaaaatcgacgtaccatctgatttacaacaccagtaat
gaacatgtcgcatccctgcccagatctgtgcgcccattggcgcggatcgttgtgaatgccgccgaaac
acttcaggtcggtatgagagccgggaggccgccatcagcaggagtttggcgagaggtgtttgatagaa
tgatgacagccttccgtgaccacgagcctactgcgacatttaatgctgcaaatcccattagaaaaatg
gtcgagacagttctacagaataatgaagagcccccgcggacgcatgctgaaatgggtaatcgccttat
gaacattatgtactggtgttgcttgggacacgcaggacaatgctcgatatggcagttgtacgagacga
atcaggccattttaagtttattagatgaagtggttatcggcacaacaaatcccttttgcaccctcgag
caatactggaagccattatgcaccgcaatcgccaacaaggggacctcatcgcttgttgaggatgccaa
agtggccgagtacctggttagcatgcgcaaattgatataacataggcacgctctgatgttacagacca
caataccgcatacatttattgtaaggttgttaataaaggtttattctatgtaagactacaatactttc
gacattgcttgtatacatattaaatactttctcaagttcctattacataaaatgggatctatcattac
attcgttaagagtctggataattttactgtttgccagcttcgatcttggaacgtactgtggatagtgc
cttacttggaatcgtgaaaatttgaaacgtccattatttggatatcttccggttgtcccatatcccgc
cctggtaccgctcggataccttgcccgtatggattcgtattgacagtcgcgcaatcggggaccaacaa
cgcgtgggtccacactcattcggaaattttccgatgattctgaatatttattgccgctcgttacgagt
cgttggacatatctgtaatacatttcttcttctgaaggatcgctgcacatttgatctatacattggcc
aggatgttcaagtctcagatgttgcattctggcacagcacaactttatggcatttccgatgtaatcgt
ccggcagccctgggggagttctatattcgcatattgggatggtaaggacaatagcagatctcgcaacc
tccagggaggctataataacgtttttaaaggatggatttctcataaaaatctgtcgcaaattacactg
agaatatcctttactagcgccgattgagagcatcgtcgtccaattttctaaatggaaagaaaacaagg
cgggcaagagtgttccaaacattttcattttcggcgaatctctcaaatcccatggcgtgcaattgatt
gcaaaattggcacttccgttcacgtttgtatctccaaactctaagacacttttaattgaaaaactacg
ttctagtgtggaaagaaacctataggcagaccatagaactatttgacaccacatatctttttgtatgt
caaactgaccatgatcgtatgttgctgaatgcactagggcaattcgctcgcgcgactccatacattga
ataattccacacgtcagctcatcggttagcaaggtccagtagttgaagtcatttatttttccccgcgg
ctggccaaatctacctctgggaatatccaagttgtcgaatatgatcgcaccggctctggtcatggtga
aggaactgtagcataaagacgcaggtatcataggggtaatatttttttattcactcacatactaaaag
taacgcatattagcaccatgtatgggctatcaattgacatttgcgtagcactacatcacgattatgta
caacataatgggacaacatatggcaagtagatgcaatttcctcacactagttgggtttatctactatt
gaattttcccctatctgtgatacacttgggagcctctacaagcatattgccatcatgtacgtttttat
ctactgtcttaacgcccatgggaacggaggcgtcgtcgtcatgtattggacggcaacataggcagcaa -continued cacaaattgcgtttaggtggggtgcatgtggactcgataccaagcccctgcagctggggaacgtctgg tggagagccgataatttgatatacgcacgccatattactgtcgttgaagtacgccttatcttctatgt tttcaaatttaggttcccaagtggacgtgagaagtgtttgtatctcacatggaatggcccaaggcatt ccagcccaggtgcctggtactttaatggcaaacaaacgttttggtagaggtattgattctattgcagt tctgcagatatctgcagccccgagtatccacaggctatacgatacgttatcggaggcaagcttgttaa ttaagtcgacggcagagtcgcagacgcccctattggacgtcaaaattgtagaggtgaagttttcaaac gatggcgaagtaacggcgacttgcgtttccaccgtcaaatctccctatagggtagaaactaattggaa agtagacctcgtagatgtaatggatgaaatttctgggaacagtcccgccggggtttttaacagtaatg agaaatggcagaaacagctgtactacagagtaaccgatggaagaacatcggtccagctaatgtgcctg tcgtgcacgagccattctccggaaccttactgtcttttcgacacgtctcttatagcgagggaaaaaga tatcgcgccagagttatactttacctctgatccgcaaacggcatactgcacaataactctgccgtccg gcgttgttccgagattcgaatggagccttaataatgtttcactgccggaatatttgacggccacgacc gttgtttcgcataccgctggccaaagtacagtgtggaagagcagcgcgagagcaggcgaggcgtggat ttctggccggggaggcaatatatacgaatgcaccgtcctcatctcagacggcactcgcgttactacgc gaaaggagaggtgcttaacaaacacatggattgcggtggaaaacggtgctgctcaggcgcagctgtat tcactcttttctggacttgtgtcaggattatgcgggagcatatctgctttgtacgcaacgctatggac cgccatttatttttgaggaatgctttttggactatcgtactgctttcttccttcgctagccagagcac cgccgccgtcacgtacgactacattttaggccgtcgcgcgctcgacgcgctaaccataccggcggttg gcccgtataacagatacctcactagggtatcaagaggctgcgacgttgtcgagctcaacccgatttct aacgtggacgacatgatatcggcggccaaagaaaaagagaagggggggccctttcgaggcctccgtcgt ctggttctacgtgattaagggcgacgacggcgaggacaagtactgtccaatctatagaaaagagtaca gggaatgtggcgacgtacaactgctatctgaatgcgccgttcaatctgcacagatgtgggcagtggac tatgttcctagcacccttgtatcgcgaaatggcgcgggactgactatattctcccccactgctgcgct ctctggccaatacttgctgaccctgaaaatcgggagatttgcgcaaacagctctcgtaactctagaag ttaacgatcgctgtttaaagatcgggtcgcagcttaactttttaccgtcgaaatgctggacaacagaa cagtatcagactggatttcaaggcgaacacctttatccgatcgcagacaccaatacacgacacgcgga cgacgtatatcggggatacgaagatattctgcagcgctggaataatttgctgaggaaaaagaatccta gcgcgccagaccctcgtccagatagcgtcccgcaagaaattcccgctgtaaccaagaaagcggaaggg cgcaccccggacgcagaaagcagcgaaaagaaggcccctccagaagactcggaggacgacatgcaggc agaggcttctggagaaaatcctgccgccctccccgaagacgacgaagtccccgaggacaccgagcacg atgatccaaactcggatcctgactattacaatgacatgcccgccgtgatcccggtggaggagactact aaaagttctaatgccgtctccatgcccatattcgcggcgttcgtagcctgcgcggtcgcgctcgtggg gctactggtttggagcatcgtaaaatgcgcgcgtagctaatcgagcctagaataggtggtttcttcct acatgccacgcctcacgctcataatataaatcacatggaatagcataccaatgcctattcattgggac gttcgaaaagcatggcatcgctacttggaactctggctctccttgccgcgacgctcgcacccttcggc gcgatgggaatcgtgatcactggaaatcacgtctccgccaggattgacgacgatcacatcgtgatcgt cgcgcctcgccccgaagctacaattcaactgcagctatttttcatgcctggccagagaccccacaaac cctactcaggaaccgtccgcgtcgcgtttcggtctgatataacaaaccagtgctaccaggaacttagc gaggagcgctttgaaaattgcactcatcgatcgtcttctgtttttgtcggctgtaaagtgaccgagta cacgttctccgcctcgaacagactaaccggacctccacacccgtttaagctcactatacgaaatcctc gtccgaacgacagcgggatgttctacgtaattgttcggctagacgacaccaaagaacccattgacgtc -continued ttcgcgatccaactatcggtgtatcaattcgcgaacaccgccgcgactcgcggactctattccaaggc ttcgtgtcgcaccttcggattacctaccgtccaacttgaggcctatctcaggaccgaggaaagttggc gcaactggcaagcgtacgttgccacggaggccacgacgaccagcgccgaggcgacaaccccgacgccc gtcactgcaaccagcgcctccgaacttgaagcggaacactttacctttccctggctagaaaatggcgt ggatcattacgaaccgacacccgcaaacgaaaattcaaacgttactgtccgtctcgggacaatgagcc ctacgctaattggggtaaccgtggctgccgtcgtgagcgcaacgatcggcctcgtcattgtaatttcc atcgtcaccagaaacatgtgcaccccgcaccgaaaattagacacggtctcgcaagacgacgaagaacg ttcccaaactagaagggaatcgcgaaaatttggacccatggttgcgtgcgaaataaacaaggggggctg accaggatagtgaacttgtggaactggttgcgattgttaacccgtctgcgctaagctcgcccgactca ataaaaatgtgattaagtctgaatgtggctctccaatcatttcgattctctaatctcccaatcctctc aaaaggggcagtatcggacacggactgggaggggcgtacacgatagttatatggtacagcagaggcct ctgaacacttaggaggagaattcagccggggagagcccctgttgagtaggcttgggagcatattgcag gatgaacatgttagtgatagttctcgcctcttgtcttgcgcgcctaacttttgcgacgcgacacgtcc tctttttggaaggcactcaggctgtcctcggggaagatgatcccagaaacgttccggaagggactgta atcaaatggacaaaagtcctgcggaacgcgtgcaagatgaaggcggccgatgtctgctcttcgcctaa ctattgctttcatgatttaatttacgacggaggaaagaaagactgcccgcccgcgggacccctgtctg caaacctggtaattttactaaagcgcggcgaaagcttcgcgccaggtcaattccctggcattatgccc agtacatgaccttatgggactttcctacttggcagtacatctacgtattagtcatcgctattaccatg gtgatgcggttttggcagtacatcaatgggcgtggatagcggtttgactcacggggatttccaagtct ccaccccattgacgtcaatgggagtttgttttggcaccaaaatcaacgggactttccaaaatgtcgta acaactccgccccattgacgcaaatgggcggtagcgtgtacggtgggaggtctatataagcagagctc gtttagtgaaccgtcagatcgcctggagacgccatccacgctgttttgacctccatagaagacaccgg ttgcgccgccaccatgggccccagaccttctaccaagaacccagtacctatgatgctgactgtccgag tcgcgctggtactgagttgcatctgtccggcaaactccattgatggcaggcctcttgcggctgcagga attgtggttacaggagacaaagccgtcaacatatacacctcatcccagacaggatcaatcatagttaa gctcctcccgaatctgcccaaggataaggaggcatgtgcgaaagccccccttggatgcatacaacagga cattgaccactttgctcaccccccttggtgactctatccgtaggatacaagagtctgtgactacatct ggagggggggagacaggggcgccttataggcgccattattggcggtgtggctcttggggttgcaactgc cgcacaaataacagcggccgcagctctgatacaagccaaacaaaatgctgccaacatcctccgactta aagagagcattgccgcaaccaatgaggctgtgcatgaggtcactgacggattatcgcaactagcagtg gcagttgggaagatgcagcagtttgttaatgaccaatttaataaaacagctcaggaattagactgcat caaaattgcacagcaagttggtgtagagctcaacctgtacctaaccgaattgactacagtattcggac cacaaatcacttcacctgctttaaacaagctgactattcaggcactttacaatctagctggtggaaat atggattacttattgactaagttaggtgtagggaacaatcaactcagctcattaatcggtagcggctt aatcaccggtaaccctattctatacgactcacagactcaactcttgggtatacaggtaactctacctt cagtcgggaagctaaataatatgcgtgccacctacttggaaaccttatccgtaagcacaaccaggga tttgcctcggcacttgtcccaaaagtggtgacacaggtcggttctgtgatagaagaacttgacacctc atactgtatagaaactgacttacatttatattgtacaagaatagtaacgttccctatgtcccctggta tttattcctgcttgagcggcaatacgtcggcctgtatgtactcaaagaccgaaggcgcacttactaca ccatacatgactatcaaaggttcagtcatcgccaactgcaagatgacaacatgtagatgtgtaaaccc -continued cccgggtatcatatcgcaaaactatggagaagccgtgtctctaatagataaacaatcatgcaatgttt tatccttaggcgggataactttaaggctcagtggggaattcgatgtaacttatcagaagaatatctca atacaagattctcaagtaataataacaggcaatcttgatatctcaactgagcttgggaatgtcaacaa ctcgatcagtaatgctttgaataagttagaggaaagcaacagaaaactagacaaagtcaatgtcaaac tgactagcacatctgctctcattacctatatcgtgttgactatcatatctcttgtttttggtatactt agcctgattctagcatgctacctaatgtacaagcaaaaggcgcaacaaaagaccttattatggcttgg gaataatactctagatcagatgagagccactacaaaaatgtgaggatctctcgaggaattctagatcc cacgtcactattgtatactctatattatactctatgttatactctgtaatcctactcaataaacgtgt cacgcctgtgaaaccgtactaagtctcccgtgtcttcttatcaccatcaggtgacatcctcgcccagg ctgtcaatcatgccggtatcgattccagtagcaccggccccacgctgacaacccactcttgcagcgtt agcagcgcccctcttaacaagccgacccccaccagcgtcgcggttactaacactcctctccccgacct gcaactagtaagcttgcctccgattctagcattacatagccggtcagtagatcctgccattcggtagc gcaaccggctacatcttcaaacagtctcacaataaatgcatctctcgttcctgccaatccggaaccgg gcataccactcccgcctgccgatttaattctcacaattgggcgatgccggcggggcaaaacgaatgtg gatttggcaaaccgacacaggtctgctgtacggactaatatgggcacacccacatcattcttcagatg ctccatgcattgttctatgagaaagatccatagggtggaggcagcgtcacgagatcgcccaggcaatc gatcgcattcgtctagtaaagtgacgagagttatcatgcacacacccatgcccacgccttccgaataa ctggagctgtggaagatcggaaacgtctttttgactgccggtctcgtactactttcgcacaggtgtat acccggacgcgtactatatattttatatcatccaacgtccgaaattacatacgtggcggcgatggaag tagatgttgagtcttcgaaagtaagtgcctcgaatatgggtattgtctgtgaaaatatcgaaagcggt acgacggttgcagaaccgtcgatgtcgccagatactagtaacaatagcttcgataacgaagacttccg tgggcctgaatacgatgtggagataaataccagaaaatctgctaatcttgatcgtatggaatcttcgt gccgtgaacaacgagcggcgtgcgaacttcgaaagtgttcgtgtcctacgtctgccgtgcgcatgcaa tacagtattctttcatctctcgctccgggttcagagggtcatgtatatatatgtactagatacgggga cgcggaccaaaaaaaatgcatagtgaaggcagtcgttggaggaaagaatcccgggagggaagtggata ttttaaaaaccatctcacataaatcaattataaaattaatccatgcctataaatggaaaaatgttgtg tgtatggcaatgcgtgtatatcgttatgatcttttcacatatattgacggagtcggccctatgcccct tcaacagatgatctatattcaacgtggactactagaggcgctagcatacatacatgaaaggggcatca ttcaccgagacgtaaagacggagaatatattcttggataatcacgaaaatgcagttttgggtgacttc ggtgctgcatgccaactaggagattgtatagatacgccccaatgttacggttggagcggaactgtgga aacaaattcgccggaattatctgcacttgatccgtattgcacaaaaacagatatttggagtgccggat tggttctatatgagatggcaattaaaaatgtaccattgtttagtaagcaggtgaaaagttcgggatct cagctgagatccataatacggtgcatgcaagtgcatgaactggagtttccccgcaacgattctaccaa cctctgtaaacatttcaaacaatatgcggttcgtgtacgaccgccttataccattcctcgagttataa gaaatgggggggatgccaatggatgttgaatatgtcatttctaaaatgcttacgtttgaccaggagttc agaccttctgctaaggaaatattgaatatgcccctatttactaaggcgccgattaacctgcttaatat cacaccctctgacagtgtctaacggtatacaggcgggagcgggtcgtggcgtcatcatcaccacttga gaatttatattttgaattgttgattgataaattaacctgattcattgagaactgaaacgccatattgg tttcttggatatgtctacaacaattagttaaattgctatgttctactgcgagtaacatttgataagtt gtaagcgacgggcgactcatgtcgaagttgacgaatataaagtacataacgtgtttagaatacccaga atccgaatagtccgcgggggcgtcttctcgcgtgagtaccaaatactgagttgaacttgaaaatgcta -continued aatctgtgacactctttgtgtgatgattattgtcaccacttcgaagatggcttcgacattcatgatgt tctggtgtttgtttggaatcgtaatagcgcttgtttcgtccaagtctgacaacaaagaaaatctgaag aattatatcacggataagtcaaccaatattagaatacccacgccattatttgtatcaacggaaaactc ttatcccacaaaacatgtaatctacgatgaaaactgtggcttcgctgtactcaatcctataagtgacc ccaaatatgtccttttgagccagcttctaatgggaaggcgcaaatatgatgcgacggtcgcgtggttt gttctcggtaaaatgtgtgccagattaatatatttgcgcgaattttataactgctcgacaaatgagcc ttttggcacatgttctatgagctctcctggatggtgggacaggcgctacgtctcaaccagtttcattt ctcgcgacgaattacagctggtttttgcagcgccgtcccgagaattagatggtttatatacgcgcgta gtagttgtcaacggggactttactacggccgatataatgtttaatgttaaagtggcatgtgccttttc aaagactggaatagaagatgatacattatgcaaaccctttcatttctttgccaatgcaacattgcaca atttaaccatgattagatcggtaactcttcgagcgcacgaaagccatttaaaggaatgggtggcacgg agaggtggtaacgtccctgcagtgctacttgagtctaccatgtatcatgcatccaatctgcctagaaa tttcagggatttctacataaagtctccagatgattataagtataatcacctagatgggccatctgtaa tgctcatcactgacagacctagtgaagatttggatgggaggctcgttcaccaaagtgacatttttact actacaagtcctataaaacaggtccggtatgaagagcatcagtcacatacaaagcagtatcctgtaaa caaaatacaagctataatttttttgatagggttaggctcgttcattggaagcatattcgtagttttgg tagtatggattatacgcagatattgcaatggagcgcggagtgggggaacgcccccccagtcctcgccgg tatgtgtataccaggctatgatcacgtgtgaaacttgggcggacctgtatcatatgtacaccgtccct attcgtttatagccagtacgtgttatctgcacatagaggaacatgtgtcatactgggatcgcatgcat ggtatgtgtgactctaatattattctgtatcataataaaaacacagtgcatggtatatagaggatcgc tggtaagcactacggtagaccaatcggctcagattgcattctttggcatcgataccgttgttaattta tatggcaaagtcttgttcatgggagatcagtatttggaggaaatatactctggaacgatggaaatact caaatggaatcaagctaaccgctgctattctattgcgcatgcaacatattacgccgactgtcctataa tcagttctacggtattcagaggatgccgggacgccgttgtttatactaggccccacagcag SEQ ID NO 29: 1332-23.7(HVT/IBDV/ILT/NDV # 4 virus)
ILT/HVT UL54.5 region (12,248 bp)
ggcgcgccactggagaacggcatgaccgcaaaaggcgttgtagagatcgatcccacgaactctcaggc gatcgtgtcagtcgccataaacagcgacgatcgtctccaggatctgaacggttttcttctcaacgatc atcagtatatgaggaactgaacctgatatttagccgagggaaacgcaggttaaaaaccctatcaagcg attgcgattttcgcgtatctagtaaaaatagatgggcttcggtactagccttcgccgccaactctgaa tatgcccttcgtggacctcatataacatggcattgtttgttggatgcggggccggaattaagaagaac attcgaaatacgagcaaaaatttcggccctggcatgtgctgcgcgagaatcggtacttcggggagaaa gttttatcggagctttgggtagtgcagaggaaactctatcttggttgaaaatgcatgcgaccctgcac ttgattctggttaaccacgatccaatttttaagacggctggcgcggtcctagataacctccgcttaaa actagccccaatattgatgtgcagatataacacagaaaaacgatcaatggaagacatgctacggcggt catctcccgaagacatcaccgattccctaacaatgtgcctgattatgttatcgcgcattcgtcgtacc atgcgcaccgcaggaaataaatatagctatatgatagatccaatgaatcgtatgtctaattacactcc aggcgaatgtatgacaggtatattgcgatatattgacgaacatgctagaaggtgtcctgatcacatat gtaatttgtatatcacatgtacacttatgccgatgtatgtgcacgggcgatatttctattgtaattca tttttttgttagtaaactaccacaggctgtccggaaatctaagttaatgaataaagtagatggttaat actcattgcttagaattggactacttttaattctctttaatgttcgtattaaataaaaacatctttaa -continued taaacttcagcctcttcgcttattgtagaaattgagtattcaaaatcatgttcaaagccgtcttcgga gagtgtactcgccacggtggttggaacatcactatgtctacacgtcaaatttaagcacgtcaggtctg tcgaggacaagaaatggttaactagtgtttcaattattcttataaacgttaagcattgtaagcccccc ggccgtccgcagcaacaatttactagtatgccgtgggctccgggactatcacggatgtccaattcgca catgcatataatttttctagggtctctcatttcgagaaatcttcggggatccatcagcaatgcgggct gtagtcccgattcccgtttcaaatgaaggtgctccaacacggtcttcaaagcaaccggcataccagca aacacagactgcaactccccgctgcaatgattggttataaacagtaatctgtcttctggaagtatatt tcgcccgacaatccacggcgcccccaaagttaaaaaccatccatgtgtatttgcgtcttctctgttaa aagaatattgactggcattttcccgttgaccgccagatatccaaagtacagcacgatgttgcacggac gactttgcagtcaccagccttcctttccacccccccaccaacaaaatgtttatcgtaggacccatatc cgtaataaggatgggtctggcagcaaccccataggcgcctcggcgtggtagttctcgaggccttaatt aagtcgacggcagagtcgcagacgcccctattggacgtcaaaattgtagaggtgaagttttcaaacga tggcgaagtaacggcgacttgcgtttccaccgtcaaatctccctatagggtagaaactaattggaaag tagacctcgtagatgtaatggatgaaatttctgggaacagtcccgccggggtttttaacagtaatgag aaatggcagaaacagctgtactacagagtaaccgatggaagaacatcggtccagctaatgtgcctgtc gtgcacgagccattctccggaaccttactgtcttttcgacacgtctcttatagcgagggaaaaagata tcgcgccagagttatactttacctctgatccgcaaacggcatactgcacaataactctgccgtccggc gttgttccgagattcgaatggagccttaataatgtttcactgccggaatatttgacggccacgaccgt tgtttcgcataccgctggccaaagtacagtgtggaagagcagcgcgagagcaggcgaggcgtggattt ctggccggggaggcaatatatacgaatgcaccgtcctcatctcagacggcactcgcgttactacgcga aaggagaggtgcttaacaaacacatggattgcggtggaaaacggtgctgctcaggcgcagctgtattc actcttttctggacttgtgtcaggattatgcgggagcatatctgctttgtacgcaacgctatggaccg ccatttatttttgaggaatgctttttggactatcgtactgctttcttccttcgctagccagagcaccg ccgccgtcacgtacgactacattttaggccgtcgcgcgctcgacgcgctaaccataccggcggttggc ccgtataacagatacctcactagggtatcaagaggctgcgacgttgtcgagctcaacccgatttctaa cgtggacgacatgatatcggcggccaaagaaaaagagaagggggccctttcgaggcctccgtcgtct ggttctacgtgattaagggcgacgacggcgaggacaagtactgtccaatctatagaaaagagtacagg gaatgtggcgacgtacaactgctatctgaatgcgccgttcaatctgcacagatgtgggcagtggacta tgttcctagcacccttgtatcgcgaaatggcgcgggactgactatattctcccccactgctgcgctct ctggccaatacttgctgaccctgaaaatcgggagatttgcgcaaacagctctcgtaactctagaagtt aacgatcgctgtttaaagatcgggtcgcagcttaactttttaccgtcgaaatgctggacaacagaaca gtatcagactggatttcaaggcgaacacctttatccgatcgcagacaccaatacacgacacgcggacg acgtatatcggggatacgaagatattctgcagcgctggaataatttgctgaggaaaaagaatcctagc gcgccagaccctcgtccagatagcgtcccgcaagaaattcccgctgtaaccaagaaagcggaagggcg caccccggacgcagaaagcagcgaaaagaaggcccctccagaagactcggaggacgacatgcaggcag aggcttctggagaaaatcctgccgccctccccgaagacgacgaagtccccgaggacaccgagcacgat gatccaaactcggatcctgactattacaatgacatgcccgccgtgatcccggtggaggagactactaa aagttctaatgccgtctccatgcccatattcgcggcgttcgtagcctgcgcggtcgcgctcgtggggc tactggtttggagcatcgtaaaatgcgcgcgtagctaatcgagcctagaataggtggtttcttcctac atgccacgcctcacgctcataatataaatcacatggaatagcataccaatgcctattcattgggacgt tcgaaaagcatggcatcgctacttggaactctggctctccttgccgcgacgctcgcacccttcggcgc -continued gatgggaatcgtgatcactggaaatcacgtctccgccaggattgacgacgatcacatcgtgatcgtcg cgcctcgccccgaagctacaattcaactgcagctatttttcatgcctggccagagaccccacaaaccc tactcaggaaccgtccgcgtcgcgtttcggtctgatataacaaaccagtgctaccaggaacttagcga ggagcgctttgaaaattgcactcatcgatcgtcttctgtttttgtcggctgtaaagtgaccgagtaca cgttctccgcctcgaacagactaaccggacctccacacccgtttaagctcactatacgaaatcctcgt ccgaacgacagcgggatgttctacgtaattgttcggctagacgacaccaaagaacccattgacgtctt cgcgatccaactatcggtgtatcaattcgcgaacaccgccgcgactcgcggactctattccaaggctt cgtgtcgcaccttcggattacctaccgtccaacttgaggcctatctcaggaccgaggaaagttggcgc aactggcaagcgtacgttgccacggaggccacgacgaccagcgccgaggcgacaaccccgacgcccgt cactgcaaccagcgcctccgaacttgaagcggaacactttacctttccctggctagaaaatggcgtgg atcattacgaaccgacacccgcaaacgaaaattcaaacgttactgtccgtctcgggacaatgagccct acgctaattggggtaaccgtggctgccgtcgtgagcgcaacgatcggcctcgtcattgtaatttccat cgtcaccagaaacatgtgcaccccgcaccgaaaattagacacggtctcgcaagacgacgaagaacgtt cccaaactagaagggaatcgcgaaaatttggacccatggttgcgtgcgaaataaacaaggggggctgac caggatagtgaacttgtggaactggttgcgattgttaacccgtctgcgctaagctcgcccgactcaat aaaaatgtgattaagtctgaatgtggctctccaatcatttcgattctctaatctcccaatcctctcaa aaggggcagtatcggacacggactgggaggggcgtacacgatagttatatggtacagcagaggcctct gaacacttaggaggagaattcagccggggagagcccctgttgagtaggcttgggagcatattgcagga tgaacatgttagtgatagttctcgcctcttgtcttgcgcgcctaacttttgcgacgcgacacgtcctc tttttggaaggcactcaggctgtcctcggggaagatgatcccagaaacgttccggaagggactgtaat caaatggacaaaagtcctgcggaacgcgtgcaagatgaaggcggccgatgtctgctcttcgcctaact attgctttcatgatttaatttacgacggaggaaagaaagactgcccgcccgcgggacccctgtctgca aacctagtaattttactaaagcgcggcgaaagcttcccgggttaattaaggccctcgaggatacatcc aaagaggttgagtattctctctacacttcttgttaaatggaaagtgcatttgcttgttcttacaatcg gcccgagtctcgttcacagcgcctcgttcacacttaaaccacaaatagtctacaggctatatgggagc cagactgaaactcacatatgactaatattcgggggtgttagtcacgtgtagcccattgtgtgcatata acgatgttggacgcgtccttattcgcggtgtacttgatactatggcagcgagcatgggatattcatcc tcgtcatcgttaacatctctacgggttcagaatgtttggcatgtcgtcgatcctttgcccatcgttgc aaattacaagtccgatcgccatgaccgcgataagcctgtaccatgtggcattagggtgacatctcgat catacattataagaccaacgtgcgagtcttccaaagacctgcacgccttcttcttcggattgtcaacg ggttcttcagaatctatgcccatatctggcgttgagaccattgtgcgtttaatgaacaataaagcggc atgccatggaaaggagggctgcagatctccattttctcacgccactatcctggacgctgtagacgata attataccatgaatatagagggggtatgtttccactgccactgtgatgataagttttctccagattgt tggatatctgcattttctgctgccgaacaaacttcatcgctatgcaaagagatgcgtgtgtacacgcg ccgttgagtatacgggaaactaaatgttcatagaggtctttgggctatatgttattaaataaaataat tgaccagtgaacaatttgtttaatgttagtttattcaatgcattggttgcaaatattcattacttctc caatcccaggtcattctttagcgagatgatgttatgacattgctgtgaaaattactacaggatatatt tttaagatgcaggagtaacaatgtgcatagtaggcgtagttatcgcagacgtgcaacgcttcgcattt gagttaccgaagtgcccaacagtgctgcggttatggtttatgcgcacagaatccatgcatgtcctaat tgaaccatccgattttttcttttaatcgcgatcgttgtttgggcaactgcgttatttcagatctaaaaa -continued atttaccctttatgaccatcacatctctctggctcataccccgcttggataagatatcatgtagattc cgccctaagaaatgcaaactaacattattgtcggttccatatacacttccatcttgtccttcgaaaat aacaaactcgcgcaatagaccgtccgtacatgcatggccgatgtgtgtcaacatcattggtctgctag atcccgatgggacgaatcgtacagtcgtcgctccagcattggcaaaaatccccagataccctccatgc ggcaaatctaaattgcgaccccgaagagactgcaccaaagtcttatcgacgcacgctgatttttttga acagcgggagcccattatcttcagtggagcgtagacgggcgaggctaattatgtgacatagcaacact gcatgtatgtttttataaatcaataagagtacataatttattacgtatcatttccgtttgtaatatac tgtatacatcatccacactattagtcagcactagcgcgcgggcgcacgttacaatagcagcgtgcccg ttatctatattgtccgatatttacacataacatttcatcgacatgattaaatacctaagtactgcaca cagatgtttaatgtatatcgtcatataaattatatcgctaggacagacccaaacgacctttatcccaa acagtcagatcctcttctcaagtgtcgatttctgttatggaatatgcataccctggcccagaaattgc acgcacgagcgtagtgaatgcgtcattggttttacatttaaaggctaaatgcacaaattctttagacg acagcacatcgttaaatagcatctctagcgttcttatgaatgctaagcattggagtcctcctggtcgg ccacaataacagctgagtatcataccctgagctccggggttgtcgcacatagcggattcgtataaaca taggattttccgcgaatccatcagttgcaaaaatctgttaggctccatcaacaacgctggatttactt cagatccacgcgtaaagtaatggtgctcgaataccgtttttagagttgtcggcatttcaaggaacaaa gaattcatttcttcattgcaacgacgcgccagaaatcccaagacctctttgggtagtatgttcttgcc tataaaacacggcgttccaagtgccaggaaccacgcatgtgttactgttggggcgtattcagaaataa agcggggtttatgcggcttttgaagctcggatatccaaagtatcgcttgctgatgaacgagcgatgta gctgttacaaaacctcctttccatcctccagtcaacataatatttatcggcctacctatgtccgtaat aagtattggtcgggcaattattccgtatgaggtcttgcaggaataagctcttagggacagccagcttg gatatggtgcgaaacagaccttctcggcttcagaatgtcgctccgcagtctcttcgtgtcggtgcatc ttagatccaccatcaatgtgtgcagcattgactcccgcccgtcgaatattccttttgttacgatgcag taatgagcacgatcatgggcggggcgatgacgttctatttgcatgtctgcgaacaatttgcgtcagtc atacagctatggagtgggccatttctggccgtcaacttaaaaacgcgaaccgcagacatatgtatttg catgcaaagacgtatcttcgtatttctgggcatcttcaaatgctctggccaatatggcaatgaatttg gattcgtttgacgccgatggtatgcagtgcaaatgtgccaatagcccacatccgaaaaagttatttgt catacaagcaggtgttaagtagcaatcacataaaggcaccagacgcctcatggcatcataatgaatag ctccttctccccactggaaccactgacaaaatctgcgagtatattccgcaaaccacattttatttctc atagaaactaccctaaatccttttaacgggaagaagaatcctagatagtgcttgaagtcatgactgtt actgctgcaataacactgtatattatttataaattccgtttgtctaggtatctgatgtaggcattccg atccatttactattgcgtcttcacgaccaaatgggaatgcgccaaaatccccacacctcatcaccctg gaggcagattgtgtattattaatatccgccgattgaagcacaaaacggtacggtactgttcctaattc tggtatagattctatggtcaaaagtctgcatatccccgacattgccatgagatcacacagtccaagta gcatgtttattgagtcactcagactgtcaacgtccctcgccgcaccaccaatcgaaaataaagtatct acgcaagttatagctccgcattttctatcgctagcagcaatcgcgacgcaaaacataaaggccatgtt gggatttgaactctctgggggcttgttatcttctgcaccgtcgcagtcgcagttttccgaaatttat gtctaatatattttccggccgtgctccaatcggccgaaaagaatctgcgtattaccagactcattgac gggccgataaagaccataaaacaaaattcctgtgcactccctcctccagttttgccatcgtccaagtc ccgtaactttttttgcgtttcgaggagcaagcgttcgttatccctacccacacttgttttccaccgtt ttcttattataagcggttgtatcgccaacgcgtcaccgcaggttgtcacatacagtgatggcatactt -continued gaacgtgcaacaacgcgctcgctttgcaaatctaagtcattgaccatcaaatcgcgttgagaggatag ccaggcatctttttttcctagtatggtgacggtgcagccaccccaactcagttcttgtaaaaaaagcta ttggcaggaatttatgttctgaggtgcattctatatttatgagtccatcaaatgccattaaccagatt cgtatttttttcgctcgacccggcatcactatggatacaatacctttctatggcccatttcagctctcg aaccaaccacacggacaattgactaacataagtatgatctttatcacagtcgcacccatctgagttat atttatggcatccgagcgctcttactgtacggtcggatacacccatggtttttcctttatatagtcgg gttatagtctgtcgggtttggcggtagcacggagtagtttgatttttaagaatcgaaaaccggcttgg agagaccactgtcgaatatttgtccgtatactctacacgtgagtgttgtccattcctaggtatattca tctgttcggataccttcaattgctgttcaggcataaccttaaagcatatgttatgttgtacatcaaaa cttggtgagttatgttcgattgccgcgcataaagaatcgtacatgagcgtttctgctaacatactatc tatattctcacacgcccctgcatatactgttcctattccaaattcacgttttgccccatcggctatct gctaccaaaaagttgtaatataggtgccgctgggtgcgaaattttcatcagttgtattcctgataaac tgaatcactttacataatttttgccacatatctgcgtgcagccatagtatcgaacccgtgggctcgga gacgacagtgcgtacaatgggtattttacctttccccaacaaaataatggtatacaagttaggtccgt acctagaccttaatgtttccaattcttctgaatcactgcactctcgtaggggagtaacggtaataatt tcgtctctgagccccgttttgcgttgaaaactaatcacattagataatgtgcaatcggtttcttttat ccggatacatctaagtattatgacatcggtggtcattgtttccatcaacgaccatcttttacgatcgc ccatactactcatggacgttgtcggtgttgaaaaatcaccagaattgcaacggatctctgggtaccat gctgctgatggaattggcggttttaattgttgtttcagtctattattgctatctttggcggggttgaa taatgtgggggagagtgattgcaggaatccgaatgggtcaataaaacgaccgtgctccgttctgccg gcgccgatccgattgaagctatatacttcgcttctctccccacttttccaatttgatccggaaataaa acggccccggacaacagtatcgtacgatccggatccggatcctgcttgcctacagaagaatcaacatc tcgccccaatattctggtcaaaactggctcgctcatggcaacgcggacgtttcccccggtggccagtc ttaatggttaatgttcttttcggcaatcttatacatcagcgggttgcgtgaatactggtcacagttca gtcatttactacacaccagcaatacgacgacggacagtaccgtcccgacgaacgcgacgcccaaaatt gctatcgcgaccgcgtccgaggcgatgtcgtacgggcggtgcggggttggatcctcggcaaagagatc ctcgtaattcggcggtgggagcggagggtaaagacgcgggtggggatctccctccggaccgcgcgccg ggcgcggttcgaaaatgctttccgcctcgctcagtgtcaacgccaagtattcgggcgggctgggggcc ggaatatctcccgcgacttcttctatcggcgcggaattggagtcgcggtcgtggcgcgcttctagcgt cgtcaacggaagtccattttcggggtctcccggtgggcgttcagcgtccatcgtcgtatatgctctaa cacacgtctcgctatattaaaaaaaagaagagtatcggtcagtgtcgagtgtcgccgacaatgtcgcg agttctcggcgatttaatttttggaactgctccctatgaatcccgtaactgtagcgcccgcgcagaaa gccgccatcagaccaactacgtgtctgttcgatgtttgcccgccgatcgctttaccgattaaggttcc ggcgagaaatgacatgctcgatccaagaacaaagtttttcgcggtaaacaacaacatagttaccgtgc gagatggagaaaccacatctcccgaattagtagaggaaagcccgcgctgtcggtttggggacatatcg atctttttttgtgtttttcctaggacccttttgccagatcgtacaaagtcgcgtcttatgagcggacgt tcttactgcagctcggtaggagtggggcagggttagatttcgtcggcgtttcggcccccgtatgcgcc gcgccaccctcttcgccgagctctttatgcgcggtgggggtgagcgcttccggagttgcgatctccga tctcgagccgcagcccggcggtgtctctttcagtggagcgttagcgccatcatgtggttcgtggcggt ggaaaggctattatgtgttaggggagagaccacgtgatcggcatgcaaatgagcaaggcgaacgcgtc -continued agcgttcgcactgcgaaccaataatatatatattatactattggctttaggtgcgaacgtccggctag tccaatagcggggtcgcgtttcgtaccacgtgttatagaccgccctaaactcgcactcgggggtccgg ccgcgcccagacagggcggagacgtgccacaggggctttaaaacaccgcttcgggcaccgttcatctc ggcgcgcc SEQ ID NO 30: 435Vec60 (HVT/IBDV/ILT/NDV # 4 virus)
mCMV IEpro-VP2-SV40pA/hCMV IEpro-F-IE(term)/HVT US2 region
(13,068 bp)

aattccagactaaatgccccggcccaatttgtcaagtgtgcagtcacggaggcgtcgaccgtgtcccc ggcattaaacaggaaagcgttaaagtttttgaatgttaggtcacaggtacaaacataaatgtttgtac aaacaggtaacaggtacaaacataaatgccccggcataaatgtcccttacggcggatcgaaacgacat taggcatactcgggtaccattttgcattccgatcagcacggatgaaattaggcaggaatgcggtttat attatgcggcattggacaaacgatatggcattgattggcagtttatgaatgtcttcatgttgggcgta aacggattcctattggttcagaagacaacgacgatatatttagagagaaaaagctacccagcatagga taaacacacattgagcattgagagacataggtatcggtatggatgggaaaactacacacgtgaacacc aaacgacttatatactcgagcggtgatactactgagcaagaatgcactgcatctgagccactgaatga agactgtgatgaaaatgtgaccatcgatggaattggagaagaatatgcgcagttcttcatgtccccgc aatgggtcccaaatctacatcgcttgagcgaggataccaaaaaggtataccgatgtatggtttccaac agactcaattattttccctattatgaggcgttcaggcggtctttgtttgatatgtatatgctaggtcg gttggggcgtcgacttaagcgatctgactgggagactattatgcatctgtcaccaacgcaaagtcggc gtctacatagaactttaagatttgtggagcgtagaattatcccatctaacagttatatacgcacatcg ggccacgttccgccttcgagggcacttccgacagatacgaatttaaagatggatgaataattaaattg gaaagagtaactacattaatcgagcgtcatgacggcgtcccgtgaaaatgggaattttctactcgaaa caccgtgacatttgacagacctggaattgttattctgatatatagtgggtgtgtctggccggcaacat acataatgtgcatgcgaaaccactttttcagtgtacgctgacattgtgcaacacggaggggtagcatc tacatacaatatatgttgattaatgattggagaaaaaactatgcagctcgccgatcatatggctaact cgccttcgtctatatggcggaccccgcgggaaaaatcgacgtaccatctgatttacaacaccagtaat gaacatgtcgcatccctgcccagatctgtgcgcccattggcgcggatcgttgtgaatgccgccgaaac acttcaggtcggtatgagagccgggaggccgccatcagcaggagtttggcgagaggtgtttgatagaa tgatgacagccttccgtgaccacgagcctactgcgacatttaatgctgcaaatcccattagaaaaatg gtcgagacagttctacagaataatgaagagcccccgcggacgcatgctgaaatgggtaatcgccttat gaacattatgtactggtgttgcttgggacacgcaggacaatgctcgatatggcagttgtacgagacga atcaggccattttaagtttattagatgaagtggttatcggcacaacaaatcccttttgcaccctcgag caatactggaagccattatgcaccgcaatcgccaacaaggggacctcatcgcttgttgaggatgccaa agtggccgagtacctggttagcatgcgcaaattgatataacataggcacgctctgatgttacagacca caataccgcatacatttattgtaaggttgttaataaaggtttattctatgtaagactacaatactttc gacattgcttgtatacatattaaatactttctcaagttcctattacataaaatgggatctatcattac attcgttaagagtctggataattttactgtttgccagcttcgatcttggaacgtactgtggatagtgc cttacttggaatcgtgaaaatttgaaacgtccattatttggatatcttccggttgtcccatatcccgc cctggtaccgctcggataccttgcccgtatggattcgtattgacagtcgcgcaatcggggaccaacaa cgcgtgggtccacactcattcggaaattttccgatgattctgaatatttattgccgctcgttacgagt cgttggacatatctgtaatacatttcttcttctgaaggatcgctgcacatttgatctatacattggcc aggatgttcaagtctcagatgttgcattctggcacagcacaactttatggcatttccgatgtaatcgt -continued ccggcagccctgggggagttctatattcgcatattgggatggtaaggacaatagcagatctcgcaacc tccagggaggctataataacgtttttaaaggatggatttctcataaaaatctgtcgcaaattacactg agaatatcctttactagcgccgattgagagcatcgtcgtccaattttctaaatggaaagaaaacaagg cgggcaagagtgttccaaacattttcattttcggcgaatctctcaaatcccatggcgtgcaattgatt gcaaaattggcacttccgttcacgtttgtatctccaaactctaagacacttttaattgaaaaactacg ttctagtgtggaaagaaacctataggcagaccatagaactatttgacaccacatatctttttgtatgt caaactgaccatgatcgtatgttgctgaatgcactagggcaattcgctcgcgcgactccatacattga ataattccacacgtcagctcatcggttagcaaggtccagtagttgaagtcatttatttttccccgcgg ctggccaaatctacctctgggaatatccaagttgtcgaatatgatcgcaccggctctggtcatggtga aggaactgtagcataaagacgcaggtatcataggggtaatatttttttattcactcacatactaaaag taacgcatattagcaccatgtatgggctatcaattgacatttgcgtagcactacatcacgattatgta caacataatgggacaacatatggcaagtagatgcaatttcctcacactagttgggtttatctactatt gaattttcccctatctgtgatacacttgggagcctctacaagcatattgccatcatgtacgtttttat ctactgtcttaacgcccatgggaacggaggcgtcgtcgtcatgtattggacggcaacataggcagcaa cacaaattgcgtttaggtggggtgcatgtggactcgataccaagcccctgcagctggggaacgtctgg tggagagccgataatttgatatacgcacgccatattactgtcgttgaagtacgccttatcttctatgt tttcaaatttaggttcccaagtggacgtgagaagtgtttgtatctcacatggaatggcccaaggcatt ccagcccaggtgcctggtactttaatggcaaacaaacgttttggtagaggtattgattctattgcagt tctgcagatatctgcagccccgagtatccacaggctatacgatacgttatcggaggcaagctgcggcc gctctagaactagtggatcccccgggctgcagcccaatgtggaattcgcccttgcacattgttactcc tgcatcttaaaaatatatcctgtagtaattttcacagcaatgtcataacatcatctcgctaaagaatg acctgggattggagaagtaatgaatatttgcaaccaatgcattgaataaactaacattaaacgaattc actagtggatcccccaactccgcccgttttatgactagaaccaatagtttttaatgccaaatgcactg aaatcccctaatttgcaaagccaaacgcccccctatgtgagtaatacggggactttttacccaatttcc caagcggaaagcccccctaatacactcatatggcatatgaatcagcacggtcatgcactctaatggcgg cccatagggactttccacataggggggcgttcaccatttcccagcataggggtggtgactcaatggcct ttacccaagtacattgggtcaatgggaggtaagccaatgggtttttcccattactggcaagcacactg agtcaaatgggactttccactgggttttgcccaagtacattgggtcaatgggaggtgagccaatggga aaaacccattgctgccaagtacactgactcaatagggactttccaatgggtttttccattgttggcaa gcatataaggtcaatgtgggtgagtcaatagggactttccattgtattctgcccagtacataaggtca ataggggtgaatcaacaggaaagtcccattggagccaagtacactgcgtcaatagggactttccatt gggttttgcccagtacataaggtcaataggggatgagtcaatgggaaaaacccattggagccaagtac actgactcaatagggactttccattgggttttgcccagtacataaggtcaataggggtgagtcaaca ggaaagtcccattggagccaagtacattgagtcaatagggactttccaatgggttttgcccagtacat aaggtcaatgggaggtaagccaatgggtttttcccattactggcacgtatactgagtcattagggact ttccaatgggttttgcccagtacataaggtcaataggggtgaatcaacaggaaagtcccattggagcc aagtacactgagtcaatagggactttccattgggttttgcccagtacaaaaggtcaataggggtgag tcaatgggtttttcccattattggcacgtacataaggtcaataggggtgagtcattgggtttttccag ccaatttaattaaaacgccatgtactttcccaccattgacgtcaatgggctattgaaactaatgcaac gtgacctttaaacggtactttcccatagctgattaatgggaaagtaccgttctcgagccaatacacgt caatgggaagtgaaagggcagccaaaacgtaacaccgccccggttttcccctggaaattccatattgg -continued cacgcattctattggctgagctgcgttctacgtgggtataagaggcgcgaccagcgtcggtaccgtcg cagtcttcggtctgaccaccgtagaacgcagagctcctcgctgcaggcggccgctctagaactcgtcg atcgcagcgatgacaaacctgcaagatcaaacccaacagattgttccgttcatacggagccttctgat gccaacaaccggaccggcgtccattccggacgacaccctggagaagcacactctcaggtcagagacct cgacctacaatttgactgtgggggacacagggtcagggctaattgtctttttccctggattccctggc tcaattgtgggtgctcactacacactgcagagcaatgggaactacaagttcgatcagatgctcctgac tgcccagaacctaccggccagctacaactactgcagactagtgagtcggagtctcacagtgaggtcaa gcacactccctggtggcgtttatgcactaaacggcaccataaacgccgtgaccttccaaggaagcctg agtgaactgacagatgttagctacaatgggttgatgtctgcaacagccaacatcaacgacaaaattgg gaatgtcctggtaggggaaggggtcactgtcctcagcctacccacatcatatgatcttgggtatgtga ggcttggtgaccccattcccgctatagggcttgacccaaaaatggtagctacatgcgacagcagtgac aggcccagagtctacaccataactgcagccgatgattaccaattctcatcacagtaccaaccaggtgg ggtaacaatcacactgttctcagccaacattgatgctatcacaagcctcagcattgggggagagctcg tgtttcaaacaagcgtccaaggccttgtactgggcgccaccatctaccttataggctttgatgggact gcggtaatcaccagagctgtagccgcagataatgggctgacggccggcaccgacaatcttatgccatt caatcttgtcattccaaccaatgagataacccagccaatcacatccatcaaactggagatagtgacct ccaaaagtggtggtcaggcaggggatcagatgtcatggtcggcaagtgggagcctagcagtgacgatc catggtggcaactatccaggggccctccgtcccgtcacactagtagcctacgaaagagtggcaacagg atccgtcgttacggtcgctggggtgagtaacttcgagctgattccaaatcctgaactagcaaagaacc tggttacagaatacggccgatttgacccaggagccatgaactacacaaaattgatactgagtgagagg gaccgtcttggcatcaagaccgtctggccaacaagggagtacactgattttcgtgagtacttcatgga ggtggccgacctcaactctcccctgaagattgcaggagcatttggcttcaaagacataatccgggcta taaggaggtaagcttgatctagagcggccgcggggatccagacatgataagatacattgatgagtttg gacaaaccacaactagaatgcagtgaaaaaaatgctttatttgtgaaatttgtgatgctattgcttta tttgtaaccattataagctgcaataaacaagttaacaacaacaattgcattcattttatgtttcaggt tcagggggaggtgtgggaggttttttcggatcctctagagtcgacaattatttcatttaataacatat agcccaaagacctctatgaacatttagtttcccgtatactcaacggcgcgtgtacacacaagggcgaa ttccacagtggatatcaagcttaattaagtaccgagctcgaattggcgcgccaggtcaattccctggc attatgcccagtacatgaccttatgggactttcctacttggcagtacatctacgtattagtcatcgct attaccatggtgatgcggttttggcagtacatcaatgggcgtggatagcggtttgactcacggggatt tccaagtctccaccccattgacgtcaatgggagtttgttttggcaccaaaatcaacgggactttccaa aatgtcgtaacaactccgccccattgacgcaaatgggcggtaggcgtgtacggtgggaggtctatata agcagagctcgtttagtgaaccgtcagatcgcctggagacgccatccacgctgttttgacctccatag aagacaccgggcgcgccggatccatgggccccagaccttctaccaagaacccagtacctatgatgctg actgtccgagtcgcgctggtactgagttgcatctgtccggcaaactccattgatggcaggcctcttgc ggctgcaggaattgtggttacaggagacaaagccgtcaacatatacacctcatcccagacaggatcaa tcatagttaagctcctcccgaatctgcccaaggataaggaggcatgtgcgaaagccccccttggatgca tacaacaggacattgaccactttgctcacccccccttggtgactctatccgtaggatacaagagtctgt gactacatctggagggggggagacaggggcgccttataggcgccattattggcggtgtggctcttgggg ttgcaactgccgcacaaataacagcggccgcagctctgatacaagccaaacaaaatgctgccaacatc -continued ctccgacttaaagagagcattgccgcaaccaatgaggctgtgcatgaggtcactgacggattatcgca actagcagtggcagttgggaagatgcagcagtttgttaatgaccaatttaataaaacagctcaggaat tagactgcatcaaaattgcacagcaagttggtgtagagctcaacctgtacctaaccgaattgactaca gtattcggaccacaaatcacttcacctgctttaaacaagctgactattcaggcactttacaatctagc tggtggaaatatggattacttattgactaagttaggtgtagggaacaatcaactcagctcattaatcg gtagcggcttaatcaccggtaaccctattctatacgactcacagactcaactcttgggtatacaggta actctaccttcagtcgggaacctaaataatatgcgtgccacctacttggaaaccttatccgtaagcac aaccaggggatttgcctcggcacttgtcccaaaagtggtgacacaggtcggttctgtgatagaagaac ttgacacctcatactgtatagaaactgacttagatttatattgtacaagaatagtaacgttccctatg tcccctggtatttattcctgcttgagcggcaatacgtcggcctgtatgtactcaaagaccgaaggcgc acttactacaccatacatgactatcaaaggttcagtcatcgccaactgcaagatgacaacatgtagat gtgtaaacccccgggtatcatatcgcaaaactatggagaagccgtgtctctaatagataaacaatca tgcaatgttttatccttaggcgggataactttaaggctcagtggggaattcgatgtaacttatcagaa gaatatctcaatacaagattctcaagtaataataacaggcaatcttgatatctcaactgagcttggga atgtcaacaactcgatcagtaatgctttgaataagttagaggaaagcaacagaaaactagacaaagtc aatgtcaaactgactagcacatctgctctcattacctatatcgttttgactatcatatctcttgtttt tggtatacttagcccgattctagcatgctacctaatgtacaagcaaaaggcgcaacaaaagaccttat tatggcttgggaataatactctagatcagatgagagccactacaaaaatgtgaggatctctcgaggaa ttctagatcccacgtcactattgtatactctatattatactctatgttatactctgtaatcctactca ataaacgtgtcacgcctgtgaaaccgtactaagtctcccgtgtcttcttatcaccatcaggtgacatc ctcgcccaggctgtcaatcatgccggtatcgattccagtagcaccggccccacgctgacaacccactc ttgcagcgttagcagcgcccctcttaacaagccgacccccaccagcgtcgcggttactaacactcctc tccccgacctgcaactagtgcggccgcagcttgcctccgattctagcattacatagccggtcagtaga tcatgccattcggtagcgcaaccggctacatcttcaaacagtctcacgataaatgcatctctcgttcc tgccaatccggaaccgggcataccactcccgcctgccgatttaattctcacaattgggcgatgccggc ggggcaaaacgaatgtggatttggcaaaccgacacaggtctgctgtacggactaatatgggcacaccc acatcattcttcagatgctccatgcattgttctatgagaaagatccatagggtggaggcagcgtcacg agatcgcccaggcaatcgatcgcattcgtctagtaaagtgacgagagttatcatgcacacacccatgc ccacgccttccgaataactggagctgtggaagatcggaaacgtctttttgactgccggtctcgtacta ctttcgcacaggtgtatacccggacgcgtactatatatttatatcatccaacgtcccgaaattacat acgtggcggcgatggaagtagatgttgagtcttcgaaagtaagtgcctcgaatatgggtattgtctgt gaaaatatcgaaagcggtacgacggttgcagaaccgtcgatgtcgccagatactagtaacaatagctt cgataacgaagacttccgtgggcctgaatacgatgtggagataaataccagaaaatctgctaatcttg atcgtatggaatcttcgtgccgtgaacaacgagcggcgtgcgaacttcgaaagtgttcgtgtcctacg tctgccgtgcgcatgcaatacagtattctttcatctctcgctccgggttcagagggtcatgtatatat atgtactagatacggggacgcggaccaaaaaaaatgcatagtgaaggcagtcgttggaggaaagaatc ccgggagggaagtggatattttaaaaaccatctcacataaatcaattataaaattaatccatgcctat aaatggaaaaatgttgtgtgtatggcaatgcgtgtatatcgttatgatcttttcacatatattgacgg agtcggccctatgccccttcaacagatgatctatattcaacgtggactactagaggcgctagcataca tacatgaaaggggcatcattcaccgagacgtaaagacggagaatatattcttggataatcacgaaaat gcagttttgggtgacttcggtgctgcatgccaactaggagattgtatagatacgccccaatgttacgg -continued ttggagcggaactgtggaaacaaattcgccggaattatctgcacttgatccgtattgcacaaaaacag
atatttggagtgccggattggttctatatgagatggcaattaaaaatgtaccattgtttagtaagcag
gtgaaaagttcgggatctcagctgagatccataatacggtgcatgcaagtgcatgaactggagtttcc
ccgcaacgattctaccaacctctgtaaacatttcaaacaatatgcggttcgtgtacgaccgccttata
ccattcctcgagttataagaaatggggggatgccaatggatgttgaatatgtcatttctaaaatgctt
acgtttgaccaggagttcagaccttctgctaaggaaatattgaatatgcccctatttactaaggcgcc
gattaacctgcttaatatcacaccctctgacagtgtctaacggtatacaggcgggagcgggtcgtggc
gtcatcatcaccacttgagaatttatatttgaattgttgattgataaattaacctgattcattgaga
actgaaacgccatattggtttcttggatatgtctacaacaattagttaaattgctatgttctactgcg
agtaacatttgataagttgtaagagacgggcgactcatgtcgaagttgacgaatataaagtacataac
gtgtttagaatacccagaatccgaatagtccgcgggggcgtcttctcgcgtgagtaccaaatactgag
ttgaacttgaaaatgctaaatctgtgacactctttgtgtgatgattattgtcaccacttcgaagatgg
cttcgacattcatgatgttctggtgtttgtttggaatcgtaatagcgcttgtttcgtccaagtctgac
aacaaagaaaatctgaagaattatatcacggataagtcaaccaatattagaatacccacgccattatt
tgtatcaacggaaaactcttatcccacaaaacatgtaatctacgatgaaaactgtggcttcgctgtac
tcaatcctataagtgaccccaaatatgtccttttgagccagcttctaatgggaaggcgcaaatatgat
gcgacggtcgcgtggtttgttctcggtaaaatgtgtgccagattaatatatttgcgcgaattttataa
ctgctcgacaaatgagccttttggcacatgttctatgagctctcctggatggtgggacaggcgctacg
tctcaaccagtttcatttctcgcgacgaattacagctggttttgcagcgccgtcccgagaattagat
ggtttatatacgcgcgtagtagttgtcaacggggactttactacggccgatataatgtttaatgttaa
agtggcatgtgccttttcaaagactggaatagaagatgatacattatgcaaaccctttcatttctttg
ccaatgcaacattgcacaatttaaccatgattagatcggtaactcttcgagcgcacgaaagccattta
aaggaatgggtggcacggagaggtggtaacgtccctgcagtgctacttgagtctaccatgtatcatgc
atccaatctgcctagaaatttcagggatttctacataaagtctccagatgattataagtataatcacc
tagatgggccatctgtaatgctcatcactgacagacctagtgaagatttggatgggaggctcgttcac
caaagtgacattttttactactacaagtcctataaaacaggtccggtatgaagagcatcagtcacatac
aaagcagtatcctgtaaacaaaatacaagctataatttttttgatagggttaggctcgttcattggaa
gcatattcgtagttttggtagtatggattatacgcagatattgcaatggagcgcggagtgggggaacg
ccccccagtcctcgccggtatgtgtataccaggctatgatcacgtgtgaaacttgggcggacctgtat
catatgtacaccgtccctattcgtttatagccagtacgtgttatctgcacatagaggaacatgtgtca
tactgggatcgcatgcatggtatgtgtgactctaatattattctgtatcataataaaaacacagtgca
tggtatatagaggatcgctggtaagcactacggtagaccaatcggctcagattgcattctttggcatc
gataccgttgttaatttatatggcaaagtcttgttcatgggagatcagtatttggaggaaatatactc
tggaacgatggaaatactcaaatggaatcaagctaaccgctgctattctattgcgcatgcaacatatt
acgccgactgtcctataatcagttctacggtattcagaggatgccgggacgccgttgtttatactagg
ccccacagcaga SEQ ID NO 31: 1332-29.4 (HVT/IBDV/ILT/NDV #5 virus)
ILT/hCMV IEpro-F-IEpA(term)/HVT UL54.5 region (14,598 bp)
cgcgccactggagaacggcatgaccgcaaaaggcgttgtagagatcgatcccacgaactctcaggcga
tcgtgtcagtcgccataaacagcgacgatcgtctccaggatctgaacggttttcttctcaacgatcat
cagtatatgaggaactgaacctgatatttagccgagggaaacgcaggttaaaaaccctatcaagcgat -continued tgcgattttcgcgtatctagtaaaaatagatgggcttcggtactagccttcgccgccaactctgaata tgcccttcgtggacctcatataacatggcattgtttgttggatgcggggccggaattaagaagaacat tcgaaatacgagcaaaaatttcggccctggcatgtgctgcgcgagaatcggtacttcggggagaaagt tttatcggagctttgggtagtgcagaggaaactctatcttggttgaaaatgcatgcgaccctgcactt gattctggttaaccacgatccaatttttaagacggctggcgcggtcctagataacctccgcttaaaac tagccccaatattgatgtgcagatataacacagaaaaacgatcaatggaagacatgctacggcggtca tctcccgaagacatcaccgattccctaacaatgtgcctgattatgttatcgcgcattcgtcgtaccat gcgcaccgcaggaaataaatatagctatatgatagatccaatgaatcgtatgtctaattacactccag gcgaatgtatgacaggtatattgcgatatattgacgaacatgctagaaggtgtcctgatcacatatgt aatttgtatatcacatgtacacttatgccgatgtatgtgcacgggcgatatttctattgtaattcatt tttttgttagtaaactaccacaggctgtccggaaatctaagttaatgaataaagtagatggttaatac tcattgcttagaattggactacttttaattctctttaatgttcgtattaaataaaaacatctttaata aacttcagcctcttcgcttattgtagaaattgagtattcaaaatcatgttcaaagccgtcttcggaga gtgtactcgccacggtggttggaacatcactatgtctacacgtcaaatttaagcacgtcaggtctgtc gaggacaagaaatggttaactagtgtttcaattattcttataaacgttaagcattgtaagcccccccgg ccgtccgcagcaacaatttactagtatgccgtgggctccgggactatcacggatgtccaattcgcaca tgcatataatttttctagggtctctcatttcgagaaatcttcggggatccatcagcaatgcgggctgt agtcccgattcccgtttcaaatgaaggtgctccaacacggtcttcaaagcaaccggcataccagcaaa cacagactgcaactccccgctgcaatgattggttataaacagtaatctgtcttctggaagtatatttc gcccgacaatccacggcgcccccaaagttaaaaaccatccatgtgtatttgcgtcttctctgttaaaa gaatattgactggcattttcccgttgaccgccagatatccaaagtacagcacgatgttgcacggacga ctttgcagtcaccagccttcctttccacccccccaccaacaaaatgtttatcgtaggacccatatccg taataaggatgggtctggcagcaaccccataggcgcctcggcgtggtagttctcgaggccttaattaa gtcgacggcagagtcgcagacgcccctattggacgtcaaaattgtagaggtgaagttttcaaacgatg gcgaagtaacggcgacttgcgtttccaccgtcaaatctccctatagggtagaaactaattggaaagta gacctcgtagatgtaatggatgaaatttctgggaacagtcccgccggggtttttaacagtaatgagaa atggcagaaacagctgtactacagagtaaccgatggaagaacatcggtccagctaatgtgcctgtcgt gcacgagccattctccggaaccttactgtcttttcgacacgtctcttatagcgagggaaaaagatatc gcgccagagttatactttacctctgatccgcaaacggcatactgcacaataactctgccgtccggcgt tgttccgagattcgaatggagccttaataatgtttcactgccggaatatttgacggccacgaccgttg tttcgcataccgctggccaaagtacagtgtggaagagcagcgcgagagcaggcgaggcgtggatttct ggccggggaggcaatatatacgaatgcaccgtcctcatctcagacggcactcgcgttactacgcgaaa ggagaggtgcttaacaaacacatggattgcggtggaaaacggtgctgctcaggcgcagctgtattcac tcttttctggacttgtgtcaggattatgcgggagcatatctgctttgtacgcaacgctatggaccgcc atttatttttgaggaatgctttttggactatcgtactgctttcttccttcgctagccagagcaccgcc gccgtcacgtacgactacattttaggccgtcgcgcgctcgacgcgctaaccataccggcggttggccc gtataacagatacctcactagggtatcaagaggctgcgacgttgtcgagctcaacccgatttctaacg tggacgacatgatatcggcggccaaagaaaaagagaagggggccctttcgaggcctccgtcgtctgg ttctacgtgattaagggcgacgacggcgaggacaagtactgtccaatctatagaaaagagtacaggga atgtggcgacgtacaactgctatctgaatgcgccgttcaatctgcacagatgtgggcagtggactatg ttcctagcacccttgtatcgcgaaatggcgcgggactgactatattctcccccactgctgcgctctct -continued ggccaatacttgctgaccctgaaaatcgggagatttgcgcaaacagctctcgtaactctagaagttaa
cgatcgctgtttaaagatcgggtcgcagcttaactttttaccgtcgaaatgctggacaacagaacagt
atcagactggatttcaaggcgaacacctttatccgatcgcagacaccaatacacgacacgcggacgac
gtatatcggggatacgaagatattctgcagcgctggaataatttgctgaggaaaaagaatcctagcgc
gccagaccctcgtccagatagcgtcccgcaagaaattcccgctgtaaccaagaaagcggaagggcgca
ccccggacgcagaaagcagcgaaaagaaggcccctccagaagactcggaggacgacatgcaggcagag
gcttctggagaaaatcctgccgccctccccgaagacgacgaagtccccgaggacaccgagcacgatga
tccaaactcggatcctgactattacaatgacatgcccgccgtgatcccggtggaggagactactaaaa
gttctaatgccgtctccatgcccatattcgcggcgttcgtagcctgcgcggtcgcgctcgtggggcta
ctggtttggagcatcgtaaaatgcgcgcgtagctaatcgagcctagaataggtggtttcttcctacat
gccacgcctcacgctcataatataaatcacatggaatagcataccaatgcctattcattgggacgttc
gaaaagcatggcatcgctacttggaactctggctctccttgccgcgacgctcgcaccccttcggcgcga
tgggaatcgtgatcactggaaatcacgtctccgccaggattgacgacgatcacatcgtgatcgtcgcg
cctcgccccgaagctacaattcaactgcagctatttttcatgcctggccagagaccccacaaacccta
ctcaggaaccgtccgcgtcgcgtttcggtctgatataacaaaccagtgctaccaggaacttagcgagg
agcgctttgaaaattgcactcatcgatcgtcttctgtttttgtcggctgtaaagtgaccgagtacacg
ttctccgcctcgaacagactaaccggacctccacacccgtttaagctcactatacgaaatcctcgtcc
gaacgacagcgggatgttctacgtaattgttcggctagacgacaccaaagaacccattgacgtcttcg
cgatccaactatcggtgtatcaattcgcgaacaccgccgcgactcgcggactctattccaaggcttcg
tgtcgcaccttcggattacctaccgtccaacttgaggcctatctcaggaccgaggaaagttggcgcaa
ctggcaagcgtacgttgccacggaggccacgacgaccagcgccgaggcgacaaccccgacgcccgtca
ctgcaaccagcgcctccgaacttgaagcggaacactttacctttccctggctagaaaatggcgtggat
cattacgaaccgacacccgcaaacgaaaattcaaacgttactgtccgtctcgggacaatgagccctac
gctaattggggtaaccgtggctgccgtcgtgagcgcaacgatcggcctcgtcattgtaatttccatcg
tcaccagaaacatgtgcaccccgcaccgaaaattagacacggtctcgcaagacgacgaagaacgttcc
caaactagaagggaatcgcgaaaatttggacccatggttgcgtgcgaaataaacaagggggctgacca
ggatagtgaacttgtggaactggttgcgattgttaacccgtctgcgctaagctcgcccgactcaataa
aaatgtgattaagtctgaatgtggctctccaatcatttcgattctctaatctcccaatcctctcaaaa
ggggcagtatcggacacggactgggaggggcgtacacgatagttatatggtacagcagaggcctctga
acacttaggaggagaattcagccggggagaacccctgttgagtaagcttgggagcatattgcaggatg
aacatgttagtgatagttctcgcctcttgtcttgcgcgcctaacttttgcgacgcgacacgtcctctt
tttggaaggcactcaggctgtcctcggggaagatgatcccagaaacgttccggaagggactgtaatca
aatggacaaaagtcctgcggaacgcgtgcaagatgaaggcggccgatgtctgctcttcgcctaactat
tgctttcatgatttaatttacgacggaggaaagaaagactgcccgcccgcgggacccctgtctgcaaa
cctggtaattttactaaagcgcggcgaaagcttcgcgccaggtcaattccctggcattatgcccagta
catgaccttatgggactttcctacttggcagtacatctacgtattagtcatcgctattaccatggtga
tgcggttttggcagtacatcaatgggcgtggatagcggtttgactcacggggatttccaagtctccac
cccattgacgtcaatgggagtttgttttggcaccaaaatcaacgggactttccaaaatgtcgtaacaa
ctccgccccattgacgcaaatgggcggtagcgtgtacggtgggaggtctatataagcagagctcgttt
agtgaaccgtcagatcgcctggagacgccatccacgctgttttgacctccatagaagacaccggttgc -continued gccgccaccatgggccccagaccttctaccaagaacccagtacctatgatgctgactgtccgagtcgc gctggtactgagttgcatctgtccggcaaactccattgatggcaggcctcttgcggctgcaggaattg tggttacaggagacaaagccgtcaacatatacacctcatcccagacaggatcaatcatagttaagctc ctcccgaatctgcccaaggataaggaggcatgtgcgaaagccccttggatgcatacaacaggacatt gaccactttgctcaccccccttggtgactctatccgtaggatacaagagtctgtgactacatctggag gggggagacaggggcgccttataggcgccattattggcggtgtggctcttggggttgcaactgccgca caaataacagcggccgcagctctgatacaagccaaacaaaatgctgccaacatcctccgacttaaaga gagcattgccgcaaccaatgaggctgtgcatgaggtcactgacggattatcgcaactagcagtggcag ttgggaagatgcagcagtttgttaatgaccaatttaataaaacagctcaggaattagactgcatcaaa attgcacagcaagttggtgtagagctcaacctgtacctaaccgaattgactacagtattcggaccaca aatcacttcacctgctttaaacaagctgactattcaggcactttacaatctagctggtggaaatatgg attacttattgactaagttaggtgtagggaacaatcaactcagctcattaatcggtagcggcttaatc accggtaaccctattctatacgactcacagactcaactcttgggtatacaggtaactctaccttcagt cgggaagctaaataatatgcgtgccacctacttggaaaccttatccgtaagcacaaccaggggatttg cctcggcacttgtcccaaaagtggtgacacaggtcggttctgtgatagaagaacttgacacctcatac tgtatagaaactgacttacatttatattgtacaagaatagtaacgttccctatgtcccctggtattta ttcctgcttgagcggcaatacgtcggcctgtatgtactcaaagaccgaaggcgcacttactacaccat acatgactatcaaaggttcagtcatcgccaactgcaagatgacaacatgtagatgtgtaaaccccccg ggtatcatatcgcaaaactatggagaagccgtgtctctaatagataaacaatcatgcaatgttttatc cttaggcgggataactttaaggctcagtggggaattcgatgtaacttatcagaagaatatctcaatac aagattctcaagtaataataacaggcaatcttgatatctcaactgagcttgggaatgtcaacaactcg atcagtaatgctttgaataagttagaggaaagcaacagaaaactagacaaagtcaatgtcaaactgac tagcacatctgctctcattacctatatcgtgttgactatcatatctcttgtttttggtatacttagcc tgattctagcatgctacctaatgtacaagcaaaaggcgcaacaaaagaccttattatggcttgggaat aatactctagatcagatgagagccactacaaaaatgtgaggatctctcgaggaattctagatcccacg tcactattgtatactctatattatactctatgttatactctgtaatcctactcaataaacgtgtcacg cctgtgaaaccgtactaagtctcccgtgtcttcttatcaccatcaggtgacatcctcgcccaggctgt caatcatgccggtatcgattccagtagcaccggccccacgctgacaacccactcttgcagcgttagca gcgcccctcttaacaagccgaccccccaccagcgtcgcggttactaacactcctctccccgacctgcaa ctagtaagcttcccgggttaattaaggccctcgaggatacatccaaagaggttgagtattctctctac acttcttgttaaatggaaagtgcatttgcttgttcttacaatcggcccgagtctcgttcacagcgcct cgttcacacttaaaccacaaatagtctacaggctatatgggagccagactgaaactcacatatgacta atattcgggggtgttagtcacgtgtagcccattgtgtgcatataacgatgttggacgcgtccttattc gcggtgtacttgatactatggcagcgagcatgggatattcatcctcgtcatcgttaacatctctacgg gttcagaatgtttggcatgtcgtcgatcctttgcccatcgttgcaaattacaagtccgatcgccatga ccgcgataagcctgtaccatgtggcattagggtgacatctcgatcatacattataagaccaacgtgcg agtcttccaaagacctgcacgccttcttcttcggattgtcaacgggttcttcagaatctatgcccata tctggcgttgagaccattgtgcgtttaatgaacaataaagcggcatgccatggaaaggagggctgcag atctccattttctcacgccactatcctggacgctgtagacgataattataccatgaatatagaggggg tatgtttccactgccactgtgatgataagttttctccagattgttggatatctgcattttctgctgcc gaacaaacttcatcgctatgcaaagagatgcgtgtgtacacgcgccgttgagtatacgggaaactaaa -continued tgttcatagaggtctttgggctatatgttattaaataaaataattgaccagtgaacaatttgtttaat gttagtttattcaatgcattggttgcaaatattcattacttctccaatcccaggtcattctttagcga gatgatgttatgacattgctgtgaaaattactacaggatatatttttaagatgcaggagtaacaatgt gcatagtaggcgtagttatcgcagacgtgcaacgcttcacatttgagttaccgaagtgcccaacagtg ctgcggttatggtttatgcgcacagaatccatgcatgtcctaattgaaccatccgattttcttttaa tcgcgatcgttgtttgggcaactgcgttatttcagatctaaaaatttaccctttatgaccatcacat ctctctggctcataccccgcttggataagatatcatgtagattccgccctaagaaatgcaaactaaca ttattgtcggttccatatacacttccatcttgtccttcgaaaataacaaactcgcgcaatagaccgtc cgtacatgcatggccgatgtgtgtcaacatcattggtctgctagatcccgatgggacgaatcgtacag tcgtcgctccagcattggcaaaaatccccagataccctccatgcggcaaatctaaattgcgaccccga agagactgcaccaaagtcttatcgacgcacgctgatttttttgaacagcgggagcccattatcttcag tggagcgtagacgggcgaggctaattatgtgacatagcaacactgcatgtatgtttttataaatcaat aagagtacataatttattacgtatcatttccgtttgtaatatactgtatacatcatccacactattag tcagcactagcgcgcgggcgcacgttacaatagcagcgtgcccgttatctatattgtccgatatttac acataacatttcatcgacatgattaaatacctaagtactgcacacagatgtttaatgtatatcgtcat ataaattatatcgctaggacagacccaaacgacctttatcccaaacagtcagatcctcttctcaagtg tcgatttctgttatggaatatgcataccctggcccagaaattgcacgcacgagcgtagtgaatgcgtc attggttttacatttaaaggctaaatgcacaaattctttagacgacagcacatcgttaaatagcatct ctagcgttcttatgaatgctaagcattggagtcctcctggtcggccacaataacagctgagtatcata ccctgagctccggggttgtcgcacatagcggattcgtataaacataggattttccgcgaatccatcag ttgcaaaaatctgttaggctccatcaacaacgctggatttacttcagatccacgcgtaaagtaatggt gctcgaataccgtttttagagttgtcggcatttcaaggaacaaagaattcatttcttcattgcaacga cgcgccagaaatcccaagacctctttgggtagtatgttcttgcctataaaacacggcgttccaagtgc caggaaccacgcatgtgttactgttggggcgtattcagaaataaagcggggtttatgcggcttttgaa gctcggatatccaaagtatcgcttgctgatgaacgagcgatgtagctgttacaaaacctcctttccat cctccagtcaacataatatttatcggcctacctatgtccgtaataagtattggtcgggcaattattcc gtatgaggtcttgcaggaataagctcttagggacagccagcttggatatggtgcgaaacagaccttct cggcttcagaatgtcgctccgcagtctcttcgtgtcggtgcatcttagatccaccatcaatgtgtgca gcattgactcccgcccgtcgaatattccttttgttacgatgcagtaatgagcacgatcatgggcgggg cgatgacgttctatttgcatgtctgcgaacaatttgcgtcagtcatacagctatggagtgggccattt ctggccgtcaacttaaaaacgcgaaccgcagacatatgtatttgcatgcaaagacgtatcttcgtatt tctgggcatcttcaaatgctctggccaatatggcaatgaatttggattcgtttgacgccgatggtatg cagtgcaaatgtgccaatagcccacatccgaaaaagttatttgtcatacaagcaggtgttaagtagca atcacataaaggcaccagacgcctcatggcatcataatgaatagctccttctccccactggaaccact gacaaaatctgcgagtatattccgcaaaccacattttatttctcatagaaactaccctaaatcctttt aacgggaagaagaatcctagatagtgcttgaagtcatgactgttactgctgcaataacactgtatatt atttataaattccgtttgtctaggtatctgatgtaggcattccgatccctttactattgcgtcttcac gaccaaatgggaatgcgccaaaatccccacacctcatcaccctggaggcagattgtgtattattaata tccgccgattgaagcacaaaacggtacggtactgttcctaattctggtatagattctatggtcaaaag tctgcatatccccgacattgccatgagatcacacagtccaagtagcatgtttattgagtcactcagac -continued tgtcaacgtccctcgccgcaccaccaatcgaaaataaagtatctacgcaagttatagctccgcatttt ctatcgctagcagcaatcgcgacgcaaaacataaaggccatgttgggatttgaactctctgggggct tgttatcttctgcaccgtcgcagtcgcagttttccgaaatttatgtctaatatattttccggccgtgc tccaatcggccgaaaagaatctgcgtattaccagactcattgacgggccgataaagaccataaaacaa aattcctgtgcactccctcctccagttttgccatcgtccaagtcccgtaactttttttgcgtttcgag gagcaagcgttcgttatccctacccacacttgttttccaccgttttcttattataagcggttgtatcg ccaacgcgtcaccgcaggttgtcacatacagtgatggcatacttgaacgtgcaacaacgcgctcgctt tgcaaatctaagtcattgaccatcaaatcgcgttgagaggatagccaggcatctttttttcctagtatg gtgacggtgcagccaccccaactcagttcttgtaaaaaaagctattggcgggaatttatgttctgagg tgcattctatatttatgagtccatcaaatgccattaaccagattcgtatttttttcgctcgacccggca tcactatggatacaatacctttctatggcccatttcagctctcgaaccaaccacacggacaattgact aacataagtatgatctttatcacagtcgcacccatctgagttatatttatggcatccgagcgctctta ctgtacggtcggatacacccatggtttttcctttatatagtcgggttatagtctgtcgggtttggcgg tagcacggagtagtttgatttttaagaatcgaaaaccggcttggagagaccactgtcgaatatttgtc cgtatactctacacgtgagtgttgtccattcctaggtatattcatctgttcggataccttcaattgct gttcaggcataaccttaaagcatatgttatgttgtacatcaaaacttggtgagttatgttcgattgcc gcgcataaagaatcgtacatgagcgtttctgctaacatactatctatattctcacacgcccctgcata tactgttcctattccaaattcacgttttgccccatcggctatctgctcccaaaaagttgtaatatagg tgccgctgggtgcgaaattttcatcagttgtattcctgataaactgaatcactttacataatttttgc cacatatctgcgtgcagccatagtatcgaacccgtgggctcggagacgacagtgcgtacaatgggtat tttacctttccccaacaaaataatggtatacaagttaggtccgtacctagaccttaatgtttccaatt cttctgaatcactgcactctcgtaggggagtaacggtaataatttcgtctctgagccccgttttgcgt tgaaaactaatcacattagataatgtgcaatcggtttcttttatccggatacatctaagtattatgac atcggtggtcattgtttccatcaacgaccatcttttacgatcgcccatactactcatggacgttgtcg gtgttgaaaaatcaccagaattgcaacggatctctgggtaccatgctgctgatggaattggcggtttt aattgttgtttcagtctattattgctatctttggcggggttgaataatgtggggggagagtgattgca ggaatccgaatgggtcaataaaacgaccgtgctccgttctgccggcgccgatccgattgaagctatat acttcgcttctctccccacttttccaatttgatccggaaataaaacggccccggacaacagtatcgta cgatccggatccggatcctgcttgcctacagaagaatcaacatctcgccccaatattctggtcaaaac tggctcgctcatggcaacgcggacgtttcccccggtggccagtcttaatggttaatgttcttttcggc aatcttatacatcagcgggttgcgtgaatactggtcacagttcagtcatttactacacaccagcaata cgacgacggacagtaccgtcccgacgaacgcgacgcccaaaattgctatcgcgaccgcgtccgaggcg atgtcgtacgggcggtgcggggttggatcctcggcaaagagatcctcgtaattcggcggtgggagcgg agggtaaagacgcgggtggggatctccctccggaccgcgcgccgggcgcggttcgaaaatgctttccg cctcgctcagtgtcaacgccaagtattcgggcgggctgggggccggaatatctcccgcgacttcttct atcggcgcggaattggagtcgcggtcgtggcgcgcttctagcgtcgtcaacggaagtccattttcggg gtctcccggtgggcgttcagcgtccatcgtcgtatatgctctaacacacgtctcgctatattaaaaaa aagaagagtatcggtcagtgtcgagtgtcgccgacaatgtcgcgagttctcggcgatttaattttgg aactgctccctatgaatcccgtaactgtagcgcccgcgcagaaagccgccatcagaccaactacgtgt ctgttcgatgtttgcccgccgatcgctttaccgattaaggttccggcgagaaatgacatgctcgatcc aagaacaaagtttttcgcggtaaacaacaacatagttaccgtgcgagatggagaaaccacatctcccg -continued aattagtagaggaaagcccgcgctgtcggtttggggacatatcgatctttttgtgtttttcctagga ccctttgccagatcgtacaaagtcgcgtcttatgagcggacgttcttactgcagctcggtaggagtg gggcagggttagatttcgtcggcgtttcggcccccgtatgcgccgcgccaccctcttcgccgagctct ttatgcgcggtgggggtgagcgcttccggagttgcgatctccgatctcgagccgcagcccggcggtgt ctctttcagtggagcgttagcgccatcatgtggttcgtggcggtggaaaggctattatgtgttagggg agagaccacgtgatcggcatgcaaatgagcaaggcgaacgcgtcagcgttcgcactgcgaaccaataa tatatatattatactattggctttaggtgcgaacgtccggctagtccaatagcggggtcgcgtttcgt accacgtgttatagaccgccctaaactcgcactcgggggtccggccgcgcccagacagggcggagacg tgccacaggggctttaaaacaccgcttcgggcaccgttcatctcgg SEQ ID NO 32: 435Vec6 (HVT/IBDV/ILT/NDV #5)
mCMV IEpro-VP2-SV40pA/HVT US2 region (10,681 bp)
aattccagactaaatgccccggcccaatttgtcaagtgtgcagtcacggaggcgtcgaccgtgtcccc ggcattaaacaggaaagcgttaaagtttttgaatgttaggtcacaggtacaaacataaatgtttgtac aaacaggtaacaggtacaaacataaatgccccggcataaatgtcccttacggcggatcgaaacgacat taggcatactcgggtaccattttgcattccgatcagcacggatgaaattaggcaggaatgcggtttat attatgcggcattggacaaacgatatggcattgattggcagtttatgaatgtcttcatgttgggcgta aacggattcctattggttcagaagacaacgacgatatatttagagagaaaaagctacccagcatagga taaacacacattgagcattgagagacataggtatcggtatggatgggaaaactacacacgtgaacacc aaacgacttatatactcgagcggtgatactactgagcaagaatgcactgcatctgagccactgaatga agactgtgatgaaaatgtgaccatcgatggaattggagaagaatatgcgcagttcttcatgtccccgc aatgggtcccaaatctacatcgcttgagcgaggataccaaaaaggtataccgatgtatggtttccaac agactcaattattttccctattatgaggcgttcaggcggtctttgtttgatatgtatatgctaggtcg gttggggcgtcgacttaagcgatctgactgggagactattatgcatctgtcaccaacgcaaagtcggc gtctacatagaactttaagatttgtggagcgtagaattatcccatctaacagttatatacgcacatcg ggccacgttccgccttcgagggcacttccgacagatacgaatttaaagatggatgaataattaaattg gaaagagtaactacattaatcgagcgtcatgacggcgtcccgtgaaaatgggaattttctactcgaaa caccgtgacatttgacagacctggaattgttattctgatatatagtgggtgtgtctggccggcaacat acataatgtgcatgcgaaaccactttttcagtgtacgctgacattgtgcaacacggaggggtagcatc tacatacaatatatgttgattaatgattggagaaaaaactatgcagctcgccgatcatatggctaact cgccttcgtctatatggcggaccccgcgggaaaaatcgacgtaccatctgatttacaacaccagtaat gaacatgtcgcatccctgcccagatctgtgcgcccattggcgcggatcgttgtgaatgccgccgaaac acttcaggtcggtatgagagccgggaggccgccatcagcaggagtttggcgagaggtgtttgatagaa tgatgacagccttccgtgaccacgagcctactgcgacatttaatgctgcaaatcccattagaaaaatg gtcgagacagttctacagaataatgaagagccccgcggacgcatgctgaaatgggtaatcgccttat gaacattatgtactggtgttgcttgggacacgcaggacaatgctcgatatggcagttgtacgagacga atcaggccattttaagtttattagatgaagtggttatcggcacaacaaatcccttttgcaccctcgag caatactggaagccattatgcaccgcaatcgccaacaaggggacctcatcgcttgttgaggatgccaa agtggccgagtacctggttagcatgcgcaaattgatataacataggcacgctctgatgttacagacca caataccgcatacatttattgtaaggttgttaataaaggtttattctatgtaagactacaatactttc gacattgcttgtatacatattaaatactttctcaagttcctattacataaaatgggatctatcattac attcgttaagagtctggataattttactgtttgccagcttcgatcttggaacgtactgtggatagtgc -continued cttacttggaatcgtgaaaatttgaaacgtccattatttggatatcttccggttgtcccatatcccgc
cctggtaccgctcggataccttgcccgtatggattcgtattgacagtcgcgcaatcggggaccaacaa
cgcgtgggtccacactcattcggaaattttccgatgattctgaatatttattgccgctcgttacgagt
cgttggacatatctgtaatacatttcttcttctgaaggatcgctgcacatttgatctatacattggcc
aggatgttcaagtctcagatgttgcattctggcacagcacaactttatggcatttccgatgtaatcgt
ccggcagccctggggagttctatattcgcatattgggatggtaaggacaatagcagatctcgcaacc
tccagggaggctataataacgtttttaaaggatggatttctcataaaaatctgtcgcaaattacactg
agaatatcctttactagcgccgattgagagcatcgtcgtccaattttctaaatggaaagaaaacaagg
cgggcaagagtgttccaaacattttcattttcggcgaatctctcaaatcccatggcgtgcaattgatt
gcaaaattggcacttccgttcacgtttgtatctccaaactctaagacacttttaattgaaaaactacg
ttctagtgtggaaagaaacctataggcagaccatagaactatttgacaccacatatctttttgtatgt
caaactgaccatgatcgtatgttgctgaatgcactagggcaattcgctcgcgcgactccatacattga
ataattccacacgtcagctcatcggttagcaaggtccagtagttgaagtcatttatttttccccgcgg
ctggccaaatctacctctgggaatatccaagttgtcgaatatgatcgcaccggctctggtcatggtga
aggaactgtagcataaagacgcaggtatcataggggtaatatttttttattcactcacatactaaaag
taacgcatattagcaccatgtatgggctatcaattgacatttgcgtagcactacatcacgattatgta
caacataatgggacaacatatggcaagtagatgcaatttcctcacactagttgggtttatctactatt
gaattttcccctatctgtgatacacttgggagcctctacaagcatattgccatcatgtacgtttttat
ctactgtcttaacgcccatgggaacggaggcgtcgtcgtcatgtattggacggcaacataggcagcaa
cacaaattgcgtttaggtggggtgcatgtggactcgataccaagcccctgcagctggggaacgtctgg
tggagagccgataatttgatatacgcacgccatattactgtcgttgaagtacgccttatcttctatgt
tttcaaatttaggttcccaagtggacgtgagaagtgtttgtatctcacatggaatggcccaaggcatt
ccagcccaggtgcctggtactttaatggcaaacaaacgttttggtagaggtattgattctattgcagt
tctgcagatatctgcagccccgagtatccacaggctatacgatacgttatcggaggcaagctgcggcc
gctctagaactagtggatcccccgggctgcagcccaatgtggaattcgcccttgcacattgttactcc
tgcatcttaaaaatatatcctgtagtaattttcacagcaatgtcataacatcatctcgctaaagaatg
acctgggattggagaagtaatgaatatttgcaaccaatgcattgaataaactaacattaaacgaattc
actagtggatcccccaactccgcccgttttatgactagaaccaatagtttttaatgccaaatgcactg
aaatcccctaatttgcaaagccaaacgcccccctatgtgagtaatacggggactttttacccaatttcc
caagcggaaagccccctaatacactcatatggcatatgaatcagcacggtcatgcactctaatggcgg
cccatagggactttccacataggggggcgttcaccatttcccagcataggggtggtgactcaatggcct
ttacccaagtacattgggtcaatgggaggtaagccaatgggtttttcccattactggcaagcacactg
agtcaaatgggactttccactgggttttgcccaagtacattgggtcaatgggaggtgagccaatggga
aaaacccattgctgccaagtacactgactcaatagggactttccaatgggtttttccattgttggcaa
gcatataaggtcaatgtgggtgagtcaatagggactttccattgtattctgcccagtacataaggtca
atagggggtgaatcaacaggaaagtcccattggagccaagtacactgcgtcaatagggactttccatt
gggttttgcccagtacataaggtcaataggggatgagtcaatgggaaaaacccattggagccaagtac
actgactcaatagggactttccattgggttttgcccagtacataaggtcaatagggggtgagtcaaca
ggaaagtcccattggagccaagtacattgagtcaatagggactttccaatgggttttgcccagtacat
aaggtcaatgggaggtaagccaatgggtttttcccattactggcacgtatactgagtcattagggact
ttccaatgggttttgcccagtacataaggtcaataggggtgaatcaacaggaaagtcccattggagcc -continued aagtacactgagtcaatagggactttccattgggttttgcccagtacaaaaggtcaatagggggtgag tcaatgggtttttcccattattggcacgtacataaggtcaataggggtgagtcattgggtttttccag ccaatttaattaaaacgccatgtactttcccaccattgacgtcaatgggctattgaaactaatgcaac gtgacctttaaacggtactttcccatagctgattaatgggaaagtaccgttctcgagccaatacacgt caatgggaagtgaaagggcagccaaaacgtaacaccgccccggttttcccctggaaattccatattgg cacgcattctattggctgagctgcgttctacgtgggtataagaggcgcgaccagcgtcggtaccgtcg cagtcttcggtctgaccaccgtagaacgcagagctcctcgctgcaggcggccgctctagaactcgtcg atcgcagcgatgacaaacctgcaagatcaaacccaacagattgttccgttcatacggagccttctgat gccaacaaccggaccggcgtccattccggacgacaccctggagaagcacactctcaggtcagagacct cgacctacaatttgactgtgggggacacagggtcagggctaattgtctttttccctggattccctggc tcaattgtgggtgctcactacacactgcagagcaatgggaactacaagttcgatcagatgctcctgac tgcccagaacctaccggccagctacaactactgcagactagtgagtcggagtctcacagtgaggtcaa gcacactccctggtggcgtttatgcactaaacggcaccataaacgccgtgaccttccaaggaagcctg agtgaactgacagatgttagctacaatgggttgatgtctgcaacagccaacatcaacgacaaaattgg gaatgtcctggtaggggaaggggtcactgtcctcagcctacccacatcatatgatcttgggtatgtga ggcttggtgaccccattcccgctatagggcttgacccaaaaatggtagctacatgcgacagcagtgac aggcccagagtctacaccataactgcagccgatgattaccaattctcatcacagtaccaaccaggtgg ggtaacaatcacactgttctcagccaacattgatgctatcacaagcctcagcattgggggagagctcg tgtttcaaacaagcgtccaaggccttgtactgggcgccaccatctaccttataggctttgatgggact gcggtaatcaccagagctgtagccgcagataatgggctgacggccggcaccgacaatcttatgccatt caatcttgtcattccaaccaatgagataacccagccaatcacatccatcaaactggagatagtgacct ccaaaagtggtggtcaggcaggggatcagatgtcatggtcggcaagtgggagcctagcagtgacgatc catggtggcaactatccaggggccctccgtcccgtcacactagtagcctacgaaagagtggcaacagg atccgtcgttacggtcgctggggtgagtaacttcgagctgattccaaatcctgaactagcaaagaacc tggttacagaatacggccgatttgacccaggagccatgaactacacaaaattgatactgagtgagagg gaccgtcttggcatcaagaccgtctggccaacaagggagtacactgattttcgtgagtacttcatgga ggtggccgacctcaactctcccctgaagattgcaggagcatttggcttcaaagacataatccgggcta taaggaggtaagcttgatctagagcggccgcggggatccagacatgataagatacattgatgagtttg gacaaaccacaactagaatgcagtgaaaaaaatgctttatttgtgaaatttgtgatgctattgcttta tttgtaaccattataagctgcaataaacaagttaacaacaacaattgcattcattttatgtttcaggt tcagggggaggtgtgggaggttttttcggatcctctagagtcgacaattattttatttaataacatat agcccaaagacctctatgaacatttagtttcccgtatactcaacggcgcgtgtacacacaagggcgaa ttccacagtggatatcaagcttagcttgcctccgattctagcattacatagccggtcagtagatcctg ccattcggtagcgcaaccggctacatcttcaaacagtctcacgataaatgcatctctcgttcctgcca atccggaaccgggcataccactcccgcctgccgatttaattctcacaattgggcgatgccggcggggc aaaacgaatgtggatttggcaaaccgacacaggtctgctgtacggactaatatgggcacacccacatc attcttcagatgctccatgcattgttctatgagaaagatccatagggtggaggcagcgtcacgagatc gcccaggcaatcgatcgcattcgtctagtaaagtgacgagagttatcatgcacacacccatgcccacg ccttccgaataactggagctgtggaagatcggaaacgtctttttgactgccggtctcgtactactttc gcacaggtgtatacccggacgcgtactatatattttatatcatccaacgtccgaaattacatacgtgg -continued cggcgatggaagtagatgttgagtcttcgaaagtaagtgcctcgaatatgggtattgtctgtgaaaat
atcgaaagcggtacgacggttgcagaaccgtcgatgtcgccagatactagtaacaatagcttcgataa
cgaagacttccgtgggcctgaatacgatgtggagataaataccagaaaatctgctaatcttgatcgta
tggaatcttcgtgccgtgaacaacgagcggcgtgcgaacttcgaaagtgttcgtgtcctacgtctgcc
gtgcgcatgcaatacagtattctttcatctctcgctccgggttcagagggtcatgtatatatatgtac
tagatacggggacgcggaccaaaaaaaatgcatagtgaaggcagtcgttggaggaaagaatcccggga
gggaagtggatattttaaaaaccatctcacataaatcaattataaaattaatccatgcctataaatgg
aaaaatgttgtgtgtatggcaatgcgtgtatatcgttatgatcttttcacatatattgacggagtcgg
ccctatgccccttcaacagatgatctatattcaacgtggactactagaggcgctagcatacatacatg
aaaggggcatcattcaccgagacgtaaagacggagaatatattcttggataatcacgaaaatgcagtt
ttgggtgacttcggtgctgcatgccaactaggagattgtatagatacgccccaatgttacggttggag
cggaactgtggaaacaaattcgccggaattatctgcacttgatccgtattgcacaaaaacagatattt
ggagtgccggattggttctatatgagatggcaattaaaaatgtaccattgtttagtaagcaggtgaaa
agttcgggatctcagctgagatccataatacggtgcatgcaagtgcatgaactggagtttccccgcaa
cgattctaccaacctctgtaaacatttcaaacaatatgcggttcgtgtacgaccgccttataccattc
ctcgagttataagaaatgggggggatgccaatggatgttgaatatgtcatttctaaaatgcttacgttt
gaccaggagttcagaccttctgctaaggaaatattgaatatgcccctatttactaaggcgccgattaa
cctgcttaatatcacaccctctgacagtgtctaacggtatacaggcgggagcgggtcgtggcgtcatc
atcaccacttgagaatttatatttgaattgttgattgataaattaacctgattcattgagaactgaa
acgccatattggtttcttggatatgtctacaacaattagttaaattgctatgttctactgcgagtaac
atttgataagttgtaagagacgggcgactcatgtcgaagttgacgaatataaagtacataacgtgttt
agaatacccagaatccgaatagtccgcgggggcgtcttctcgcgtgagtaccaaatactgagttgaac
ttgaaaatgctaaatctgtgacactctttgtgtgatgattattgtcaccacttcgaagatggcttcga
cattcatgatgttctggtgtttgtttggaatcgtaatagcgcttgtttcgtccaagtctgacaacaaa
gaaaatctgaagaattatatcacggataagtcaaccaatattagaatacccacgccattatttgtatc
aacggaaaactcttatcccacaaaacatgtaatctacgatgaaaactgtggcttcgctgtactcaatc
ctataagtgacccaaatatgtccttttgagccagcttctaatgggaaggcgcaaatatgatgcgacg
gtcgcgtggtttgttctcggtaaaatgtgtgccagattaatatatttgcgcgaattttataactgctc
gacaaatgagccttttggcacatgttctatgagctctcctggatggtgggacaggcgctacgtctcaa
ccagtttcatttctcgcgacgaattacagctggtttttgcagcgccgtcccgagaattagatggttta
tatacgcgcgtagtagttgtcaacggggactttactacggccgatataatgtttaatgttaaagtggc
atgtgccttttcaaagactggaatagaagatgatacattatgcaaacccttcatttctttgccaatg
caacattgcacaatttaaccatgattagatcggtaactcttcgagcgcacgaaagccatttaaaggaa
tgggtggcacggagaggtggtaacgtccctgcagtgctacttgagtctaccatgtatcatgcatccaa
tctgcctagaaatttcagggatttctacataaagtctccagatgattataagtataatcacctagatg
ggccatctgtaatgctcatcactgacagacctagtgaagatttggatgggaggctcgttcaccaaagt
gacatttttactactacaagtcctataaaacaggtccggtatgaagagcatcagtcacatacaaagca
gtatcctgtaaacaaaatacaagctataatttttttgatagggttaggctcgttcattggaagcatat
tcgtagttttggtagtatggattatacgcagatattgcaatggagcgcggagtgggggaacgcccccc
agtcctcgccggtatgtgtataccaggctatgatcacgtgtgaaacttgggcggacctgtatcatatg
tacaccgtccctattcgtttatagccagtacgtgttatctgcacatagaggaacatgtgtcatactgg -continued gatcgcatgcatggtatgtgtgactctaatattattctgtatcataataaaaacacagtgcatggtat atagaggatcgctggtaagcactacggtagaccaatcggctcagattgcattctttggcatcgatacc gttgttaatttatatggcaaagtcttgttcatgggagatcagtatttggaggaaatatactctggaac gatggaaatactcaaatggaatcaagctaaccgctgctattctattgcgcatgcaacatattacgccg actgtcctataatcagttctacggtattcagaggatgccgggacgccgttgtttatactaggccccac agcag The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

It is further to be understood that all base sizes or amino acid sizes, and all molecular weight or molecular mass values, given for nucleic acids or polypeptides are approximate, and are provided for description.

We claim:

1. A recombinant herpesvirus of turkeys (rHVT) that comprises a first heterologous nucleic acid and a second heterologous nucleic acid;

wherein the first heterologous nucleic acid is located in a first nonessential site in the rHVT genome, and the second heterologous nucleic acid is located in a second nonessential site in the rHVT genome;

wherein the first nonessential site is the UL54.5 site and the second nonessential site is the US2 site;

wherein the first heterologous nucleic acid encodes an Infectious Bursal Disease Virus viral protein 2 (IBDV VP2), an Infectious Laryngotracheitis Virus glycoprotein D (ILTV gD) and an Infectious Laryngotracheitis Virus glycoprotein I (ILTV gI), and wherein the second heterologous encodes a Newcastle Disease Virus fusion protein (NDV F); and wherein the first heterologous nucleic acid is configured to be transcribed in the opposite direction relative to a UL54.5 gene of the rHVT.

2. The rHVT of claim 1, wherein the ILTV gD comprises an amino acid sequence that has greater than 90%, greater than 95%, greater than 98%, greater than 99%, or 100% identity to the amino acid sequence of SEQ ID NO: 2.

3. The rHVT of claim 1, wherein the ILTV gI comprises an amino acid sequence that has greater than 90%, greater than 95%, greater than 98%, greater than 99%, or 100% identity to the amino acid sequence of SEQ ID NO: 4.

4. The rHVT of claim 1, wherein the IBDV VP2 comprises an amino acid sequence that has greater than 90%, greater than 95%, greater than 98%, greater than 99%, or 100% identity to the amino acid sequence of SEQ ID NO: 6.

5. The rHVT of claim 1, wherein the NDV F comprises an amino acid sequence that has greater than 90%, greater than 95%, greater than 98%, greater than 99%, or 100% identity to the amino acid sequence of SEQ ID NO: 8 or SEQ ID NO: 10.

6. The rHVT of claim 1, wherein the ILTV gD comprises an amino acid sequence that has greater than 95% identity to the amino acid sequence of SEQ ID NO: 2; wherein the ILTV gI comprises an amino acid sequence that has greater than 95% identity to the amino acid sequence of SEQ ID NO: 4; wherein the IBDV VP2 comprises an amino acid sequence that has greater than 95% identity to the amino acid sequence of SEQ ID NO: 6; and wherein the NDV F comprises an amino acid sequence that has greater than 95% identity to the amino acid sequence of SEQ ID NO: 8 or SEQ ID NO: 10.

7. The rHVT of claim 6, wherein the coding sequence of the IBDV VP2 is operatively under the control of a murine cytomegalovirus immediate early 1 gene (mCMV-IE1) promoter; the coding sequence of the ILTV gD is operatively under the control of an endogenous ILTV gD promoter; the coding sequence of the ILTV gI is operatively under the control of an endogenous ILTV gI promoter; and the coding sequence of the NDV F is operatively under the control of a human cytomegalovirus immediate early 1 gene (hCMV-IE1) promoter.

8. A vaccine comprising the rHVT of claim 7.

9. A method for aiding in the protection of a chicken against a virus selected from the group consisting of Newcastle Disease Virus (NDV), Infectious Laryngotracheitis Virus (ILTV), Infectious Bursal Disease Virus (IBDV), Marek's Disease Virus (MDV) and any combination thereof comprising administering to the chicken the vaccine of claim 8.

10. A recombinant herpesvirus of turkeys (rHVT) that comprises a first heterologous nucleic acid that comprises the nucleotide sequence of SEQ ID NO: 21 and a second heterologous nucleic acid that comprises the nucleotide sequence of SEQ ID NO: 22, wherein the first heterologous nucleic acid comprises an Infectious Bursal Disease Virus viral protein 2 (IBDV VP2) gene, an Infectious Laryngotracheitis Virus glycoprotein D (ILTV gD) gene and an Infectious Laryngotracheitis Virus glycoprotein I (ILTV gI) gene configured to be transcribed in the opposite direction relative to a UL54.5 gene of the rHVT.

11. A vaccine comprising the rHVT of claim 10.

12. A method for aiding in the protection of a chicken against a virus selected from the group consisting of Newcastle Disease Virus (NDV), Infectious Laryngotracheitis Virus (ILTV), Infectious Bursal Disease Virus (IBDV), Marek's Disease Virus (MDV), and any combination thereof comprising administering to the chicken the vaccine of claim 11.

* * * * *

UNITED STATES PATENT AND TRADEMARK OFFICE

CERTIFICATE OF CORRECTION

PATENT NO. : 12,239,704 B2
APPLICATION NO. : 17/544044
DATED : March 4, 2025
INVENTOR(S) : Stephanie M. Cook, Mohamad Morsey and Ian Tarpey It is certified that error appears in the above-identified patent and that said Letters Patent is hereby corrected as shown below:

On the Title Page

Related U.S. Application Data (63) reads:
"(63) Continuation of application No. 16/753,133, filed as application No. PCT/EP2018/077725 on Oct. 11, 2018, now Pat. No. 11,229,698."

Should read:
--(63) Continuation of application No. 16/753,133, filed 04/02/2020, as a national phase entry of application No. PCT/EP2018/077725 filed on Oct. 11, 2018, now Pat. No. 11,229,698.--

Signed and Sealed this
Third Day of June, 2025

Coke Morgan Stewart
*Acting Director of the United States Patent and Trademark Office*